(12) United States Patent
Reddy et al.

(10) Patent No.: US 7,666,855 B2
(45) Date of Patent: Feb. 23, 2010

(54) 2'-C-METHYL NUCLEOSIDE DERIVATIVES

(75) Inventors: K. Raja Reddy, San Diego, CA (US); Mark D. Erion, Del Mar, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 100 days.

(21) Appl. No.: 11/589,363

(22) Filed: Oct. 30, 2006

(65) Prior Publication Data
US 2007/0042989 A1 Feb. 22, 2007

Related U.S. Application Data

(62) Division of application No. 10/903,215, filed on Jul. 29, 2004, now abandoned.

(60) Provisional application No. 60/544,743, filed on Feb. 13, 2004.

(51) Int. Cl.
*A61K 31/70* (2006.01)
*A01N 43/04* (2006.01)

(52) U.S. Cl. .......... 514/48; 514/45

(58) Field of Classification Search ........ None
See application file for complete search history.

(56) References Cited

U.S. PATENT DOCUMENTS

| | | | |
|---|---|---|---|
| 3,018,302 A | 1/1962 | Arnold et al. | |
| 6,312,662 B1 * | 11/2001 | Erion et al. | 424/9.1 |
| 6,752,981 B1 | 6/2004 | Erion et al. | |
| 6,777,395 B2 | 8/2004 | Bhat et al. | |
| 6,864,244 B2 | 3/2005 | Connolly et al. | |
| 6,914,054 B2 | 7/2005 | Sommadossi et al. | |
| 7,105,493 B2 * | 9/2006 | Sommadossi et al. | 514/42 |
| 2003/0225277 A1 | 12/2003 | Kopcho et al. | |
| 2003/0229225 A1 | 12/2003 | Reddy et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0092476 A1 | 5/2004 | Boyer et al. | |
| 2004/0147464 A1 | 7/2004 | Roberts et al. | |
| 2004/0192651 A1 | 9/2004 | Reddy et al. | |
| 2005/0090463 A1 | 4/2005 | Roberts et al. | |
| 2005/0107312 A1 | 5/2005 | Keicher et al. | |
| 2005/0182252 A1 | 8/2005 | Reddy et al. | |
| 2007/0060498 A1 * | 3/2007 | Gosselin et al. | 514/2 |

FOREIGN PATENT DOCUMENTS

| | | |
|---|---|---|
| GB | 2337262 A | 11/1999 |
| WO | WO 97/26883 A1 | 7/1997 |
| WO | WO 97/41211 A1 | 11/1997 |
| WO | WO 98/16184 A2 | 4/1998 |
| WO | WO 98/16186 A2 | 4/1998 |
| WO | WO 98/22458 A1 | 5/1998 |
| WO | WO 98/22496 A2 | 5/1998 |
| WO | WO 98/29430 A1 | 7/1998 |
| WO | WO 98/30223 A1 | 7/1998 |
| WO | WO 98/38888 A1 | 9/1998 |
| WO | WO 98/46630 A1 | 10/1998 |
| WO | WO 99/00399 A1 | 1/1999 |
| WO | WO 99/04908 A1 | 2/1999 |
| WO | WO 99/07733 A2 | 2/1999 |
| WO | WO 99/07734 A2 | 2/1999 |
| WO | WO 99/36074 A1 | 7/1999 |
| WO | WO 99/43691 A1 | 9/1999 |
| WO | WO 99/50230 A1 | 10/1999 |
| WO | WO 99/60855 A1 | 12/1999 |
| WO | WO 99/64442 A1 | 12/1999 |
| WO | WO 00/09543 | 2/2000 |
| WO | WO 00/24693 | 5/2000 |
| WO | WO 00/25780 | 5/2000 |
| WO | WO 00/44388 | 8/2000 |
| WO | WO 00/59929 | 10/2000 |
| WO | WO 01/00622 A1 | 1/2001 |
| WO | WO 01/27114 A1 | 4/2001 |
| WO | WO 01/45509 A1 | 6/2001 |
| WO | WO 01/45642 A2 | 6/2001 |
| WO | WO 01/46212 A1 | 6/2001 |
| WO | WO 01/47883 A1 | 7/2001 |
| WO | WO 01/60379 A1 | 8/2001 |
| WO | WO 01/60381 A1 | 8/2001 |
| WO | WO 01/68034 A2 | 9/2001 |
| WO | WO 01/68663 A1 | 9/2001 |
| WO | WO 01/77091 A2 | 10/2001 |
| WO | WO 01/79246 A2 | 10/2001 |
| WO | WO 02/03997 A1 | 1/2002 |
| WO | WO 02/04425 A2 | 1/2002 |
| WO | WO 02/06246 A1 | 1/2002 |

(Continued)

OTHER PUBLICATIONS

Stella, "Prodrugs as Therapeutics", Expert Opinion Ther. Patents (2004) 14(3), pp. 277-280.*

(Continued)

*Primary Examiner*—Traviss C McIntosh, III
(74) *Attorney, Agent, or Firm*—Saliwanchik, Lloyd & Saliwanchik

(57) ABSTRACT

Compounds of Formula I, stereoisomers, and pharmaceutically acceptable salts or prodrugs thereof, their preparation, and their uses for the treatment of hepatitis C viral infection are described:

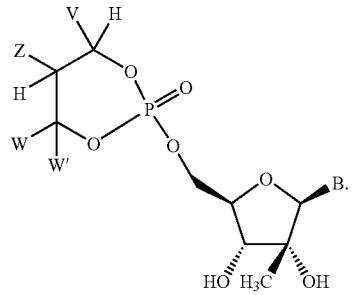

Formula I

37 Claims, No Drawings

FOREIGN PATENT DOCUMENTS

| | | |
|---|---|---|
| WO | WO 02/15904 A1 | 2/2002 |
| WO | WO 02/16382 A1 | 2/2002 |
| WO | WO 02/18404 A2 | 3/2002 |
| WO | WO 02/20497 A | 3/2002 |
| WO | WO 02/32920 A2 | 4/2002 |
| WO | WO 02/48116 A2 | 6/2002 |
| WO | WO 02/48165 A2 | 6/2002 |
| WO | WO 02/48172 A2 | 6/2002 |
| WO | WO 02/051425 A1 | 7/2002 |
| WO | WO 02/057287 A2 | 7/2002 |
| WO | WO 02/057425 A2 | 7/2002 |
| WO | WO 02/100415 A2 | 12/2002 |
| WO | WO 02/102307 A2 | 12/2002 |
| WO | WO03/062255 * | 1/2003 |
| WO | WO 03/014821 A2 | 2/2003 |
| WO | WO 03/014822 A2 | 2/2003 |
| WO | WO 03/026589 A2 | 4/2003 |
| WO | WO 03/026675 A1 | 4/2003 |
| WO | WO 03/034690 A2 | 4/2003 |
| WO | WO 03/034709 A1 | 4/2003 |
| WO | WO 03/037908 A1 | 5/2003 |
| WO | WO 03/051881 A1 | 6/2003 |
| WO | WO 03/051896 A1 | 6/2003 |
| WO | WO 03/051897 A1 | 6/2003 |
| WO | WO 03/051898 A1 | 6/2003 |
| WO | WO 03/051899 A1 | 6/2003 |
| WO | WO 03/052053 A2 | 6/2003 |
| WO | WO 03/057287 A1 | 7/2003 |
| WO | WO 03/062255 A2 | 7/2003 |
| WO | WO 03/062256 A1 | 7/2003 |
| WO | WO 03/093290 A2 | 11/2003 |
| WO | WO 2004/002422 A2 | 1/2004 |
| WO | WO 2004/002999 A2 | 1/2004 |
| WO | WO 2004/003000 A2 | 1/2004 |
| WO | WO 2004/013300 A2 | 2/2004 |
| WO | WO 2004/028481 A2 | 4/2004 |
| WO | WO2004/041834 * | 5/2004 |
| WO | WO 2004/046331 A2 | 6/2004 |
| WO | WO 2005/016927 A1 | 2/2005 |
| WO | WO 2005/037214 A2 | 4/2005 |

OTHER PUBLICATIONS

Allison, A. C. and Eugui, E. M., "Immunosuppressive and other anti-rheumatic activities of mycophenolate mofetil," *Variability in Response to Anti-Rheumatic Drugs* 1993, 165-188.

Aleksiuk, O. et al., "Proximal intraannular modifications of calix[4]arene via its spirodienone derivative," *J. Chem. Soc., Chem. Comm.* 1993, 11-13.

Anderson, R. C. and Shapiro, M. J., "2-Chloro-4(R),5(R)-dimethyl-2-oxo-1,3,2-dioxphospholane, a new chiral derivatizing agent," *J. Org. Chem.* 1984, 49, 1304-1305.

Aso, M. et al., "Synthesis of a new class of spin-labeled purine ribonucleosides and development of novel nucleophilic reaction to form 2,6,8-trifunctionalized purine derivatives," *J. Chem. Soc., Perkin Trans.* 2000, 2, 1637-1638.

Beigelman, L. N. et al., "New synthesis of 2'-C-Methylnucleotides starting from $_D$-glucose and $_D$-ribose," *Carbohydrate Research* 1987, 166,219-232.

Bentrude, W. G. et al., "Stereo- and regiochemistries of the oxidations of 2-methoxy-5-tert-butyl-1,3,2-dioxaphosphorinanes and the cyclic methyl 3',5'-phosphite of thymidine by $H_2O/I_2$ and $O_2/AIBN$ to p-chiral phosphates. $^{17}O$ NMR assignment of phosphorus configuration to the diastereomeric thymidine cyclic methyl 3',5'-monophosphates," *J. Am. Chem. Soc.* 1989, 111, 3981-3987.

Bertocchio, R. And Dreux, J., *Mémoires Présentés a la Société Chimique* 1962, 307, 1809-1813.

Corey, E. J. and Reichard, G. A., "Enantioselective and practical synthesis of R- and S-fluoxetines," *Tet. Lett.* 1989, 30(39), 5207-5210.

Cullis, P. M., "The stereochemical course of iodine-water oxidation of dinucleoside phosphite triesters," *J. Chem. Soc., Chem. Comm.* 1984, 1510-1512.

Curran, D. P. and Fenk, C. J., "Thermolysis of bis[2-[(trimethylsilyl)oxy]prop-2-yl]furoxan(TOP-furoxan). The first practical method for intermolecular cycloaddition of an in situ generated nitrile oxide with 1,2-di- and trisubstituted olefins," *J. Am. Chem. Soc.* 1985, 107, 6023-6028.

Dornow, A. et al., *Chem. Ber.* 1949, 3, 254-257.

Dymock, B. W., "Emerging therapies for hepatitis C virus infection," *Emerging Drugs* 2001, 6(1), 13-42.

Freer, R. et al., "A new route to famciclovir via palladium catalysed allylation," *Tetrahedron* 2000, 56, 4589-4595.

Hanson, R. L., "Regioslective enzymatic aminoacylation of lobucavir to give an intermediate for lobucavir prodrug," *Biorganic & Medicinal Chemistry* 2000, 8, 2681-2687.

Harry-O'kuru, R. E. et al., "A short, flexible route toward 2'-C-branched ribonucleosides," *J. Org. Chem.* 1997, 62, 1754-1759.

Hoeffler, J. F. et al., "Chemical synthesis of enantiopure 2-C-methyl-D-erythritol 4-phosphate, the key intermediate in the mevalonate-independent pathway for isoprenoid biosynthesis," *Tetrahedron* 2000, 56, 1485-1489.

Iwata, C. et al., "Asymmetric functionalization at a prochiral carbon center by the aid of sulfinyl chirality: a selective formation of 6-substituted $(3R,S_S)$- and $(3R,S_S)$-3-hydroxymethyl-3, 4-dihydro-5-(p-tolyl)sulfinyl-2H-pyrans," *Tet. Lett.* 1987, 28(27), 3131-3134.

Kimura, J. et al., "Studies on Nucleosides and Nucleotides," *Bulletin of the Chemical Society of Japan* 1979, 52(4), 1191-1196.

Kirschbaum, J., "Amantadine," *Anal Profiles Drug Subs.* 1983, 12; 1-36.

Mikolajczyk, M. and Luczak, J., "Dimethyl selenoxide oxidation of trivalent phosphorus compounds, thio-and selenophosphoryl compounds, and thiocarbonyl compounds. Stereochemical studies and selective modification of the thiocarbonyl-containing nucleic acid components," *J. Org. Chem.* 1978, 43(11), 2132-2138.

Mosbo, J. A. and Verkade, J. G., "Dipole moment, nuclear magnetic resonance, and infrared studies of phosphorus configurations and equilibria in 2-R-2-Oxo-1,3,2-dioxaphosphorinanes," *J. Org. Chem.* 1977, 42(9), 1549-1555.

Ogilvie, K. K. et al., "A general transesterification method for the synthesis of mixed trialkyl phosphates," *J. Am. Chem. Soc.* 1977, 99(4), 1277-1278.

Pankiewicz, K. W. et al., "Nucleosides," *J. Org. Chem.* 1985, 50, 3319-3322.

Patois, C. et al., "2-Alkyl-5,5-dimethyl-1,3,2-dioxaphosphorinan-2-ones α-lithiated carbanions," *J. Chem. Soc., Perkin Trans.* 1990, 1577-1581.

Perich, J. W. and Johns, R. B., "Di-tert-butyl N,N-diethylphosphoramidite," *Synthesis* 1988, 2, 142-144.

Perich, J. W. and Johns, R. B., "Synthesis of casein-related peptides and phosphopeptides," *Aust. J. Chem.* 1990, 43, 1623-1632.

Robins, R. K. and Revankar, G. R., "Design and synthesis of β-D-ribofuranosyl nucleosides active against RNA viral infections," *Advances in Drug Design*, vol. 1, 1993, 39-85.

Shih, Y. and Wang, J., "Synthesis and structure of 6-phenylcyclophosphamides," *Heterocycles* 1986, 24(6), 1599-1603.

Silverberg, L. J. et al., "A simple, rapid and efficient protocol for the selective phosphorylation of phenols with dibenzyl phosphite," *Tet. Lett.* 1996, 37(6), 771-774.

Thuong, N. T. et al., *Bulletin of the Chemical Society of France* 1974, 130,667-671.

Tsuchiya, H. et al., *The Chemical Society of Japan*, 10, 1968-1973.

Verürth, U. and Ugi, I., *Chem. Ber.* 1991, 124, 1627-1634.

Waga, T. et al., "Synthesis of 4'-C-Methylnucleosides," *Biosco. Biotch. Biochem.* 1993, 57(9), 1433-1438.

Wolfe, M. S. and Harry-O'kuru, R. E. "A Concise Synthesis of 2'-C-Methylribonucleosides," *Tet. Lett.* 1995, 36(42), 7611-7614.

Alexander et al., i"Preparation of 9—(Phosphonomethoxy-ethyl) Adenine Esters as Potential Prodrugs," Collect, Czech. Chem. Commun. 1994, 59, p. 1853-1869.

* cited by examiner

2'-C-METHYL NUCLEOSIDE DERIVATIVES

RELATED APPLICATIONS

This application is a divisional of U.S. application Ser. No. 10/903,215, filed Jul. 29, 2004, which claims the benefit of U.S. Provisional Application No. 60/544,743 filed Feb. 13, 2004 and which are incorporated by reference herein in their entirely, including figures.

FIELD OF THE INVENTION

The present invention is directed towards novel 2'-C-methyl nucleoside 5'-monophosphate derivatives, their preparation and their uses. More specifically, the novel compounds are useful to treat hepatitis C viral infections.

BACKGROUND

The following description of the background of the invention is provided to aid in understanding the invention, but is not admitted to be, or to describe, prior art to the invention. All publications are incorporated by reference in their entirety.

Hepatitis C is a viral disease that causes inflammation of the liver that may lead to cirrhosis, primary liver cancer and other long-term complications. Nucleosides are a well-recognized class of compounds shown to be effective against a variety of viral infections, including hepatitis B, HIV, and herpes. A few nucleosides are reported to inhibit hepatitis C (HCV) virus replication, including ribavirin, which currently is marketed as a drug combination with various interferons, and nucleosides containing a 2'-C-methyl ribose sugar.

Nucleosides are generally effective as antiviral agents following conversion of the nucleoside to the corresponding nucleoside 5'-triphosphate (NTP). Conversion occurs inside cells through the action of various intracellular kinases. The first step, i.e. conversion of the nucleoside to the 5'-monophosphate (NMP) is generally the slow step and involves a nucleoside kinase, which is encoded by either the virus or host. Conversion of the NMP to the NTP is generally catalyzed by host nucleotide kinases. The NTP interferes with viral replication through inhibition of viral polymerases and/or via incorporation into a growing strand of DNA or RNA followed by chain termination.

Use of nucleosides to treat viral liver infections is often complicated by one of two problems. In some cases, the desired nucleoside is a good kinase substrate and accordingly produces NTP in the liver as well as other cells and tissues throughout the body. Since NTP production is often associated with toxicity, efficacy can be limited by extrahepatic toxicities. In other cases, the desired nucleoside is a poor kinase substrate so is not efficiently converted into the NMP and ultimately into the NTP.

For instance, U.S. Pat. No. 6,312,662 discloses the use of certain phosphate prodrugs for the liver-specific delivery of various drugs including nucleosides for the treatment of patients with liver diseases such as hepatitis C, hepatitis B and hepatocellular carcinoma.

SUMMARY OF THE INVENTION

The present invention is directed towards novel 2'-C-methyl nucleoside 5'-monophosphate derivatives, their preparation and their uses for the treatment of hepatitis C viral infections.

In one aspect, the present invention relates to compounds of Formula I, and pharmaceutically acceptable salts and prodrugs thereof.

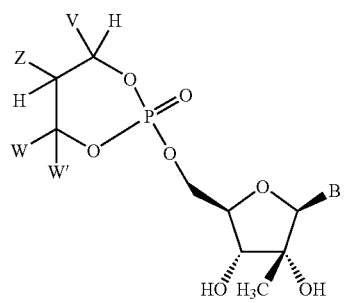

Formula I wherein:

B is selected from the group consisting of

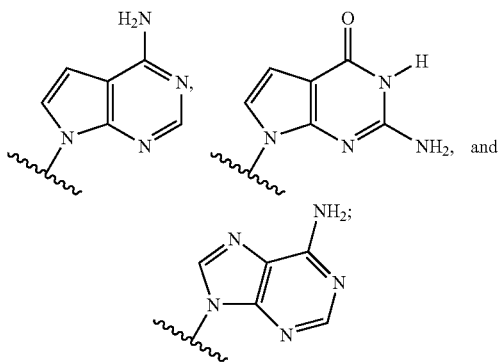

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4{}_2$, —$CO_2R^5$, —$SO_2R^5$, —$SO_2NR^4{}_2$, —$OR^4$, —$SR^4$, —$R^4$, —$NR^4{}_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^3$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3.

In another aspect, the invention relates to compounds of Formula I, and pharmaceutically acceptable salts and prodrugs thereof:

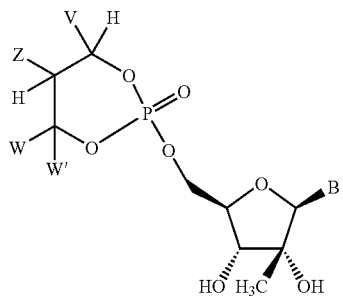

(I)

wherein:
B is

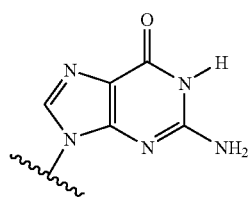

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4{}_2$, —$CO_2R^5$, —$SO_2R^5$, —$SO_2NR^4{}_2$, —$OR^4$, —$SR^4$, —$R^4$, —$NR^4{}_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^5$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3.

Some of the compounds of Formula I have asymmetric centers where the stereochemistry is unspecified, and the diastereomeric mixtures of these compounds are included, as well as the individual stereoisomers when referring to a compound of Formula I generally.

Some of the compounds described herein may exist as tautomers such as keto-enol tautomers and imine-enamine tautomers. The individual tautomers as well as mixtures thereof are encompassed with compounds of Formula I. An example of keto-enol tautomers which are intended to be encompassed within the compounds of the present invention is illustrated below:

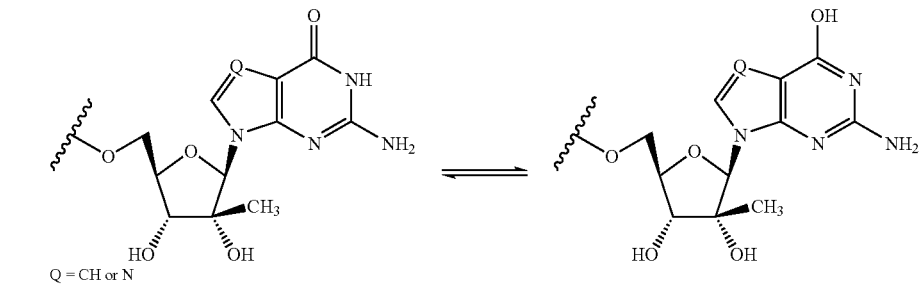

An example of imine-enamine tautomers which are intended to be encompassed within the compounds of the present invention is illustrated below:

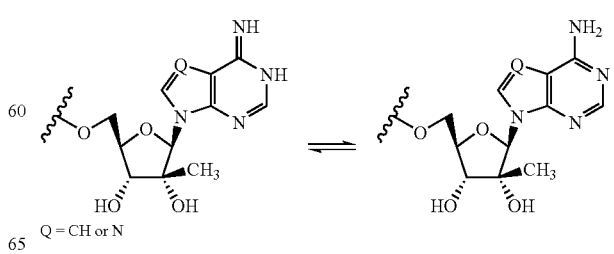

Also provided are pharmaceutical compositions comprising compounds of Formula I, pharmaceutically acceptable salts or prodrugs thereof; in association with pharmaceutically acceptable excipients or carriers.

Also provided are methods for inhibiting viral replication comprising the step of administering to a patient a therapeutically effective amount of a compound of Formula I, pharmaceutically acceptable salts or prodrugs thereof.

Also provided are methods for inhibiting RNA-dependent RNA viral replication comprising the step of administering to a patient a therapeutically effective amount of a compound of Formula I, or pharmaceutically acceptable salts or prodrugs thereof.

Also provided are methods for inhibiting HCV replication comprising the step of administering to a patient a therapeutically effective amount of a compound of Formula I, pharmaceutically acceptable salts or prodrugs thereof.

Also provided are methods for treating viral infections comprising the step of administering to a patient a therapeutically effective amount of a compound of Formula I, or pharmaceutically acceptable salts or prodrugs thereof.

Also provided are methods for treating viral infections of the liver comprising the step of administering to a patient a therapeutically effective amount of a compound of Formula I, or pharmaceutically acceptable salts or prodrugs thereof.

Also provided are methods for treating RNA-dependent RNA viral infection comprising the step of administering to a patient a therapeutically effective amount of a compound of Formula I, a pharmaceutically acceptable salts or prodrugs thereof.

Also provided are methods for treating HCV infection comprising the step of administering to a patient a therapeutically effective amount of a compound of Formula I, pharmaceutically acceptable salts or prodrugs thereof.

Also provided are methods for preparing compounds of Formula I, stereoisomers, and pharmaceutically acceptable salts or prodrugs thereof.

DEFINITIONS

In accordance with the present invention and as used herein, the following terms are defined with the following meanings, unless explicitly stated otherwise.

The term "alkyl" refers to saturated aliphatic groups including straight-chain, branched chain and cyclic groups, up to and including 10 carbon atoms. Suitable alkyl groups include methyl, ethyl, n-propyl, isopropyl, and cyclopropyl. The alkyl may be optionally substituted with 1-3 substituents.

The term "aryl" refers to aromatic groups which have 5-14 ring atoms and at least one ring having a conjugated pi electron system and includes carbocyclic aryl, heterocyclic aryl and biaryl groups, all of which may be optionally substituted. The aryl group may be optionally substituted with 1-6 substituents.

Carbocyclic aryl groups are groups which have 6-14 ring atoms wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups which have 5-14 ring atoms wherein 1 to 4 heteroatoms are ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The term "monocyclic aryl" refers to aromatic groups which have 5-6 ring atoms and includes carbocyclic aryl and heterocyclic aryl. Suitable aryl groups include phenyl, furanyl, pyridyl, and thienyl. Aryl groups may be substituted.

The term "monocyclic heteroaryl" refers to aromatic groups which have 5-6 ring atoms wherein 1 to 4 heteroatoms are ring atoms in the aromatic ring and the remainder of the ring atoms being carbon atoms. Suitable heteroatoms include oxygen, sulfur, and nitrogen.

The term "biaryl" represents aryl groups which have 5-14 atoms containing more than one aromatic ring including both fused ring systems and aryl groups substituted with other aryl groups. Such groups may be optionally substituted. Suitable biaryl groups include naphthyl and biphenyl.

The term "optionally substituted" or "substituted" includes groups substituted by one to four substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, and lower aralkyloxyalkyl. "Substituted aryl" and "substituted heteroaryl" refers to aryl and heteroaryl groups substituted with 1-6 substituents. These substituents are selected from the group consisting of lower alkyl, lower alkoxy, lower perhaloalkyl, halogen, hydroxy, cyano, and amino.

The term "-aralkyl" refers to an alkylene group substituted with an aryl group. Suitable aralkyl groups include benzyl, picolyl, and the like, and may be optionally substituted. The aryl portion may have 5-14 ring atoms and the alkyl portion may have up to and including 10 carbon atoms. "Heteroaralkyl" refers to an alkylene group substituted with a heteroaryl group.

The term "alkylaryl-" refers to an aryl group substituted with an alkyl group. "Lower alkylaryl-" refers to such groups where alkyl is lower alkyl. The aryl portion may have 5-14 ring atoms and the alkyl portion may have up to and including 10 carbon atoms. The term "lower" referred to herein in connection with organic radicals or compounds respectively defines such as with up to and including 10, in one aspect up to and including 6, and in another aspect one to four carbon atoms. Such groups may be straight chain, branched, or cyclic.

The term "cyclic alkyl" or "cycloalkyl" refers to alkyl groups that are cyclic of 3 to 10 carbon atoms, and in one aspect are 3 to 6 carbon atoms. Suitable cyclic groups include norbornyl and cyclopropyl. Such groups may be substituted.

The term "heterocyclic", "heterocyclic alkyl" or "heterocycloalkyl" refer to cyclic groups of 3 to 10 atoms, and in one aspect are 3 to 6 atoms, containing at least one heteroatom, in a further aspect are 1 to 3 heteroatoms. Suitable heteroatoms include oxygen, sulfur, and nitrogen. Heterocyclic groups may be attached through a nitrogen or through a carbon atom in the ring. The heterocyclic alkyl groups include unsaturated cyclic, fused cyclic and spirocyclic groups. Suitable heterocyclic groups include pyrrolidinyl, morpholino, morpholinoethyl, and pyridyl.

The terms "arylamino" (a), and "aralkylamino" (b), respectively, refer to the group —NRR' wherein respectively, (a) R is aryl and R' is hydrogen, alkyl, aralkyl, heterocycloalkyl, or aryl, and (b) R is aralkyl and R' is hydrogen, aralkyl, aryl, alkyl or heterocycloalkyl.

The term "acyl" refers to —C(O)R where R is alkyl, heterocycloalkyl, or aryl. The term "lower acyl" refers to where R is lower alkyl. The term $C_1$-$C_4$ acyl refers to where R is $C_1$-$C_4$.

The term "carboxy esters" refers to —C(O)OR where R is alkyl, aryl, aralkyl, cyclic alkyl, or heterocycloalkyl, all optionally substituted.

The term "carboxyl" refers to —C(O)OH.

The term "oxo" refers to =O in an alkyl or heterocycloalkyl group.

The term "amino" refers to —NRR' where R and R' are independently selected from hydrogen, alkyl, aryl, aralkyl and heterocycloalkyl, all except H are optionally substituted; and R and R' can form a cyclic ring system.

The term "-carboxylamido" refers to —CONR$_2$ where each R is independently hydrogen or alkyl.

The term "-sulphonylamido" or "-sulfonylamido" refers to —S(=O)$_2$NR$_2$ where each R is independently hydrogen or alkyl.

The term "halogen" or "halo" refers to —F, —Cl, —Br and —I.

The term "alkylaminoalkylcarboxy" refers to the group alkyl-NR-alk-C(O)—O— where "alk" is an alkylene group, and R is a H or lower alkyl.

The term "sulphonyl" or "sulfonyl" refers to —SO$_2$R, where R is H, alkyl, aryl, aralkyl, or heterocycloalkyl.

The term "sulphonate" or "sulfonate" refers to —SO$_2$OR, where R is —H, alkyl, aryl, aralkyl, or heterocycloalkyl.

The term "alkenyl" refers to unsaturated groups which have 2 to 12 atoms and contain at least one carbon-carbon double bond and includes straight-chain, branched-chain and cyclic groups. Alkenyl groups may be optionally substituted. Suitable alkenyl groups include allyl. "1-Alkenyl" refers to alkenyl groups where the double bond is between the first and second carbon atom. If the 1-alkenyl group is attached to another group, e.g. it is a W substituent attached to the cyclic phosphate, it is attached at the first carbon.

The term "alkynyl" refers to unsaturated groups which have 2 to 12 atoms and contain at least one carbon-carbon triple bond and includes straight-chain, branched-chain and cyclic groups. Alkynyl groups may be optionally substituted. Suitable alkynyl groups include ethynyl. "1-Alkynyl" refers to alkynyl groups where the triple bond is between the first and second carbon atom. If the 1-alkynyl group is attached to another group, e.g. it is a W substituent attached to the cyclic phosphate, it is attached at the first carbon.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched or cyclic. The alkylene may be optionally substituted with 1-3 substituents.

The term "acyloxy" refers to the ester group —O—C(O)R, where R is H, alkyl, alkenyl, alkynyl, aryl, aralkyl, or heterocycloalkyl.

The term "aminoalkyl-" refers to the group NR$_2$-alk- wherein "alk" is an alkylene group and R is selected from —H, alkyl, aryl, aralkyl, and heterocycloalkyl.

The term "alkylaminoalkyl-" refers to the group alkyl-NR-alk- wherein each "alk" is an independently selected alkylene, and R is H or lower alkyl. "Lower alkylaminoalkyl-" refers to groups where the alkyl and the alkylene group is lower alkyl and alkylene, respectively.

The term "arylaminoalkyl-" refers to the group aryl-NR-alk- wherein "alk" is an alkylene group and R is —H, alkyl, aryl, aralkyl, or heterocycloalkyl. In "lower arylaminoalkyl-", the alkylene group is lower alkylene.

The term "alkylaminoaryl-" refers to the group alkyl-NR-aryl- wherein "aryl" is a divalent group and R is —H, alkyl, aralkyl, or heterocycloalkyl. In "lower alkylaminoaryl-", the alkyl group is lower alkyl.

The term "alkoxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "alkoxy-" or "alkyloxy-" refers to the group alkyl-O—.

The term "alkoxyalkyl-" or "alkyloxyalkyl-" refer to the group alkyl-O-alk- wherein "alk" is an alkylene group. In "lower alkoxyalkyl-", each alkyl and alkylene is lower alkyl and alkylene, respectively.

The terms "alkylthio-" refers to the group alkyl-S—.

The term "alkylthioalkyl-" refers to the group alkyl-S-alk- wherein "alk" is an alkylene group. In "lower alkylthioalkyl-" each alkyl and alkylene is lower alkyl and alkylene, respectively.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "amido" refers to the NR$_2$ group next to an acyl or sulfonyl group as in NR$_2$—C(O)—, RC(O)—NR$^1$—, NR$_2$—S(=O)$_2$— and RS(=O)$_2$—NR$^1$—, where R and R$^1$ include —H, alkyl, aryl, aralkyl, and heterocycloalkyl.

The term "carboxamido" refer to NR$_2$—C(O)— and RC(O)—NR$^1$—, where R and R$^1$ include —H, alkyl, aryl, aralkyl, and heterocycloalkyl. The term does not include urea, —NR—C(O)—NR—.

The terms "sulphonamido" or "sulfonamido" refer to NR$_2$—S(=O)$_2$— and RS(=O)$_2$—NR$^1$—, where R and R$^1$ include —H, alkyl, aryl, aralkyl, and heterocycloalkyl. The term does not include sulfonylurea, —NR—S(=O)$_2$—NR—.

The term "carboxamidoalkylaryl" and "carboxamidoaryl" refers to an aryl-alk-NR$^1$—C(O), and ar-NR$^1$—C(O)-alk-, respectively where "ar" is aryl, "alk" is alkylene, R$^1$ and R include H, alkyl, aryl, aralkyl, and heterocycloalkyl.

The term "sulfonamidoalkylaryl" and "sulfonamidoaryl" refers to an aryl-alk-NR$^1$—S(=O)$_2$—, and ar-NR$^1$—S(=O)$_2$—, respectively where "ar" is aryl, "alk" is alkylene, R$^1$ and R include —H, alkyl, aryl, aralkyl, and heterocycloalkyl.

The term "hydroxyalkyl" refers to an alkyl group substituted with one —OH.

The term "haloalkyl" refers to an alkyl group substituted with one halogen.

The term "cyano" refers to —C≡N.

The term "nitro" refers to —NO$_2$.

The term "acylalkyl" refers to an alkyl-C(O)-alk-, where "alk" is alkylene.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "heteroarylalkyl" refers to an alkylene group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "heterocyclic base B" refers to

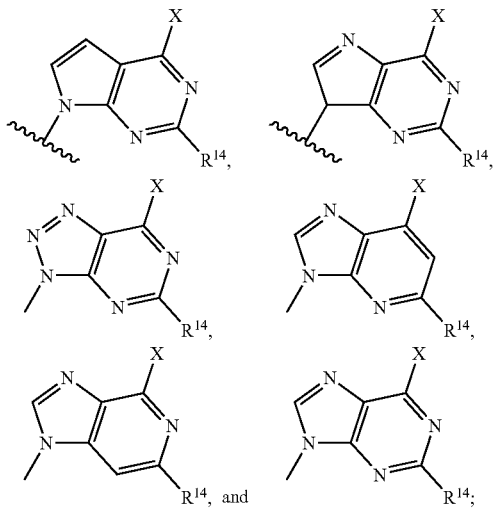

wherein:

R$^{14}$ is independently selected from the group consisting of H and NH$_2$; and X is selected from the group consisting of NH$_2$, NHCH$_3$, N(CH$_3$)$_2$, OCH$_3$, SCH$_3$, OH, and SH.

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition.

The term "pharmaceutically acceptable salt" includes salts of compounds of Formula I and its prodrugs derived from the combination of a compound of this invention and an organic or inorganic acid or base. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

The term "naturally-occurring L-amino acid" refers to those amino acids routinely found as components of proteinaceous molecules in nature, including alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine and histidine. In one aspect, this term is intended to encompass L-amino acids having only the amine and carboxylic acid as charged functional groups, i.e., alanine, valine, leucine, isoleucine, proline, phenylalanine, tryptophan, methionine, glycine, serine, threonine, cysteine and tyrosine. In another aspect they are alanine, valine, leucine, isoleucine, proline, phenylalanine, and glycine. In a further aspect, it is valine.

The term "patient" refers to an animal being treated including a mammal, such as a dog, a cat, a cow, a horse, a sheep, and a human. Another aspect includes a mammal, both male and female.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, R$_2$N—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The term "prodrug" herein also includes but is not limited to esterase cleavable prodrugs of the 2' and 3'-hydroxy groups of compounds of Formula I (Anastasi et al., *Curr. Med. Chem.*, 2003, 10, 1825). Standard groups include acyl and alkoxycarbonyl groups, and esters of natural L-amino acid derivatives (Perry, et al., *Drugs*, 1996, 52, 754). Also included is a cyclic carbonate derivative formed by carbonylation of the 2' and 3'-hydroxy groups, which upon activation by esterase activity in vivo results in compounds of Formula I.

In the case of bases, "prodrugs" are preferred at the 6-position of purine analogs. Such substitution may include H, halogen, amino, acetoxy or azido groups. Hydrogen substituted prodrugs at the 6-position of guanosine analogs undergo oxidation in vivo by aldehyde oxidase or xanthine oxidase to give the required functionality (Rashidi et al., *Drug Metab. Dispos.* 1997, 25, 805). While esterases unmask acetoxy groups, amine and halogen substituents are known to be substrates for deaminases. 6-Azido substituted compounds are also known to give the corresponding amino derivatives by the action of reductases (Koudriakova, et al., *J. Med Chem.*, 1996, 39, 4676).

The structure

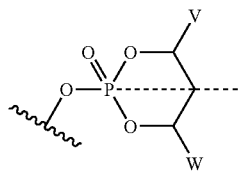

has a plane of symmetry running through the phosphorus-oxygen double bond when V=W and V and W are either both pointing up or both pointing down.

The term "cyclic phosphate ester of 1,3-propanediol", "cyclic phosphate diester of 1,3-propanediol", "2 oxo $2\lambda^5$[1,3,2]dioxaphosphorinane", "2-oxo-[1,3,2]-dioxaphosphorinane", or "dioxaphosphorinane" refers to the following:

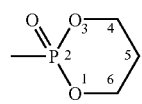

The phrase "together V and Z are connected via an additional 3-5 atoms to form a cyclic group, optionally containing one heteroatom, that is fused to an aryl group attached at the beta and gamma position to the O attached to the phosphorus" includes the following:

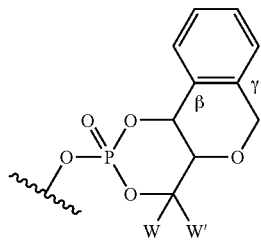

As shown above together V and Z are connected via 4 additional atoms.

The phrase "together W and W' are connected via an additional 2-5 atoms to form a cyclic group, optionally containing 0-2 heteroatoms, and V must be aryl, substituted aryl, heteroaryl, or substituted heteroaryl" includes the following:

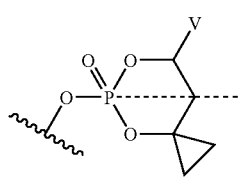

As shown above together W and W' are connected via an additional 2 atoms.

The structure above has V=aryl, and a spiro-fused cyclopropyl group for W and W'.

The term "cyclic phosphate" refers to

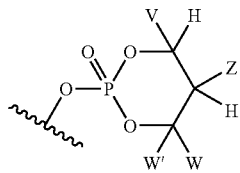

The carbon attached to V must have a C—H bond. The carbon attached to Z must also have a C—H bond.

The term "cis" stereochemistry refers to the spatial relationship of the V group and the substituent attached to the phosphorus atom via an exocyclic single bond on the six membered 2-oxo-phosphorinane ring. The structures A and B below show two possible cis-isomers of 2- and 4-substituted 2-oxo-phosphorinane. Structure A shows cis-isomer of (2S, 4R)-configuration whereas structure B shows cis-isomer of (2R,4S)-configuration.

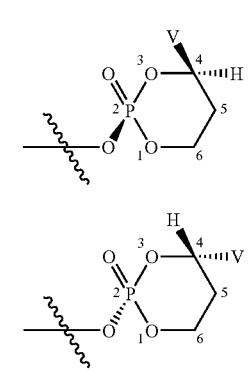

The term "trans" stereochemistry refers to the spatial relationship of the V group and the substituent attached to the phosphorus atom via an exocyclic single bond on the six membered 2-oxo-phosphorinane ring. The structures C and D below show two possible trans-isomers of 2- and 4-substituted 2-oxo-phosphorinane. Structure C shows trans-isomer of (2S,4S)-configuration whereas structure D shows trans-isomer of (2R,4R)-configuration.

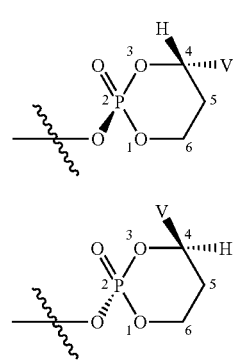

The term "percent enantiomeric excess (% ee)" refers to optical purity. It is obtained by using the following formula:

$$\frac{[R]-[S]}{[R]+[S]} \times 100 = \% R - \% S$$

where [R] is the amount of the R isomer and [S] is the amount of the S isomer. This formula provides the % ee when R is the dominant isomer.

The term "enantioenriched" or "enantiomerically enriched" refers to a sample of a chiral compound that consists of more of one enantiomer than the other. The extent to which a sample is enantiomerically enriched is quantitated by the enantiomeric ratio or the enantiomeric excess.

The term "liver" refers to liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug. In an additional aspect the increase in oral bioavailability of the prodrug (compared to the parent drug) is at least 100%, that is a doubling of the absorption. Measurement of oral bioavailability usually refers to measurements of the prodrug, drug, or drug metabolite in blood, plasma, tissues, or urine following oral administration compared to measurements following parenteral administration.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biological activity of the drug and the ability of an agent to bypass this resistance through the use of alternative pathways or the failure of the agent to induce changes that tend to resistance.

The terms "treating" or "treatment" of a disease includes inhibiting the disease (slowing or arresting its development), providing relief from the symptoms or side-effects of the disease (including palliative treatment), and relieving the disease (causing regression of the disease).

DETAILED DESCRIPTION

The present invention relates to compounds of Formula I, stereoisomers, pharmaceutically acceptable salts or prodrugs thereof or pharmaceutically acceptable salts of the prodrugs as represented by Formula I:

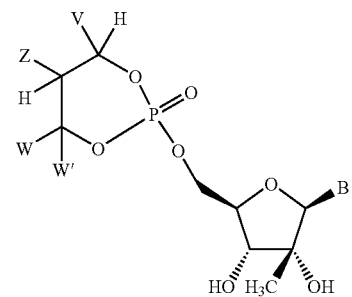

wherein:

B is selected from the group consisting of

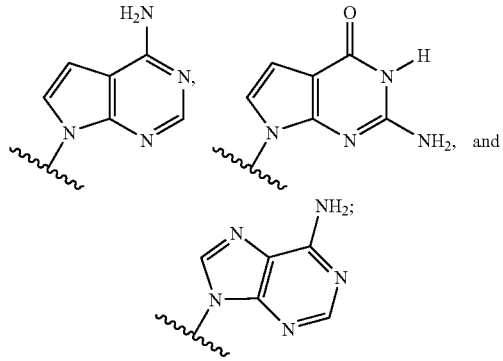

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4{}_2$, —$CO_2R^5$, —$SO_2R^5$, —$SO_2NR^4{}_2$, —$OR^4$, —$SR^4$, —$R^4$, —$NR^4{}_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^3$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3;
or pharmaceutically acceptable prodrugs or salts thereof.

In one aspect, the invention comprises compounds of Formula I:

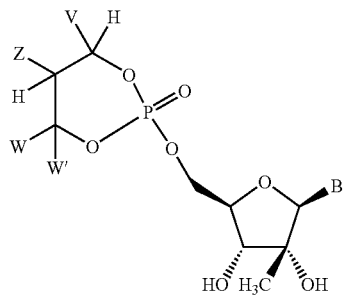

(I)

wherein:
B is

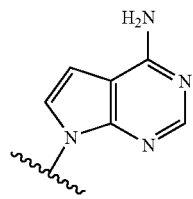

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4{}_2$, —$CO_2R^5$, —$SO_2R^5$, —$SO_2NR^4{}_2$, —$OR^4$, —$SR^4$, —$R^4$, —$NR^4{}_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^5$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3;

or pharmaceutically acceptable prodrugs or salts thereof.

In another aspect, the invention comprises compounds of Formula I:

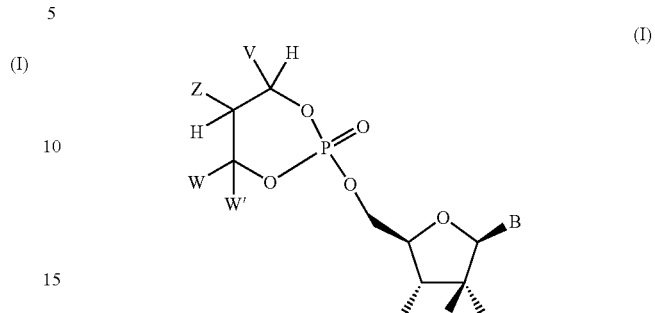

(I)

wherein:
B is

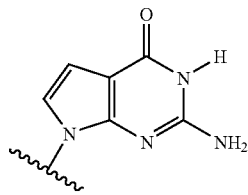

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4{}_2$, —$CO_2R^5$, —$SO_2R^5$, —$SO_2NR^4{}_2$, —$OR^4$, —$SR^4$, —$R^4$, —$NR^4{}_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^5$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3;

or pharmaceutically acceptable prodrugs or salts thereof.

In another aspect, the invention comprises compounds of Formula I:

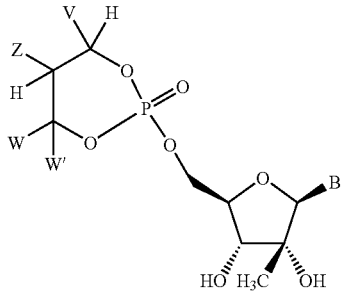

(I)

wherein:
B is

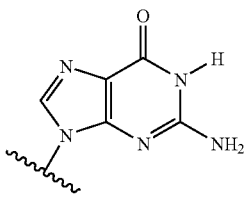

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4_2$, —$CO_2R^5$, —$SO_2R^5$, —$SO_2NR^4_2$, —$OR^4$, —$SR^4$, —$R^4$, —$NR^4_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^5$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3;

or pharmaceutically acceptable prodrugs or salts thereof.

In yet another aspect, the invention comprises compounds of Formula I:

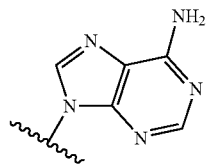

(I)

wherein:
B is

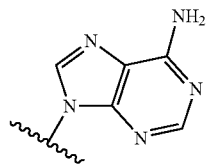

V is selected from the group consisting of optionally substituted monocyclic aryl and optionally substituted monocyclic heteroaryl;

W and W' are independently selected from the group consisting of —$R^2$, optionally substituted monocyclic aryl, and optionally substituted monocyclic heteroaryl;

Z is selected from the group consisting of halogen, —CN, —$COR^5$, —$CONR^4_2$, —$CO_2R^5$, —$SO_2R^5$, —$SO_2NR^4_2$, —$OR^4$, —$SR^4$, —$R^4$, —$NR^4_2$, —$OCOR^5$, —$OCO_2R^5$, —$SCOR^5$, —$SCO_2R^5$, —$NHCOR^4$, —$NHCO_2R^5$, —$(CH_2)_p$—$OR^6$, and —$(CH_2)_p$—$SR^6$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group, optionally containing 0-2 heteroatoms;

$R^2$ is selected from the group consisting of $R^3$ and hydrogen;

$R^3$ is selected from the group consisting of alkyl, aryl, heterocycloalkyl, and aralkyl;

$R^4$ is selected from the group consisting of $R^5$ and hydrogen;

$R^5$ is selected from the group consisting of alkyl, aryl, heterocycloalkyl, and aralkyl;

$R^6$ is selected from the group consisting of hydrogen, and lower acyl;

$R^{12}$ is selected from the group consisting of hydrogen, and lower acyl; and p is an integer 2 or 3;

or pharmaceutically acceptable prodrugs or salts thereof.

In one aspect, V is selected from the group consisting of phenyl, substituted phenyl with 1-3 substituents independently selected from the group consisting of halogen, $C_1$-$C_6$ alkyl, —$CF_3$, —$OR^3$, —$OR^{12}$, —$COR^3$, —$CO_2R^3$, —$NR^3_2$, —$NR^{12}_2$, —$CO_2NR_2^2$, —$SR^3$, —$SO_2R^3$, —$SO_2NR_2^2$ and —CN, monocyclic heteroaryl, and substituted monocyclic heteroaryl with 1-2 substituents independently selected from the group consisting of halogen, $C_1$-$C_6$ alkyl, —$CF_3$, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, —$SO_2NR_2{}^2$ and —CN, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 3-5 atoms to form a cyclic group, optionally containing 1 heteroatom, that is fused to an aryl group at the beta and gamma position to the O attached to the phosphorus; and $R^3$ is $C_1$-$C_6$ alkyl.

In another aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 4 atoms to form a 6-membered ring that is fused to a phenyl or substituted phenyl at the beta and gamma position to the O attached to the phosphorus.

In yet another aspect, V is selected from the group consisting of phenyl; substituted phenyl with 1-2 substituents independently selected from the group consisting of —Cl, —Br, —F, $C_1$-$C_3$ alkyl, and —$CF_3$; pyridyl; substituted pyridyl with 1 substituent independently selected from the group consisting of —Cl, —Br, —F, $C_1$-$C_3$ alkyl, and —$CF_3$; furanyl; substituted furanyl with 1 substituent independently selected from the group consisting of —Cl, —Br, —F, $C_1$-$C_3$ alkyl, and —$CF_3$; thienyl; and substituted thienyl with 1 substituent independently selected from the group consisting of —Cl, —Br, —F, $C_1$-$C_3$ alkyl, and —$CF_3$.

In a further aspect, V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl. In another aspect, V is selected from the group consisting of 3-chlorophenyl, 3-bromophenyl, 2-bromophenyl, 3,5-dichlorophenyl, 3-pyridyl, and 4-pyridyl.

In another aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OH, —OMe, —$NH_2$, —$NMe_2$, —OEt, —COOH, —$CO_2$t-butyl, —$CO_2NH_2$, —SMe, —$SO_2Me$, —$SO_2NH_2$ and —CN; monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OH, —OMe, —$NH_2$, —$NMe_2$, —OEt, —COOH, —$CO_2$t-butyl, —$CO_2NH_2$, —SMe, —$SO_2Me$, —$SO_2NH_2$ and —CN; and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 4 atoms to form a 6-membered ring that is fused to a phenyl or substituted phenyl at the beta and gamma position to the O attached to the phosphorus.

In one aspect, Z is selected from the group consisting of —H, —OMe, —OEt, phenyl, $C_1$-$C_3$ alkyl, —$NR^4{}_2$, —$SR^4$, —$(CH_2)_p$—$OR^6$, —$(CH_2)_p$—$SR^6$ and —$OCOR^5$; $R^4$ is $C_1$-$C_4$ alkyl; $R^5$ is selected from the group consisting of $C_1$-$C_4$ alkyl, monocyclic aryl, and monocyclic aralkyl; and $R^6$ is $C_1$-$C_4$ acyl. In a further aspect, Z is selected from the group consisting of —H, —OMe, —OEt, and phenyl.

In an additional aspect, W and W' are independently selected from the group consisting of —H, $C_1$-$C_6$ alkyl, and phenyl; or together W and W' are connected via an additional 2-5 atoms to form a cyclic group. In yet another aspect, W and W' are independently selected from the group consisting of —H, methyl, and V, or W and W' are each methyl, with the proviso that when W is V, then W' is H.

In one aspect, V is selected from the group consisting of optionally substituted monocyclic aryl and optionally substituted monocyclic heteroaryl;

W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4{}_2$, —$SR^4$, —$(CH_2)_p$—$OR^6$, —$(CH_2)_p$—$SR^6$ and —$OCOR^5$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group; and $R^4$ is $C_1$-$C_4$ alkyl; $R^5$ is selected from the group consisting of $C_1$-$C_4$ alkyl, monocyclic aryl, and monocyclic aralkyl; and $R^6$ is $C_1$-$C_4$ acyl.

In another aspect, V is selected from the group consisting of phenyl, substituted phenyl with 1-3 substituents independently selected from the group consisting of halogen, $C_1$-$C_6$ alkyl, —$CF_3$, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, —$SO_2NR_2{}^2$ and —CN, monocyclic heteroaryl, and substituted monocyclic heteroaryl with 1-2 substituents independently selected from the group consisting of halogen, $C_1$-$C_6$ alkyl, —$CF_3$, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, —$SO_2NR_2{}^2$ and —CN, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4_2$, —$SR^4$, —$(CH_2)_p$—$OR^6$, —$(CH_2)_p$—$SR^6$ and —$OCOR^5$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group; and $R^3$ is $C_1$-$C_6$ alkyl; $R^4$ is $C_1$-$C_4$ alkyl; $R^5$ is selected from the group consisting of $C_1$-$C_4$ alkyl, monocyclic aryl, and monocyclic aralkyl; and $R^6$ is $C_1$-$C_4$ acyl.

In a further aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S; and b) when there are two heteroatoms and one is S, then the other can not be O or S; or W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4_2$, —$SR^4$, —$(CH_2)_p$—$OR^6$, —$(CH_2)_p$—$SR^6$ and —$OCOR^5$; or together V and Z are connected via an additional 4 atoms to form a 6-membered ring that is fused to a phenyl or substituted phenyl at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group; and $R^4$ is $C_1$-$C_4$ alkyl; $R^5$ is selected from the group consisting of $C_1$-$C_4$ alkyl, monocyclic aryl, and monocyclic aralkyl; and $R^6$ is $C_1$-$C_4$ acyl.

In yet another aspect, V is selected from the group consisting of phenyl; substituted phenyl with 1-2 substituents independently selected from the group consisting of —Cl, —Br, —F, $C_1$-$C_3$ alkyl, and —$CF_3$; pyridyl; substituted pyridyl with 1 substituent independently selected from the group consisting of —Cl, —Br, —F, $C_1$-$C_3$ alkyl, and —$CF_3$; furanyl; substituted furanyl with 1 substituent independently selected from the group consisting of —Cl, —Br, —F, $C_1$-$C_3$ alkyl, and —$CF_3$; thienyl; and substituted thienyl with 1 substituent independently selected from the group consisting of —Cl, —Br, —F, $C_1$-$C_3$ alkyl, and —$CF_3$;

W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4_2$, —$SR^4$, —$(CH_2)_p$—$OR^6$, —$(CH_2)_p$—$SR^6$ and —$OCOR^5$; or together Z and W are connected via an additional 3-5 atoms to form a cyclic group, optionally containing one heteroatom; or together W and W' are connected via an additional 2-5 atoms to form a cyclic group; and $R^4$ is $C_1$-$C_4$ alkyl; $R^5$ is selected from the group consisting of $C_1$-$C_4$ alkyl, monocyclic aryl, and monocyclic aralkyl; and $R^6$ is $C_1$-$C_4$ acyl.

In a further aspect, V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl; and Z is selected from the group consisting of —H, OMe, OEt, and phenyl; and W and W' are independently selected from the group consisting of —H and phenyl, or W and W' are each methyl.

In one aspect, Z, W, and W' are each —H. In another aspect, V and W are the same and each is selected from the group consisting of optionally substituted monocyclic aryl and optionally substituted monocyclic heteroaryl.

In another aspect, B is

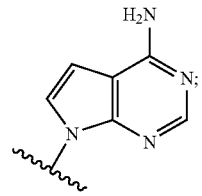

V is selected from the group consisting of 3-chlorophenyl, 3-bromophenyl, 2-bromophenyl, 3,5-dichlorophenyl, and 4-pyridyl; and Z, W, and W' are each —H.

In yet another aspect, B is

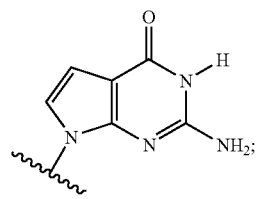

V is selected from the group consisting of 3-chlorophenyl, 3-bromophenyl, 2-bromophenyl, 3,5-dichlorophenyl, and 4-pyridyl; and Z, W, and W' are each —H.

In a further aspect, B is

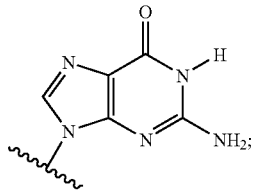

V is selected from the group consisting of 3-chlorophenyl, 3-bromophenyl, 2-bromophenyl, 3,5-dichlorophenyl, and 4-pyridyl; and Z, W, and W' are each —H.

In an additional aspect, B is

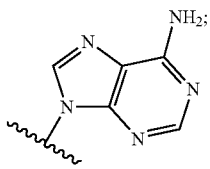

V is selected from the group consisting of 3-chlorophenyl, 3-bromophenyl, 2-bromophenyl, 3,5-dichlorophenyl, and 4-pyridyl; and Z, W, and W' are each —H.

A further aspect of this invention includes compounds of Formula V:

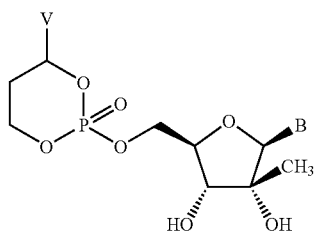

wherein:
V and the 5'oxymethylene group of the ribose sugar moiety are cis to one another
B is selected from the group consisting of

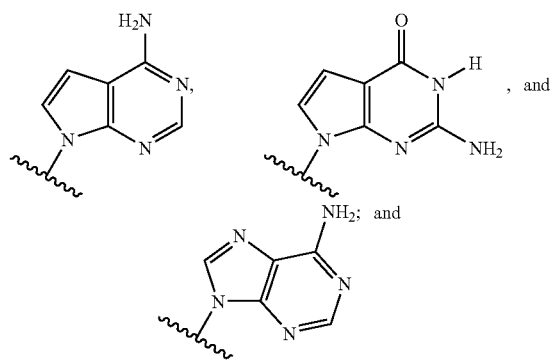

V is selected from the group consisting of optionally substituted monocyclic aryl and optionally substituted monocyclic heteroaryl; or pharmaceutically acceptable prodrugs or salts thereof.

In a further aspect, this invention includes compounds of Formula V:

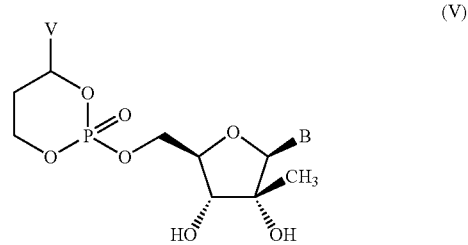

wherein:
V and the 5'oxymethylene group of the ribose sugar moiety are cis to one another;
B is

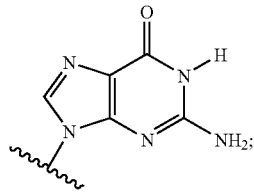

V is selected from the group consisting of optionally substituted monocyclic aryl and optionally substituted monocyclic heteroaryl; or pharmaceutically acceptable prodrugs or salts thereof.

In an additional aspect, V is selected from the group consisting of phenyl, substituted phenyl with 1-3 substituents independently selected from the group consisting of halogen, $C_1$-$C_6$ alkyl, —$CF_3$, —$OR^3$, —$OR^{12}$, —$COR^3$, —$CO_2R^3$, —$NR^3_2$, —$NR^{12}_2$, —$CO_2NR_2^2$, —$SR^3$, —$SO_2R^3$, —$SO_2NR_2^2$ and —CN, monocyclic heteroaryl, and substituted monocyclic heteroaryl with 1-2 substituents independently selected from the group consisting of halogen, $C_1$-$C_6$ alkyl, —$CF_3$, —$OR^3$, —$OR^{12}$, —$COR^3$, —$CO_2R^3$, —$NR^3_2$, —$NR^{12}_2$, —$CO_2NR_2^2$, —$SR^3$, —$SO_2R^3$, —$SO_2NR_2^2$ and —CN, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; and $R^3$ is $C_1$-$C_6$ alkyl.

In a further aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2$Me, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2$Me, —$SO_2NH_2$ and —CN and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 4 atoms to form a 6-membered ring that is fused to a phenyl or substituted phenyl at the beta and gamma position to the O attached to the phosphorus.

In an additional aspect, V is selected from the group consisting of phenyl; substituted phenyl with 1-2 substituents independently selected from the group consisting of —Cl, —Br, —F, $C_1$-$C_3$ alkyl, and —$CF_3$; pyridyl; substituted pyridyl with 1 substituent independently selected from the group consisting of —Cl, —Br, —F, $C_1$-$C_3$ alkyl, and —$CF_3$; furanyl; substituted furanyl with 1 substituent independently selected from the group consisting of —Cl, —Br, —F, $C_1$-$C_3$ alkyl, and —$CF_3$; thienyl; and substituted thienyl with 1 substituent independently selected from the group consisting of —Cl, —Br, —F, $C_1$-$C_3$ alkyl, and —$CF_3$.

In yet another aspect, V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl. In another aspect, V is selected from the group consisting of 3-chlorophenyl, 3-bromophenyl, 2-bromophenyl, 3,5-dichlorophenyl, 3-pyridyl, and 4-pyridyl.

In a further aspect, this invention includes compounds of Formula II:

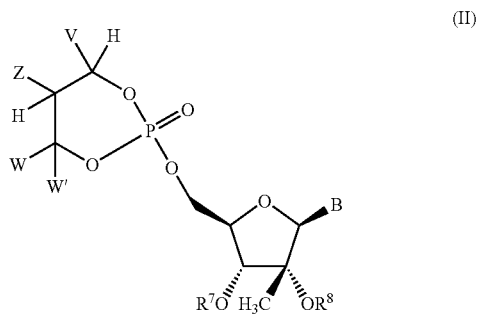

(II)

wherein:
B is selected from the group consisting of:

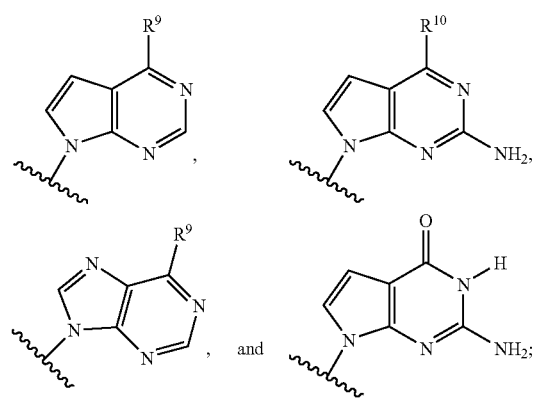

V is selected from the group consisting of optionally substituted monocyclic aryl and optionally substituted monocyclic heteroaryl;

W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4_2$, —$SR^4$, —$(CH_2)_p$—$OR^6$, —$(CH_2)_p$—$SR^6$ and —$OCOR^5$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group;

$R^4$ is $C_1$-$C_4$ alkyl;

$R^5$ is selected from the group consisting of $C_1$-$C_4$ alkyl, monocyclic aryl, and monocyclic aralkyl; and $R^6$ is $C_1$-$C_4$ acyl;

$R^7$ and $R^8$ are independently selected from the group consisting of hydrogen, $C_1$-$C_4$ acyl, $C_1$-$C_4$ alkoxycarbonyl, and a naturally-occurring L-amino acid connected via its carbonyl group to form an ester; or together $R^7$ and $R^8$ form a cyclic carbonate;

$R^9$ is selected from the group consisting of amino, azido, —N=CHN$(R^4)_2$, —NHC(O)$R^4$, and —NHC(O)O$R^4$; and $R^{10}$ is selected from the group consisting of O$R^6$, halogen, and H.

In another aspect, the invention comprises compounds of Formula II:

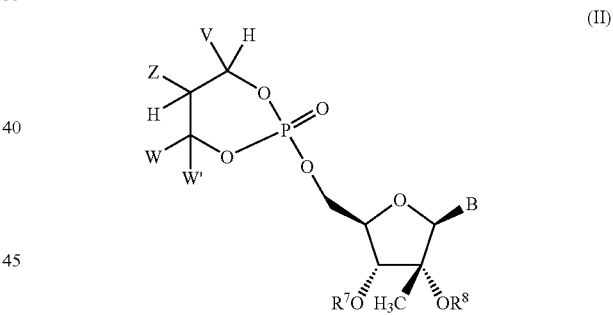

(II)

wherein:
B is selected from the group consisting of

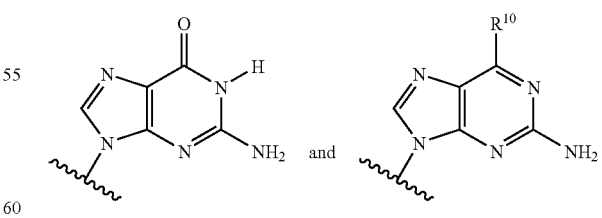

V is selected from the group consisting of optionally substituted monocyclic aryl and optionally substituted monocyclic heteroaryl;

W and W' are independently selected from the group consisting of —H, methyl, and V, or W and W' are each methyl, with the proviso that when W is V, then W' is H;

Z is selected from the group consisting of —H, —OMe, —OEt, phenyl, $C_1$-$C_3$ alkyl, —$NR^4_2$, —$SR^4$, —$(CH_2)_p$—$OR^6$, —$(CH_2)_p$—$SR^6$ and —$OCOR^5$; or together V and Z are connected via an additional 3-5 atoms to form a cyclic group, optionally containing 1 heteroatom, that is fused to an aryl group at the beta and gamma position to the O attached to the phosphorus; or together Z and W are connected via an additional 3-5 atoms to form a cyclic group, optionally containing one heteroatom; or together W and W' are connected via an additional 2-5 atoms to form a cyclic group;

$R^4$ is $C_1$-$C_4$ alkyl;

$R^5$ is selected from the group consisting of $C_1$-$C_4$ alkyl, monocyclic aryl, and monocyclic aralkyl; and $R^6$ is $C_1$-$C_4$ acyl;

$R^7$ and $R^8$ are independently selected from the group consisting of hydrogen, $C_1$-$C_4$ acyl, $C_1$-$C_4$ alkoxycarbonyl, and a naturally-occurring L-amino acid connected via its carbonyl group to form an ester; or together $R^7$ and $R^8$ form a cyclic carbonate; and $R^{10}$ is selected from the group consisting of $OR^4$, $OR^6$, halogen, and H.

A further aspect of the invention comprises compounds of Formula III:

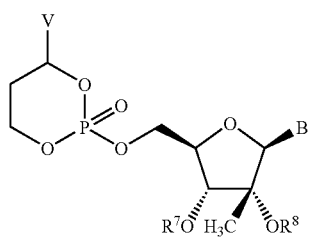

wherein:

V and the 5'oxymethylene group of the ribose sugar moiety are cis to one another;

B is selected from the group consisting of:

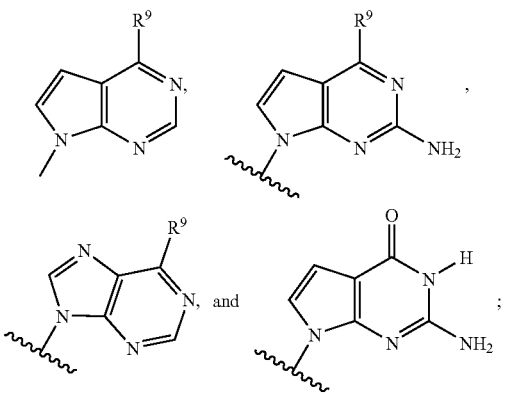

V is selected from the group consisting of optionally substituted monocyclic aryl and optionally substituted monocyclic heteroaryl;

$R^4$ is $C_1$-$C_4$ alkyl;

$R^6$ is $C_1$-$C_4$ acyl;

$R^7$ and $R^8$ are independently selected from the group consisting of hydrogen, $C_1$-$C_4$ acyl, $C_1$-$C_4$ alkoxycarbonyl, and a naturally-occurring L-amino acid connected via its carbonyl group to form an ester; or together $R^7$ and $R^8$ form a cyclic carbonate;

$R^9$ is selected from the group consisting of amino, azido, —N=$CHN(R^4)_2$, —$NHC(O)R^4$, and —$NHC(O)OR^4$; and $R^{10}$ is selected from the group consisting of $OR^6$, halogen, and H.

In one aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN. In another aspect, V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl.

In another aspect, the invention comprises compounds of Formula III:

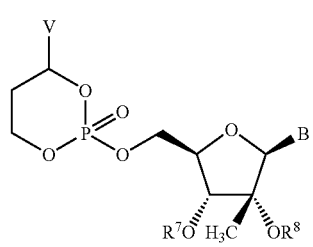

wherein:

V and the 5'oxymethylene group of the ribose sugar moiety are cis to one another;

B is selected from the group consisting of

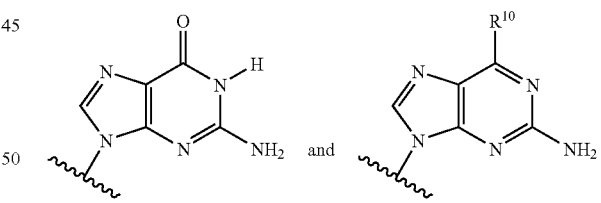

V is selected from the group consisting of optionally substituted monocyclic aryl and optionally substituted monocyclic heteroaryl;

$R^4$ is $C_1$-$C_4$ alkyl;

$R^6$ is $C_1$-$C_4$ acyl;

$R^7$ and $R^8$ are independently selected from the group consisting of hydrogen, $C_1$-$C_4$ acyl, $C_1$-$C_4$ alkoxycarbonyl, and a naturally-occurring L-amino acid connected via its carbonyl group to form an ester; or together $R^7$ and $R^8$ form a cyclic carbonate; and $R^{10}$ is selected from the group consisting of $OR^4$, $OR^6$, $NH_2$, $NHR^4$, halogen, and H.

In one aspect, V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN. In another aspect, V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl.

In a further aspect, the compounds of this invention are compounds of Formula VI:

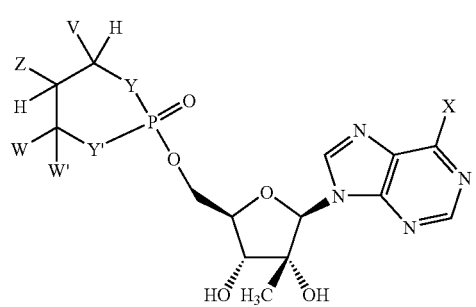

Formula VI wherein X is selected from the group consisting of $NH_2$, $NHCH_3$, $N(CH_3)_2$, $OCH_3$, and $SCH_3$;

Y and Y' are independently O or NH;

V, W, and W' are independently hydrogen, alkyl, alkenyl, alkynyl, aryl, alkaryl, each of which is optionally substituted; and Z is hydrogen, CHWOH, CHWOCOW', SW, or $CH_2$aryl.

In another aspect, the invention comprises compounds of Formula VII:

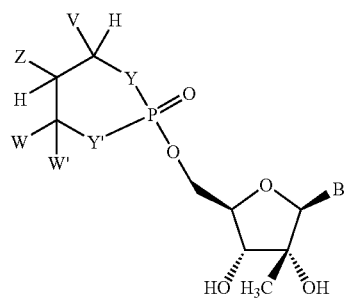

Formula VII wherein B is selected from the group consisting of:

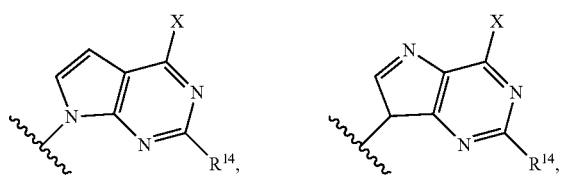

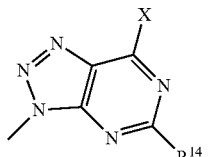

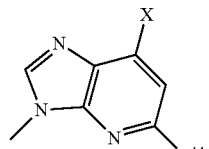

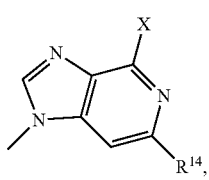

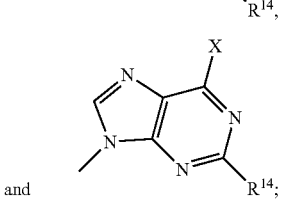

and

X is selected from the group consisting of $NH_2$, $NHCH_3$, $N(CH_3)_2$, $OCH_3$, $SCH_3$, OH, and SH;

Y and Y' are independently O or NH;

$R^{14}$ is independently selected from the group consisting of H and $NH_2$;

the heterocyclic base may be further substituted at any position on the heterocyclic base with a substituent of a molecular weight of less than 150 and selected from the group consisting of halogen, alkyl, alkenyl, alkynyl, aryl, alkaryl, cycloalkyl, acyl, and alkoxy, and wherein said substituents may be coupled to the 6-position of the heterocyclic base via a carbon, sulfur, oxygen, or selenium;

V, W, and W' are independently hydrogen, alkyl, alkenyl, alkynyl, aryl, alkaryl, each of which is optionally substituted; and Z is hydrogen, CHWOH, CHWOCOW', SW, or $CH_2$aryl.

In another aspect, B is selected from the group consisting of:

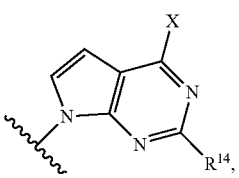

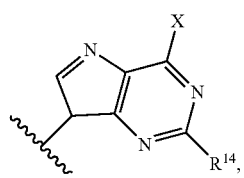

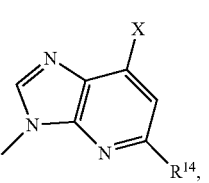

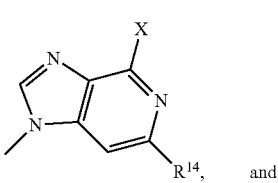

and

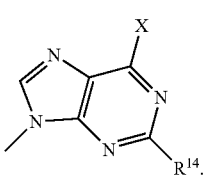

In yet another aspect, B is selected from the groups consisting of:

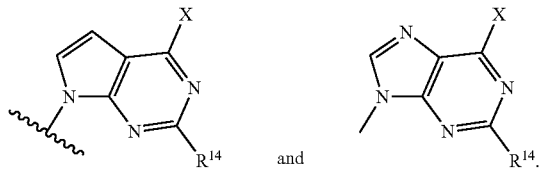

In another aspect, X is NH$_2$.
In a further aspect, the invention comprises:

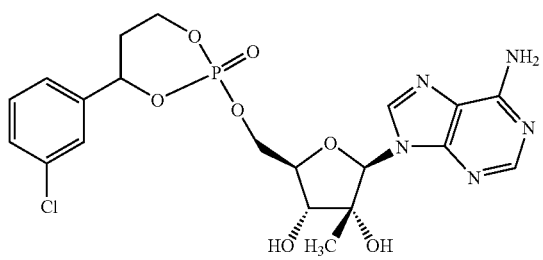

In another aspect, the invention comprises:

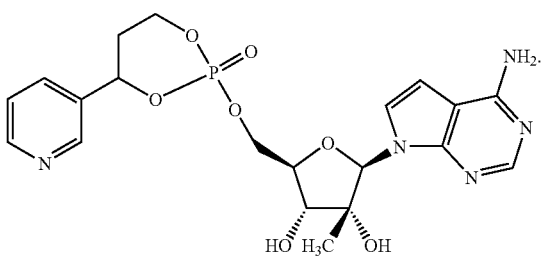

In a further aspect, the invention comprises:

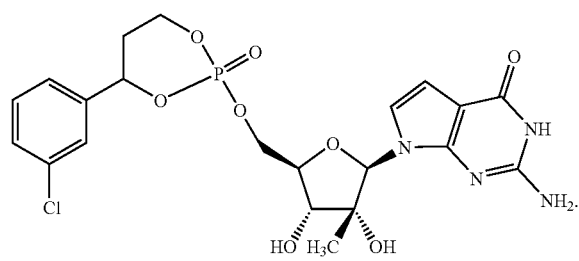

In another aspect, the invention comprises:

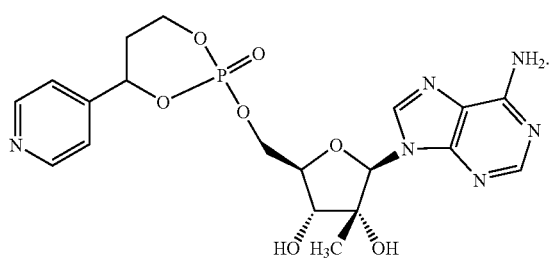

In a further aspect, the invention comprises:

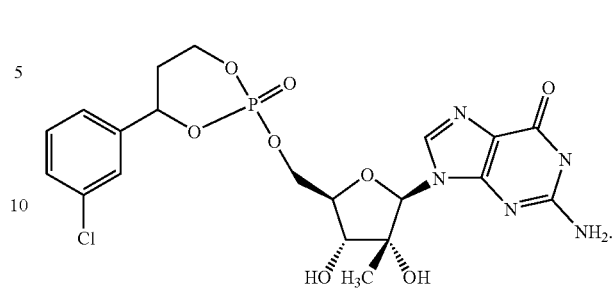

In another aspect of the invention the compounds of this invention have R-stereochemistry at the V-attached carbon and have S-stereochemistry at the phosphorus center. In another aspect of the invention the compounds of this invention have S-stereochemistry at the V-attached carbon and have R-stereochemistry at the phosphorus center.

In one aspect the following compounds are included in the invention but the compounds are not limited to these illustrative compounds.

The following prodrugs are preferred compounds of the invention. The compounds are shown without depiction of stereochemistry since the compounds are biologically active as the diastereomeric mixture or as a single stereoisomer. Compounds named in Table 1 are designated by numbers assigned to the variables of formula using the following convention: M1.V.L1.L2. M1 is a variable that represents nucleosides of Formula I which are attached via 5'-hydroxyl group that is phosphorylated with a group P(O)(O—CH(V)CH$_2$CH$_2$—O) to make compounds of Formula VI. V is an aryl or heteroaryl group that has 2 substituents, L1 and L2, at the designated positions. V may have additional substituents.

Formula VI

Variable M1:

1)

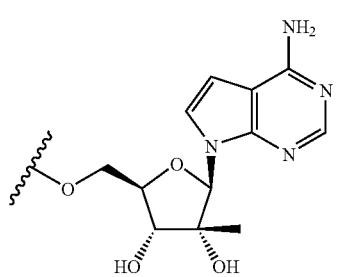

2)

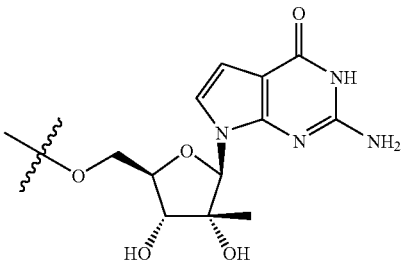

3)

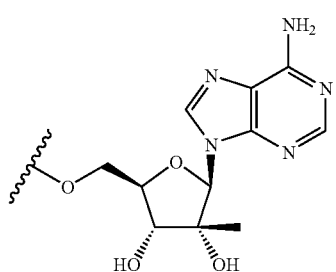

4)

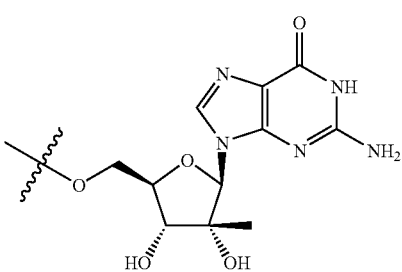

Variable V: Group V1
1) 2-(L1)-3(L2)-phenyl
2) 2-(L1)-4(L2)-phenyl
3) 2-(L1)-5(L2)-phenyl
4) 2-(L1)-6(L2)-phenyl
5) 3-(L1)-4(L2)-phenyl
6) 3-(L1)-5(L2)-phenyl
7) 3-(L1)-6(L2)-phenyl
8) 2-(L1)-6(L2)-3-chlorophenyl
9) 4-(L1)-5(L2)-3-chlorophenyl Variable V: Group V2
1) 2-(L1)-3(L2)-4-pyridyl
2) 2-(L1)-5(L2)-4-pyridyl
3) 2-(L1)-6(L2)-4-pyridyl
4) 3-(L1)-5(L2)-4-pyridyl
5) 3-(L1)-6(L2)-4-pyridyl
6) 2-(L1)-4(L2)-3-pyridyl
7) 2-(L1)-5(L2)-3-pyridyl
8) 2-(L1)-6(L2)-3-pyridyl
9) 4-(L1)-5(L2)-3-pyridyl Variable V: Group V3
1) 4-(L1)-6(L2)-3-pyridyl
2) 5-(L1)-6(L2)-3-pyridyl
3) 3-(L1)-4(L2)-2-pyridyl
4) 3-(L1)-5(L2)-2-pyridyl
5) 3-(L1)-6(L2)-2-pyridyl
6) 4-(L1)-5(L2)-2-pyridyl
7) 4-(L1)-6(L2)-2-pyridyl
8) 3-(L1)-4(L2)-2-thienyl
9) 3-(L1)-4(L2)-2-furanyl Variable L1
1) hydrogen
2) chloro
3) bromo
4) fluoro
5) methyl
6) trifluoromethyl
7) methoxy
8) dimethylamino
9) cyano Variable L2
1) hydrogen
2) chloro
3) bromo
4) fluoro
5) methyl
6) trifluoromethyl
7) methoxy
8) dimethylamino
9) cyano Preferred compounds are compounds listed in Table 1 using variables M1 and V1 and L1 and L2 listed in that order. For example, compound 1.3.6.7 represents structure 1 of variable M1, i.e., 7-deaza-2'-methyl adenosine; structure 3 of group V1, i.e., 2-(L1)-5-(L2) phenyl; structure 6 of variable L1, i.e., trifluoromethyl; and structure 7 of variable L2, i.e., methoxy. The compound 1.3.6.7. therefore is 7-deaza-2'-methyladenosine with the P(O)(O—CH(V)CH$_2$CH$_2$O) attached to the 5'-primary hydroxyl group being {[1-(2-trifluoromethyl-5-methoxyphenyl)-1,3-propyl]phosphoryl.

Preferred compounds are also compounds listed in Table 1 using variables M1 and V2 wherein the four digit number represents M1.V2.L1.L2.

Preferred compounds are also compounds listed in Table 1 using variables M1 and V3 wherein the four digit number represents M1.V3.L1.L2.

TABLE 1

| | | | | | | | | | |
|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.1.1.8 | 1.1.1.9 | 1.1.2.1 |
| 1.1.2.2 | 1.1.2.3 | 1.1.2.4 | 1.1.2.5 | 1.1.2.6 | 1.1.2.7 | 1.1.2.8 | 1.1.2.9 | 1.1.3.1 | 1.1.3.2 |
| 1.1.3.3 | 1.1.3.4 | 1.1.3.5 | 1.1.3.6 | 1.1.3.7 | 1.1.3.8 | 1.1.3.9 | 1.1.4.1 | 1.1.4.2 | 1.1.4.3 |
| 1.1.4.4 | 1.1.4.5 | 1.1.4.6 | 1.1.4.7 | 1.1.4.8 | 1.1.4.9 | 1.1.5.1 | 1.1.5.2 | 1.1.5.3 | 1.1.5.4 |
| 1.1.5.5 | 1.1.5.6 | 1.1.5.7 | 1.1.5.8 | 1.1.5.9 | 1.1.6.1 | 1.1.6.2 | 1.1.6.3 | 1.1.6.4 | 1.1.6.5 |
| 1.1.6.6 | 1.1.6.7 | 1.1.6.8 | 1.1.6.9 | 1.1.7.1 | 1.1.7.2 | 1.1.7.3 | 1.1.7.4 | 1.1.7.5 | 1.1.7.6 |
| 1.1.7.7 | 1.1.7.8 | 1.1.7.9 | 1.1.8.1 | 1.1.8.2 | 1.1.8.3 | 1.1.8.4 | 1.1.8.5 | 1.1.8.6 | 1.1.8.7 |
| 1.1.8.8 | 1.1.8.9 | 1.1.9.1 | 1.1.9.2 | 1.1.9.3 | 1.1.9.4 | 1.1.9.5 | 1.1.9.6 | 1.1.9.7 | 1.1.9.8 |
| 1.1.9.9 | 1.2.1.1 | 1.2.1.2 | 1.2.1.3 | 1.2.1.4 | 1.2.1.5 | 1.2.1.6 | 1.2.1.7 | 1.2.1.8 | 1.2.1.9 |
| 1.2.2.1 | 1.2.2.2 | 1.2.2.3 | 1.2.2.4 | 1.2.2.5 | 1.2.2.6 | 1.2.2.7 | 1.2.2.8 | 1.2.2.9 | 1.2.3.1 |
| 1.2.3.2 | 1.2.3.3 | 1.2.3.4 | 1.2.3.5 | 1.2.3.6 | 1.2.3.7 | 1.2.3.8 | 1.2.3.9 | 1.2.4.1 | 1.2.4.2 |
| 1.2.4.3 | 1.2.4.4 | 1.2.4.5 | 1.2.4.6 | 1.2.4.7 | 1.2.4.8 | 1.2.4.9 | 1.2.5.1 | 1.2.5.2 | 1.2.5.3 |

TABLE 1-continued

| | | | | | | | | | |
|---|---|---|---|---|---|---|---|---|---|
| 1.2.5.4 | 1.2.5.5 | 1.2.5.6 | 1.2.5.7 | 1.2.5.8 | 1.2.5.9 | 1.2.6.1 | 1.2.6.2 | 1.2.6.3 | 1.2.6.4 |
| 1.2.6.5 | 1.2.6.6 | 1.2.6.7 | 1.2.6.8 | 1.2.6.9 | 1.2.7.1 | 1.2.7.2 | 1.2.7.3 | 1.2.7.4 | 1.2.7.5 |
| 1.2.7.6 | 1.2.7.7 | 1.2.7.8 | 1.2.7.9 | 1.2.8.1 | 1.2.8.2 | 1.2.8.3 | 1.2.8.4 | 1.2.8.5 | 1.2.8.6 |
| 1.2.8.7 | 1.2.8.8 | 1.2.8.9 | 1.2.9.1 | 1.2.9.2 | 1.2.9.3 | 1.2.9.4 | 1.2.9.5 | 1.2.9.6 | 1.2.9.7 |
| 1.2.9.8 | 1.2.9.9 | 1.3.1.1 | 1.3.1.2 | 1.3.1.3 | 1.3.1.4 | 1.3.1.5 | 1.3.1.6 | 1.3.1.7 | 1.3.1.8 |
| 1.3.1.9 | 1.3.2.1 | 1.3.2.2 | 1.3.2.3 | 1.3.2.4 | 1.3.2.5 | 1.3.2.6 | 1.3.2.7 | 1.3.2.8 | 1.3.2.9 |
| 1.3.3.1 | 1.3.3.2 | 1.3.3.3 | 1.3.3.4 | 1.3.3.5 | 1.3.3.6 | 1.3.3.7 | 1.3.3.8 | 1.3.3.9 | 1.3.4.1 |
| 1.3.4.2 | 1.3.4.3 | 1.3.4.4 | 1.3.4.5 | 1.3.4.6 | 1.3.4.7 | 1.3.4.8 | 1.3.4.9 | 1.3.5.1 | 1.3.5.2 |
| 1.3.5.3 | 1.3.5.4 | 1.3.5.5 | 1.3.5.6 | 1.3.5.7 | 1.3.5.8 | 1.3.5.9 | 1.3.6.1 | 1.3.6.2 | 1.3.6.3 |
| 1.3.6.4 | 1.3.6.5 | 1.3.6.6 | 1.3.6.7 | 1.3.6.8 | 1.3.6.9 | 1.3.7.1 | 1.3.7.2 | 1.3.7.3 | 1.3.7.4 |
| 1.3.7.5 | 1.3.7.6 | 1.3.7.7 | 1.3.7.8 | 1.3.7.9 | 1.3.8.1 | 1.3.8.2 | 1.3.8.3 | 1.3.8.4 | 1.3.8.5 |
| 1.3.8.6 | 1.3.8.7 | 1.3.8.8 | 1.3.8.9 | 1.3.9.1 | 1.3.9.2 | 1.3.9.3 | 1.3.9.4 | 1.3.9.5 | 1.3.9.6 |
| 1.3.9.7 | 1.3.9.8 | 1.3.9.9 | 1.4.1.1 | 1.4.1.2 | 1.4.1.3 | 1.4.1.4 | 1.4.1.5 | 1.4.1.6 | 1.4.1.7 |
| 1.4.1.8 | 1.4.1.9 | 1.4.2.1 | 1.4.2.2 | 1.4.2.3 | 1.4.2.4 | 1.4.2.5 | 1.4.2.6 | 1.4.2.7 | 1.4.2.8 |
| 1.4.2.9 | 1.4.3.1 | 1.4.3.2 | 1.4.3.3 | 1.4.3.4 | 1.4.3.5 | 1.4.3.6 | 1.4.3.7 | 1.4.3.8 | 1.4.3.9 |
| 1.4.4.1 | 1.4.4.2 | 1.4.4.3 | 1.4.4.4 | 1.4.4.5 | 1.4.4.6 | 1.4.4.7 | 1.4.4.8 | 1.4.4.9 | 1.4.5.1 |
| 1.4.5.2 | 1.4.5.3 | 1.4.5.4 | 1.4.5.5 | 1.4.5.6 | 1.4.5.7 | 1.4.5.8 | 1.4.5.9 | 1.4.6.1 | 1.4.6.2 |
| 1.4.6.3 | 1.4.6.4 | 1.4.6.5 | 1.4.6.6 | 1.4.6.7 | 1.4.6.8 | 1.4.6.9 | 1.4.7.1 | 1.4.7.2 | 1.4.7.3 |
| 1.4.7.4 | 1.4.7.5 | 1.4.7.6 | 1.4.7.7 | 1.4.7.8 | 1.4.7.9 | 1.4.8.1 | 1.4.8.2 | 1.4.8.3 | 1.4.8.4 |
| 1.4.8.5 | 1.4.8.6 | 1.4.8.7 | 1.4.8.8 | 1.4.8.9 | 1.4.9.1 | 1.4.9.2 | 1.4.9.3 | 1.4.9.4 | 1.4.9.5 |
| 1.4.9.6 | 1.4.9.7 | 1.4.9.8 | 1.4.9.9 | 1.5.1.1 | 1.5.1.2 | 1.5.1.3 | 1.5.1.4 | 1.5.1.5 | 1.5.1.6 |
| 1.5.1.7 | 1.5.1.8 | 1.5.1.9 | 1.5.2.1 | 1.5.2.2 | 1.5.2.3 | 1.5.2.4 | 1.5.2.5 | 1.5.2.6 | 1.5.2.7 |
| 1.5.2.8 | 1.5.2.9 | 1.5.3.1 | 1.5.3.2 | 1.5.3.3 | 1.5.3.4 | 1.5.3.5 | 1.5.3.6 | 1.5.3.7 | 1.5.3.8 |
| 1.5.3.9 | 1.5.4.1 | 1.5.4.2 | 1.5.4.3 | 1.5.4.4 | 1.5.4.5 | 1.5.4.6 | 1.5.4.7 | 1.5.4.8 | 1.5.4.9 |
| 1.5.5.1 | 1.5.5.2 | 1.5.5.3 | 1.5.5.4 | 1.5.5.5 | 1.5.5.6 | 1.5.5.7 | 1.5.5.8 | 1.5.5.9 | 1.5.6.1 |
| 1.5.6.2 | 1.5.6.3 | 1.5.6.4 | 1.5.6.5 | 1.5.6.6 | 1.5.6.7 | 1.5.6.8 | 1.5.6.9 | 1.5.7.1 | 1.5.7.2 |
| 1.5.7.3 | 1.5.7.4 | 1.5.7.5 | 1.5.7.6 | 1.5.7.7 | 1.5.7.8 | 1.5.7.9 | 1.5.8.1 | 1.5.8.2 | 1.5.8.3 |
| 1.5.8.4 | 1.5.8.5 | 1.5.8.6 | 1.5.8.7 | 1.5.8.8 | 1.5.8.9 | 1.5.9.1 | 1.5.9.2 | 1.5.9.3 | 1.5.9.4 |
| 1.5.9.5 | 1.5.9.6 | 1.5.9.7 | 1.5.9.8 | 1.5.9.9 | 1.6.1.1 | 1.6.1.2 | 1.6.1.3 | 1.6.1.4 | 1.6.1.5 |
| 1.6.1.6 | 1.6.1.7 | 1.6.1.8 | 1.6.1.9 | 1.6.2.1 | 1.6.2.2 | 1.6.2.3 | 1.6.2.4 | 1.6.2.5 | 1.6.2.6 |
| 1.6.2.7 | 1.6.2.8 | 1.6.2.9 | 1.6.3.1 | 1.6.3.2 | 1.6.3.3 | 1.6.3.4 | 1.6.3.5 | 1.6.3.6 | 1.6.3.7 |
| 1.6.3.8 | 1.6.3.9 | 1.6.4.1 | 1.6.4.2 | 1.6.4.3 | 1.6.4.4 | 1.6.4.5 | 1.6.4.6 | 1.6.4.7 | 1.6.4.8 |
| 1.6.4.9 | 1.6.5.1 | 1.6.5.2 | 1.6.5.3 | 1.6.5.4 | 1.6.5.5 | 1.6.5.6 | 1.6.5.7 | 1.6.5.8 | 1.6.5.9 |
| 1.6.6.1 | 1.6.6.2 | 1.6.6.3 | 1.6.6.4 | 1.6.6.5 | 1.6.6.6 | 1.6.6.7 | 1.6.6.8 | 1.6.6.9 | 1.6.7.1 |
| 1.6.7.2 | 1.6.7.3 | 1.6.7.4 | 1.6.7.5 | 1.6.7.6 | 1.6.7.7 | 1.6.7.8 | 1.6.7.9 | 1.6.8.1 | 1.6.8.2 |
| 1.6.8.3 | 1.6.8.4 | 1.6.8.5 | 1.6.8.6 | 1.6.8.7 | 1.6.8.8 | 1.6.8.9 | 1.6.9.1 | 1.6.9.2 | 1.6.9.3 |
| 1.6.9.4 | 1.6.9.5 | 1.6.9.6 | 1.6.9.7 | 1.6.9.8 | 1.6.9.9 | 1.7.1.1 | 1.7.1.2 | 1.7.1.3 | 1.7.1.4 |
| 1.7.1.5 | 1.7.1.6 | 1.7.1.7 | 1.7.1.8 | 1.7.1.9 | 1.7.2.1 | 1.7.2.2 | 1.7.2.3 | 1.7.2.4 | 1.7.2.5 |
| 1.7.2.6 | 1.7.2.7 | 1.7.2.8 | 1.7.2.9 | 1.7.3.1 | 1.7.3.2 | 1.7.3.3 | 1.7.3.4 | 1.7.3.5 | 1.7.3.6 |
| 1.7.3.7 | 1.7.3.8 | 1.7.3.9 | 1.7.4.1 | 1.7.4.2 | 1.7.4.3 | 1.7.4.4 | 1.7.4.5 | 1.7.4.6 | 1.7.4.7 |
| 1.7.4.8 | 1.7.4.9 | 1.7.5.1 | 1.7.5.2 | 1.7.5.3 | 1.7.5.4 | 1.7.5.5 | 1.7.5.6 | 1.7.5.7 | 1.7.5.8 |
| 1.7.5.9 | 1.7.6.1 | 1.7.6.2 | 1.7.6.3 | 1.7.6.4 | 1.7.6.5 | 1.7.6.6 | 1.7.6.7 | 1.7.6.8 | 1.7.6.9 |
| 1.7.7.1 | 1.7.7.2 | 1.7.7.3 | 1.7.7.4 | 1.7.7.5 | 1.7.7.6 | 1.7.7.7 | 1.7.7.8 | 1.7.7.9 | 1.7.8.1 |
| 1.7.8.2 | 1.7.8.3 | 1.7.8.4 | 1.7.8.5 | 1.7.8.6 | 1.7.8.7 | 1.7.8.8 | 1.7.8.9 | 1.7.9.1 | 1.7.9.2 |
| 1.7.9.3 | 1.7.9.4 | 1.7.9.5 | 1.7.9.6 | 1.7.9.7 | 1.7.9.8 | 1.7.9.9 | 1.8.1.1 | 1.8.1.2 | 1.8.1.3 |
| 1.8.1.4 | 1.8.1.5 | 1.8.1.6 | 1.8.1.7 | 1.8.1.8 | 1.8.1.9 | 1.8.2.1 | 1.8.2.2 | 1.8.2.3 | 1.8.2.4 |
| 1.8.2.5 | 1.8.2.6 | 1.8.2.7 | 1.8.2.8 | 1.8.2.9 | 1.8.3.1 | 1.8.3.2 | 1.8.3.3 | 1.8.3.4 | 1.8.3.5 |
| 1.8.3.6 | 1.8.3.7 | 1.8.3.8 | 1.8.3.9 | 1.8.4.1 | 1.8.4.2 | 1.8.4.3 | 1.8.4.4 | 1.8.4.5 | 1.8.4.6 |
| 1.8.4.7 | 1.8.4.8 | 1.8.4.9 | 1.8.5.1 | 1.8.5.2 | 1.8.5.3 | 1.8.5.4 | 1.8.5.5 | 1.8.5.6 | 1.8.5.7 |
| 1.8.5.8 | 1.8.5.9 | 1.8.6.1 | 1.8.6.2 | 1.8.6.3 | 1.8.6.4 | 1.8.6.5 | 1.8.6.6 | 1.8.6.7 | 1.8.6.8 |
| 1.8.6.9 | 1.8.7.1 | 1.8.7.2 | 1.8.7.3 | 1.8.7.4 | 1.8.7.5 | 1.8.7.6 | 1.8.7.7 | 1.8.7.8 | 1.8.7.9 |
| 1.8.8.1 | 1.8.8.2 | 1.8.8.3 | 1.8.8.4 | 1.8.8.5 | 1.8.8.6 | 1.8.8.7 | 1.8.8.8 | 1.8.8.9 | 1.8.9.1 |
| 1.8.9.2 | 1.8.9.3 | 1.8.9.4 | 1.8.9.5 | 1.8.9.6 | 1.8.9.7 | 1.8.9.8 | 1.8.9.9 | 1.9.1.1 | 1.9.1.2 |
| 1.9.1.3 | 1.9.1.4 | 1.9.1.5 | 1.9.1.6 | 1.9.1.7 | 1.9.1.8 | 1.9.1.9 | 1.9.2.1 | 1.9.2.2 | 1.9.2.3 |
| 1.9.2.4 | 1.9.2.5 | 1.9.2.6 | 1.9.2.7 | 1.9.2.8 | 1.9.2.9 | 1.9.3.1 | 1.9.3.2 | 1.9.3.3 | 1.9.3.4 |
| 1.9.3.5 | 1.9.3.6 | 1.9.3.7 | 1.9.3.8 | 1.9.3.9 | 1.9.4.1 | 1.9.4.2 | 1.9.4.3 | 1.9.4.4 | 1.9.4.5 |
| 1.9.4.6 | 1.9.4.7 | 1.9.4.8 | 1.9.4.9 | 1.9.5.1 | 1.9.5.2 | 1.9.5.3 | 1.9.5.4 | 1.9.5.5 | 1.9.5.6 |
| 1.9.5.7 | 1.9.5.8 | 1.9.5.9 | 1.9.6.1 | 1.9.6.2 | 1.9.6.3 | 1.9.6.4 | 1.9.6.5 | 1.9.6.6 | 1.9.6.7 |
| 1.9.6.8 | 1.9.6.9 | 1.9.7.1 | 1.9.7.2 | 1.9.7.3 | 1.9.7.4 | 1.9.7.5 | 1.9.7.6 | 1.9.7.7 | 1.9.7.8 |
| 1.9.7.9 | 1.9.8.1 | 1.9.8.2 | 1.9.8.3 | 1.9.8.4 | 1.9.8.5 | 1.9.8.6 | 1.9.8.7 | 1.9.8.8 | 1.9.8.9 |
| 1.9.9.1 | 1.9.9.2 | 1.9.9.3 | 1.9.9.4 | 1.9.9.5 | 1.9.9.6 | 1.9.9.7 | 1.9.9.8 | 1.9.9.9 | 2.1.1.1 |
| 2.1.1.2 | 2.1.1.3 | 2.1.1.4 | 2.1.1.5 | 2.1.1.6 | 2.1.1.7 | 2.1.1.8 | 2.1.1.9 | 2.1.2.1 | 2.1.2.2 |
| 2.1.2.3 | 2.1.2.4 | 2.1.2.5 | 2.1.2.6 | 2.1.2.7 | 2.1.2.8 | 2.1.2.9 | 2.1.3.1 | 2.1.3.2 | 2.1.3.3 |
| 2.1.3.4 | 2.1.3.5 | 2.1.3.6 | 2.1.3.7 | 2.1.3.8 | 2.1.3.9 | 2.1.4.1 | 2.1.4.2 | 2.1.4.3 | 2.1.4.4 |
| 2.1.4.5 | 2.1.4.6 | 2.1.4.7 | 2.1.4.8 | 2.1.4.9 | 2.1.5.1 | 2.1.5.2 | 2.1.5.3 | 2.1.5.4 | 2.1.5.5 |
| 2.1.5.6 | 2.1.5.7 | 2.1.5.8 | 2.1.5.9 | 2.1.6.1 | 2.1.6.2 | 2.1.6.3 | 2.1.6.4 | 2.1.6.5 | 2.1.6.6 |
| 2.1.6.7 | 2.1.6.8 | 2.1.6.9 | 2.1.7.1 | 2.1.7.2 | 2.1.7.3 | 2.1.7.4 | 2.1.7.5 | 2.1.7.6 | 2.1.7.7 |
| 2.1.7.8 | 2.1.7.9 | 2.1.8.1 | 2.1.8.2 | 2.1.8.3 | 2.1.8.4 | 2.1.8.5 | 2.1.8.6 | 2.1.8.7 | 2.1.8.8 |
| 2.1.8.9 | 2.1.9.1 | 2.1.9.2 | 2.1.9.3 | 2.1.9.4 | 2.1.9.5 | 2.1.9.6 | 2.1.9.7 | 2.1.9.8 | 2.1.9.9 |
| 2.2.1.1 | 2.2.1.2 | 2.2.1.3 | 2.2.1.4 | 2.2.1.5 | 2.2.1.6 | 2.2.1.7 | 2.2.1.8 | 2.2.1.9 | 2.2.2.1 |
| 2.2.2.2 | 2.2.2.3 | 2.2.2.4 | 2.2.2.5 | 2.2.2.6 | 2.2.2.7 | 2.2.2.8 | 2.2.2.9 | 2.2.3.1 | 2.2.3.2 |
| 2.2.3.3 | 2.2.3.4 | 2.2.3.5 | 2.2.3.6 | 2.2.3.7 | 2.2.3.8 | 2.2.3.9 | 2.2.4.1 | 2.2.4.2 | 2.2.4.3 |
| 2.2.4.4 | 2.2.4.5 | 2.2.4.6 | 2.2.4.7 | 2.2.4.8 | 2.2.4.9 | 2.2.5.1 | 2.2.5.2 | 2.2.5.3 | 2.2.5.4 |
| 2.2.5.5 | 2.2.5.6 | 2.2.5.7 | 2.2.5.8 | 2.2.5.9 | 2.2.6.1 | 2.2.6.2 | 2.2.6.3 | 2.2.6.4 | 2.2.6.5 |
| 2.2.6.6 | 2.2.6.7 | 2.2.6.8 | 2.2.6.9 | 2.2.7.1 | 2.2.7.2 | 2.2.7.3 | 2.2.7.4 | 2.2.7.5 | 2.2.7.6 |
| 2.2.7.7 | 2.2.7.8 | 2.2.7.9 | 2.2.8.1 | 2.2.8.2 | 2.2.8.3 | 2.2.8.4 | 2.2.8.5 | 2.2.8.6 | 2.2.8.7 |
| 2.2.8.8 | 2.2.8.9 | 2.2.9.1 | 2.2.9.2 | 2.2.9.3 | 2.2.9.4 | 2.2.9.5 | 2.2.9.6 | 2.2.9.7 | 2.2.9.8 |
| 2.2.9.9 | 2.3.1.1 | 2.3.1.2 | 2.3.1.3 | 2.3.1.4 | 2.3.1.5 | 2.3.1.6 | 2.3.1.7 | 2.3.1.8 | 2.3.1.9 |
| 2.3.2.1 | 2.3.2.2 | 2.3.2.3 | 2.3.2.4 | 2.3.2.5 | 2.3.2.6 | 2.3.2.7 | 2.3.2.8 | 2.3.2.9 | 2.3.3.1 |

TABLE 1-continued

| | | | | | | | | | |
|---|---|---|---|---|---|---|---|---|---|
| 2.3.3.2 | 2.3.3.3 | 2.3.3.4 | 2.3.3.5 | 2.3.3.6 | 2.3.3.7 | 2.3.3.8 | 2.3.3.9 | 2.3.4.1 | 2.3.4.2 |
| 2.3.4.3 | 2.3.4.4 | 2.3.4.5 | 2.3.4.6 | 2.3.4.7 | 2.3.4.8 | 2.3.4.9 | 2.3.5.1 | 2.3.5.2 | 2.3.5.3 |
| 2.3.5.4 | 2.3.5.5 | 2.3.5.6 | 2.3.5.7 | 2.3.5.8 | 2.3.5.9 | 2.3.6.1 | 2.3.6.2 | 2.3.6.3 | 2.3.6.4 |
| 2.3.6.5 | 2.3.6.6 | 2.3.6.7 | 2.3.6.8 | 2.3.6.9 | 2.3.7.1 | 2.3.7.2 | 2.3.7.3 | 2.3.7.4 | 2.3.7.5 |
| 2.3.7.6 | 2.3.7.7 | 2.3.7.8 | 2.3.7.9 | 2.3.8.1 | 2.3.8.2 | 2.3.8.3 | 2.3.8.4 | 2.3.8.5 | 2.3.8.6 |
| 2.3.8.7 | 2.3.8.8 | 2.3.8.9 | 2.3.9.1 | 2.3.9.2 | 2.3.9.3 | 2.3.9.4 | 2.3.9.5 | 2.3.9.6 | 2.3.9.7 |
| 2.3.9.8 | 2.3.9.9 | 2.4.1.1 | 2.4.1.2 | 2.4.1.3 | 2.4.1.4 | 2.4.1.5 | 2.4.1.6 | 2.4.1.7 | 2.4.1.8 |
| 2.4.1.9 | 2.4.2.1 | 2.4.2.2 | 2.4.2.3 | 2.4.2.4 | 2.4.2.5 | 2.4.2.6 | 2.4.2.7 | 2.4.2.8 | 2.4.2.9 |
| 2.4.3.1 | 2.4.3.2 | 2.4.3.3 | 2.4.3.4 | 2.4.3.5 | 2.4.3.6 | 2.4.3.7 | 2.4.3.8 | 2.4.3.9 | 2.4.4.1 |
| 2.4.4.2 | 2.4.4.3 | 2.4.4.4 | 2.4.4.5 | 2.4.4.6 | 2.4.4.7 | 2.4.4.8 | 2.4.4.9 | 2.4.5.1 | 2.4.5.2 |
| 2.4.5.3 | 2.4.5.4 | 2.4.5.5 | 2.4.5.6 | 2.4.5.7 | 2.4.5.8 | 2.4.5.9 | 2.4.6.1 | 2.4.6.2 | 2.4.6.3 |
| 2.4.6.4 | 2.4.6.5 | 2.4.6.6 | 2.4.6.7 | 2.4.6.8 | 2.4.6.9 | 2.4.7.1 | 2.4.7.2 | 2.4.7.3 | 2.4.7.4 |
| 2.4.7.5 | 2.4.7.6 | 2.4.7.7 | 2.4.7.8 | 2.4.7.9 | 2.4.8.1 | 2.4.8.2 | 2.4.8.3 | 2.4.8.4 | 2.4.8.5 |
| 2.4.8.6 | 2.4.8.7 | 2.4.8.8 | 2.4.8.9 | 2.4.9.1 | 2.4.9.2 | 2.4.9.3 | 2.4.9.4 | 2.4.9.5 | 2.4.9.6 |
| 2.4.9.7 | 2.4.9.8 | 2.4.9.9 | 2.5.1.1 | 2.5.1.2 | 2.5.1.3 | 2.5.1.4 | 2.5.1.5 | 2.5.1.6 | 2.5.1.7 |
| 2.5.1.8 | 2.5.1.9 | 2.5.2.1 | 2.5.2.2 | 2.5.2.3 | 2.5.2.4 | 2.5.2.5 | 2.5.2.6 | 2.5.2.7 | 2.5.2.8 |
| 2.5.2.9 | 2.5.3.1 | 2.5.3.2 | 2.5.3.3 | 2.5.3.4 | 2.5.3.5 | 2.5.3.6 | 2.5.3.7 | 2.5.3.8 | 2.5.3.9 |
| 2.5.4.1 | 2.5.4.2 | 2.5.4.3 | 2.5.4.4 | 2.5.4.5 | 2.5.4.6 | 2.5.4.7 | 2.5.4.8 | 2.5.4.9 | 2.5.5.1 |
| 2.5.5.2 | 2.5.5.3 | 2.5.5.4 | 2.5.5.5 | 2.5.5.6 | 2.5.5.7 | 2.5.5.8 | 2.5.5.9 | 2.5.6.1 | 2.5.6.2 |
| 2.5.6.3 | 2.5.6.4 | 2.5.6.5 | 2.5.6.6 | 2.5.6.7 | 2.5.6.8 | 2.5.6.9 | 2.5.7.1 | 2.5.7.2 | 2.5.7.3 |
| 2.5.7.4 | 2.5.7.5 | 2.5.7.6 | 2.5.7.7 | 2.5.7.8 | 2.5.7.9 | 2.5.8.1 | 2.5.8.2 | 2.5.8.3 | 2.5.8.4 |
| 2.5.8.5 | 2.5.8.6 | 2.5.8.7 | 2.5.8.8 | 2.5.8.9 | 2.5.9.1 | 2.5.9.2 | 2.5.9.3 | 2.5.9.4 | 2.5.9.5 |
| 2.5.9.6 | 2.5.9.7 | 2.5.9.8 | 2.5.9.9 | 2.6.1.1 | 2.6.1.2 | 2.6.1.3 | 2.6.1.4 | 2.6.1.5 | 2.6.1.6 |
| 2.6.1.7 | 2.6.1.8 | 2.6.1.9 | 2.6.2.1 | 2.6.2.2 | 2.6.2.3 | 2.6.2.4 | 2.6.2.5 | 2.6.2.6 | 2.6.2.7 |
| 2.6.2.8 | 2.6.2.9 | 2.6.3.1 | 2.6.3.2 | 2.6.3.3 | 2.6.3.4 | 2.6.3.5 | 2.6.3.6 | 2.6.3.7 | 2.6.3.8 |
| 2.6.3.9 | 2.6.4.1 | 2.6.4.2 | 2.6.4.3 | 2.6.4.4 | 2.6.4.5 | 2.6.4.6 | 2.6.4.7 | 2.6.4.8 | 2.6.4.9 |
| 2.6.5.1 | 2.6.5.2 | 2.6.5.3 | 2.6.5.4 | 2.6.5.5 | 2.6.5.6 | 2.6.5.7 | 2.6.5.8 | 2.6.5.9 | 2.6.6.1 |
| 2.6.6.2 | 2.6.6.3 | 2.6.6.4 | 2.6.6.5 | 2.6.6.6 | 2.6.6.7 | 2.6.6.8 | 2.6.6.9 | 2.6.7.1 | 2.6.7.2 |
| 2.6.7.3 | 2.6.7.4 | 2.6.7.5 | 2.6.7.6 | 2.6.7.7 | 2.6.7.8 | 2.6.7.9 | 2.6.8.1 | 2.6.8.2 | 2.6.8.3 |
| 2.6.8.4 | 2.6.8.5 | 2.6.8.6 | 2.6.8.7 | 2.6.8.8 | 2.6.8.9 | 2.6.9.1 | 2.6.9.2 | 2.6.9.3 | 2.6.9.4 |
| 2.6.9.5 | 2.6.9.6 | 2.6.9.7 | 2.6.9.8 | 2.6.9.9 | 2.7.1.1 | 2.7.1.2 | 2.7.1.3 | 2.7.1.4 | 2.7.1.5 |
| 2.7.1.6 | 2.7.1.7 | 2.7.1.8 | 2.7.1.9 | 2.7.2.1 | 2.7.2.2 | 2.7.2.3 | 2.7.2.4 | 2.7.2.5 | 2.7.2.6 |
| 2.7.2.7 | 2.7.2.8 | 2.7.2.9 | 2.7.3.1 | 2.7.3.2 | 2.7.3.3 | 2.7.3.4 | 2.7.3.5 | 2.7.3.6 | 2.7.3.7 |
| 2.7.3.8 | 2.7.3.9 | 2.7.4.1 | 2.7.4.2 | 2.7.4.3 | 2.7.4.4 | 2.7.4.5 | 2.7.4.6 | 2.7.4.7 | 2.7.4.8 |
| 2.7.4.9 | 2.7.5.1 | 2.7.5.2 | 2.7.5.3 | 2.7.5.4 | 2.7.5.5 | 2.7.5.6 | 2.7.5.7 | 2.7.5.8 | 2.7.5.9 |
| 2.7.6.1 | 2.7.6.2 | 2.7.6.3 | 2.7.6.4 | 2.7.6.5 | 2.7.6.6 | 2.7.6.7 | 2.7.6.8 | 2.7.6.9 | 2.7.7.1 |
| 2.7.7.2 | 2.7.7.3 | 2.7.7.4 | 2.7.7.5 | 2.7.7.6 | 2.7.7.7 | 2.7.7.8 | 2.7.7.9 | 2.7.8.1 | 2.7.8.2 |
| 2.7.8.3 | 2.7.8.4 | 2.7.8.5 | 2.7.8.6 | 2.7.8.7 | 2.7.8.8 | 2.7.8.9 | 2.7.9.1 | 2.7.9.2 | 2.7.9.3 |
| 2.7.9.4 | 2.7.9.5 | 2.7.9.6 | 2.7.9.7 | 2.7.9.8 | 2.7.9.9 | 2.8.1.1 | 2.8.1.2 | 2.8.1.3 | 2.8.1.4 |
| 2.8.1.5 | 2.8.1.6 | 2.8.1.7 | 2.8.1.8 | 2.8.1.9 | 2.8.2.1 | 2.8.2.2 | 2.8.2.3 | 2.8.2.4 | 2.8.2.5 |
| 2.8.2.6 | 2.8.2.7 | 2.8.2.8 | 2.8.2.9 | 2.8.3.1 | 2.8.3.2 | 2.8.3.3 | 2.8.3.4 | 2.8.3.5 | 2.8.3.6 |
| 2.8.3.7 | 2.8.3.8 | 2.8.3.9 | 2.8.4.1 | 2.8.4.2 | 2.8.4.3 | 2.8.4.4 | 2.8.4.5 | 2.8.4.6 | 2.8.4.7 |
| 2.8.4.8 | 2.8.4.9 | 2.8.5.1 | 2.8.5.2 | 2.8.5.3 | 2.8.5.4 | 2.8.5.5 | 2.8.5.6 | 2.8.5.7 | 2.8.5.8 |
| 2.8.5.9 | 2.8.6.1 | 2.8.6.2 | 2.8.6.3 | 2.8.6.4 | 2.8.6.5 | 2.8.6.6 | 2.8.6.7 | 2.8.6.8 | 2.8.6.9 |
| 2.8.7.1 | 2.8.7.2 | 2.8.7.3 | 2.8.7.4 | 2.8.7.5 | 2.8.7.6 | 2.8.7.7 | 2.8.7.8 | 2.8.7.9 | 2.8.8.1 |
| 2.8.8.2 | 2.8.8.3 | 2.8.8.4 | 2.8.8.5 | 2.8.8.6 | 2.8.8.7 | 2.8.8.8 | 2.8.8.9 | 2.8.9.1 | 2.8.9.2 |
| 2.8.9.3 | 2.8.9.4 | 2.8.9.5 | 2.8.9.6 | 2.8.9.7 | 2.8.9.8 | 2.8.9.9 | 2.9.1.1 | 2.9.1.2 | 2.9.1.3 |
| 2.9.1.4 | 2.9.1.5 | 2.9.1.6 | 2.9.1.7 | 2.9.1.8 | 2.9.1.9 | 2.9.2.1 | 2.9.2.2 | 2.9.2.3 | 2.9.2.4 |
| 2.9.2.5 | 2.9.2.6 | 2.9.2.7 | 2.9.2.8 | 2.9.2.9 | 2.9.3.1 | 2.9.3.2 | 2.9.3.3 | 2.9.3.4 | 2.9.3.5 |
| 2.9.3.6 | 2.9.3.7 | 2.9.3.8 | 2.9.3.9 | 2.9.4.1 | 2.9.4.2 | 2.9.4.3 | 2.9.4.4 | 2.9.4.5 | 2.9.4.6 |
| 2.9.4.7 | 2.9.4.8 | 2.9.4.9 | 2.9.5.1 | 2.9.5.2 | 2.9.5.3 | 2.9.5.4 | 2.9.5.5 | 2.9.5.6 | 2.9.5.7 |
| 2.9.5.8 | 2.9.5.9 | 2.9.6.1 | 2.9.6.2 | 2.9.6.3 | 2.9.6.4 | 2.9.6.5 | 2.9.6.6 | 2.9.6.7 | 2.9.6.8 |
| 2.9.6.9 | 2.9.7.1 | 2.9.7.2 | 2.9.7.3 | 2.9.7.4 | 2.9.7.5 | 2.9.7.6 | 2.9.7.7 | 2.9.7.8 | 2.9.7.9 |
| 2.9.8.1 | 2.9.8.2 | 2.9.8.3 | 2.9.8.4 | 2.9.8.5 | 2.9.8.6 | 2.9.8.7 | 2.9.8.8 | 2.9.8.9 | 2.9.9.1 |
| 2.9.9.2 | 2.9.9.3 | 2.9.9.4 | 2.9.9.5 | 2.9.9.6 | 2.9.9.7 | 2.9.9.8 | 2.9.9.9 | 3.1.1.1 | 3.1.1.2 |
| 3.1.1.3 | 3.1.1.4 | 3.1.1.5 | 3.1.1.6 | 3.1.1.7 | 3.1.1.8 | 3.1.1.9 | 3.1.2.1 | 3.1.2.2 | 3.1.2.3 |
| 3.1.2.4 | 3.1.2.5 | 3.1.2.6 | 3.1.2.7 | 3.1.2.8 | 3.1.2.9 | 3.1.3.1 | 3.1.3.2 | 3.1.3.3 | 3.1.3.4 |
| 3.1.3.5 | 3.1.3.6 | 3.1.3.7 | 3.1.3.8 | 3.1.3.9 | 3.1.4.1 | 3.1.4.2 | 3.1.4.3 | 3.1.4.4 | 3.1.4.5 |
| 3.1.4.6 | 3.1.4.7 | 3.1.4.8 | 3.1.4.9 | 3.1.5.1 | 3.1.5.2 | 3.1.5.3 | 3.1.5.4 | 3.1.5.5 | 3.1.5.6 |
| 3.1.5.7 | 3.1.5.8 | 3.1.5.9 | 3.1.6.1 | 3.1.6.2 | 3.1.6.3 | 3.1.6.4 | 3.1.6.5 | 3.1.6.6 | 3.1.6.7 |
| 3.1.6.8 | 3.1.6.9 | 3.1.7.1 | 3.1.7.2 | 3.1.7.3 | 3.1.7.4 | 3.1.7.5 | 3.1.7.6 | 3.1.7.7 | 3.1.7.8 |
| 3.1.7.9 | 3.1.8.1 | 3.1.8.2 | 3.1.8.3 | 3.1.8.4 | 3.1.8.5 | 3.1.8.6 | 3.1.8.7 | 3.1.8.8 | 3.1.8.9 |
| 3.1.9.1 | 3.1.9.2 | 3.1.9.3 | 3.1.9.4 | 3.1.9.5 | 3.1.9.6 | 3.1.9.7 | 3.1.9.8 | 3.1.9.9 | 3.2.1.1 |
| 3.2.1.2 | 3.2.1.3 | 3.2.1.4 | 3.2.1.5 | 3.2.1.6 | 3.2.1.7 | 3.2.1.8 | 3.2.1.9 | 3.2.2.1 | 3.2.2.2 |
| 3.2.2.3 | 3.2.2.4 | 3.2.2.5 | 3.2.2.6 | 3.2.2.7 | 3.2.2.8 | 3.2.2.9 | 3.2.3.1 | 3.2.3.2 | 3.2.3.3 |
| 3.2.3.4 | 3.2.3.5 | 3.2.3.6 | 3.2.3.7 | 3.2.3.8 | 3.2.3.9 | 3.2.4.1 | 3.2.4.2 | 3.2.4.3 | 3.2.4.4 |
| 3.2.4.5 | 3.2.4.6 | 3.2.4.7 | 3.2.4.8 | 3.2.4.9 | 3.2.5.1 | 3.2.5.2 | 3.2.5.3 | 3.2.5.4 | 3.2.5.5 |
| 3.2.5.6 | 3.2.5.7 | 3.2.5.8 | 3.2.5.9 | 3.2.6.1 | 3.2.6.2 | 3.2.6.3 | 3.2.6.4 | 3.2.6.5 | 3.2.6.6 |
| 3.2.6.7 | 3.2.6.8 | 3.2.6.9 | 3.2.7.1 | 3.2.7.2 | 3.2.7.3 | 3.2.7.4 | 3.2.7.5 | 3.2.7.6 | 3.2.7.7 |
| 3.2.7.8 | 3.2.7.9 | 3.2.8.1 | 3.2.8.2 | 3.2.8.3 | 3.2.8.4 | 3.2.8.5 | 3.2.8.6 | 3.2.8.7 | 3.2.8.8 |
| 3.2.8.9 | 3.2.9.1 | 3.2.9.2 | 3.2.9.3 | 3.2.9.4 | 3.2.9.5 | 3.2.9.6 | 3.2.9.7 | 3.2.9.8 | 3.2.9.9 |
| 3.3.1.1 | 3.3.1.2 | 3.3.1.3 | 3.3.1.4 | 3.3.1.5 | 3.3.1.6 | 3.3.1.7 | 3.3.1.8 | 3.3.1.9 | 3.3.2.1 |
| 3.3.2.2 | 3.3.2.3 | 3.3.2.4 | 3.3.2.5 | 3.3.2.6 | 3.3.2.7 | 3.3.2.8 | 3.3.2.9 | 3.3.3.1 | 3.3.3.2 |
| 3.3.3.3 | 3.3.3.4 | 3.3.3.5 | 3.3.3.6 | 3.3.3.7 | 3.3.3.8 | 3.3.3.9 | 3.3.4.1 | 3.3.4.2 | 3.3.4.3 |
| 3.3.4.4 | 3.3.4.5 | 3.3.4.6 | 3.3.4.7 | 3.3.4.8 | 3.3.4.9 | 3.3.5.1 | 3.3.5.2 | 3.3.5.3 | 3.3.5.4 |
| 3.3.5.5 | 3.3.5.6 | 3.3.5.7 | 3.3.5.8 | 3.3.5.9 | 3.3.6.1 | 3.3.6.2 | 3.3.6.3 | 3.3.6.4 | 3.3.6.5 |
| 3.3.6.6 | 3.3.6.7 | 3.3.6.8 | 3.3.6.9 | 3.3.7.1 | 3.3.7.2 | 3.3.7.3 | 3.3.7.4 | 3.3.7.5 | 3.3.7.6 |
| 3.3.7.7 | 3.3.7.8 | 3.3.7.9 | 3.3.8.1 | 3.3.8.2 | 3.3.8.3 | 3.3.8.4 | 3.3.8.5 | 3.3.8.6 | 3.3.8.7 |
| 3.3.8.8 | 3.3.8.9 | 3.3.9.1 | 3.3.9.2 | 3.3.9.3 | 3.3.9.4 | 3.3.9.5 | 3.3.9.6 | 3.3.9.7 | 3.3.9.8 |

TABLE 1-continued

| | | | | | | | | |
|---|---|---|---|---|---|---|---|---|
| 3.3.9.9 | 3.4.1.1 | 3.4.1.2 | 3.4.1.3 | 3.4.1.4 | 3.4.1.5 | 3.4.1.6 | 3.4.1.7 | 3.4.1.8 | 3.4.1.9 |
| 3.4.2.1 | 3.4.2.2 | 3.4.2.3 | 3.4.2.4 | 3.4.2.5 | 3.4.2.6 | 3.4.2.7 | 3.4.2.8 | 3.4.2.9 | 3.4.3.1 |
| 3.4.3.2 | 3.4.3.3 | 3.4.3.4 | 3.4.3.5 | 3.4.3.6 | 3.4.3.7 | 3.4.3.8 | 3.4.3.9 | 3.4.4.1 | 3.4.4.2 |
| 3.4.4.3 | 3.4.4.4 | 3.4.4.5 | 3.4.4.6 | 3.4.4.7 | 3.4.4.8 | 3.4.4.9 | 3.4.5.1 | 3.4.5.2 | 3.4.5.3 |
| 3.4.5.4 | 3.4.5.5 | 3.4.5.6 | 3.4.5.7 | 3.4.5.8 | 3.4.5.9 | 3.4.6.1 | 3.4.6.2 | 3.4.6.3 | 3.4.6.4 |
| 3.4.6.5 | 3.4.6.6 | 3.4.6.7 | 3.4.6.8 | 3.4.6.9 | 3.4.7.1 | 3.4.7.2 | 3.4.7.3 | 3.4.7.4 | 3.4.7.5 |
| 3.4.7.6 | 3.4.7.7 | 3.4.7.8 | 3.4.7.9 | 3.4.8.1 | 3.4.8.2 | 3.4.8.3 | 3.4.8.4 | 3.4.8.5 | 3.4.8.6 |
| 3.4.8.7 | 3.4.8.8 | 3.4.8.9 | 3.4.9.1 | 3.4.9.2 | 3.4.9.3 | 3.4.9.4 | 3.4.9.5 | 3.4.9.6 | 3.4.9.7 |
| 3.4.9.8 | 3.4.9.9 | 3.5.1.1 | 3.5.1.2 | 3.5.1.3 | 3.5.1.4 | 3.5.1.5 | 3.5.1.6 | 3.5.1.7 | 3.5.1.8 |
| 3.5.1.9 | 3.5.2.1 | 3.5.2.2 | 3.5.2.3 | 3.5.2.4 | 3.5.2.5 | 3.5.2.6 | 3.5.2.7 | 3.5.2.8 | 3.5.2.9 |
| 3.5.3.1 | 3.5.3.2 | 3.5.3.3 | 3.5.3.4 | 3.5.3.5 | 3.5.3.6 | 3.5.3.7 | 3.5.3.8 | 3.5.3.9 | 3.5.4.1 |
| 3.5.4.2 | 3.5.4.3 | 3.5.4.4 | 3.5.4.5 | 3.5.4.6 | 3.5.4.7 | 3.5.4.8 | 3.5.4.9 | 3.5.5.1 | 3.5.5.2 |
| 3.5.5.3 | 3.5.5.4 | 3.5.5.5 | 3.5.5.6 | 3.5.5.7 | 3.5.5.8 | 3.5.5.9 | 3.5.6.1 | 3.5.6.2 | 3.5.6.3 |
| 3.5.6.4 | 3.5.6.5 | 3.5.6.6 | 3.5.6.7 | 3.5.6.8 | 3.5.6.9 | 3.5.7.1 | 3.5.7.2 | 3.5.7.3 | 3.5.7.4 |
| 3.5.7.5 | 3.5.7.6 | 3.5.7.7 | 3.5.7.8 | 3.5.7.9 | 3.5.8.1 | 3.5.8.2 | 3.5.8.3 | 3.5.8.4 | 3.5.8.5 |
| 3.5.8.6 | 3.5.8.7 | 3.5.8.8 | 3.5.8.9 | 3.5.9.1 | 3.5.9.2 | 3.5.9.3 | 3.5.9.4 | 3.5.9.5 | 3.5.9.6 |
| 3.5.9.7 | 3.5.9.8 | 3.5.9.9 | 3.6.1.1 | 3.6.1.2 | 3.6.1.3 | 3.6.1.4 | 3.6.1.5 | 3.6.1.6 | 3.6.1.7 |
| 3.6.1.8 | 3.6.1.9 | 3.6.2.1 | 3.6.2.2 | 3.6.2.3 | 3.6.2.4 | 3.6.2.5 | 3.6.2.6 | 3.6.2.7 | 3.6.2.8 |
| 3.6.2.9 | 3.6.3.1 | 3.6.3.2 | 3.6.3.3 | 3.6.3.4 | 3.6.3.5 | 3.6.3.6 | 3.6.3.7 | 3.6.3.8 | 3.6.3.9 |
| 3.6.4.1 | 3.6.4.2 | 3.6.4.3 | 3.6.4.4 | 3.6.4.5 | 3.6.4.6 | 3.6.4.7 | 3.6.4.8 | 3.6.4.9 | 3.6.5.1 |
| 3.6.5.2 | 3.6.5.3 | 3.6.5.4 | 3.6.5.5 | 3.6.5.6 | 3.6.5.7 | 3.6.5.8 | 3.6.5.9 | 3.6.6.1 | 3.6.6.2 |
| 3.6.6.3 | 3.6.6.4 | 3.6.6.5 | 3.6.6.6 | 3.6.6.7 | 3.6.6.8 | 3.6.6.9 | 3.6.7.1 | 3.6.7.2 | 3.6.7.3 |
| 3.6.7.4 | 3.6.7.5 | 3.6.7.6 | 3.6.7.7 | 3.6.7.8 | 3.6.7.9 | 3.6.8.1 | 3.6.8.2 | 3.6.8.3 | 3.6.8.4 |
| 3.6.8.5 | 3.6.8.6 | 3.6.8.7 | 3.6.8.8 | 3.6.8.9 | 3.6.9.1 | 3.6.9.2 | 3.6.9.3 | 3.6.9.4 | 3.6.9.5 |
| 3.6.9.6 | 3.6.9.7 | 3.6.9.8 | 3.6.9.9 | 3.7.1.1 | 3.7.1.2 | 3.7.1.3 | 3.7.1.4 | 3.7.1.5 | 3.7.1.6 |
| 3.7.1.7 | 3.7.1.8 | 3.7.1.9 | 3.7.2.1 | 3.7.2.2 | 3.7.2.3 | 3.7.2.4 | 3.7.2.5 | 3.7.2.6 | 3.7.2.7 |
| 3.7.2.8 | 3.7.2.9 | 3.7.3.1 | 3.7.3.2 | 3.7.3.3 | 3.7.3.4 | 3.7.3.5 | 3.7.3.6 | 3.7.3.7 | 3.7.3.8 |
| 3.7.3.9 | 3.7.4.1 | 3.7.4.2 | 3.7.4.3 | 3.7.4.4 | 3.7.4.5 | 3.7.4.6 | 3.7.4.7 | 3.7.4.8 | 3.7.4.9 |
| 3.7.5.1 | 3.7.5.2 | 3.7.5.3 | 3.7.5.4 | 3.7.5.5 | 3.7.5.6 | 3.7.5.7 | 3.7.5.8 | 3.7.5.9 | 3.7.6.1 |
| 3.7.6.2 | 3.7.6.3 | 3.7.6.4 | 3.7.6.5 | 3.7.6.6 | 3.7.6.7 | 3.7.6.8 | 3.7.6.9 | 3.7.7.1 | 3.7.7.2 |
| 3.7.7.3 | 3.7.7.4 | 3.7.7.5 | 3.7.7.6 | 3.7.7.7 | 3.7.7.8 | 3.7.7.9 | 3.7.8.1 | 3.7.8.2 | 3.7.8.3 |
| 3.7.8.4 | 3.7.8.5 | 3.7.8.6 | 3.7.8.7 | 3.7.8.8 | 3.7.8.9 | 3.7.9.1 | 3.7.9.2 | 3.7.9.3 | 3.7.9.4 |
| 3.7.9.5 | 3.7.9.6 | 3.7.9.7 | 3.7.9.8 | 3.7.9.9 | 3.8.1.1 | 3.8.1.2 | 3.8.1.3 | 3.8.1.4 | 3.8.1.5 |
| 3.8.1.6 | 3.8.1.7 | 3.8.1.8 | 3.8.1.9 | 3.8.2.1 | 3.8.2.2 | 3.8.2.3 | 3.8.2.4 | 3.8.2.5 | 3.8.2.6 |
| 3.8.2.7 | 3.8.2.8 | 3.8.2.9 | 3.8.3.1 | 3.8.3.2 | 3.8.3.3 | 3.8.3.4 | 3.8.3.5 | 3.8.3.6 | 3.8.3.7 |
| 3.8.3.8 | 3.8.3.9 | 3.8.4.1 | 3.8.4.2 | 3.8.4.3 | 3.8.4.4 | 3.8.4.5 | 3.8.4.6 | 3.8.4.7 | 3.8.4.8 |
| 3.8.4.9 | 3.8.5.1 | 3.8.5.2 | 3.8.5.3 | 3.8.5.4 | 3.8.5.5 | 3.8.5.6 | 3.8.5.7 | 3.8.5.8 | 3.8.5.9 |
| 3.8.6.1 | 3.8.6.2 | 3.8.6.3 | 3.8.6.4 | 3.8.6.5 | 3.8.6.6 | 3.8.6.7 | 3.8.6.8 | 3.8.6.9 | 3.8.7.1 |
| 3.8.7.2 | 3.8.7.3 | 3.8.7.4 | 3.8.7.5 | 3.8.7.6 | 3.8.7.7 | 3.8.7.8 | 3.8.7.9 | 3.8.8.1 | 3.8.8.2 |
| 3.8.8.3 | 3.8.8.4 | 3.8.8.5 | 3.8.8.6 | 3.8.8.7 | 3.8.8.8 | 3.8.8.9 | 3.8.9.1 | 3.8.9.2 | 3.8.9.3 |
| 3.8.9.4 | 3.8.9.5 | 3.8.9.6 | 3.8.9.7 | 3.8.9.8 | 3.8.9.9 | 3.9.1.1 | 3.9.1.2 | 3.9.1.3 | 3.9.1.4 |
| 3.9.1.5 | 3.9.1.6 | 3.9.1.7 | 3.9.1.8 | 3.9.1.9 | 3.9.2.1 | 3.9.2.2 | 3.9.2.3 | 3.9.2.4 | 3.9.2.5 |
| 3.9.2.6 | 3.9.2.7 | 3.9.2.8 | 3.9.2.9 | 3.9.3.1 | 3.9.3.2 | 3.9.3.3 | 3.9.3.4 | 3.9.3.5 | 3.9.3.6 |
| 3.9.3.7 | 3.9.3.8 | 3.9.3.9 | 3.9.4.1 | 3.9.4.2 | 3.9.4.3 | 3.9.4.4 | 3.9.4.5 | 3.9.4.6 | 3.9.4.7 |
| 3.9.4.8 | 3.9.4.9 | 3.9.5.1 | 3.9.5.2 | 3.9.5.3 | 3.9.5.4 | 3.9.5.5 | 3.9.5.6 | 3.9.5.7 | 3.9.5.8 |
| 3.9.5.9 | 3.9.6.1 | 3.9.6.2 | 3.9.6.3 | 3.9.6.4 | 3.9.6.5 | 3.9.6.6 | 3.9.6.7 | 3.9.6.8 | 3.9.6.9 |
| 3.9.7.1 | 3.9.7.2 | 3.9.7.3 | 3.9.7.4 | 3.9.7.5 | 3.9.7.6 | 3.9.7.7 | 3.9.7.8 | 3.9.7.9 | 3.9.8.1 |
| 3.9.8.2 | 3.9.8.3 | 3.9.8.4 | 3.9.8.5 | 3.9.8.6 | 3.9.8.7 | 3.9.8.8 | 3.9.8.9 | 3.9.9.1 | 3.9.9.2 |
| 3.9.9.3 | 3.9.9.4 | 3.9.9.5 | 3.9.9.6 | 3.9.9.7 | 3.9.9.8 | 4.1.1.1 | 4.1.1.2 | 4.1.1.3 |
| 4.1.1.4 | 4.1.1.5 | 4.1.1.6 | 4.1.1.7 | 4.1.1.8 | 4.1.1.9 | 4.1.2.1 | 4.1.2.2 | 4.1.2.3 | 4.1.2.4 |
| 4.1.2.5 | 4.1.2.6 | 4.1.2.7 | 4.1.2.8 | 4.1.2.9 | 4.1.3.1 | 4.1.3.2 | 4.1.3.3 | 4.1.3.4 | 4.1.3.5 |
| 4.1.3.6 | 4.1.3.7 | 4.1.3.8 | 4.1.3.9 | 4.1.4.1 | 4.1.4.2 | 4.1.4.3 | 4.1.4.4 | 4.1.4.5 | 4.1.4.6 |
| 4.1.4.7 | 4.1.4.8 | 4.1.4.9 | 4.1.5.1 | 4.1.5.2 | 4.1.5.3 | 4.1.5.4 | 4.1.5.5 | 4.1.5.6 | 4.1.5.7 |
| 4.1.5.8 | 4.1.5.9 | 4.1.6.1 | 4.1.6.2 | 4.1.6.3 | 4.1.6.4 | 4.1.6.5 | 4.1.6.6 | 4.1.6.7 | 4.1.6.8 |
| 4.1.6.9 | 4.1.7.1 | 4.1.7.2 | 4.1.7.3 | 4.1.7.4 | 4.1.7.5 | 4.1.7.6 | 4.1.7.7 | 4.1.7.8 | 4.1.7.9 |
| 4.1.8.1 | 4.1.8.2 | 4.1.8.3 | 4.1.8.4 | 4.1.8.5 | 4.1.8.6 | 4.1.8.7 | 4.1.8.8 | 4.1.8.9 | 4.1.9.1 |
| 4.1.9.2 | 4.1.9.3 | 4.1.9.4 | 4.1.9.5 | 4.1.9.6 | 4.1.9.7 | 4.1.9.8 | 4.1.9.9 | 4.2.1.1 | 4.2.1.2 |
| 4.2.1.3 | 4.2.1.4 | 4.2.1.5 | 4.2.1.6 | 4.2.1.7 | 4.2.1.8 | 4.2.1.9 | 4.2.2.1 | 4.2.2.2 | 4.2.2.3 |
| 4.2.2.4 | 4.2.2.5 | 4.2.2.6 | 4.2.2.7 | 4.2.2.8 | 4.2.2.9 | 4.2.3.1 | 4.2.3.2 | 4.2.3.3 | 4.2.3.4 |
| 4.2.3.5 | 4.2.3.6 | 4.2.3.7 | 4.2.3.8 | 4.2.3.9 | 4.2.4.1 | 4.2.4.2 | 4.2.4.3 | 4.2.4.4 | 4.2.4.5 |
| 4.2.4.6 | 4.2.4.7 | 4.2.4.8 | 4.2.4.9 | 4.2.5.1 | 4.2.5.2 | 4.2.5.3 | 4.2.5.4 | 4.2.5.5 | 4.2.5.6 |
| 4.2.5.7 | 4.2.5.8 | 4.2.5.9 | 4.2.6.1 | 4.2.6.2 | 4.2.6.3 | 4.2.6.4 | 4.2.6.5 | 4.2.6.6 | 4.2.6.7 |
| 4.2.6.8 | 4.2.6.9 | 4.2.7.1 | 4.2.7.2 | 4.2.7.3 | 4.2.7.4 | 4.2.7.5 | 4.2.7.6 | 4.2.7.7 | 4.2.7.8 |
| 4.2.7.9 | 4.2.8.1 | 4.2.8.2 | 4.2.8.3 | 4.2.8.4 | 4.2.8.5 | 4.2.8.6 | 4.2.8.7 | 4.2.8.8 | 4.2.8.9 |
| 4.2.9.1 | 4.2.9.2 | 4.2.9.3 | 4.2.9.4 | 4.2.9.5 | 4.2.9.6 | 4.2.9.7 | 4.2.9.8 | 4.2.9.9 | 4.3.1.1 |
| 4.3.1.2 | 4.3.1.3 | 4.3.1.4 | 4.3.1.5 | 4.3.1.6 | 4.3.1.7 | 4.3.1.8 | 4.3.1.9 | 4.3.2.1 | 4.3.2.2 |
| 4.3.2.3 | 4.3.2.4 | 4.3.2.5 | 4.3.2.6 | 4.3.2.7 | 4.3.2.8 | 4.3.2.9 | 4.3.3.1 | 4.3.3.2 | 4.3.3.3 |
| 4.3.3.4 | 4.3.3.5 | 4.3.3.6 | 4.3.3.7 | 4.3.3.8 | 4.3.3.9 | 4.3.4.1 | 4.3.4.2 | 4.3.4.3 | 4.3.4.4 |
| 4.3.4.5 | 4.3.4.6 | 4.3.4.7 | 4.3.4.8 | 4.3.4.9 | 4.3.5.1 | 4.3.5.2 | 4.3.5.3 | 4.3.5.4 | 4.3.5.5 |
| 4.3.5.6 | 4.3.5.7 | 4.3.5.8 | 4.3.5.9 | 4.3.6.1 | 4.3.6.2 | 4.3.6.3 | 4.3.6.4 | 4.3.6.5 | 4.3.6.6 |
| 4.3.6.7 | 4.3.6.8 | 4.3.6.9 | 4.3.7.1 | 4.3.7.2 | 4.3.7.3 | 4.3.7.4 | 4.3.7.5 | 4.3.7.6 | 4.3.7.7 |
| 4.3.7.8 | 4.3.7.9 | 4.3.8.1 | 4.3.8.2 | 4.3.8.3 | 4.3.8.4 | 4.3.8.5 | 4.3.8.6 | 4.3.8.7 | 4.3.8.8 |
| 4.3.8.9 | 4.3.9.1 | 4.3.9.2 | 4.3.9.3 | 4.3.9.4 | 4.3.9.5 | 4.3.9.6 | 4.3.9.7 | 4.3.9.8 | 4.3.9.9 |
| 4.4.1.1 | 4.4.1.2 | 4.4.1.3 | 4.4.1.4 | 4.4.1.5 | 4.4.1.6 | 4.4.1.7 | 4.4.1.8 | 4.4.1.9 | 4.4.2.1 |
| 4.4.2.2 | 4.4.2.3 | 4.4.2.4 | 4.4.2.5 | 4.4.2.6 | 4.4.2.7 | 4.4.2.8 | 4.4.2.9 | 4.4.3.1 | 4.4.3.2 |
| 4.4.3.3 | 4.4.3.4 | 4.4.3.5 | 4.4.3.6 | 4.4.3.7 | 4.4.3.8 | 4.4.3.9 | 4.4.4.1 | 4.4.4.2 | 4.4.4.3 |
| 4.4.4.4 | 4.4.4.5 | 4.4.4.6 | 4.4.4.7 | 4.4.4.8 | 4.4.4.9 | 4.4.5.1 | 4.4.5.2 | 4.4.5.3 | 4.4.5.4 |
| 4.4.5.5 | 4.4.5.6 | 4.4.5.7 | 4.4.5.8 | 4.4.5.9 | 4.4.6.1 | 4.4.6.2 | 4.4.6.3 | 4.4.6.4 | 4.4.6.5 |
| 4.4.6.6 | 4.4.6.7 | 4.4.6.8 | 4.4.6.9 | 4.4.7.1 | 4.4.7.2 | 4.4.7.3 | 4.4.7.4 | 4.4.7.5 | 4.4.7.6 |

TABLE 1-continued

| | | | | | | | | | |
|---|---|---|---|---|---|---|---|---|---|
| 4.4.7.7 | 4.4.7.8 | 4.4.7.9 | 4.4.8.1 | 4.4.8.2 | 4.4.8.3 | 4.4.8.4 | 4.4.8.5 | 4.4.8.6 | 4.4.8.7 |
| 4.4.8.8 | 4.4.8.9 | 4.4.9.1 | 4.4.9.2 | 4.4.9.3 | 4.4.9.4 | 4.4.9.5 | 4.4.9.6 | 4.4.9.7 | 4.4.9.8 |
| 4.4.9.9 | 4.5.1.1 | 4.5.1.2 | 4.5.1.3 | 4.5.1.4 | 4.5.1.5 | 4.5.1.6 | 4.5.1.7 | 4.5.1.8 | 4.5.1.9 |
| 4.5.2.1 | 4.5.2.2 | 4.5.2.3 | 4.5.2.4 | 4.5.2.5 | 4.5.2.6 | 4.5.2.7 | 4.5.2.8 | 4.5.2.9 | 4.5.3.1 |
| 4.5.3.2 | 4.5.3.3 | 4.5.3.4 | 4.5.3.5 | 4.5.3.6 | 4.5.3.7 | 4.5.3.8 | 4.5.3.9 | 4.5.4.1 | 4.5.4.2 |
| 4.5.4.3 | 4.5.4.4 | 4.5.4.5 | 4.5.4.6 | 4.5.4.7 | 4.5.4.8 | 4.5.4.9 | 4.5.5.1 | 4.5.5.2 | 4.5.5.3 |
| 4.5.5.4 | 4.5.5.5 | 4.5.5.6 | 4.5.5.7 | 4.5.5.8 | 4.5.5.9 | 4.5.6.1 | 4.5.6.2 | 4.5.6.3 | 4.5.6.4 |
| 4.5.6.5 | 4.5.6.6 | 4.5.6.7 | 4.5.6.8 | 4.5.6.9 | 4.5.7.1 | 4.5.7.2 | 4.5.7.3 | 4.5.7.4 | 4.5.7.5 |
| 4.5.7.6 | 4.5.7.7 | 4.5.7.8 | 4.5.7.9 | 4.5.8.1 | 4.5.8.2 | 4.5.8.3 | 4.5.8.4 | 4.5.8.5 | 4.5.8.6 |
| 4.5.8.7 | 4.5.8.8 | 4.5.8.9 | 4.5.9.1 | 4.5.9.2 | 4.5.9.3 | 4.5.9.4 | 4.5.9.5 | 4.5.9.6 | 4.5.9.7 |
| 4.5.9.8 | 4.5.9.9 | 4.6.1.1 | 4.6.1.2 | 4.6.1.3 | 4.6.1.4 | 4.6.1.5 | 4.6.1.6 | 4.6.1.7 | 4.6.1.8 |
| 4.6.1.9 | 4.6.2.1 | 4.6.2.2 | 4.6.2.3 | 4.6.2.4 | 4.6.2.5 | 4.6.2.6 | 4.6.2.7 | 4.6.2.8 | 4.6.2.9 |
| 4.6.3.1 | 4.6.3.2 | 4.6.3.3 | 4.6.3.4 | 4.6.3.5 | 4.6.3.6 | 4.6.3.7 | 4.6.3.8 | 4.6.3.9 | 4.6.4.1 |
| 4.6.4.2 | 4.6.4.3 | 4.6.4.4 | 4.6.4.5 | 4.6.4.6 | 4.6.4.7 | 4.6.4.8 | 4.6.4.9 | 4.6.5.1 | 4.6.5.2 |
| 4.6.5.3 | 4.6.5.4 | 4.6.5.5 | 4.6.5.6 | 4.6.5.7 | 4.6.5.8 | 4.6.5.9 | 4.6.6.1 | 4.6.6.2 | 4.6.6.3 |
| 4.6.6.4 | 4.6.6.5 | 4.6.6.6 | 4.6.6.7 | 4.6.6.8 | 4.6.6.9 | 4.6.7.1 | 4.6.7.2 | 4.6.7.3 | 4.6.7.4 |
| 4.6.7.5 | 4.6.7.6 | 4.6.7.7 | 4.6.7.8 | 4.6.7.9 | 4.6.8.1 | 4.6.8.2 | 4.6.8.3 | 4.6.8.4 | 4.6.8.5 |
| 4.6.8.6 | 4.6.8.7 | 4.6.8.8 | 4.6.8.9 | 4.6.9.1 | 4.6.9.2 | 4.6.9.3 | 4.6.9.4 | 4.6.9.5 | 4.6.9.6 |
| 4.6.9.7 | 4.6.9.8 | 4.6.9.9 | 4.7.1.1 | 4.7.1.2 | 4.7.1.3 | 4.7.1.4 | 4.7.1.5 | 4.7.1.6 | 4.7.1.7 |
| 4.7.1.8 | 4.7.1.9 | 4.7.2.1 | 4.7.2.2 | 4.7.2.3 | 4.7.2.4 | 4.7.2.5 | 4.7.2.6 | 4.7.2.7 | 4.7.2.8 |
| 4.7.2.9 | 4.7.3.1 | 4.7.3.2 | 4.7.3.3 | 4.7.3.4 | 4.7.3.5 | 4.7.3.6 | 4.7.3.7 | 4.7.3.8 | 4.7.3.9 |
| 4.7.4.1 | 4.7.4.2 | 4.7.4.3 | 4.7.4.4 | 4.7.4.5 | 4.7.4.6 | 4.7.4.7 | 4.7.4.8 | 4.7.4.9 | 4.7.5.1 |
| 4.7.5.2 | 4.7.5.3 | 4.7.5.4 | 4.7.5.5 | 4.7.5.6 | 4.7.5.7 | 4.7.5.8 | 4.7.5.9 | 4.7.6.1 | 4.7.6.2 |
| 4.7.6.3 | 4.7.6.4 | 4.7.6.5 | 4.7.6.6 | 4.7.6.7 | 4.7.6.8 | 4.7.6.9 | 4.7.7.1 | 4.7.7.2 | 4.7.7.3 |
| 4.7.7.4 | 4.7.7.5 | 4.7.7.6 | 4.7.7.7 | 4.7.7.8 | 4.7.7.9 | 4.7.8.1 | 4.7.8.2 | 4.7.8.3 | 4.7.8.4 |
| 4.7.8.5 | 4.7.8.6 | 4.7.8.7 | 4.7.8.8 | 4.7.8.9 | 4.7.9.1 | 4.7.9.2 | 4.7.9.3 | 4.7.9.4 | 4.7.9.5 |
| 4.7.9.6 | 4.7.9.7 | 4.7.9.8 | 4.7.9.9 | 4.8.1.1 | 4.8.1.2 | 4.8.1.3 | 4.8.1.4 | 4.8.1.5 | 4.8.1.6 |
| 4.8.1.7 | 4.8.1.8 | 4.8.1.9 | 4.8.2.1 | 4.8.2.2 | 4.8.2.3 | 4.8.2.4 | 4.8.2.5 | 4.8.2.6 | 4.8.2.7 |
| 4.8.2.8 | 4.8.2.9 | 4.8.3.1 | 4.8.3.2 | 4.8.3.3 | 4.8.3.4 | 4.8.3.5 | 4.8.3.6 | 4.8.3.7 | 4.8.3.8 |
| 4.8.3.9 | 4.8.4.1 | 4.8.4.2 | 4.8.4.3 | 4.8.4.4 | 4.8.4.5 | 4.8.4.6 | 4.8.4.7 | 4.8.4.8 | 4.8.4.9 |
| 4.8.5.1 | 4.8.5.2 | 4.8.5.3 | 4.8.5.4 | 4.8.5.5 | 4.8.5.6 | 4.8.5.7 | 4.8.5.8 | 4.8.5.9 | 4.8.6.1 |
| 4.8.6.2 | 4.8.6.3 | 4.8.6.4 | 4.8.6.5 | 4.8.6.6 | 4.8.6.7 | 4.8.6.8 | 4.8.6.9 | 4.8.7.1 | 4.8.7.2 |
| 4.8.7.3 | 4.8.7.4 | 4.8.7.5 | 4.8.7.6 | 4.8.7.7 | 4.8.7.8 | 4.8.7.9 | 4.8.8.1 | 4.8.8.2 | 4.8.8.3 |
| 4.8.8.4 | 4.8.8.5 | 4.8.8.6 | 4.8.8.7 | 4.8.8.8 | 4.8.8.9 | 4.8.9.1 | 4.8.9.2 | 4.8.9.3 | 4.8.9.4 |
| 4.8.9.5 | 4.8.9.6 | 4.8.9.7 | 4.8.9.8 | 4.8.9.9 | 4.9.1.1 | 4.9.1.2 | 4.9.1.3 | 4.9.1.4 | 4.9.1.5 |
| 4.9.1.6 | 4.9.1.7 | 4.9.1.8 | 4.9.1.9 | 4.9.2.1 | 4.9.2.2 | 4.9.2.3 | 4.9.2.4 | 4.9.2.5 | 4.9.2.6 |
| 4.9.2.7 | 4.9.2.8 | 4.9.2.9 | 4.9.3.1 | 4.9.3.2 | 4.9.3.3 | 4.9.3.4 | 4.9.3.5 | 4.9.3.6 | 4.9.3.7 |
| 4.9.3.8 | 4.9.3.9 | 4.9.4.1 | 4.9.4.2 | 4.9.4.3 | 4.9.4.4 | 4.9.4.5 | 4.9.4.6 | 4.9.4.7 | 4.9.4.8 |
| 4.9.4.9 | 4.9.5.1 | 4.9.5.2 | 4.9.5.3 | 4.9.5.4 | 4.9.5.5 | 4.9.5.6 | 4.9.5.7 | 4.9.5.8 | 4.9.5.9 |
| 4.9.6.1 | 4.9.6.2 | 4.9.6.3 | 4.9.6.4 | 4.9.6.5 | 4.9.6.6 | 4.9.6.7 | 4.9.6.8 | 4.9.6.9 | 4.9.7.1 |
| 4.9.7.2 | 4.9.7.3 | 4.9.7.4 | 4.9.7.5 | 4.9.7.6 | 4.9.7.7 | 4.9.7.8 | 4.9.7.9 | 4.9.8.1 | 4.9.8.2 |
| 4.9.8.3 | 4.9.8.4 | 4.9.8.5 | 4.9.8.6 | 4.9.8.7 | 4.9.8.8 | 4.9.8.9 | 4.9.9.1 | 4.9.9.2 | 4.9.9.3 |
| 4.9.9.4 | 4.9.9.5 | 4.9.9.6 | 4.9.9.7 | 4.9.9.8 | 4.9.9.9 | | | | |

Another group of preferred compounds are named in Table 2 and designated by numbers assigned to the variables of Formula I using the following convention: M1.V/Z/W. The compounds are shown without depiction of stereochemistry since the compounds are biologically active as the diastereomeric mixture or as a single stereoisomer. M1 is a variable that represents nucleosides of Formula I which are attached via 5'-hydroxyl group that is phosphorylated with a group P(O)(O—CH(V)CH(Z)C(WW')—O) to make compounds of Formula I.

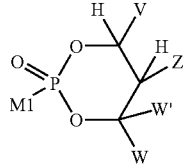

The structures for variable M1 are the same as described above.

Variable V/Z/W: Group 1 of V/Z/W
1) V=3-chlorophenyl; Z=methyl; W=hydrogen
2) V=3,5-dichlorophenyl; Z=methyl; W=hydrogen
3) V=4-pyridyl; Z=methyl; W=hydrogen
4) V=3-chlorophenyl; Z=methoxy; W=hydrogen
5) V=3,5-dichlorophenyl; Z=methoxy; W=hydrogen
6) V=4-pyridyl; Z=methoxy; W=hydrogen
7) V=3-chlorophenyl; Z=hydrogen; W=3-chlorophenyl
8) V=3,5-dichlorophenyl; Z=hydrogen; W=3,5-dichlorophenyl
9) V=4-pyridyl; Z=hydrogen; W=4-pyridyl Variable V/Z/W: Group 2 of V/Z/W
1) V=3-chlorophenyl; Z=NHAc; W=hydrogen
2) V=3,5-dichlorophenyl; Z=NHAc; W=hydrogen
3) V=4-pyridyl; Z=NHAc; W=hydrogen
4) V=3-chlorophenyl; Z=hydrogen; W=methyl
5) V=3,5-dichlorophenyl; Z=hydrogen; W=methyl
6) V=4-pyridyl; Z=hydrogen; W=methyl
7) V=3-chlorophenyl; Z=acetoxy; W=hydrogen
8) V=3,5-dichlorophenyl; Z=acetoxy; W=hydrogen
9) V=4-pyridyl; Z=acetoxy; W=hydrogen Variable V/Z/W: Group 3 of V/Z/W
1) V=phenyl; Z=phenyl; W=hydrogen
2) V=phenyl; Z=—CH$_2$—CH$_2$— fused to phenyl at V to form a 6-membered ring; W=hydrogen
3) V=phenyl; Z=H; W=—CH$_2$—CH$_2$— fused to phenyl at V to form a 6-membered ring
4) V=phenyl; Z=H; W=W'=methyl
5) V=phenyl; Z=H; W and W'=—CH$_2$—CH$_2$—CH$_2$— to form a 6-membered ring 6) V=phenyl; Z and W=—CH$_2$—CH$_2$—CH$_2$—CH$_2$— to form a 6-membered ring
7) V=3-chlorophenyl; Z=CH$_2$CH$_2$CH$_2$OC(O)OCH$_3$; W=hydrogen
8) V=3-chlorophenyl; Z=CH$_2$CH$_2$CH$_2$SC(O)CH$_3$; W=hydrogen
9) V=4-pyridyl; Z=CH$_2$CH$_2$CH$_2$OC(O)OCH$_3$; W=hydrogen
10) V=4-pyridyl; Z=CH$_2$CH$_2$CH$_2$SC(O)CH$_3$; W=hydrogen W' is hydrogen when not specified.

Preferred compounds are compounds listed in Table 2 using groups M1 and Group 1 of V/Z/W. For example, compound 1.3 represents structure 1 of group M1, i.e., 7-deaza-2'-methyl adenosine; and structure 3 of Group 1 of V/Z/W, i.e., V=4-pyridyl, Z=methyl and W =hydrogen. The compound 1.3 therefore is 7-deaza-2'-methyladenosine with the P(O)(O—CH(4-pyridyl)CH(CH$_3$)CH$_2$O) attached to the primary hydroxyl.

Preferred compounds are also compounds listed in Table 2 using groups M1 and Group 2 of V/Z/W.

Preferred compounds are also compounds listed in Table 2 using groups M1 and Group 3 of V/Z/W.

TABLE 2

| | | | | | | | | | | | | | | | | | | |
|---|---|---|---|---|---|---|---|---|---|---|---|---|---|---|---|---|---|---|
| 1.1 | 1.2 | 1.3 | 1.4 | 1.5 | 1.6 | 1.7 | 1.8 | 1.9 | 2.1 | 2.2 | 2.3 | 2.4 | 2.5 | 2.6 | 2.7 | 2.8 | 2.9 | |
| 3.1 | 3.2 | 3.3 | 3.4 | 3.5 | 3.6 | 3.7 | 3.8 | 3.9 | 4.1 | 4.2 | 4.3 | 4.4 | 4.5 | 4.6 | 4.7 | 4.8 | 4.9 | |

Preferred compounds are also compounds of Tables 1 and 2 of formulae VI-VIII where R$^7$ is an L-valinyl group attached via a carbonyl and R$^7$ and R$^8$ form a 5-membered cyclic carbonate.

Moreover, the compounds of the present invention can be used for inhibiting viral replication. In another aspect, the compounds of this invention can be used for inhibiting RNA-dependent RNA viral replication. In a further aspect, the compounds of this invention can be used for inhibiting HCV replication.

In another aspect, the compounds of the present invention can be used for treating viral infections. In a further aspect, compounds of this invention can be used for treating RNA-dependent RNA viral infection. In another aspect, compounds of this invention can be used for treating HCV infection.

In another aspect, the compounds of the present invention can be used for treating viral infections of the liver. In a further aspect, compounds of this invention can be used for treating RNA-dependent RNA viral infection in the liver. In another aspect, compounds of this invention can be used for treating HCV infection in the liver.

In one aspect, inhibition of viral replication is measured in serum. Increased viral titer reduction is associated with decreased generation of viral mutants which are associated with drug resistance.

In another aspect, the compounds of the present invention can be used for preventing the onset of symptoms associated with a viral infection.

Activation of prodrugs of this invention results in the production of a nucleoside monophosphate (NMP). NMPs are frequently further phosphorylated inside the hepatocyte to the biologically active nucleoside triphosphate (NTP). Drug elimination from the hepatocyte typically entails degradation of phosphorylated metabolites back to a species capable of being transported out of the hepatocyte and into the blood for elimination by the kidney or into the bile for biliary excretion. Often with nucleoside-based drug the phophorylated metabolites are dephosphorylated to the uncharged nucleoside.

Nucleosides that leak back into the systemic circulation result in systemic exposure. If the nucleoside is active systemically, e.g. through entry into virally infected cells and phosphorylation to the active species, escape of the nucleoside from the liver leads to biological activity outside of the liver (i.e. extrahepatic tissues, blood cells). In this case, prodrugs of the invention can be effective for treating diseases outside of the liver, e.g. viral infections. Since many nucleosides exhibit poor oral bioavailability due to breakdown in the gastrointestinal tract either enzymatically (e.g. deamination by adenosine deaminase) or chemically (e.g. acid instability), the prodrug can be used for oral drug delivery. Moreover, given that the prodrugs in some cases are broken down slowly relative to e.g. most ester based prodrugs, the prodrugs could advantageously result in slow, sustained systemic release of the nucleoside.

In other cases, however, systemic exposure to the nucleoside can result in toxicity. This can be minimized by selecting nucleosides that are preferentially excreted through the bile or nucleosides that are unable to undergo phosphorylation in tissues or nucleosides that undergo rapid intrahepatic metabolism to a biologically inactive metabolite. Some enzymes in the hepatocyte are present that can degrade nucleosides and therefore minimize exposure (e.g. Phase I and Phase II enzymes). One example is adenosine deaminase, which can deaminate some adenosine-based nucleosides to produce the corresponding inosine analogue. Rapid intracellular deamination of the nucleoside following its dephosphorylation to the nucleoside limits systemic exposure to the nucleoside and diminishes the risk of toxicity.

Methods described in Examples A-D were used to test activation of compounds of this invention. Methods used in Example E were used to evaluate the ability of compounds of the invention to generate NTPs.

HCV replication in human liver tissue was evaluated as in Example F. Liver specificity of the prodrugs relative to the nucleosides was measured by methods in Example G.

Tissue distribution can be determined according to methods in Example H. Oral bioavailability was determined by methods described in Example I. The susceptibility of nucleoside analogs to metabolism can be determined as in Example J.

In one aspect of the present invention, the RNA-dependent RNA viral infection is a positive-sense single-stranded RNA-dependent viral infection. In another aspect, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infections hepatitis C virus infection.

In a further aspect, compounds of the present invention can be used to enhance the oral bioavailability of the parent drug. In another aspect, compounds of the present invention can be used to enhance the oral bioavailability of the parent drug by at least 5%. In another aspect, compounds of the present invention can be used to enhance the oral bioavailability of the parent drug by at least 10%. In another aspect, oral bioavailability is enhanced by 50% compared to the parent drug administered orally. In a further aspect, the oral bioavailability is enhanced by at least 100%.

In another aspect, compounds of the present invention can be used to increase the therapeutic index of a drug.

In one aspect, compounds of the present invention can be used to bypass drug resistance.

In another aspect, compounds of the present invention can be used to treat cancer.

Formulations

Compounds of the invention are administered in a total daily dose of 0.01 to 1000 mg/kg. In one aspect the range is about 0.1 mg/kg to about 100 mg/kg. In another aspect the range is 0.5 to 20 mg/kg. The dose may be administered in as many divided doses as is convenient.

Compounds of this invention when used in combination with other antiviral agents may be administered as a daily dose or an appropriate fraction of the daily dose (e.g., bid). Administration of the prodrug may occur at or near the time in which the other antiviral is administered or at a different time. The compounds of this invention may be used in a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Intravenous administration is generally preferred.

Pharmaceutically acceptable salts include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfosalicylate, tannate, tartrate, terphthalate, tosylate, and triethiodide.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachid oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachid oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/h can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Formulations suitable for parenteral administration may be administered in a continuous infusion manner via an indwelling pump or via a hospital bag. Continuous infusion includes the infusion by an external pump. The infusions may be done through a Hickman or PICC or any other suitable means of administering a formulation either parenterally or i.v.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Another aspect of the present invention is concerned with a method of inhibiting HCV replication or treating HCV infection with a compound of the present invention in combination with one or more agents useful for treating HCV infection. Such agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine is a liver-targeting prodrug analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

Also included within the scope of the invention is a pharmaceutical composition comprising a compound of Formula I or prodrug or pharmaceutically acceptable salt thereof and at least one agent useful for treating a viral infection, particularly an HCV infection.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, U.S. Pat. Nos. 6,323,180, and 6,410,531. Specific embodiments of NS3 protease inhibitors for combination with the compounds of the present invention are BILN 2061 (Boehringer Ingelheim) and VX-950/LY-570310. HCV NS3 protease as a target for the development of inhibitors of HCV replication and for the treatment of HCV infection is discussed in B. W. Dymock, "Emerging therapies for hepatitis C virus infection," Emerging Drugs, 6: 13-42 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497 (merimepodib), which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, Agents Action, 44 (Suppl.): 165 (1993)].

For the treatment of HCV infection, the compounds of the present invention may also be administered in combination with the antiviral agent amantadine (1-aminoadamantane) and its hydrochloride salt [for a comprehensive description of this agent, see J. Kirschbaum, Anal. Profiles Drug Subs. 12: 1-36 (1983)].

The compounds of the present invention may also be combined for the treatment of HCV infection with antiviral 1'-C, 2'-C-, or 3'-C-branched ribonucleosides disclosed in R. E. Harry-O'kuru, et al., J. Org. Chem., 62: 1754-1759 (1997); M. S. Wolfe, et al., Tetrahedron Lett., 36: 7611-7614 (1995); U.S. Pat. No. 3,480,613 (Nov. 25, 1969); International Publication Number WO 01/90121 (29 Nov. 2001); International Publication Number WO 01/92282 (6 Dec. 2001); and International Publication Number WO 02/32920 (25 Apr. 2002); the contents of each of which are incorporated by reference in their entirety. Such branched ribonucleosides include, but are not limited to, 2'-C-methylcytidine, 2'-C-methyluridine, 2'-C-methyladenosine, 2'-C-methylguanosine, and 9-(2-C-methyl-β-D-ribofuranosyl)-2,6-diaminopurine, and prodrugs thereof.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920 (25 Apr. 2002), and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/057287 (25 Jul. 2002), assigned to Merck & Co. and Isis Pharmaceuticals; and WO 02/057425 (25 Jul. 2002), assigned to Merck & Co. and Isis Pharmaceuticals.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; and WO 02/20497 (3 Mar. 2002). WO 01/47883 discloses a large number of benzimidazole derivatives, such as JTK-003, which is claimed to be an orally active inhibitor of NS5B that is currently undergoing clinical evaluation.

Synthesis of Compounds of 2'-C-Methyl Derivatives

Synthesis of the 5'-nucleoside monophosphate (NMP) prodrugs of the present invention is organized into two sections: 1. synthesis of phosphorylation precursors; 2. synthesis of prodrugs via coupling of nucleosides and prodrug moiety.

Synthesis of Phosphorylation Precursors:

Synthesis of phosphorylation precursors is attained in two stages: 1. Synthesis of 1,3-diols and 2. Synthesis of phosphorylation precursor.

Synthesis of 1,3-Diols:

A variety of synthetic methods are known to prepare the following types of 1,3-diols: a) 1-substituted; b) 2-substituted; and c) 1,2- or 1,3-annulated in their racemic or enantioenriched form. The V, W, Z groups of Formula I can be introduced or modified either during synthesis of diols or after the synthesis of prodrugs.

Synthesis of 1-(aryl)-Propane-1,3-Diols:

The suitable methods to prepare 1,3-diols are divided into two types as following: 1) synthesis of racemic 1-(aryl)-propane-1,3-diols; 2) synthesis of enantioenriched 1-(aryl)-propane-1,3-diols.

Synthesis of Racemic 1-(aryl)-Propane-1,3-Diol:

1,3-Dihydroxy compounds can be synthesized by several well-known methods from the literature. Substituted aromatic aldehydes are utilized to synthesize racemic 1-(aryl) propane-1,3-diols via addition of lithium enolate of alkyl acetate followed by ester reduction (path A) (Turner, J. Org. Chem. 55:4744 (1990)). Alternatively, aryl lithium or aryl Grignard additions to 1-hydroxy propan-3-al also give 1-(arylsubstituted)propane-1,3-diols (path B). This method will enable conversion of various substituted aryl halides to 1-(arylsubstituted)-1,3-propane diols (Coppi, et al., *J. Org. Chem.* 53:911(1988)). Aryl halides can also be used to synthesize 1-substituted propane diols by Heck coupling of 1,3-diox-4-ene followed by reduction and hydrolysis (Sakamoto, et al., *Tetrahedron Lett.* 33:6845 (1992)). Pyridyl-, quinolyl-, isoquinolyl- propan-3-ol derivatives can be hydroxylated to 1-substituted-1,3-diols by N-oxide formation followed by rearrangement in the presence of acetic anhydride (path C) (Yamamoto, et al., *Tetrahedron* 37:1871 (1981)). A variety of aromatic aldehydes can also be converted to 1-substituted-1, 3-diols by vinyl lithium or vinyl Grignard addition followed by hydroboration reaction (path D).

condensation (Turner, et al., *J. Org. Chem.* 54:4229 (1989)) or from aryl halides (Kobayashi, et al., *Tetrahedron Lett.* 27:4745 (1986)). Alternatively, 1,3-diols of high enantiomeric purity can be obtained by enantioselective borane reduction of β-hydroxyethyl aryl ketone derivatives or β-keto acid derivatives (path B) (Ramachandran, et al., *Tetrahedron Lett.* 38:761 (1997)). In another method, commercially available cinnamyl alcohols may be converted to epoxy alcohols under catalytic asymmetric epoxidation conditions. These epoxy alcohols are reduced by Red-Al to result in 1,3-diols with high ee's (path C) (Gao, et al., *J. Org. Chem.* 53:4081 (1980)). Enantioselective aldol condensation is another well-described method for synthesis of 1,3-oxygenated functionality with high ee's starting from aromatic aldehydes. (path D) (Mukaiyama, *Org. React.* 28:203 (1982)).

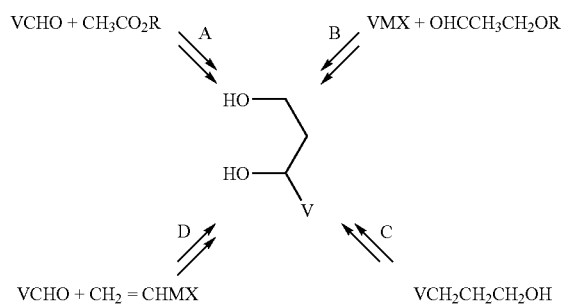

V = Aryl,
R = Alkyl,
R' = benzyl,
M = Mg or Li,
X = Halide or null

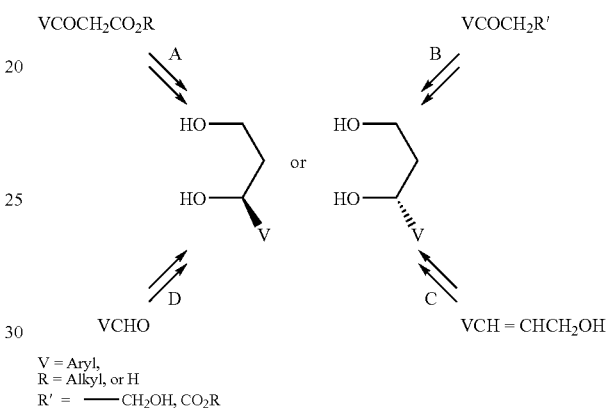

V = Aryl,
R = Alkyl, or H
R' = ——CH$_2$OH, CO$_2$R

Synthesis of Enantioenriched 1-(aryl)-Propane-1,3-Diol:

A variety of known methods for resolution of secondary alcohols via chemical or enzymatic agents may be utilized for preparation of diol enantiomers (Harada, et al., *Tetrahedron Lett.* 28:4843 (1987)). Transition metal catalyzed hydrogenation of substituted 3-aryl-3-oxo-propionic acids or esters is an efficient method to prepare R- or S-isomers of beta hydroxy acids or esters in high enantiomeric purity (*Comprehensive Asymmetric Catalysis*, Jacobsen, E. N., Pfaltz, A., Yamamoto, H. (Eds), Springer, (1999); *Asymmetric Catalysis in Organic Synthesis*, Noyori, R., John Wiley, (1994)). These beta hydroxy acid or ester products can be further reduced to give required 1-(aryl)-propane-1,3-diols in high enantiomeric excess (ee). (path A). The β-keto acid or ester substrates for high pressure hydrogenation or hydrogen transfer reactions may be prepared by a variety of methods such as condensation of acetophenone with dimethylcarbonate in the presence of a base (Chu, et al., *J. Het Chem.* 22:1033 (1985)), by ester Synthesis of 2-Substituted 1,3-Diols:

Various 2-substituted-1,3-diols can be made from commercially available 2-(hydroxymethyl)-1,3-propane-diol. Pentaerythritol can be converted to triol via decarboxylation of diacid followed by reduction (path a) (Werle, et al., *Liebigs. Ann. Chem.*, 1986, 944) or diol-monocarboxylic acid derivatives can also be obtained by decarboxylation under known conditions (Iwata, et. al., *Tetrahedron Lett.* 1987, 28, 3131). Nitrotriol is also known to give triol by reductive elimination (path b) (Latour, et. al., *Synthesis*, 1987, 8, 742). The triol can be derivatized by mono acylation or carbonate formation by treatment with alkanoyl chloride, or alkylchloroformate (path d) (Greene and Wuts, *Protective groups in organic synthesis*, John Wiley, New York, 1990). Aryl substitution can be affected by oxidation to aldehyde and aryl Grignard additions (path c). Aldehydes can also be converted to substituted amines by reductive amination reaction (path e).

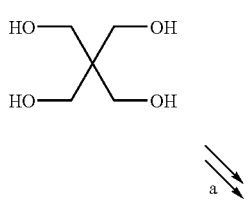

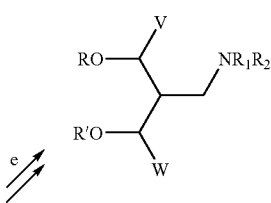

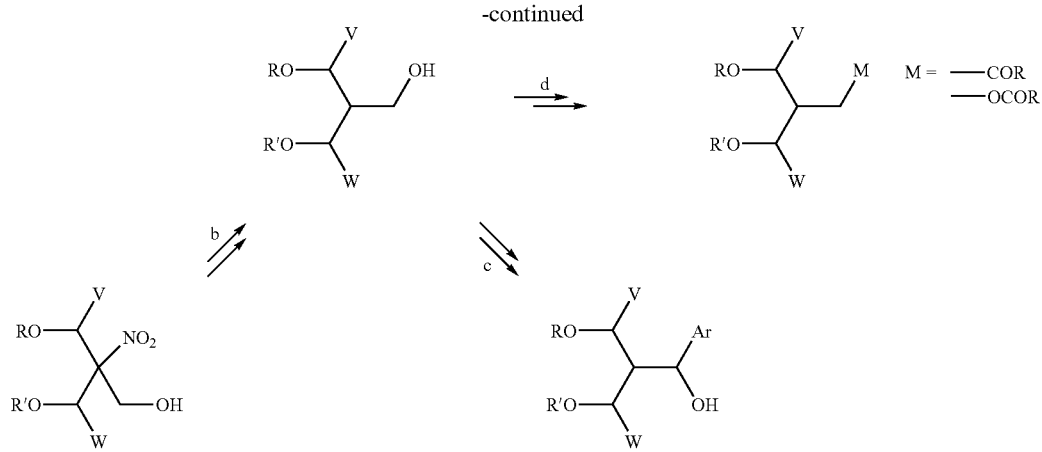

Synthesis of cyclic-1,3-diols:

Compounds of Formula 1 where V-Z or V—W are fused by four carbons are made from cyclohexane diol derivatives. Commercially available cis, cis-1,3,5-cyclohexane-triol can be used as is or modified as described in case of 2-substituted propan-1,3-diols to give various analogues. These modifications can either be made before or after ester formation. Various 1,3-cyclohexane-diols can be made by Diels-Alder methodology using pyrone as diene (Posner, et. al., *Tetrahedron Lett.*, 1991, 32, 5295). Cyclohexanediol derivatives are also made by nitrile oxide-olefin additions (Curran, et. al., *J. Am. Chem. Soc.*, 1985, 107, 6023). Alternatively, cyclohexyl precursors are also made from commercially available quinic acid (Rao, et. al., *Tetrahedron Lett.*, 1991, 32, 547.)

Synthesis of Substituted 1,3-hydroxyamines and 1,3-diamines:

A large number of synthetic methods are available for the preparation of substituted 1,3-hydroxyamines and 1,3-diamines due to the ubiquitous nature of these functionalities in naturally occurring compounds. Following are some of these methods organized into: 1. synthesis of substituted 1,3-hydroxy amines; 2. synthesis of substituted 1,3-diamines and 3. synthesis of chiral substituted 1,3-hydroxyamines and 1,3-diamines.

Synthesis of Substituted 1,3-hydroxy amines:

1,3-Diols described in the earlier section can be converted selectively to either hydroxy amines or to corresponding diamines by converting hydroxy functionality to a leaving group and treating with anhydrous ammonia or required primary or secondary amines (Corey, et al., *Tetrahedron Lett.*, 1989, 30, 5207: Gao, et al., *J. Org. Chem.*, 1988, 53, 4081). A similar transformation may also be achieved directly from alcohols under Mitsunobu type of reaction conditions (Hughes, D. L., *Org. React.*, 1992, 42).

A general synthetic procedure for 3-aryl-3-hydroxy-propan-1-amine type of prodrug moiety involves aldol type condensation of aryl esters with alkyl nitriles followed by reduction of resulting substituted benzoylacetonitrile (Shih et al., *Heterocycles*, 1986, 24, 1599). The procedure can also be adapted for formation of 2-substituted aminopropanols by using substituted alkylnitrile. In another approach, 3-aryl-3-amino-propan-1-ol type of prodrug groups are synthesized from aryl aldehydes by condensation of malonic acid in presence of ammonium acetate followed by reduction of resulting substituted β-amino acids. Both these methods enable to introduce wide variety of substitution of aryl group (Shih, et al., *Heterocycles.*, 1978, 9, 1277). In an alternate approach, β-substituted organolithium compounds of 1-amino-1-aryl ethyl dianion generated from styrene type of compounds undergo addition with carbonyl compounds to give variety of W, W' substitution by variation of the carbonyl compounds (Barluenga, et al., *J. Org. Chem.*, 1979, 44, 4798).

Synthesis of Substituted 1,3-diamines:

Substituted 1,3-diamines are synthesized starting from a variety of substrates. Arylglutaronitriles can be transformed to 1-substituted diamines by hydrolysis to amide and Hofmann rearrangement conditions (Bertochio, et al., *Bull. Soc. Chim. Fr*, 1962, 1809). Whereas, malononitrile substitution will enable variety of Z substitution by electrophile introduction followed by hydride reduction to corresponding diamines. In another approach, cinnamaldehydes react with hydrazines or substituted hydrazines to give corresponding pyrazolines which upon catalytic hydrogenation result in substituted 1,3-diamines (Weinhardt, et al., *J. Med. Chem.*, 1985, 28, 694). High trans-diastereoselectivity of 1,3-substitution is also attainable by aryl Grignard addition on to pyrazolines followed by reduction (Alexakis, et al., *J. Org. Chem.*, 1992, 576, 4563). 1-Aryl-1,3-diaminopropanes are also prepared by diborane reduction of 3-amino-3-arylacrylonitriles which in turn are made from nitrile substituted aromatic compounds (Dornow, et al., *Chem Ber.*, 1949, 82, 254). Reduction of 1,3-diimines obtained from corresponding 1,3-carbonyl compounds are another source of 1,3-diamine prodrug moiety which allows a wide variety of activating groups V and/or Z (Barluenga, et al., *J. Org. Chem.*, 1983, 48, 2255).

Synthesis of Chiral Substituted 1,3-hydroxyamines and 1,3-diamines:

Enantiomerically pure 3-aryl-3-hydroxypropan-1-amines are synthesized by CBS enantioselective catalytic reaction of β-chloropropiophenone followed by displacement of halo group to make secondary or primary amines as required (Corey, et al., *Tetrahedron Lett.*, 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., *J. Org. Chem.*, 1982, 47, 4005). Chiral induction in 1,3-polar additions to form substituted isoxazolidines is also attained by chiral phosphine palladium complexes resulting in enantioselective formation of amino alcohols (Hori, et al., *J. Org. Chem.*, 1999, 64, 5017).

Alternatively, optically pure 1-aryl substituted amino alcohols are obtained by selective ring opening of corresponding chiral epoxy alcohols with desired amines (Canas et al., *Tetrahedron Lett.*, 1991, 32, 6931).

Several methods are known for diastereoselective synthesis of 1,3-disubstituted aminoalcohols. For example, treatment of (E)-N-cinnamyltrichloroacetamide with hypochlorous acid results in trans-dihydrooxazine which is readily hydrolysed to erythro-β-chloro-γ-hydroxy-γ-phenylpropanamine in high diastereoselectivity (Commercon et al., *Tetrahedron Lett.*, 1990, 31, 3871). Diastereoselective formation of 1,3-aminoalcohols is also achieved by reductive amination of optically pure 3-hydroxy ketones (Haddad et al., *Tetrahedron Lett.*, 1997, 38, 5981). In an alternate approach, 3-aminoketones are transformed to 1,3-disubstituted aminoalcohols in high stereoselectivity by a selective hydride reduction (Barluenga et al., *J. Org. Chem.*, 1992, 57, 1219).

Synthesis of Phosphorylation Precursors:

Synthesis of phosphorylation precursors is divided in to two sections: a. synthesis of P(III) phosphorylation precursor, b. stereoselective synthesis of P(V) phosphorylation precursors.

Synthesis of P(III) Phosphorylation Precursors:

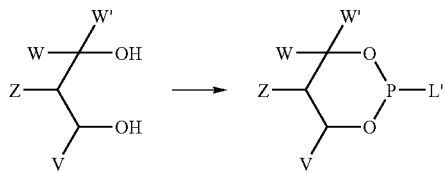

Phosphorylation of 5'-alcohol is achieved using cyclic 1',3'-propanyl esters of phosphorylating agents where the agent is in the P(III) oxidation state. One preferred phosphorylating agent is a chloro phospholane (L'=chloro). Cyclic chlorophospholanes are prepared under mild conditions by reaction of phosphorus trichloride with substituted 1,3-diols (Wissner, et al, *J. Med. Chem.*, 1992, 35, 1650). Alternatively phosphoramidites can be used as the phosphorylating agent (Beaucage, et al., *Tetrahedron*, 1993, 49, 6123). Appropriately substituted phosphoramidites can be prepared by reacting cyclic chlorophospholanes with N,N-dialkylamine (Perich, et al., *Aust. J. Chem.*, 1990, 43, 1623. Perich, et al, Synthesis, 1988, 2, 142) or by reaction of commercially available dialkylaminophosphorochloridate with substituted propane-1,3-diols.

Synthesis of P(V) Phosphorylation Precursors:

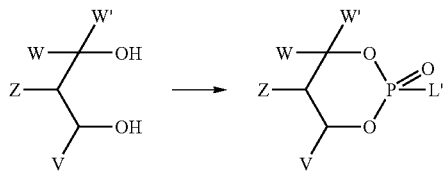

In general, synthesis of phosphate esters is achieved by coupling the alcohol with the corresponding activated phosphate precursor for example, Chlorophosphate (L'=chloro) condensation with 5'-hydroxy of nucleoside is a well known method for preparation of nucleoside phosphate monoesters. The activated precursor can be prepared by several well known methods. Chlorophosphates useful for synthesis of the prodrugs are prepared from the substituted-1,3-propanediol (Wissner, et al, *J. Med Chem.*, 1992, 35, 1650). Chlorophosphates are made by oxidation of the corresponding chlorophospholanes (Anderson, et al, *J. Org. Chem.*, 1984, 49, 1304), which are obtained by reaction of the substituted diol with phosphorus trichloride. Alternatively, the chlorophosphate agent is made by treating substituted-1,3-diols with phosphorus oxychloride (Patois, et al, *J. Chem. Soc. Perkin Trans. I*, 1990, 1577). Chlorophosphate species may also be generated in situ from corresponding cyclic phosphites (Silverburg, et al., *Tetrahedron Lett.*, 1996, 37, 771), which in turn can be either made from a chlorophospholane or phosphoramidate intermediate. Phosphorofluoridate intermediate prepared either from pyrophosphate or phosphoric acid may also act as precursor in preparation of cyclic prodrugs (Watanabe et al., *Tetrahedron Lett.*, 1988, 29, 5763).

Phosphoramidates (L'=NRR') are also well-known intermediates for the synthesis of phosphate esters. Monoalkyl or dialkylphosphoramidate (Watanabe, et al, *Chem Pharm Bull.*, 1990, 38, 562), triazolophosphoramidate (Yamakage, et al., *Tetrahedron*, 1989, 45, 5459) and pyrrolidinophosphoramidate (Nakayama, et al, *J. Am. Chem. Soc.*, 1990, 112, 6936) are some of the known intermediates used for the preparation of phosphate esters. Another effective phosphorylating procedure is a metal catalyzed addition of cyclic chlorophosphate adduct of 2-oxazolone. This intermediate attains high selectivity in phosphorylation of primary hydroxy group in presence of secondary hydroxyl group (Nagamatsu, et al, *Tetrahedron Lett.*, 1987, 28, 2375). These agents are obtained by reaction of a chlorophosphate with the amine or alternatively by formation of the corresponding phosphoramidite followed by oxidation.

Synthesis of Enantiomerically Enriched P(V) Phosphorylation Precursors:

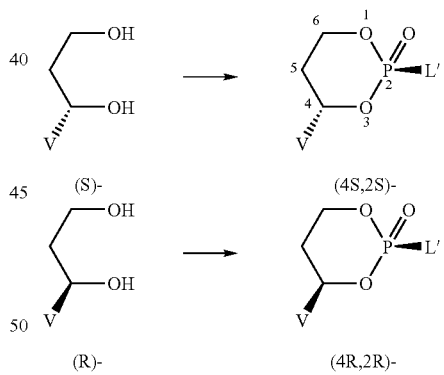

The enantioenriched activated phosphorylating agent is synthesized by phosphorylation of an enantioenriched 1-(V)-1,3-propanediol with phosphorodichloridates of formula L-P(O)Cl$_2$ in the presence of a base (Ferroni, et al., *J. Org. Chem.* 64(13), 4943 (1999)). Phosphorylation of an enantiomerically pure substituted diol with, for example, a commercially available phosphorodichloridate R—OP(O)Cl$_2$, where RO is a leaving group, preferably aryl substituted with electron withdrawing groups, such as a nitro or a chloro, produces two diastereomeric intermediates. The relative configuration of the phosphorus atom is easily determined by comparison of the $^{31}$P NMR spectra. The chemical shift of the equatorial phosphoryloxy moiety (trans-isomer) is always more upfield than the one of the axial isomer (cis-isomer) (Verkade, et al, *J.*

Org. Chem., 1977, 42, 1549). These diastereomers can be further equilibrated to give a trans-2,4-substituted phosphorylating agents in presence of a base such as triethyl amine or DBU. The equilibration to complete inversion of 2,4-cis-diastereomer is also achieved in presence of appropriately substituted sodium phenoxide. The equilibration step results in greater than 95% ee of the isolated trans-phosphorylating agent.

Synthesis of Nucleosides.

All nucleoside moieties of Formula I are well described in the literature. 2'-C-methyl-adenosine and 2'-C-methyl-guanosine analogs are made by Lewis acid catalyzed reactions of the persilylated base and 1'-acetate or benzoate sugar intermediate (Walton et al., *J. Am. Chem. Soc.*, 1966, 88, 4524; Harry-O'Kuru et al., *J. Org. Chem.*, 1997, 62, 1754, WO01/90121). The 7-deaza analogs are made as described earlier from 1'-bromo sugar intermediate via reaction of sodium salt of the bases (US2002-0147160A1 or WO02/057827). The glycosylation products are subjected to deprotection and amination via ammonolysis reaction.

The nucleoside moieties and derivatives thereof of Formulae VI-VIII of the present invention may be synthesized by many well-established general methods described in the nucleoside literature. Several nucleosides analogs described herein are synthesized as illustrated in WO04/046331 and by the methods cited therein. These compounds of the present invention can also be made from a wide variety of commercial bases utilizing the 2'-methyl riboglycosylation precursor (US2002-0147160A1 or WO02/057827) via a range of well-known glycosylation reactions (Vorbruggen and Ruh-Pohlenz, *Handbook of Nucleoside Synthesis*, Wiley, N.Y., 2001). Furthermore, deaza and aza nucleoside analogs may be prepared utilizing the methods reported in the case of corresponding ribo- analogs by glycosylation with 2'-methyl glycosylation precursor (Robins, et al., *Advances in Antiviral Drug Design*, Vol. 1, p 39-85, De Clercq, ed., JAI Press, Greenwich, Conn., 1993). In addition, new base analogs of the nucleosides can be synthesized by modification of the available nucleosides or via synthesis of new bases followed by glycosylation (*Chemistry of Nucleosides and Nucleotides*, Vols. 1-3, Townsend, ed., Plenum, N.Y., 1988 and *Nucleic Acid Chemistry*, Vols. 1-4, Townsend and Tipson Eds., Wiley, N.Y., 1986).

Synthesis of Prodrugs via Coupling of Nucleosides and Prodrug Moiety.

The following procedures on the preparation of prodrugs illustrate the general procedures used to prepare the NMP prodrugs. Prodrugs can be introduced at different stages of the synthesis. Most often they are made at a later stage, because of the general sensitivity of these groups to various reaction conditions. Optically pure prodrugs containing single isomer at phosphorus center are made by coupling of enantiomerically enriched activated phosphate intermediates.

All the procedures described herein, where Y and Y' are oxygen are also applicable for the preparation of the prodrugs where Y and and/or Y' are NH by appropriate substitution or protection of nitrogen.

The preparation of prodrugs is further organized into, 1) synthesis via P(III) intermediates, 2) synthesis via P(V) intermediates, and 3) miscellaneous methods.

Synthesis of Prodrugs via P(III) Intermediates:

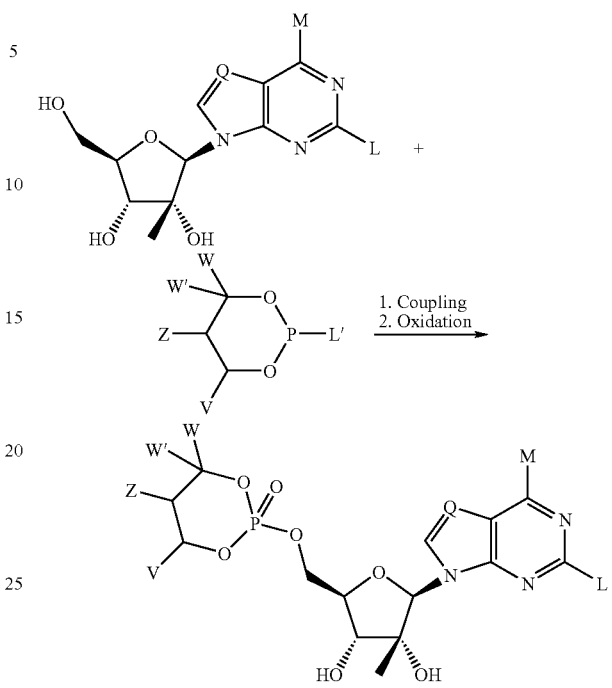

wherein Q is N or CH; and L is H and M is $NH_2$ or M is OH and L is $NH_2$.

Chlorophospholanes are used to phosphorylate alcohols on nucleosides in the presence of an organic base (e.g., triethylamine, pyridine). Alternatively, the phosphite can be obtained by coupling the nucleoside with a phosphoramidate in the presence of a coupling promoter such as tetrazole or benzimidazolium triflate (Hayakawa et al., *J. Org. Chem.*, 1996, 61, 7996). Phosphite diastereomers may be isolated by column chromatography or crystallization (Wang, et al, *Tetrahedron Lett*, 1997, 38, 3797; Bentridge et al., *J. Am. Chem. Soc.*, 1989, 111, 3981). Since condensation of alcohols with chlorophospholanes or phosphoramidites is an $S_N2(P)$ reaction, the product is expected to have an inverted configuration. This allows for the stereoselective synthesis of cyclic phosphites. Isomeric mixtures of phosphorylation reactions can also be equilibrated (e.g. thermal equilibration) to a more thermodynamically stable isomer.

The resulting phosphites are subsequently oxidized to the corresponding phosphate prodrugs using an oxidant such as molecular oxygen or t-butylhydroperoxide (Meier et al., *Bioorg, Med. Chem. Lett.*, 1997, 7, 1577). Oxidation of optically pure phosphites is expected to stereoselectively provide optically active prodrugs (Mikolajczyk, et al., *J. Org. Chem.*, 1978, 43, 2132. Cullis, P. M. *J. Chem. Soc., Chem Commun.*, 1984, 1510, Verfurth, et al., *Chem. Ber.*, 1991, 129, 1627).

Synthesis of Prodrugs via P(V) Intermediates:

For the synthesis of cis-prodrugs of Formula I, the prodrug moiety can be introduced at different stages of the synthesis. Most often the cyclic phosphates are introduced at a later stage, because of the general sensitivity of these groups to various reaction conditions. The synthesis can also proceed through using a protected or unprotected nucleoside or nucleoside analog depending on the reactivity of the functional groups present in the compound. Single stereoisomers of the cis-prodrugs can be made either by separation of the diastereoisomers/enantiomers by a combination of column chromatography and/or crystallization, or by enantiospecific or enantioselective synthesis using enantioenriched activated phosphate intermediates.

Synthesis of Enantiomerically Enriched Prodrugs:

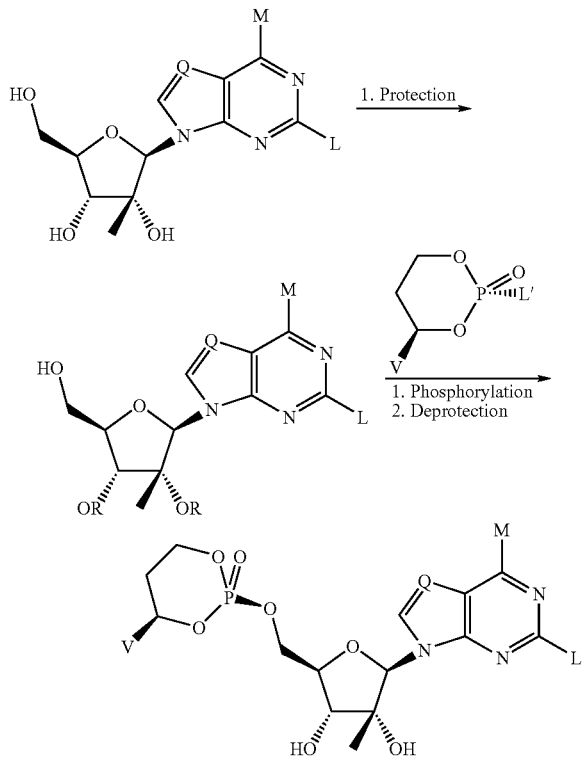

wherein Q is N or CH; and L is H and M is NH$_2$ or M is OH and L is NH$_2$.

The general procedure for the phosphorylation of protected nucleosides is accomplished by reacting a suitably protected nucleoside with a base and reacting the alkoxide generated with the phosphorylating reagent. The protected nucleoside can be prepared by one skilled in the art using one of the many procedures described for the protection of nucleosides (Greene T. W., Protective Groups in Organic Chemistry, John Wiley & Sons, New York (1999)). The nucleoside is protected in such a way as to expose the hydroxyl group on which to add the phosphate group while protecting all the remaining hydroxyls and other functional groups on the nucleoside that may interfere with the phosphorylation step or lead to regioisomers. In one aspect, the protecting groups selected are resistant to strong bases, e.g., ethers, silyl ethers and ketals. In one aspect, the protecting groups are optionally substituted MOM ethers, MEM ethers, trialkylsilyl ethers and symmetrical ketals. In another aspect, the protecting groups are t-butyldimethylsilyl ether and isopropylidene. Further protection entails masking of the amino group of the base moiety, if present, so as to eliminate any acidic protons. In one aspect the selected N-protecting groups are selected from the groups of dialkyl formamidines, mono and dialkyl imines, mono and diaryl imines. In one aspect, the N-protecting groups are selected from the groups of dialkyl formamidines and monoalkyl imine and mono aryl imine. In one aspect the monoalkyl imine is benzylimine and the mono-aryl imine is phenylimine. In another aspect, the N-protecting group is a symmetrical dialkyl formamidine selected from the group of dimethyl formamidine and diethyl formamidine.

Generation of the alkoxide of the exposed hydroxyl group on the suitably protected nucleoside is accomplished with a base in an aprotic solvent that is not base sensitive such as THF, dialkyl and cyclic formamides, ether, toluene and mixtures of those solvents. In one aspect, the solvents are DMF, DMA, DEF, N-methylpyrrolidinone, THF, and mixture of those solvents.

Many different bases have been used for the phosphorylation of nucleosides and non-nucleoside compounds with cyclic and acyclic phosphorylating agents. For example trialkylamines such as triethylamine (Roodsari et al., J. Org. Chem. 64(21), 7727 (1999)) or N,N-diisopropylethylamine (Meek et al., J. Am. Chem. Soc. 110(7), 2317 (1988)); nitrogen containing heterocyclic amines such as pyridine (Hoefler et al., Tetrahedron 56(11), 1485 (2000)), N-methylimidazole (Vankayalapati et al., J. Chem. Soc. Perk T 1 14, 2187(2000)), 1,2,4-triazole (Takaku et al., Chem. Lett. (5), 699 (1986)) or imidazole (Dyatkina et al., Tetrahedron Lett. 35(13), 1961 (1994)); organometallic bases such as potassium t-butoxide (Postel et al., J. Carbohyd. Chem. 19(2), 171 (2000)), butyllithium (Torneiro et al., J. Org. Chem. 62(18), 6344 (1977)), t-butylmagnesium chloride (Hayakawa et al., Tetrahedron Lett. 28(20), 2259 (1987)) or LDA (Aleksiuk et al., J. Chem. Soc. Chem. Comm. (1), 11 (1993)); inorganic bases such as cesium fluoride (Takaku et al., Nippon Kagaku Kaishi (10), 1968 (1985)), sodium hydride (Hanaoka et al., Heterocycles 23(11), 2927 (1985)), sodium iodide (Stromberg et al., J. Nucleos. Nucleot. 6(5), 815 (1987)), iodine (Stromberg et al., J. Nucleos. Nucleot. 6(5), 815 (1987)) or sodium hydroxide (Attanasi et al., Phosphorus Sulfur 35(1-2), 63 (1988)); metals such as copper (Bhatia et al., Tetrahedron Lett. 28(3), 271 (1987)). However, no reaction or racemization at the phosphorus stereogenic center was observed when coupling of phosphorylating reagent was attempted using the previously described procedures. Especially, no reaction was observed with bases previously used with substituted cyclic phosphorylating agent to give the corresponding cyclic phosphate in high yield such as sodium hydride (Thuong et al., Bull. Soc. Chim. Fr. 667 (1974)), pyridine (Ayral-Kaloustian et al., Carbohydr. Res. 187(1991)), butyl-lithium (Hulst et al., Tetrahedron Lett. 1339 (1993)), DBU (Merckling et al., Tetrahedron Lett. 2217 (1996)), triethylamine (Hadvary et al., Helv. Chim. Acta, 1986, 69(8), 1862), N-methylimidazole (Li et al., Tetrahedron Lett. 6615 (2001)) or sodium methoxide (Gorenstein et al., J. Am. Chem. Soc. 5077 (1980)). It was found that the use of Grignard reagents promoted phosphorylation with minimal epimerization of the phosphorus center. In one aspect, Grignard reagents are alkyl and aryl Grignards. In another aspect, the Grignard reagents are t-butyl magnesium halides and phenyl magnesium halides. In another aspect, the Grignard reagents are t-butylmagnesium chloride and phenylmagnesium chloride.

In another aspect magnesium alkoxides are used to generate the magnesium 5'-alkoxide of the nucleoside. In one aspect magnesium alkoxides are selected from the group of Mg(O-t-Bu)$_2$, and Mg(O-iPr)$_2$.

The protected prodrugs generated as described above are then subjected to a deprotection step to remove all the protecting groups using one of the many methods known to those skilled in the art (Greene T. W., Protective Groups in Organic Chemistry, John Wiley & Sons, New York (1999)) and that are compatible with the stability of the phosphate prodrug. In one aspect, deprotection reagents include fluoride salts to remove silyl protecting groups, mineral or organic acids to remove acid labile protecting groups such as silyl and/or ketals and N-protecting groups, if present. In another aspect, reagents are tetrabutylammonium fluoride (TBAF), hydrochloric acid solutions and aqueous TFA solutions. Isolation and purification of the final prodrugs, as well as all intermediates, are accomplished by a combination of column chromatography and/or crystallization.

The sequence provides methods to synthesize single isomers of compounds of Formula I. Due to the presence of a stereogenic center at the carbon where V is attached on the cyclic phosphate reagent, this carbon atom can have two distinct orientations, namely R or S. As such the trans-phosphate reagent prepared from a racemic diol can exist as either the S-trans or R-trans configuration and results in a S-cis and R-cis prodrug mixture. The reaction of the C'-S-trans-phosphate reagent generates the C'-S-cis-prodrug of the nucleoside while reaction with the C'-R-trans-phosphate reagent generates the C'-R-cis-prodrug.

Synthesis of 6-, 2'-, and/or 3'- Substituted Prodrugs:

Synthesis of 6-, 2'- and/or 3-'substituted prodrugs of Formula II or III can be accomplished starting from compounds of Formula I. For example, selective 3'-acylation of nucleoside monophosphate cyclic prodrugs of Formula I may be achieved by several methods as described in the literature (*Protective groups in organic synthesis*, Greene and Wuts, John Wiley, New York, 1991). Additionally, selective 3'-acylation can be attained by various esterification methods in the presence of tertiary hydroxy functionality at the 2'-position without protection. Acylation may also be accomplished efficiently by utilizing amine protected amino acids as described earlier (WO 04/002422, Hanson et al., *Bioorg. Med Chem.* 2000, 8, 2681) and the amine protective groups are removed under mild acidic conditions. 2',3-Cyclic carbonate formation is another well-known transformation for ribofuranosyl nucleosides. Compounds of formula I undergo carbonate formation under neutral conditions to result in compounds of Formula II or III (Pankiewicz, et al., *J. Org. Chem.*, 1985, 50, 3319).

Prodrugs at 6-position may be prepared from the corresponding halo derivatives of the nucleosides. The prodrug substitution is made at the nucleoside stage (before 5'-prodrug formation) from the corresponding chloro or hydroxy functionalities in case of compounds of Formula II or III where $R^9$ or $R^{10}$ is substituted (e.g., $N_3$, H, —COR). Synthesis of such nucleoside precursors are attained as described earlier (WO 02/057287). Preparation of these purine analogs by azido displacement (Aso et al., *J. Chem Soc Perkin Trans II*, 2000, 8 1637) or hydrogention (Freer et al., *Tetrahedron*, 2000, 56, 45) are well known methods. Subsequently, these prodrug functionality substituted nucleosides are transformed to corresponding monophosphate cyclic prodrugs of Formula II or III.

Miscellaneous Methods:

Coupling of activated phosphates with alcohols is accomplished in the presence of an organic base. For example, chlorophosphates synthesized as described in the earlier section react with an alcohol in the presence of a base such as pyridine or N-methylimidazole. In some cases phosphorylation is enhanced by in situ generation of iodophosphate from chlorophosphate (Stomberg, et al., *Nucleosides & Nucleotides.*, 1987, 5: 815). Phosphorofluoridate intermediates have also been used in phosphorylation reactions in the presence of a base such as CsF or n-BuLi to generate cyclic prodrugs (Watanabe et al., *Tetrahedron Lett.*, 1988, 29, 5763). Phosphoramidate intermediates are known to couple by transition metal catalysis (Nagamatsu, et al., *Tetrahedron Lett.*, 1987, 28, 2375).

Reaction of the optically pure diastereomer of phosphoramidate intermediate with the hydroxyl of nucleoside in the presence of an acid produces the optically pure phosphate prodrug by direct $S_N2(P)$ reaction (Nakayama, et al., *J. Am. Chem. Soc.*, 1990, 112, 6936). Alternatively, reaction of the optically pure phosphate precursor with a fluoride source, preferably cesium fluoride or TBAF, produces the more reactive phosphorofluoridate which reacts with the hydroxyl of the nucleoside to give the optically pure prodrug by overall retention of configuration at the phosphorus atom (Ogilvie, et al., *J. Am. Chem. Soc.*, 1977, 99, 1277).

Prodrugs of Formula I are synthesized by reaction of the corresponding phosphodichloridate and an alcohol (Khamnei, et al., *J. Med. Chem.*, 1996, 39: 4109). For example, the reaction of a phosphodichloridate with substituted 1,3-diols in the presence of base (such as pyridine and triethylamine) yields compounds of Formula I.

Such reactive dichloridate intermediates can be prepared from the corresponding acids and the chlorinating agents such as thionyl chloride (Starrett, et al, *J. Med. Chem.*, 1994, 1857), oxalyl chloride (Stowell, et al., *Tetrahedron Lett.*, 1990, 31: 3261), and phosphorus pentachloride (Quast, et al., *Synthesis*, 1974, 490).

Phosphorylation of an alcohol is also achieved under Mitsunobu reaction conditions using the cyclic 1',3'-propanyl ester of phosphoric acid in the presence of triphenylphosphine and diethyl azodicarboxylate (Kimura et al., *Bull. Chem. Soc. Jpn.*, 1979, 52, 1191). The procedure can be extended to prepare enantiomerically pure phosphates from the corresponding phosphoric acids. Phosphate prodrugs are also prepared from the free acid by Mitsunobu reactions (Mitsunobu, *Synthesis*, 1981, 1; Campbell, *J. Org. Chem.*, 1992, 52: 6331), and other acid coupling reagents including, but not limited to, carbodiimides (Alexander, et al., *Collect. Czech. Chem. Commun.*, 1994, 59: 1853; Casara, et al., *Bioorg. Med. Chem. Lett.*, 1992, 2: 145; Ohashi, et al., *Tetrahedron Lett.*, 1988, 29: 1189), and benzotriazolyloxytris-(dimethylamino)phosphonium salts (Campagne, et al., *Tetrahedron Lett.*, 1993, 34: 6743). Cyclic-1,3-propanyl prodrugs of phosphates are also synthesized from NMP and substituted propane-1,3-diols using a coupling reagent such as 1,3-dicyclohexylcarbodiimide (DCC) in presence of a base (e.g., pyridine). Other carbodiimide based coupling agents such as 1,3-diisopropylcarbodiimide and the water soluble reagent, 1-(3-dimethylaminopropyl)-3-ethylcarbodiimide hydrochloride (EDCI) can also be utilized for the synthesis of cyclic prodrugs.

Phosphate prodrugs can be prepared by an alkylation reaction between the phosphate corresponding tetrabutylammonium salts and substituted-1,3-diiodopropanes made from 1,3-diols (Farquhar, et al., *Tetrahedron Lett.*, 1995 36, 655). Furthermore, phosphate prodrugs can be made by conversion of nucleoside to the dichloridate intermediate with phosphoryl chloride in presence of triethylphosphite and quenching with substituted- 1,3-propanediols (Farquhar et al., *J. Org. Chem.*, 1983, 26, 1153).

Phosphorylation can also be achieved by making the mixed anhydride of the cyclic diester of phosphoric acid and a sulfonyl chloride, preferably 8-quinolinesulfonyl chloride, and reacting the hydroxyl of the nucleoside in the presence of a base, preferably N-methylimidazole (Takaku, et al., *J. Org. Chem.*, 1982, 47, 4937). In addition, starting from an enantiomerically pure cyclic diester of a phosphoric acid, obtained by resolution (Wynberg, et al., *J. Org. Chem.*, 1985, 50, 4508), one can obtain enantiomerically pure phosphates.

EXAMPLES

The compounds used in this invention and their preparation can be understood further by the Examples, which illustrate some of the processes by which these compounds are prepared. These Examples should not however be construed as specifically limiting the invention, and variations of the compounds, now known or later developed, are considered to fall within the scope of the present invention as hereinafter claimed.

Compounds of Formula I are prepared as outlined below. The TLC conditions given are utilizing plates of Analtech UNIPLATE, silica gel GHLF, scored 10×20 cm, 250 micron.

Synthesis of Racemic 1-(Aryl)Propane-1,3-Diols

Example 1

Preparation of 1-(2'-Furanyl)-Propane-1,3-Diol via Grignard Addition and Hydroboration To a solution of 2-furaldehyde (3 g, 31.2 mmol) in THF (60 mL) was added 1 M vinyl magnesium bromide in THF (34 mL) at 0° C. After stirring for an hour, a solution of 1 M BH$_3$THF complex in THF was added. The reaction was quenched with 3N NaOH (20 mL) and 30% hydrogen peroxide (10 mL) at 0° C. The organic fraction was separated and concentrated. The crude product was chromatographed by eluting with 5% methanol-dichloromethane to give 1-(2'-furyl)propane-1,3-diol (1 g).

Example 2

Preparation of 1-(2'-Pyridyl)-Propane-1,3-Diol via Benzylic Oxidation

Step A: (*J. Org. Chem.* 22:589 (1957))

To a solution of 3-(2'-pyridyl)propan-1-ol (10 g, 72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of the reaction. Chromatography of the mixture by eluting with methanol-methylene chloride (1:9) resulted in 10.5 g of pure diacetate.

Step B:

To a solution of diacetate (5 g, 21.1 mmol) in methanol-water (3:1, 40 mL) was added potassium carbonate (14.6 g, 105.5 mmol). After stirring for 3 h at room temperature, the reaction mixture was concentrated. The residue was chromatographed by eluting with methanol-methylene chloride (1:9) to give 2.2 g of crystalline diol.

Example 3

Preparation of 1-(Aryl)-Propane-1,3-Diol from Propane-1,3-Diol via Grignard Addition Step A: (*J. Org. Chem.* 53:911 (1988))

To a solution of oxalyl chloride (5.7 mL, 97 mmol) in dichloromethane (200 mL) at −78° C. was added dimethyl sulfoxide (9.2 mL, 130 mmol). The reaction mixture was stirred at −78° C. for 20 min before addition of 3-(benzyloxy)propan-1-ol (11 g, 65 mmol) in dichloromethane (25 mL). After an hour at −78° C., reaction was quenched with triethylamine (19 mL, 260 mmol) and warmed to room temperature. Work-up and column chromatography by elution with dichloromethane resulted in 8 g of 3-(benzyloxy)propan-1-al.

Step B:

To a solution of 3-(benzyloxy)propan-1-al (1 g, 6.1 mmol) in THF at 0° C. was added a 1 M solution of 4-fluorophenylmagnesium bromide in THF (6.7 mL, 6.7 mmol). The reaction was warmed to room temperature and stirred for 1 h. Work-up and column chromatography by elution with dichloromethane resulted in 0.7 g of alcohol.

Step C:

To a solution of benzyl ether (500 mg) in ethyl acetate (10 mL) was added 10% Pd(OH)$_2$C (100 mg). The reaction was stirred under hydrogen gas for 16 h. The reaction mixture was filtered through Celite and concentrated. Chromatography of the residue by elution with ethyl acetate-dichloromethane (1:1) resulted in 340 mg of product.

Example 4

General Procedure for Preparation of 1-Aryl Substituted-Propane-1,3-Diol From Aryl Aldehyde Step A: (*J. Ore. Chem.* 55:4744 (1990))

To a −78° C. solution of diisopropylamine (2 mmol) in THF (0.7 mL/mmol diisopropylamine) was slowly added n-butyllithium (2 mmol, 2.5 M solution in hexanes). The reaction was then stirred for 15 min at −78° C. before a solution of ethyl acetate (2 mmol) in THF (0.14 mL/mmol ethyl acetate) was slowly introduced. After stirring an additional 30 min at −78° C., a THF solution containing the aryl aldehyde (1.0 mmol in 0.28 mL THF) was added. The reaction was then stirred at −78° C. for 30 min, warmed to room temperature and stirred an additional 2 h. After aqueous work up (0.5 M HCl), the organic layer was concentrated to a crude oil (beta-hydroxyester).

Step B:

The crude hydroxyester was dissolved in ether (2.8 mL/mmol), cooled to ice bath temperature, and lithium aluminum hydride (3 mmol) was added batch wise. The reaction was stirred allowing the cooling bath to melt and the reaction to reach room temperature. After stirring overnight at room temperature, the reaction was cooled back to ice bath temperature and quenched with ethyl acetate. Aqueous work up (0.5 M HCl) afforded the crude diol, which was purified either by chromatography or distillation.

Example 4a

Synthesis of 1-(3-methoxycarbonylphenyl)-1,3-propanediol 1-(3-bromophenyl)-1,3-propane diol was prepared as Example 4 and further derivatized as follows:

A pressure vessel was charged with 1-(3-bromophenyl)-1, 3-propanediol (2 g, 8.6 mmol), methanol (30 mL), triethylamine (5 mL) and bis(triphenylphosphine)palladium dichloride (0.36 g, 05 mmol). The sealed vessel was pressurize with carbon monoxide at 55 psi and heated at 85° C. for 24 h. The cooled vessel was opened and the reaction mixture was filtered through Celite and rinsed with methanol. The combined filtrates were concentrated under reduced pressure and the residue was purified by column chromatography (silica gel, hexanes/ethyl acetate 1/1) to afford the title compound (1.2 g)
TLC: hexanes/ethyl acetate 2/8; Rf=0.5
$^1$H NMR (CDCl$_3$, Varian Gemini 200 MHz): 5.05-4.95 (m, 1H), 3.9 (s, 3H), 2-1.8 (m, 2H).

Example 4b

Synthesis of
1-(4-methoxycarbonylphenyl)-1,3-propanediol 1-(4-bromophenyl)-1,3-propane diol was prepared as Example 4 and further derivatized as Example 4a.
TLC: hexanes/ethyl acetate 3/7; Rf=0.35
$^1$H NMR (CDCl$_3$, Varian Gemini 200 MHz): 5.1-5 (m, 1H), 3.91 (s, 3H), 2.05-1.9 (m, 2H).

Synthesis of Enantioenriched 1-(Aryl)-Propane-1,3-Diols

Example 5

General Procedure for Resolution of Racemic 1,3-diols

Racemic diols synthesized as in Examples 1-4 may be resolved to yield both enantiomers as described in the following procedure.

Step A:
To a solution of diol (1.0 mmol) in THF (1.0 ml) was added hexamethyldisilazane(2.1 mmol) followed by a catalytic amount of trimethylsilyltriflate (2-3 drops). After stirring at room temperature for 1 h, the reaction was diluted with hexane (4 mL) and subjected to work up with ice-cold water. The resulting disilylether was either purified by chromatography or, if sufficiently pure, used crude in the next reaction.

Step B:
To a solution of disilylether (1.0 mmol) and (−)-menthone (1.1 mmol) in dichloromethane (2.0 ml) at −40° C., was slowly added trimethylsilyltriflate (0.11 mmol). The reaction was then kept at −50° to −60° C. for 48 h, at which time pyridine was added to quench the reaction. After warming to room temperature, the crude mixture was diluted with hexane (4.0 ml) and subjected to aqueous work up. The two ketals were separated by chromatography.

Step C:
The separated ketals were hydrolyzed by adding a catalytic amount of concentrated hydrochloric acid to a methanol (4.0 mL/mmol) solution of each. After stirring overnight at room temperature, the methanol was removed under vacuum and the residue was subjected to aqueous work up. The resolved diols were further purified by either chromatography or distillation.

Example 6

Synthesis of Enantioenriched
1-(3'-chlorophenyl)-1,3-dihydroxypropane via Sharpless Asymmetric Epoxidation Step A:
To a dispersion of m-chloro-cinnamic acid (25 g, 137 mmol) in ethanol (275 mL) was added conc. sulfuric acid (8 mL) at room temperature. The reaction was refluxed over-night and concentrated. Ice-cold water was added to the crude and precipitated white solid was filtered and washed with cold water. The precipitate was dried under vacuum overnight to give 25 g of ester. (Rf=0.5 in dichloromethane on silica)

Step B:
To a solution of ethyl-m-chlorocinnamate (23 g, 109.5 mmol) in dichloromethane at −78° C. was added 1 M DIBAL-H in dichloromethane (229 mL, 229 mmol) dropwise over 1 h. The reaction was stirred at −78° C. for an additional 3 h. Ethylacetate was added to quench excess DIBAL-H and saturated aq. potassium sodium tartrate was added and the reaction was stirred at room temperature for 3 h. The organic layer was separated and salts were washed with ethyl acetate. The combined organic extracts were concentrated and distilled at 120° C./0.1 mm to give 14 g of pure allylic alcohol. (Rf=0.38 in 1:1 ethylacetate:hexane on silica)

Step C:
To a solution of m-chlorocinnamyl alcohol (5 g, 29.76 mmol) in dichloromethane (220 mL) was added activated 4 Å molecular sieves powder (2.5 g) and the mixture was cooled to −20° C. (+)-Diethyl tartrate (0.61 mL, 3.57 mmol) was added at −20° C. and stirred for 15 min before adding titanium tetraisopropoxide (0.87 g, 2.97 mmol). The reaction was stirred for additional 30 min and 5-6 M solution of t-butylhydroperoxide in heptane (10 mL, 60 mmol) was added dropwise while maintaining the internal temperature at −20 to −25° C. The mixture was stirred for an additional 3 h at −20° C. and a 10% sodium hydroxide in saturated aq. sodium chloride (7.5 mL) followed by ether (25 mL) were added. The reaction was warmed to 10° C. and stirred for 15 min before adding anhydrous magnesium sulfate (10 g) and Celite (1.5 g). The mixture was further stirred for additional 15 min, filtered and concentrated at 25° C. to give crude epoxy alcohol. (Rf=0.40 in 1:1 ethylacetate:hexane on silica)

Step D:
To a solution of crude m-chloroepoxycinnamyl alcohol obtained from earlier reaction in dimethoxyethane (300 mL) was added a 65% Red-Al solution in toluene (18.63 mL, 60 mmol) dropwise under nitrogen at 0° C. After stirring at room temperature for 3 h, the solution was diluted with ethyl acetate (400 mL) and quenched with aq. saturated sodium sulfate solution (50 mL). After stirring at room temperature for 30 min, the resulting white precipitate formed was filtered and washed with ethylacetate. The filtrate was dried and concentrated. The crude product was distilled at 125-130° C./0.1 mm to give 3.75 g of enantioenriched (R)-1-(3'-chlorophenyl)-1,3-dihydroxypropane. (Rf=0.40 in 1:1 ethylacetate:dichloromethane)

Enantiomeric excesses were defined as diacetates (prepared by treatment of diols with acetic anhydride, triethylamine, cat.DMAP in dichloromethane) by HPLC ((S,S) Whelko-0, 250 cm×4.0 mm ID purchased from Regis).

(R)-1-(3'-chlorophenyl)-1,3-dihydroxypropane: 91% ee
(+)Diisopropyltartrate provided >96% ee in (R)-1-(3'-chlorophenyl)-1,3-dihydroxypropane.
(S)-1-(3'-chlorophenyl)-1,3-dihydroxypropane was also prepared under identical conditions via asymmetric epoxidation and reduction protocol utilizing (−)-tartrate in similar yields. (S)-3-(3'-chlorophenyl)-1,3-dihydroxypropane was obtained with 79% ee.

Example 7

Synthesis of Enantioenriched 1-(3'-chlorophenyl)-1,3-hihydroxypropane via Hydrogen Transfer Reaction Step A: Preparation of methyl 3-(3'-chlorophenyl)-3-oxopropanoate:

A 22 L, 3-neck round bottom flask was equipped with a mechanical stirrer, thermowell/thermometer and nitrogen inlet (bubbler in-line). The flask was flushed with nitrogen and charged sequentially with THF (6 L), potassium t-butoxide (1451 g), and THF (0.5 L). The resulting mixture was stirred at ambient temperature for 15 min. and a 20° C. water bath was applied. A 3 L round bottom flask was charged with 3'-chloroacetophenone (1000 g) and diethylcarbonate (1165 g), and the resulting yellow solution was added slowly to the stirred potassium t-butoxide solution, maintaining the temperature between 16 and 31° C. After the addition was complete (1 h, 10 min.), the cooling bath was removed and the solution was stirred for 1 h, 30 min. TLC indicated that the reaction was complete. A 5 gallon stationary separatory funnel was charged with ice water (4 L) and concentrated hydrochloric acid (1.3 L of 12 M solution). The dark red reaction solution was quenched into the aqueous acid and the mixture was stirred for 15 min. The layers were separated and the aqueous phase (lower) was extracted again with toluene (4 L). The combined organic extracts were washed with saturated brine (2×3 L, 10 min. stirring time each), dried (MgSO$_4$), filtered and concentrated under reduced pressure to provide 1480 g of a brown oil. The oil was placed under high vacuum (10 torr) overnight to give 1427 g. The material was vacuum distilled (short path column, fraction cutter receiver) and the fraction at 108-128° C./1-0.5 torr was collected to provide 1273.9 g of a yellow oil. (Rf=0.36 in 20% ethyl acetate/hexanes).

Step B: Preparation of methyl (S)-3-(3'-chlorophenyl)-3-hydroxypropionate:

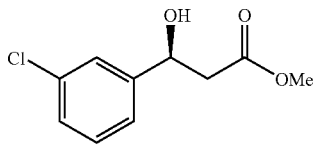

A 12 L, 3-neck round bottom flask was equipped with a mechanical stirrer, thermometer, addition funnel (500 mL) and nitrogen inlet (bubbler in-line). The flask was flushed with nitrogen and charged with formic acid (292 mL, 350 g). Triethylamine (422 mL, 306 g) was charged to the addition funnel, then added slowly with stirring, maintaining the temperature less than 45° C. After the addition was complete (1 h, 30 min), the solution was stirred with the ice bath applied for 20 min., then at ambient temperature for an additional 1 h. The flask was charged sequentially with methyl 3-(3-chlorophenyl)-3-oxo-propanoate (1260 g), DMF (2.77 L including rinsing volume) and (S,S)-Ts-DPEN-Ru-Cl-(p-cymene) (3.77 g). The flask was equipped with a heating mantle and the addition funnel was replaced with a condenser (5 C circulating coolant for condenser). The stirred reaction solution was slowly heated to 60° C. (90 min. to attain 60° C.) and the contents were maintained at 60° C. for 4.25 h. HPLC indicated 3% starting material remained. The solution was stirred at 60° C. for an additional 8 h, then gradually cooled to ambient temperature overnight. HPLC indicated 0.5% starting material. A 5 gallon stationary separatory funnel was charged with water (10 L) and MTBE (1 L). The reaction solution was poured into the aqueous mixture and the reaction flask was rinsed into the separatory funnel with an additional 1 L of MTBE. The contents were stirred for several minutes and the layers were separated. The aqueous phase was extracted with additional MTBE (2×1 L), and the combined organic extracts were washed with brine (1 L), and concentrated under reduced pressure to provide 1334 g of a red oil. The oil was used without further purification for the next step.

The crude hydroxyester (10 mg, 0.046 mmol) was dissolved in dichloromethane (1 mL). Acetic anhydride (22 μL, 0.23 mmol) and 4-(dimethylamino)pyridine (22 mg, 0.18 mmol) were added and the solution was stirred at ambient temperature for 15 min. The solution was diluted with dichloromethane (10 mL) and washed with 1 M hydrochloric acid (3×3 mL). The organic phase was dried (MgSO$_4$), filtered and concentrated under reduced pressure. The residual oil was dissolved in methanol and analyzed by chiral HPLC (Zorbax Rx-C 18, 250×4.6 mm; mobile phase: 65/35 (v/v) water/acetonitrile, isocratic; flow rate=1.5 mL/min; inj. volume=15 μL; UV detection at 220 nm. Retention times: Product=9.3 min, starting material=17.2 min). The hydroxyester was derivatized to the acetate for analysis by chiral HPLC and shown to give 91% ee. (HPLC conditions: Column: Pirkle covalent (S,S) Whelk-O 10/100 krom FEC, 250×4.6 mm; mobile phase: 70/30 (v/v) methanol/water, isocratic; flow rate: 1.5 mL/min; inj. volume=10 μL; UV detection at 220 nm. Retention times: S-hydroxyester (acetate)=9.6 min, R-hydroxyester (acetate)=7.3 min.)

Step C: Preparation of (S)-3-(3'-chlorophenyl)-3-hydroxypropanoic acid:

To the crude hydroxyester in a 10 L rotary evaporator flask was added sodium hydroxide solution (2.5 L of 2 M solution). The resulting solution was stirred on the rotary evaporator at ambient pressure and temperature for 2 h. HPLC indicated 5% starting material still remained (HPLC conditions: Column: Zorbax Rx-C18, 250×4.6 mm; mobile phase: 65/35 (v/v) water/acetonitrile, isocratic; flow rate=1.5 mL/min; inj. volume=15 μL; UV detection at 220 nm. Retention times: Product=3.8 min, starting material=18.9 min.). The pH of the solution was 11 (wide range pH paper). Additional 2 M NaOH solution was added to adjust the pH to 14 (approx. 100 mL), and the solution was stirred for an additional 30 min. HPLC indicated the reaction was complete. The solution was transferred to a 5 gallon stationary separatory funnel and extracted with MTBE (2 L). The layers were separated and the organic extract was discarded. The aqueous phase was transferred back to the separatory funnel and acidified with 12 M HCl solution (600 mL). The mixture was extracted with MTBE (1×2 L, 2×1 L). The combined acidic organic extracts were dried (MgSO$_4$), filtered and concentrated under reduced pressure to give 1262 g of a brown, oily semi-solid. The residue was slurried with ethyl acetate (1 L) and transferred to a 12 L, 3-neck round bottom flask equipped with a mechanical stirrer, heating mantle, condenser and thermometer. The stirred mixture was heated to dissolve all solids (28° C.) and the dark solution was cooled to 10° C. (a precipitate formed at 11° C.). The mixture was slowly diluted with hexanes (4 L over 1 h) and the resulting mixture was stirred at <10° C. for 2 h. The mixture was filtered and the collected solid was washed with cold 4/1 hexanes/ethyl acetate (1 L), and dried to constant weight (−30 in. Hg, 50° C., 4 h). Recovery=837 g of a beige solid. mp=94.5-95.5° C.

A 50 mg sample of hydroxyacid was reduced to the diol with borane-THF (see Step D). The resulting crude diol was diacetylated (as described in Step B)) and analyzed by chiral HPLC. Retention times: S-diol (diacetate)=12.4 min, R-diol (diacetate)=8.8 min.) ee=98%

A second crop of hydroxyacid was isolated. The filtrate from above was concentrated under reduced pressure to give 260 g of a brown sludge. The material was dissolved in ethyl acetate (250 mL) and the stirred dark solution was slowly diluted with hexanes (1000 mL) and the resulting mixture was stirred at ambient temperature overnight. The mixture was filtered and the collected solid was washed with 5/1 hexanes/ethyl acetate (200 mL), and dried to constant weight (−30 in. Hg, 50° C., 16 h). Recovery=134 g of a beige solid. ee=97%

Step D: Preparation of (S)-(−)-1-(3-chlorophenyl)-1,3-propanediol:

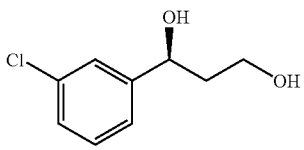

A 22 L, 3-neck round bottom flask was equipped with a mechanical stirrer, thermowell/thermometer and nitrogen inlet (outlet to bubbler). The flask was charged with 2 M borane-THF (3697 g, 4.2 L) and the stirred solution was cooled to 5° C. A solution of (S)-3-(3-chlorophenyl)-3-hydroxypropanoic acid (830 g) in THF (1245 mL) was prepared with stirring (slightly endothermic). The reaction flask was equipped with an addition funnel (1 L) and the hydroxyacid solution was slowly added to the stirred borane solution, maintaining the temperature ≦16° C. After the addition was complete (3 h), the mixture was stirred at ice bath temperature for 1.5 h. The reaction was quenched by careful addition of water (2.5 L). After the addition was complete (30 min), 3 M NaOH solution (3.3 L) was added (temperature increased to 35° C.) and the resulting mixture was stirred for an additional 20 min. (temperature=30° C.). The reaction mixture was transferred to a 5 gallon stationary separatory funnel and the layers were separated. The aqueous phase was extracted with MTBE (2.5 L) and the combined organic extracts (THF and MTBE) were washed with 20 wt % NaCl solution (2 L) and stirred with MgSO$_4$ (830 g) for 30 min. The mixture was filtered through Celite and concentrated under reduced pressure to provide 735 g of a thick, brown oil.

The oil was purified by vacuum distillation and the fraction at 135-140° C./0.2 mm Hg was collected to provide 712.2 g of a colorless oil.

The diol was diacetylated and analyzed by chiral HPLC (e.e.=98%) (see Step B). Retention times: S-diol (diacetate)=12.4 min, R-diol (diacetate)=8.9 min. [α]$_D$=−51.374 (5 mg/mL in CHCl$_3$)

Example 8

Synthesis of Enantioenriched 1-(4'-pyridyl)-1,3-Dihydroxypropane via Hydrogen Transfer Reaction Step A: Synthesis of methyl 3-oxo-3-(pyridin-4-yl)-propanoate A 50 L, 3-neck flask was equipped with an overhead stirrer, heating mantle, and nitrogen inlet. The flask was charged with THF (8 L), potassium t-butoxide (5 kg, 44.6 mol), and THF (18 L). 4-Acetylpyridine (2.5 kg, 20.6 mol) was added, followed by dimethylcarbonate (3.75 L, 44.5 mol). The reaction mixture was stirred without heating for 2.5 h then with heating to 57-60° C. for 3 h. The heat was turned off and the mixture cooled slowly overnight (15 h). The mixture was filtered through a 45 cm Buchner funnel. The solid was returned to the 50 L flask and diluted with aqueous acetic acid (3 L acetic acid in 15 L of water). The mixture was extracted with MTBE (1×16 L, 1×12 L). The combined organic layers were washed with aqueous Na$_2$CO$_3$ (1750 g in 12.5 L water), saturated aqueous NaHCO$_3$ (8 L), and brine (8 L) then dried over MgSO$_4$ (500 g) overnight (15 h). The solution was filtered and the solvent removed by rotary evaporation to a mass of 6.4 kg. The resulting suspension was cooled in an ice bath with stirring for 2 h. The solid was collected by filtration, washed with MTBE (500 mL), and dried in a vacuum oven at 20° C. for 15 h, giving 2425 g of the keto ester as a pale yellow solid.

The MTBE mother liquor was concentrated to approximately 1 L. The resulting suspension was cooled in an ice bath for 1 h. The solid was collected by filtration, washed with MTBE (2×150 mL), and dried in a vacuum oven to give 240 g of a second crop.

TLC. Merck silica gel plates, 1:2 THF/hexane, UV lamp, Rf of SM=0.25, Rf of product=0.3.

Melting Point: 74-76° C.

Step B: Synthesis of S-methyl-3-hydroxy-3-(pyridin-4-yl)-propanoate

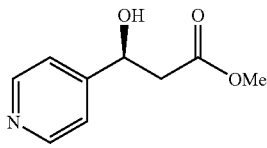

A 22 L, 3-neck round bottom flask was equipped with an overhead stirrer, thermowell/thermometer, addition funnel (1 L), and cooling vessel (empty). The flask was flushed with nitrogen, charged with formic acid (877 g) and cooled with an ice bath. Triethylamine (755 g) was charged to the addition funnel and added slowly over 50 min. to the stirred formic acid. After the addition was complete, the cooling bath was removed and the reaction solution was diluted with DMF (5.0 L). The ketoester (2648 g) was added in one portion, followed by an additional 0.5 L of DMF. The flask was equipped with a heating mantle and the stirred mixture was heated gradually to 16° C. to dissolve all solids. The catalyst (S,S)-Ts-DPEN-Ru-Cl-(p-cymene) (18.8 g) was added in one portion and the stirred mixture was heated to 55° C. over 1 h. The resulting dark solution was stirred at 55° C. for 16 h. TLC indicated the reaction was complete. The solvent was evaporated under reduced pressure (Buchi R152 rotary evaporator under high vacuum, bath temp=60° C.) to give 3574 g of a brown oil. The oil was dissolved in dichloromethane (10 L) and transferred to a 5 gal. stationary separatory funnel. The dark solution was washed with saturated sodium bicarbonate solution (3.0 L) and the aqueous phase was back extracted with dichloromethane (3.0 L). The combined dichloromethane extracts were dried over MgSO$_4$ (300 g), filtered, and concentrated under reduced pressure to provide 3362 g of a brown oil.

Column: Chiralpak AD, 0.46×25 cm; mobile phase=10:90, ethanol:hexane, isocratic; flow rate=1.5 mL/min; injection volume=10 μL UV detection at 254 nm.

Retention times: R-hydroxy ester=19.9 min.

S-hydroxy ester=21.7 min.

Retention times:

R-diol=14.2 min.

S-diol=15.5 min

Hydroxy Ester:

$^1$H NMR (CDCl$_3$): δ 2.73 (d, 2H, J=1.5 Hz), 3.73 (s, 3H), 4.35 (s, 1H), 5.11-5.19 (m, 1H), 7.31 (d, 2H, J=6.6 Hz), 8.53 (d, 2H, J=6.0 Hz)

Merck silica gel 60 plates, 2.5×7.5 cm, 250 micron; UV lamp: 5% MeOH in CH$_2$Cl$_2$; Rf of S.M.=0.44, Rf of product=0.15.

e.e.=87% S isomer of hydroxy ester.

Step C: Synthesis of S-(−)-1-(Pyrid-4-yl)-1,3-propanediol

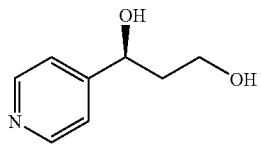

A 22 L, 4-neck round bottom flask was equipped with an overhead stirrer, thermowell/thermometer, addition funnel (2 L), condenser and cooling vessel (empty). The flask was flushed with nitrogen and charged sequentially with sodium borohydride (467 g, 12.3 mol), 1-butanol (9.0 L), and water (148 mL, 8.23 mol) The crude hydroxyester was dissolved in 1-butanol (1.0 L) and the solution was charged to the addition funnel. The solution was added over 3.25 h, using cooling as necessary to keep the temperature below 62° C. After addition was complete, the mixture was stirred for 0.5 h then the flask was equipped with a heating mantle and the stirred mixture was heated to 90° C. over 0.75 h. The mixture was stirred at 90-93° C. for 2.25 h, then cooled over 1.5 h to 28° C. The reaction mixture was quenched with aqueous potassium carbonate solution (10 wt/vol %, 6 L) and the mixture was stirred for 10 min. The layers were separated and the butanol phase was washed with aqueous potassium carbonate solution (10 wt/vol %, 2 L) and sodium chloride solution (15 wt/vol %, 2 L). The solvent was removed under reduced pressure (Buchi R152 rotary evaporator, high vacuum, bath temperature=60° C.) until a concentrated solution resulted and 10.5 L of distillate had been collected. Acetonitrile (3 L) was fed into the evaporator flask and the solvent was evaporated under reduced pressure. Acetonitrile (9 L) was again fed into the evaporator flask and the slurry was stirred (rotation on the rotary evaporator) at ~60° C. (bath temperature=70° C., atmospheric pressure) for 15 min. The hot slurry was filtered through Celite 521 (250 g as a slurry in 1 L of acetonitrile was prepacked on a 24 cm Buchner funnel). The filtrate was partially concentrated under reduced pressure (5 L of distillate were collected) and the resulting slurry was heated at atmospheric pressure on the rotary evaporator to dissolve all solids (bath temp=65° C.). The heat source was turned off and the resulting solution was stirred on the rotary evaporator for 10 h, with gradual cooling to ambient temperature. The resulting mixture was filtered and the collected solid was washed with acetonitrile (2×200 mL) and dried to constant weight (−30 in. Hg, 55° C., 4 h), giving S-(−)-1-(4-pyridyl)-1,3-propanediol as a yellow solid weighing 496 g.

Melting point=98-100° C.

HPLC conditions:

Column: Chiralpak AD, 0.46×25 cm; mobile phase=10:90, ethanol:hexane, isocratic; flow rate=1.5 mL/min; injection volume=10 μL UV detection at 254 nm.

Retention times:

R-diol=14.2 min.

S-diol =15.5 min.

Merck silica gel 60 plates, 2.5×7.5 cm, 250 micron; UV lamp; 15% MeOH in CH$_2$Cl$_2$; Rf of starting material=0.38, Rf of product=0.17, Rf of boron complex=0.26.

Example 9

Synthesis of (S)-3-(3'-chlorophenyl)-1,3-dihydroxypropane via (−)-β-chlorodiisopinocampheylborane (DIPCl) Reduction Step A: Preparation of 3-(3-chlorophenyl)-3-oxo-propanoic acid:

A 12 L, 3-neck round bottom flask was equipped with a mechanical stirrer and addition funnel (2 L). The flask was flushed with nitrogen and charged with diisopropylamine (636 mL) and THF (1.80 L). A thermocouple probe was immersed in the reaction solution and the stirred contents were cooled to −20° C. n-Butyllithium (1.81 L of a 2.5 M solution in hexanes) was charged to the addition funnel and added slowly with stirring, maintaining the temperature between −20 and −28° C. After the addition was complete (30 min), the addition funnel was rinsed with hexanes (30 mL) and the stirred solution was cooled to −62° C. Trimethylsilyl acetate (300 g) was added slowly with stirring, maintaining the temperature <−60° C. After the addition was complete (30 min), the solution was stirred at −60° C. for 15 min. 3-Chlorobenzoyl chloride (295 mL) was added slowly with stirring, maintaining the temperature <−60° C. After the addition was complete (65 min), the cooling bath was removed and the reaction solution was stirred for 1.25 h, with gradual warming to 0° C. The reaction flask was cooled with an ice bath, then water (1.8 L) was added to the stirred solution. The reaction mixture was stirred for 10 min., then diluted with t-butyl methyl ether (1.0 L). The lower aqueous phase was separated and transferred to a 12 L, 3-neck round bottom flask equipped with a mechanical stirrer. t-Butyl methyl ether was added (1.8 L) and the stirred mixture was cooled to <10° C. (ice bath). Concentrated HCl solution (300 mL of 12 M solution) was added and the mixture was vigorously stirred. The layers were separated and aqueous phase was further acidified with con. HCl (30 mL) and extracted again with t-butyl methyl ether (1.0 L). The combined MTBE extracts were washed with brine (1 L), dried (MgSO4, 70 g), filtered and concentrated under reduced pressure to give 827 g of a yellow solid. The crude solid was slurried in hexanes (2.2 L) and transferred to a 5 L, 3-neck round bottom flask equipped with a mechanical stirrer. The mixture was stirred at <10° C. (ice bath) for 1 h, then filtered, washed with hexanes (4×100 mL) and dried to constant weight (−30 in. Hg, ambient temperature, 14 h). Recovery=309 g of a pale yellow powder.

Step B: Preparation of (S)-3-(3-chlorophenyl)-3-hydroxypropanoic acid:

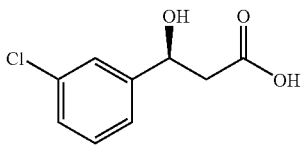

A 12 L, 3-neck round bottom flask was equipped with a mechanical stirrer and addition funnel (1 L). The flask was flushed with nitrogen and charged with 3-(3-chlorophenyl)-3-oxo-propanoic acid (275.5 g) and dichloromethane (2.2 L). A thermocouple probe was immersed in the reaction slurry and the stirred contents were cooled to −20° C. Triethylamine (211 mL) was added over 5 min. to the stirred slurry and all solids dissolved. A dichloromethane solution of (−)-β-chlorodiisopinocampheylborane (1.60 M, 1.04 L) was charged to the addition funnel, then added slowly with stirring, maintaining the temperature between −20 and −25° C. After the addition was complete (35 min), the solution was warmed to ice bath temperature (2-3° C.) and stirred for 4 h. Water (1.2 L) was added to the cloudy orange reaction mixture, followed by 3 M NaOH solution (1.44 L). The mixture was vigorously stirred for 5 min, then transferred to a separatory funnel. The layers were separated and the basic aqueous phase was washed with ethyl acetate (1.0 L). The aqueous phase was acidified with conc. HCl (300 mL) and extracted with ethyl acetate (2×1.3 L). The two acidic ethyl acetate extracts were combined, washed with brine (600 mL), dried (MgSO₄, 130 g), filtered and concentrated under reduced pressure to provide 328 g of a yellow oil (the oil crystallized on standing). The solid was slurried in ethyl acetate (180 mL) and transferred to a 2 L, 3-neck round bottom flask, equipped with a mechanical stirrer. The stirred mixture was cooled to <10° C. (ice bath), then diluted with hexanes (800 mL). The resulting mixture was stirred at ice bath temperature for 4 h, then filtered. The collected solid was washed with 4:1 hexanes: ethyl acetate (3×50 mL) and dried to constant weight (−30 in. Hg, ambient temperature, 12 h). Recovery=207.5 g of a white powder.

Step C: Preparation of (S)-(−)-1-(3-chlorophenyl)-1,3-propanediol:

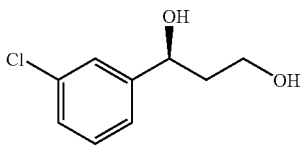

The compound was prepared as described in Example 7, Step D.

The residue was dissolved in methanol (1 mL) and analyzed by chiral HPLC (see, Example 7; Step B). ee >98%.

Example 10

The Preparation of 1,3-Diols via Catalytic Asymmetric Hydrogenation

Step A:
Beta-ketoester starting material was synthesized as described in Example 7, step A.

Step B:
A solution containing beta-ketoester (1 mmol) in either methanol or ethanol (5-10 mL/mmol ketoester) was degassed through several pump/vent (N₂) cycles at room temperature. The degassed solution was moved into a glove bag and under an atmosphere of N₂ was poured into a stainless steel bomb containing a stir bar and 1.0 mole % Ru-BINAP catalyst. The bomb was sealed, removed from the glove bag and purged with H₂ prior to stirring 18-24 h at room temperature and 150 psi H₂. After venting the hydrogen pressure, the bomb was opened and the reaction mixture was removed and concentrated. The crude beta-hydroxyester was used for hydrolysis.

Step C:
Crude beta-hydroxy ester was hydrolyzed as described in Example 7, step C.

Step D:
Optically active beta-hydroxy acid was reduced as described in Example 7, step D.

Synthesis of racemic phosphorylating agents:

Example 11

General Procedure for the Synthesis of trans-4-(aryl)-2-(4-nitrophenoxy)-2-oxo-1,3,2-dioxaphosphorinanes

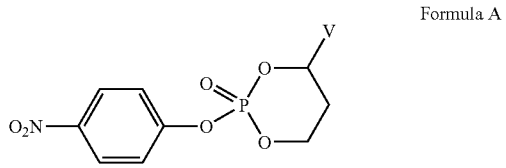

Formula A

Example 11.1

Synthesis of trans-4-(3-chlorophenyl)-2-(4-nitrophenoxy)-2-oxo-1,3,2-dioxaphosphorinane A solution of 1-(3-chlorophenyl)-1,3-propane diol (25 g, 134 mmol) and triethylamine (62.5 mL, 442 mmol) in THF was added to a solution of 4-nitrophenyl-phosphorodichloridate (37.7 g, 147 mmol) in THF at room temperature and the resulting solution was heated at reflux. After 2 h, TLC indicated complete consumption of the starting diol and formation of the cis and trans isomers in a 60/40 ratio (HPLC). The clear yellow solution was cooled to 30° C., sodium 4-nitrophenoxide (56 g, 402 mmol)) was added and the reaction mixture was heated at reflux. After 90 min. the reddish reaction mixture was cooled to room temperature and stirred at room temperature for 2 h then placed in the refrigerator overnight. The final ratio was determined by HPLC to be 96/4 trans/cis. The reaction mixture was quenched with a saturated solution of ammonium chloride and diluted with ethyl acetate. The layers were separated and the organics were washed 4 times with 0.3 N sodium hydroxide to remove the nitrophenol, then saturated sodium chloride and dried over sodium sulfate. The filtered solution was concentrated under reduced pressure and the resulting solid was recrystallized from ethyl acetate to give large off white needles (45 g, mp=115-116° C., purity 98 A %).

¹H NMR (CDCl₃, Varian Gemini 200 MHz): C'-proton: cis-isomer 5.6-5.8 (m, 1H), trans-isomer 5.5-5.6 9 (m, 1H).

TLC conditions: Merck silica gel 60 F254 plates, 250 μm thickness; mobile phase=60/40 hexanes/ethyl acetate; $R_f$: diol=0.1, cis-phosphate=0.2, trans-phosphate=0.35.

HPLC conditions: Column=Waters μ Bondapack C18 3.9×300 mm; mobile phase=40/60 acetonitrile/phosphate buffer pH 6.2; flow rate=1.4 mL/min; detection=UV@270 nm; retention times in min: cis-isomer=14.46, trans-isomer=16.66, 4-nitrophenol=4.14.

Example 11.2

Syntiesis of trans-4-(3-pyrid-3-yl)-2-(4-nitrophenoxy)-2-oxo-1,3,2-dioxaphosphorinane Same as Example 11.1
$^1$H NMR (CDCl$_3$, Varian Gemini 200 MHz): C'-proton: trans-isomer 5.6-5.8 (m, 1H).

Example 11.3

Synthesis of trans-4-(3,-5-difluorophenyl)-2-(4-nitrophenoxy)-2-oxo-1,3,2-dioxaphosphorinane Same as Example 11.1
TLC conditions: Merck silica gel 60 F254 plates, 250 μm thickness; mobile phase=50/50 hexanes/ethyl acetate; $R_f$: diol=0.1, cis-phosphate=0.25, trans-phosphate=0.4. $^1$H NMR (CDCl$_3$, Varian Gemini 200 MHz): C'-proton: trans-isomer 5.7-5.5 (m, 1H).

Example 11.4

Synthesis of trans-4-(4-methylphenyl)-2-(4-nitrophenoxy)-2-oxo-1,3,2-dioxaphosphorinane Same as Example 11.1 starting with 1-(4-methylphenyl)-1,3-propanediol
TLC: 50/50 hexanes/ethyl acetate; Rf: cis-phosphate=0.25; trans-phosphate=0.35. 1H NMR (CDCl3, Varian Gemini 200 MHz): C'-proton: trans-isomer 5.65-5.5 (m, 1H).

Example 11.5

Synthesis of trans-4-(3,5-dimethylphenyl)-2-(4-nitrophenoxy)-2-oxo-1,3,2-dioxaphosphorinane Same as Example 11.1 starting with 1-(3,5-dimethylphenyl)-1,3-propanediol
TLC: 50/50 hexanes/ethyl acetate; Rf: cis-phosphate=0.2; trans-phosphate=0.3. 1H NMR (CDCl3, Varian Gemini 200 MHz): C'-proton: trans-isomer 5.6-5.45 (m, 1H).

Example 11.6

Synthesis of trans-4-(3,5-dichlorophenyl)-2-(4-nitrophenoxy)-2-oxo-1,3,2-dioxaphosphorinane Same as Example 11.1 starting with 1-(3,5-dichlorophenyl)-1,3-propanediol
TLC: 70/30 hexanes/ethyl acetate; Rf: cis-phosphate=0.3; trans-phosphate=0.5. 1H NMR (CDCl3, Varian Gemini 200 MHz): C'-proton: trans-isomer 5.85-5.7 (m, 1H).

Example 11.7

Synthesis of trans-4-(pyrid-4-yl)-2-(4-nitrophenoxy)-2-oxo-1,3,2-dioxaphosphorinane Same as Example 11.1 starting with 1-(pyrid-4-yl)-1,3-propanediol
TLC: 95/5 dichloromethane/ethanol; Rf: trans-phosphate=0.35. $^1$H NMR (CDCl$_3$, Varian Gemini 200 MHz): C'-proton: trans-isomer 5.7-5.55 (m, 1H).

Example 11.8

Synthesis of trans-4-(3-methoxycarbonylphenyl)-2-(4-nitrophenoxy)-2-oxo-1,3,2-dioxaphosphorinane Same as Example 11.1 starting with 1-(3-methoxycarbonylphenyl)-1,3-propanediol
TLC: 30/70 hexanes/ethyl acetate; Rf: cis-phosphate=0.5; trans-phosphate=0.6. $^1$H NMR (CDCl$_3$, Varian Gemini 200 MHz): C'-proton: trans-isomer 5.7-5.6 (m, 1H).

Example 11.9

Synthesis of trans-4-(4-methoxycarbonylphenyl)-2-(4-nitrophenoxy)-2-oxo-1,3,2-dioxaphosphorinane Same as Example 11.1 starting with 1-(4-methoxycarbonylphenyl)-1,3-propanediol
TLC: 30/70 hexanes/ethyl acetate; Rf: cis-phosphate=0.35; trans-phosphate=0.5.
$^1$H NMR (CDCl$_3$, Varian Gemini 200 MHz): C'-proton: trans-isomer 5.7-5.6 (m, 1H).

Example 11.10

Synthesis of trans-4-(5-bromopyrid-3-yl)-2-(4-nitrophenoxy)-2-oxo-1,3,2-dioxaphosphorinane Same as Example 11.1 starting with 1-(5-bromopyrid-3-yl)-1,3-propanediol
$^1$H NMR (CDCl$_3$, Varian Gemini 200 MHz): C'-proton: trans-isomer 5.8-5.65 (m, 1H).

Example 11.11

Synthesis of trans-4-(2,3-dichlorophenyl)-2-(4-nitrophenoxy)-2-oxo-1,3,2-dioxaphosphorinane Same as Example 11.1 starting with 1-(2,3-dichlorophenyl)-1,3-propanediol except that the isomerization was conducted with 4-nitrophenol and lithium hydride as in Example 13a.
$^1$H NMR (CDCl$_3$, Varian Gemini 200 MHz): C'-proton: trans-isomer 6-5.9 (m, 1H).

Example 11.12

Synthesis of trans-4-(2,3,5-trichlorophenyl)-2-(4-nitrophenoxy)-2-oxo-1,3,2-dioxaphosphorinane Same as Example 11.1 starting with 1-(2,3,5-trichlorophenyl)-1,3-propanediol except that the isomerization was conducted with 4-nitrophenol and triethylamine as in Example 13b.

$^1$H NMR (CDCl$_3$, Varian Gemini 200 MHz): C'-proton: trans-isomer 5.9-5.7 (m, 1H).

Example 11.13

Synthesis of trans-4-(2-chlorophenyl)-2-(4-nitrophenoxy)-2-oxo-1,3,2-dioxaphosphorinane Same as Example 11.1 starting with 1-(2-chlorophenyl)-1,3-propanediol except that the isomerization was conducted with 4-nitrophenol and lithium hydride as in Example 13a.

$^1$H NMR (CDCl$_3$, Varian Gemini 200 MHz): C'-proton: trans-isomer 6-5.9 (m, 1H).

Example 11.14

Synthesis of trans-4-(3,5-dimethoxyphenyl)-2-(4-nitrophenoxy)-2-oxo-1,3,2-dioxaphosphorinane Same as Example 11.1 starting with 1-(3,5-dimethoxyphenyl)-1,3-propanediol except that the isomerization was conducted with 4-nitrophenol and triethylamine as in Example 13b.

$^1$H NMR (CDCl$_3$, Varian Gemini 200 MHz): C'-proton: trans-isomer 5.55-5.45 (m, 1H), 3.3 (s, 6H).

Example 11.15

Synthesis of trans-4-(2-bromophenyl)-2-(4-nitrophenoxy)-2-oxo-1,3,2-dioxaphosphorinane Same as Example 11.1 starting with 1-(2-bromophenyl)-1,3-propanediol except that the isomerization was conducted with 4-nitrophenol and triethylamine as in Example 13a.

$^1$H NMR (CDCl$_3$, Varian Gemini 200 MHz): C'-proton: trans-isomer 5.95-5.85 (m, 1H).

Example 11.16

Synthesis of trans-4-(3-bromo-5-ethoxyphenyl)-2-(4-nitrophenoxy)-2-oxo-1,3,2-dioxaphosphorinane Same as Example 11.1 starting with 1-(3-bromo-5-ethoxyphenyl)-1,3-propanediol except that the isomerization was conducted with 4-nitrophenol and triethylamine as in Example 13b.

$^1$H NMR (CDCl$_3$, Varian Gemini 200 MHz): C'-proton: trans-isomer 5.9-5.75 (m, 1H), 4.04 (q, 2H), 1.39 (t, 3H).

Example 11.17

Synthesis of trans-4-(2-trifluoromethylphenyl)-2-(4-nitrophenoxy)-2-oxo-1,3,2-dioxaphosphorinane Same as Example 11.1 starting with 1-(2-trifluoromethylphenyl)-1,3-propanediol except that the isomerization was conducted with 4-nitrophenol and triethylamine as in Example 13b.

$^1$H NMR (CDCl$_3$, Varian Gemini 200 MHz): C'-proton: trans-isomer 6-5.75 (m, 1H).

Example 11.18

Synthesis of trans-4-(4-chlorophenyl)-2-(4-nitrophenoxy)-2-oxo-1,3,2-dioxaphosphorinane Same as Example 11.1 starting with 1-(4-chlorophenyl)-1,3-propanediol except that the trans-isomer was isolated from the cis/trans mixture without isomerization.

TLC: hexanes/ethyl acetate 1/1; Rf: cis-phosphate=0.2; trans-phosphate=0.6.

$^1$H NMR (CDCl$_3$, Varian Gemini 200 MHz): C'-proton: trans-isomer 5.6-5.5 (m, 1H).

Example 11.19

Synthesis of trans-4-(3-methylphenyl)-2-(4-nitrophenoxy)-2-oxo-1,3,2-dioxaphosphorinane Same as Example 11.1 starting with 1-(3-methylphenyl)-1,3-propanediol except that the trans-isomer was isolated from the cis/trans mixture without isomerization.

TLC: hexanes/ethyl acetate 6/4; Rf: cis-phosphate=0.2; trans-phosphate=0.5.

$^1$H NMR (CDCl$_3$, Varian Gemini 200 MHz): C'-proton: trans-isomer 5.65-5.5 (m, 1H).

Example 11.20

Synthesis of trans-4-(4-fluorophenyl)-2-(4-nitrophenoxy)-2-oxo-1,3,2-dioxaphosphorinanes Same as Example 11.1 starting with 1-(4-fluorophenyl)-1,3-propanediol except that the trans-isomer was isolated from the cis/trans mixture without isomerization.

$^1$H NMR (DMSO-d$_6$, Varian Gemini 200 MHz): C'-proton: trans-isomer 5.78-5.85 (m, 1H).

Example 11.21

Synthesis of trans-4-(2-fluorophenyl)-2-(4-nitrophenoxy)-2-oxo-1,3,2-dioxaphosphorinane Same as Example 11.1 starting with 1-(2-fluorophenyl)-1,3-propanediol except that the trans-isomer was isolated from the cis/trans mixture without isomerization.

$^1$H NMR (DMSO-d$_6$, Varian Gemini 200 MHz): C'-proton: trans-isomer 5.9-6.1 (m, 1H).

Example 11.22

Synthesis of trans-4-(3-fluorophenyl)-2-(4-nitrophenoxy)-2-oxo-1,3,2-dioxaphosphorinane Same as Example 11.1 starting with 1-(3-fluorophenyl)-1,3-propanediol except that the trans-isomer was isolated from the cis/trans mixture without isomerization.

$^1$H NMR (DMSO-d$_6$, Varian Gemini 200 MHz): C'-proton: trans-isomer 5.8-5.9 (m, 1H).

Example 11.23

Synthesis of trans-4-[4-(4-chlorophenoxy)phenyl]-2-(4-nitrophenoxy)-2-oxo-1,3,2-dioxaphosphorinane Same as Example 11.1 starting with 1-[4-(4-chlorophenoxy)phenyl]-1,3-propanediol except that the trans-isomer was isolated from the cis/trans mixture without isomerization.

¹H NMR (DMSO-d₆, Varian Gemini 200 MHz): C'-proton: trans-isomer 5.75-5.9 (m, 1H).

Example 11.24

Synthesis of trans-4-(3-bromophenyl)-2-(4-nitrophenoxy)-2-oxo-1,3,2-dioxaphosphorinane Same as Example 11.1 starting with 1-(3-bromophenyl)-1,3-propanediol except that the trans-isomer was isolated from the cis/trans mixture without isomerization.

TLC: hexanes/ethyl acetate 1/1; Rf: cis-phosphate=0.25; trans-phosphate=0.5.

¹H NMR (DMSO-d₆, Varian Gemini 200 MHz): C'-proton: trans-isomer 5.8-5.95 (m, 1H).

Example 11.25

Synthesis of trans-4-(3,4-ethylenedioxyphenyl)-2-(4-nitrophenoxy)-2-oxo-1,3,2-dioxaphosphorinane Same as Example 11.1 starting with 1-(3,4-ethylenedioxyphenyl)-1,3-propanediol except that the trans-isomer was isolated from the cis/trans mixture without isomerization.

TLC: hexanes/ethyl acetate 1/1; Rf: trans-phosphate=0.6.

¹H NMR (DMSO-d₆, Varian Gemini 200 MHz): C'-proton: trans-isomer 5.8-5.9 (m, 1H).

Example 11.26

Synthesis of trans-4-(2-fluoro-4-chlorophenyl)-2-(4-nitrophenoxy)-2-oxo-1,3,2-dioxaphosphorinane Same as Example 11.1 starting with 1-(2-fluoro-4-chlorophenyl)-1,3-propanediol except that the trans-isomer was isolated from the cis/trans mixture without isomerization.

TLC: hexanes/ethyl acetate 1/1; Rf: trans-phosphate=0.7.

¹H NMR (DMSO-d₆, Varian Gemini 200 MHz): C'-proton: trans-isomer 5.9-6 (m, 1H).

Example 11.27

Synthesis of trans-4-(2,6-dichlorophenyl)-2-(4-nitrophenoxy)-2-oxo-1,3,2-dioxaphosphorinane Same as Example 11.1 starting with 1-(2,6-dichlorophenyl)-1,3-propanediol except that the trans-isomer was isolated from the cis/trans mixture without isomerization.

TLC: hexanes/ethyl acetate 1/1; Rf: trans-phosphate=0.65.

¹H NMR (DMSO-d₆, Varian Gemini 200 MHz): C'-proton: trans-isomer 6.2-6.4 (m, 1H).

Example 11.28

Synthesis of trans-4-(2-fluoro-5-methoxyphenyl)-2-(4-nitrophenoxy)-2-oxo-1,3,2-dioxaphosphorinane Same as Example 11.1 starting with 1-(2-fluoro-5-methoxyphenyl)-1,3-propanediol except that the trans-isomer was isolated from the cis/trans mixture without isomerization.

¹H NMR (CDCl₃, Varian Gemini 200 MHz): C'-proton: trans-isomer 5.8-5.95 (m, 1H), 3.8 (s, 3H).

Example 11.29

Synthesis of trans-4-(3-fluoro-4-chlorophenyl)-2-(4-nitrophenoxy)-2-oxo-1,3,2-dioxaphosphorinane Same as Example 11.1 starting with 1-(3-fluoro-4-chlorophenyl)-1,3-propanediol except that the isomerization was conducted with 4-nitrophenol and triethylamine as in Example 13b.

¹H NMR (CDCl₃, Varian Gemini 200 MHz): C'-proton: trans-isomer 5.4-5.6 (m, 1H).

Example 11.30

Synthesis of trans-4-(3-chloro-4-fluorophenyl)-2-(4-nitrophenoxy)-2-oxo-1,3,2-dioxaphosphorinane Same as Example 11.1 starting with 1-(3-chloro-4-fluorophenyl)-1,3-propanediol except that the isomerization was conducted with 4-nitrophenol and triethylamine as in Example 13b.

¹H NMR (CDCl₃, Varian Gemini 200 MHz): C'-proton: trans-isomer 5.5-5.6 (m, 1H).

Example 11.31

Synthesis of trans-4-(2-fluoro-5-bromophenyl)-2-(4-nitrophenoxy)-2-oxo-1,3,2-dioxaphosphorinane Same as Example 11.1 starting with 1-(2-fluoro-5-bromophenyl)-1,3-propanediol except that the isomerization was conducted with 4-nitrophenol and triethylamine as in Example 13b.

¹H NMR (CDCl₃, Varian Gemini 200 MHz): C'-proton: trans-isomer 5.8-5.9 (m, 1H).

Example 11.32

Synthesis of trans-4-(2,3,5,6-tetrafluorophenyl)-2-(4-nitrophenoxy)-2-oxo-1,3,2-dioxaphosphorinane Same as Example 11.1 starting with 1-(2,3,5,6-tetrafluorophenyl)-1,3-propanediol except that the isomerization was conducted with 4-nitrophenol and triethylamine as in Example 13b.

¹H NMR (CDCl₃, Varian Gemini 200 MHz): C'-proton: trans-isomer 5.9-6 (m, 1H).

Example 11.33

Synthesis of trans-4-(2,3,6-trifluorophenyl)-2-(4-nitrophenoxy)-2-oxo-1,3,2-dioxaphosphorinane Same as Example 11.1 starting with 1-(2,3,6-trifluorophenyl)-1,3-propanediol except that the isomerization was conducted with 4-nitrophenol and triethylamine as in Example 13b.

¹H NMR (CDCl₃, Varian Gemini 200 MHz): C'-proton: trans-isomer 5.9-6 (m, 1H).

Example 11.34

Synthesis of trans-4(R)-(phenyl)-2-(4-chlorophenoxy)-2-oxo-1,3,2-dioxaphosphorinane Same as Example 11.1 starting with 1(R)-(phenyl)-1,3-propanediol isolated by column without the isomerization.

Rf=0.5 (50% EtOAc in Hexanes). mp 90-92° C. Anal calcd for $C_{15}H_{14}ClO_4P$: C, 55.49; H, 4.35. Found: C, 55.64; H, 3.94.

Example 11.35

Synthesis of trans-4(R)-(phenyl)-2-(4-nitrophenoxy)-2-oxo-1,3,2-dioxaphosphorinane Same as Example 11.1 starting with 1(R)-(phenyl)-1,3-propanediol isolated by column without the isomerization.
Rf=0.4 (50% EtOAc in Hexanes). mp 130-131° C. Anal calcd for $C_{15}H_{14}NO_6P$: C, 53.74; H, 4.21; N, 4.18. Found: C, 53.86; H, 4.07; N, 4.00.

Example 11.36

Synthesis of trans-4(S)-(phenyl)-2-(4-nitrophenoxy)-2-oxo-1,3,2-dioxaphosphorinane Same as Example 11.1 starting with 1(S)-(phenyl)-1,3-propanediol.
Rf=0.2 (5% EtOAc in $CH_2Cl_2$). mp 128-129° C. Anal calcd for $C_{15}H_{14}NO_6P$: C, 53.74; H, 4.21; N, 4.18. Found: C, 53.69; H, 4.53; N, 4.23.

Example 11.37

Synthesis of trans-4-(3-trifluoromethylphenyl)-2-(4-nitrophenoxy)-2-oxo-1,3,2-dioxaphosphorinane Same as Example 11.1 starting with 1-(3-trifluoromethylphenyl)-1,3-propanediol.
Rf=0.32(35% EtOAc in hexanes). mp 78-81° C. Anal calcd for $C_{16}H_{13}F_3NO_6P$: C, 47.66; H, 3.25; N, 3.47. Found: C, 47.69; H, 3.77; N, 3.52.

Example 11.38

Synthesis of trans-4-(2,4-dichlorophenyl)-2-(4-nitrophenoxy)-2-oxo-1,3,2-dioxaphosphorinane Same as Example 11.1 starting with 1-(2,4-dichlorophenyl)-1,3-propanediol.
Rf=0.32(35% EtOAc in hexanes). mp 154-157° C. Anal calcd for $C_{15}H_{12}C_2NO_6P$: C, 44.58; H, 2.99; N, 3.47. Found: C, 44.63; H, 3.07; N, 3.47.

Example 11.39

Synthesis of trans-4-(3-bromo-4-fluorophenyl)-2-(4-nitrophenoxy)-2-oxo-1,3,2-dioxaphosphorinane Same as Example 11.1 starting with 1-(3-bromo-4-fluorophenyl)-1,3-propanediol. Rf=0.2 (5% EtOAc in $CH_2Cl_2$). mp 108° C. Anal calcd for $C_{15}H_{12}NO_6BrFP$: C, 41.69; H, 2.80; N, 3.24. Found: C, 41.90; H, 2.76; N, 3.05.

Example 11.40

Synthesis of trans-4-(2-pyridyl)-2-(4-nitrophenoxy)-2-oxo-1,3,2-dioxaphosphorinane Same as Example 11.1 starting with 1-(2-pyridyl)-1,3-propanediol. mp 99-102° C. Anal calcd for $C_{14}H_{13}N_2O_6P$: C, 50.01; H, 3.90; N, 8.33. Found: C, 49.84; H, 3.41; N, 8.14.

Example 11.41

Synthesis of trans-4-(3,4-dichlorophenyl)-2-(4-nitrophenoxy)-2-oxo-1,3,2-dioxaphosphorinane Same as Example 11.1 starting with 1-(3,4-dichlorophenyl)-1,3-propanediol. Rf=0.15 (35% EtOAc in Hexanes). mp 126-129° C. Anal calcd for $C_{15}H_{12}Cl_2NO_6P$: C, 44.58; H, 2.99; N, 3.47. Found: C, 44.71; H, 3.49; N, 3.41.

Example 11.42

Synthesis of trans-4-(4tert-butylphenyl)-2-(4-nitrophenoxy)-2-oxo-1,3,2-dioxaphosphorinane Same as Example 11.1 starting with 1-(4-tert-butylphenyl)-1,3-propanediol. Rf=0.20 (35% EtOAc in Hexanes). mp 108-111° C. Anal calcd for $C_{19}H_{22}NO_6P$: C, 58.31; H, 5.67; N, 3.58. Found: C, 58.04; H, 5.67; N, 3.55.

Example 11.43

Synthesis of trans-4-(3-thiophenyl)-2-(4-nitrophenoxy)-2-oxo-1,3,2-dioxaphosphorinane Same as Example 11.1 starting with 1-(3-thiophenyl)-1,3-propanediol. mp 94-96° C. Anal calcd for $C_{13}H_{12}NO_6PS$: C, 45.75; H, 3.54; N, 4.10. Found: C, 45.65; H, 3.21; N, 4.24.

Example 11.44

Synthesis of trans-4-(3-furanyl)-2-(4-nitrophenoxy)-2-oxo-1,3,2-dioxaphosphorinane Same as Example 11.1 starting with 1-(3-furanyl)-1,3-propanediol. mp 108-111° C. Anal calcd for $C_{13}H_{12}NO_7P$: C, 48.01; H, 3.72; N, 4.31. Found: C, 48.06; H, 3.61; N, 4.26.

Example 11.45

Synthesis of trans-4-(2-bromo-5-chlorophenyl)-2-(4-nitrophenoxy)-2-oxo-1,3,2-dioxaphosphorinane Same as Example 11.1 starting with 1-(2-bromo-5-chlorophenyl)-1,3-propanediol. Rf=0.20 (5% MeOH in $CH_2Cl_2$). mp 105-106° C. Anal calcd for $C_{15}H_{12}NO_6BrClP$: C, 40.16; H, 2.70; N, 3.12. Found: C, 39.97; H, 2.86; N, 3.06.

Example 11.46

Synthesis of trans-4-(2,5-difluorophenyl)-2-(4-nitrophenoxy)-2-oxo-1,3,2-dioxaphosphorinane Same as Example 11.1 starting with 1-(2,5-difluorophenyl)-1,3-propanediol. Rf=0.50 (50% EtOAc in Hexanes). mp 120-122° C. Anal calcd for $C_{15}H_{12}F_2NO_6P$: C, 48.53; H, 3.26; N, 3.77. Found: C, 48.46; H, 3.52; N, 3.87.

Example 11.47

Synthesis of trans-4-(2,4-difluorophenyl)-2-(4-nitrophenoxy)-2-oxo-1,3,2-dioxaphosphorinane Same as Example 11.1 starting with 1-(2,4-difluorophenyl)-1,3-propanediol. Rf=0.50 (50% EtOAc in Hexanes). mp 85-87° C. Anal calcd for $C_{15}H_{12}F_2NO_6P$: C, 48.53; H, 3.26; N, 3.77. Found: C, 48.82; H, 3.55; N, 3.84.

Example 11.48

Synthesis of trans-4-cis-6-(diphenyl)-2-(4-nitrophenoxy)-2-oxo-1,3,2-dioxaphosphorinane Same as Example 11.1 starting with trans-1,3-diphenyl-1,3-propanediol (Yamamura, H., Araki, S., *Tetrahedron*, 1997, 53, 46, 15685-15690) without equilibration. Rf=0.29 (35% EtOAc in Hexanes). mp 118-121° C. Anal calcd for $C_{21}H_{18}NO_6P$: C, 61.32; H, 4.41; N, 3.41. Found: C, 60.94; H, 4.44; N, 3.53.

Example 11.49

Synthesis of trans-4-trans-6-(diphenyl)-2-(4-nitrophenoxy)-2-oxo-1,3,2-dioxaphosphorinane Same as Example 11.1 starting with cis-1,3-diphenyl-1,3-propanediol (Yamamura, H., Araki, S., *Tetrahedron*, 1997, 53, 46, 15685-15690) without equilibration. Rf=0.65 (5% EtOAc in $CH_2Cl_2$). mp 144-147° C. Anal calcd for $C_{21}H_{18}NO_6P$: C, 61.32; H, 4.41; N, 3.41. Found: C, 61.21; H, 4.58; N, 3.36.

Example 11.50

Synthesis of cis-4-cis-6-(diphenyl)-2-(4-nitrophenoxy)-2-oxo-1,3,2-dioxaphosphorinane Same as Example 11.1 starting with cis-1,3-diphenyl-1,3-propanediol (Yamamura, H., Araki, S., *Tetrahedron*, 1997, 53, 46, 15685-15690) without equilibration. Rf=0.3 (5% EtOAc in $CH_2Cl_2$). mp 135-138° C. Anal calcd for $C_{21}H_{18}NO_6P$: C, 61.32; H, 4.41; N, 3.41. Found: C, 61.29; H, 4.77; N, 3.46.

Example 11.51

Synthesis of cis-4-cis-5-(diphenyl)-2-(4-nitrophenoxy)-2-oxo-1,3,2-dioxaphosphorinane Same as Example 11.1 starting with cis-1,2-diphenyl-1,3-propanediol (Kristersson, P, Lindquist, K., *Acta Chem. Scand. B* 1980, 34, 3, 213-234) without equilibration. Rf=0.35 (5% EtOAc in $CH_2Cl_2$). mp 136-139° C. Anal calcd for $C_{21}H_{18}NO_6P$: C, 61.32; H, 4.41; N, 3.41. Found: C, 60.95; H, 4.41; N, 3.82.

Example 11.52

Synthesis of trans-4-trans-5-(diphenyl)-2-(4-nitrophenoxy)-2-oxo-1,3,2-dioxaphosphorinane Same as Example 11.1 starting with cis-1,2-diphenyl-1,3-propanediol (Kristersson, P, Lindquist, K., *Acta Chem. Scand. B* 1980, 34, 3, 213-234) without equilibration. Rf=0.65 (5% EtOAc in $CH_2Cl_2$). mp 176-178° C. Anal calcd for $C_{21}H_{18}NO_6P$: C, 61.32; H, 4.41; N, 3.41. Found: C, 61.09; H, 4.46; N, 3.80.

Example 11.53

Synthesis of trans-4-4-dimethyl-6-(phenyl)-2-(4-nitrophenoxy)-2-oxo-1,3,2-dioxaphosphorinane Step A:

To a solution of diisopropylamine (58.4 g, 577 mmol) in dry ether (500 mL) at −78° C. under nitrogen was added n-BuLi (215 mL, 2.5 M in hexane, 538 mmol) over 30 min. The reaction was stirred for 10 min before addition of ethyl acetate (55 mL, 558 mmol) over a period 30 min. Freshly distilled benzaldehyde (47 mL, 443 mmol) in ether (50 mL) was slowly added over 30 min and the mixture was allowed to warm to room temperature. The reaction was quenched with saturated ammonium chloride (150 mL) at 0° C. The organic layer was washed, dried (anhydrous $Na_2SO_4$) and concentrated to give the crude addition product.

Step B:

To a solution of crude condensation product (10.6 g, 54.6 mmol) in dry ether at −78° C. was added MeMgBr (60 mL, 3.0 M in THF, 180 mmol). The mixture was allowed to warm to room temperature and stirred overnight. The reaction was quenched with ammonium chloride (50 mL) at 0° C. and diluted with EtOAc (350 mL). The organic layer was washed, dried (anhydrous $Na_2SO_4$) and concentrated. The crude product was purified by column chromatography (0-10% EtOAc in $CH_2Cl_2$) to give 3, 3-dimethyl-1-phenyl-1,3-propanediol (7 g) as a pale yellow oil.

Step C:

Same as Example 11.1 starting with 3,3-dimethyl-1-phenyl-1,3-propanediol without equilibration. Rf=0.18 (35% EtOAc in hexanes). mp 131-133° C. Anal calcd for $C_{17}H_{18}NO_6P$: C, 56.20; H, 4.99; N, 3.86. Found: C, 56.00; H, 5.03; N, 3.86.

Example 11.54

Synthesis of cis-4-(3-chlorophenyl)-cis-5-methoxy-(-2-(4-nitrophenoxy)-2-oxo-1,3,2-dioxaphosphorinane and trans-4-(3-chlorophenyl)-cis-5-methoxy-(-2-(4-nitrophenoxy)-2-oxo-1,3,2-dioxaphosphorinane (11.55)

Step A:

To a solution of lithium diisopropylamide (356 mmol) in THF (500 mL) at −78° C. was slowly added 2-methoxy-methyl acetate (38.8 mL, 392 mmol) via an addition funnel. The reaction was stirred at −78° C. for 30 min before 3-chlorobenzaldehyde (20.1 mL, 178 mmol) was added. The reaction was allowed to warm to room temperature and quenched with saturated aq $NH_4Cl$ (500 mL). The mixture was extracted with EtOAc (3×200 mL) and the combined organic extracts were washed with water and dried (anhydrous $Na_2SO_4$). The crude product was purified by column chromatography (5-50% EtOAc in hexanes) to yield 3-(3-chlorophenyl)-3-hydroxy-2-methoxy-methyl proprionate (39 g) as pale yellow oil.

Step B:

To a solution of the ester (39 g, 159 mmol) obtained from step A in ethanol (500 mL) was added sodiumborohydride (6.2 g, 159 mmol) in three portions, over 10 min. The reaction was refluxed for 3 h and the ethanol was evaporated under reduced pressure. The residue was dissolved in EtOAc (500 mL), washed with water and dried (anhydrous $Na_2SO_4$). The crude product was purified by column chromatography (1-5% MeOH-CH$_2$Cl$_2$) to give the diol (28 g) as colorless oil.

Step C:

To a solution of diol (28 g, 129 mmol) in acetone (250 mL) was added trimethyl orthoformate (10 mL) followed by p-toluenesulfonic acid (500 mg, 2.64 mmol) and the reaction was heated to reflux overnight. The reaction was cooled to room temperature and the acetone was removed under vacuum. The residue was dissolved in ethyl acetate and washed with NaHCO$_3$, water and dried (anhydrous Na$_2$SO$_4$). The ketals were separated by column chromatography (5-10% EtOAc in hexanes) to give 1,2-cis (7.26 g) and 1,2-trans ketal (0.9 g) diastereomers.

Step D:

The 1,2-cis ketal (4.5 g, 17.5 mmol) was dissolved in 70% aq TFA (10 mL) and allowed to react overnight at room temperature. The reaction was diluted with acetonitrile (30 mL) and volatiles were removed under reduced pressure. The residue was dissolved in EtOAc (300 mL) and the organic layer was washed with saturated aq NaHCO$_3$, water and dried (anhydrous Na$_2$SO$_4$). The crude product was purified by column chromatography (1-5% MeOH-CH$_2$Cl$_2$) to give 1,2-cis diol diastereomer (3.5 g).

The 1,2-trans ketal diastereomer was also hydrolyzed following the above procedure to give 1,2-trans-diol diastereomer.

Step E:

1,2-cis-diol diastereomer was subjected to phosphorylation using the procedure described in Example 11.1 without equilibration to give the following two isomers.

11.54: Rf=0.57 (5% EtOAc in CH$_2$Cl$_2$). mp 110-112° C. Anal calcd for C$_{16}$H$_{15}$NO$_7$PCl: C, 48.08; H, 3.78; N, 3.50. Found: C, 48.35; H, 3.56; N, 3.69.

11.55: Rf=0.34 (5% EtOAc in CH$_2$Cl$_2$). mp 131-134° C. Anal calcd for C$_{16}$H$_{15}$NO$_7$PCl.0.3 H$_2$O: C, 47.44; H, 3.88; N, 3.46. Found: C, 47.23; H, 4.01; N, 3.46.

Example 12

General procedure for the synthesis of trans-4-(aryl)-2-(4-nitrophenoxy)-2-oxo-1,3,2-dioxaphosphorinanes using phosphorus oxychloride Phosphorus oxychloride (3.4 mL, 36.3 mmol) was added to a solution of 1-(3-chlorophenyl)-1,3-propanediol in dichloromethane at 0° C. followed by triethylamine (10.2 mL, 73 mmol). After 2 h, sodium 4-nitrophenoxide (10.63 g, 66 mmol) was added to the solution of cis/trans phosphorochloridate reagent and the orange reaction mixture was heated at reflux for 1 h. The cooled solution was partitioned with ethyl acetate and a saturated solution of ammonium chloride. The organics were separated and dried over sodium sulfate, filtered and concentrated under reduced pressure. The residue was taken up in THF, sodium 4-nitrophenoxide (10.63 g, 66 mmol) was added and the orange reaction mixture was heated to reflux for 3 h (HPLC, 95/5 trans/cis). The cooled solution was partitioned with ethyl acetate and a saturated solution of ammonium chloride. The organics were separated and washed with 0.3 N solution of sodium hydroxide and brine, dried over sodium sulfate and concentrated under reduced pressure. Recrystallization from ethyl acetate as in Example 10 gave the phosphate reagent.

Example 13

Procedures for the Enrichment in Trans-Isomer of a cis/trans Mixture of 4-(aryl)-2-(4-nitrophenoxy)-2-oxo-1,3,2-dioxaphosphorinane A cis/trans mixture of 4-(3-chlorophenyl)-2-(4-nitrophenoxy)-2-oxo-1,3,2-dioxaphosphorinanes was prepared as in Example 11, except that the cis and trans isomers were separated by column chromatography prior to the addition of 4-nitrophenol.

Cis-4-(3-chlorophenyl)-2-(4-nitrophenoxy)-2-oxo-1,3,2-dioxaphosphorinane was isomerized to the trans isomer by adding a solution of the cis-isomer to a solution of 4-nitrophenoxide prepared with the following bases.

Example 13a

Lithium hydride (19.4 mg, 2.44 mmol) was added to a solution of 4-nitrophenol in THF at room temperature. The yellow solution was stirred at room temperature for 30 min. A solution of cis-4-(3-chlorophenyl)-2-(4-nitrophenoxy)-2-oxo-1,3,2-dioxaphosphorinane (300 mg, 0.813 mmol) in THF was added to the solution of lithium 4-nitrophenoxide. The orange reaction mixture was stirred a room temperature. After 5 h the ratio was 92.9/5.4 trans/cis (HPLC determination).

Example 13b

Same as above using triethylamine instead of lithium hydride. After 20 h the trans/cis ratio was 90.8/5.3.

Example 13c

Same as above using DBU instead of lithium hydride. After 3 h the trans/cis ratio was 90.8/5.3.

Synthesis of enantioenriched phosphorylating agents

Example 14

General procedure for the Synthesis of enantioenriched trans-4-(aryl)-2-(4-nitrophenoxy)-2-oxo-1,3,2-dioxaphosphorinanes

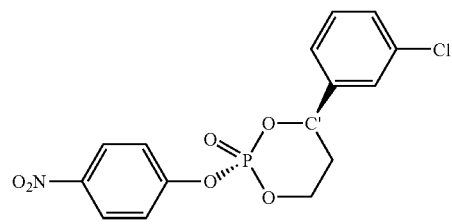

Example 14a

Synthesis of (+)-(4R)-trans-4-(3-chlorophenyl)-2-(4-nitrophenoxy)-2-oxo-1,3,2-dioxaphosphorinane A solution of (+)-(R)-1-(3-chlorophenyl)-1,3-propanediol (3 g, 16.1 mmol) and triethylamine (6.03 ml, 59.6 mmol) in THF (80 mL) was added dropwise to a solution of 4-nitrophenoxyphosphorodichloridate (7.63 g, 29.8 mmol) in 150 mL of THF at 0° C. After about 2 h, the starting diol was consumed, with the formation of two isomeric 4-nitrophenylphosphates, and additional triethylamine (8.31 mL) followed by of 4-nitrophenol (8.29 g, 59.6 mmol) were added. The reaction mixture was stirred overnight. The solvent was evaporated under reduced pressure and the residue was partitioned between ethyl acetate and water. The organic phase was washed (0.4 M NaOH, water and sat'd NaCl solution) and dried over $MgSO_4$. Concentration and chromatography of the residue using 30% ethyl acetate in hexanes yielded 4.213 g of the desired product.

HNMR (200 MHz, $CDCl_3$): 8.26 (2H, d, J=9.7 Hz), 7.2-7.5 (6H, m), 5.56 (1H, apparent d, J=11.7 Hz), 4.4-4.7 (2H, m), 2.2-2.6 (1H, m), 2.0-2.2 (1H, m). mp: 114-115° C. $[\alpha]_D$=+91.71. Elemental Analysis: Calculated for $C_{15}H_{13}NO_6ClP$: C: 48.73, H: 3.54, N: 3.79. Found: C: 48.44, H: 3.20, N: 3.65

Example 14b

Synthesis of (−)-(4S)-trans-4-(3-chlorophenyl)-2-(4-nitrophenoxy)-2-oxo-1,3,2-dioxaphosphorinane

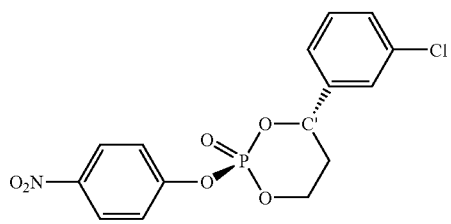

In a similar manner, from 3.116 g of (−)-(S)-1-(3-chlorophenyl)-1,3-propane diol was obtained 4.492 g of the desired phosphate.

HNMR (200 MHz, $CDCl_3$): 8.26 (2H, d, J=9.7 Hz), 7.2-7.5 (6H, m), 5.56 (1H, apparent d, J=11.7 Hz), 4.4-4.7 (2H, m), 2.2-2.6 (1H, m), 2.0-2.2 (1H, m).

mp: 114-115° C. $[\alpha]_D$=−91.71. Elemental Analysis: Calculated for $C_{15}H_{13}NO_6ClP$: C: 48.73, H: 3.54, N: 3.79. Found: C: 48.61, H: 3.36, N: 3.66.

Example 14c

Synthesis of (−)-(4S)-trans-phenyl-2-(4-nitrophenoxy)-2-oxo-1,3,2-dioxaphosphorinane Same as Example 11.1 starting with S-(−)-1-phenyl-1,3-propanediol except that the isomerization was conducted with 4-nitrophenol and triethylamine as in Example 13b.

TLC: hexanes/ethyl acetate 4/1); Rf=0.4 $^1$H NMR (DMSO-$d_6$, Varian Gemini 300 MHz): C'-proton: trans-isomer 5.85-5.75 (m, 1H).

Example 15

General procedures for maintaining enantiomeric excess during synthesis of enantioenriched phosphorylating reagent

Example 15a

Synthesis of (−)-(4S)-trans-(pyrid-4-yl)-2-(4-nitrophenoxy)-2-oxo-1,3,2-dioxaphosphorinane

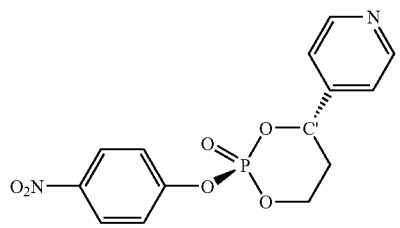

A 12 L round bottom flask equipped with an overhead stirrer and nitrogen inlet was charged with (S)-(−)-1-(pyrid-4-yl)-1,3-propanediol (1.2 kg, 7.83 mol) and pyridine (6 L) The mixture was vigorously stirred at room temperature for 0.5 h until all the solids had dissolved. Meanwhile, a 22 L, 3-neck flask was equipped with an overhead stirrer, thermocouple, cooling bath, and nitrogen inlet. This vessel was charged with 4-nitrophenyl phosphorodichloridate (2.01 kg, 7.83 mol) and pyridine (6 L). The resulting mixture was cooled to 3.3° C. After the diol was completely dissolved (0.5 h), triethylamine (190 mL, 1.36 mol) was added and the slightly cloudy, yellow-brown solution was transferred in portions to a 2 L addition funnel on the 22 L flask. The solution was added to the cold phosphorodichloridate solution over 3.25 h. After the addition was complete, the cooling bath was drained and stirring was continued for 3 h. During this time, a 50 L, 3-neck flask was equipped with an overhead stirrer, thermocouple, addition funnel, cooling bath (ice water) and nitrogen inlet. This flask was then charged with sodium hydride (180 g, 4.5 mol) and THF (1 L) and the addition funnel was charged with a solution of 4-nitrophenol (817 g, 5.87 mol) in THF (1 L). The nitrophenol solution was slowly added to the cold suspension of sodium hydride. After the addition was complete, the resulting bright orange suspension was stirred at room temperature for 1 h. After the diol-dichloridate reaction was judged complete the dark suspension was subjected to vacuum filtration. The glassware and filter cake (triethylamine-HCl) were rinsed with THF (1 L) and the combined filtrate and rinse were poured into the orange, sodium 4-nitrophenoxide suspension. The resulting mixture was then heated at 40° C. for 3.5 h at which time the heating mantle was turned off and the reaction was stirred an additional 11 h at room temperature. The crude reaction mixture was concentrated on a rotary evaporator at 45-50° C. at reduced pressure (oil pump). The resulting thick, black, foamy tar was dissolved in 1.5 M aq HCl (12 L) and ethyl acetate (8 L). The mixture was transferred to a 12.5-gallon separatory funnel, stirred 10 min, and the phases separated. The ethyl acetate layer was washed with an additional 1.3 L of 1.5 M aq HCl. To the combined aqueous layers was added dichloromethane (8 L) and the vigorously stirred mixture was carefully neutralized with solid sodium bicarbonate. The layers were separated and the aqueous layer was extracted with dichloromethane (8 L). The combined organic layers were dried over magnesium sulfate (600 g) and filtered. The solution was concentrated on a rotary evaporator until most of the solvent was removed and a thick suspension resulted. 2-Propanol (5 L) was added and evaporation continued until 4 L of distillate were collected. 2-Propanol (3 L) was added and evaporation continued until 3 L of distillate were collected. The thick slurry was diluted with 2-propanol (2 L) and the mixture stirred with cooling (ice bath) for 1 h. The solid was collected by filtration, washed with 2-propanol (2 L), and dried in a vacuum oven (−30 in. Hg, 55° C., 18 h) to a constant weight of 1.86 kg. mp 140-142° C.

Specific Rotation=−80.350 (c=1.0, MeOH); ee=99+% trans

HPLC conditions:

Column: Chiralpak AD, 0.46×25 cm; mobile phase=50:50, 2-propanol:hexane, isocratic; flow rate=1.0 mL/min; injection volume=10 μL UV detection at 254 nm.

The cis/trans equilibration was monitored by HPLC. Stopped at 92% trans, 6.6% cis, r.t.=trans isomer 6.9 min. and cis isomer 10.9 min.

$^1$HNMR (DMSO-d$_6$): δ=2.23-2.29 (m, 2H), 4.56-4.71 (m, 2H), 5.88-5.95 (m, 1H), 7.44 (d, 2H, J=5.8 Hz), 7.59 (d, 2H, J=9.2 Hz), 8.34 (d, 2H, J=9.4 Hz), 8.63 (d, 2H J=5.8 Hz)

Example 15b

Synthesis of (−)-(4S)-(−)-(pyrid-4-yl)-2-(4-nitrophenoxy)-2-oxo-1,3,2-dioxaphosphorinane A 1 liter 3-neck round bottom flask was equipped with a mechanical stirrer, addition funnel, a thermometer and a N$_2$ inlet. The flask is charged with S-(−)-1-(pyrid-4-yl)-propane-1,3-diol (25 g, 163.4 mmol) and ethyl acetate (250 mL) and the resulting suspension was treated slowly with a 4N HCl solution in dioxane (43 mL, 176 mmol) over a period of 15 min. After stirring for 30 min at room temperature, 4-nitrophenylphosphorodichloridate (41.81 g, 163.4 mmol) was added as a solid as quickly as possible under a positive flow of N2. The internal temperature of the reaction mixture was adjusted to −10° C. with the help of a dry ice-acetone cooling bath. A solution of triethylamine (79 mL, 572 mmol) in ethyl acetate (100 mL) was added maintaining the reaction temperature at <−5° C. Thirty minutes after the complete addition of the triethylamine solution, the cooling bath was removed and the reaction mixture was stirred at room temperature for 1 h. The reaction mixture was filtered to remove triethylamine-hydrochloride salt, which is washed with ethyl acetate (3×30 mL) until the filtrate shows only faint absorption. The filtrate was evaporated down to a volume of 150-175 mL under reduced pressure. 4-nitrophenol (7.5 g, 54.3 mmol) and triethylamine (9 mL) were added to the concentrated solution and the resulting orange reaction mixture was stirred at room temperature for 24 h. The solid formed in the reaction mixture was collected by filtration, washed with ethyl acetate (2×25 mL) and methyl t-butyl ether (25 mL) and dried under vacuum at 55° C. to give 31.96 g of the desired product. Same analytical data as Example 14a.

Example 16

Preparation of Prodrugs of 2'-C-beta-methyl-7-deazaadenosine via trans-transphosphate Addition 16.1: 4-amino-7-(cis-5'-O-[4-(3-chlorophenyl)-2-oxo-1,3,2-dioxaphosphorinan-2-yl]-2'-C-methyl-beta-D-ribofuranosyl)-7H-pyrrolo[2,3-d]pyrimidine

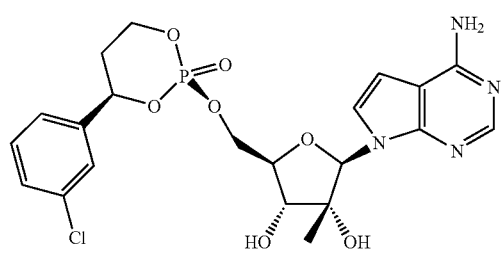

Step A:

To a solution of 4-amino-7-(2-C-methyl-beta-D-ribofuranosyl)-7H-pyrrolo[2,3-d]pyrimidine (US2002-0147160A1, WO 02/057827) (10 g, 0.356 mol) in anhydrous acetone (145 mL) and anhydrous DMF (35 mL) were added p-toluene sulfonic acid monohydrate (33.8 g, 0.18 moles) and triethyl orthoformate (31.2 mL, 28.5 moles) at room temperature. The reaction was warmed to ~80° C. and allowed to stir for 3 h under nitrogen. The mixture was evaporated under reduced pressure. The oily residue was purified by column chromatography (5% MeOH in CH$_2$Cl$_2$) to give the isopropylidene derivative (8.6 g) as a white solid.

Step B:

To a solution of 2',3'-O-isopropylidene-4-amino-7-(2-C-methyl-beta-D-ribofuranosyl)-7H-pyrrolo[2,3-d]pyrimidine (0.094 g, 0.29 mmol) in DMF (1.5 mL) was added t-butyl magnesium chloride and stirred under nitrogen for 30 min. The reaction mixture was then cooled to −55° C. and the phosphorylating agent (whose preparation is described in example 11.1) (0.13 g, 0.35 mmol) in DMF (1.5 mL) was added dropwise. The reaction was allowed to warm to room temperature and stirred under nitrogen for 2 h. The mixture was evaporated under reduced pressure and purified by chromatography (5% MeOH in CH$_2$Cl$_2$) to yield 0.070 g of the 2',3'-O-isopropylidene protected prodrug as a yellow solid.

Step C:

The prodrug (0.15 g, 0.27 mmol) obtained from the above step was dissolved in pre-cooled 75% TFA/H2O (20 mL) and allowed to stir at 0° C. for 2 h. The reaction mixture was evaporated under reduced pressure. The crude product was purified by flash chromatography (1% aq.NH$_4$OH in 10%MeOH in CH$_2$Cl$_2$) to give 0.142 g of the title compound as an off-white solid.

R$_f$=0.40 (10% MeOH in CH$_2$Cl$_2$). mp 138-141° C. Anal calcd for C$_{21}$H$_{24}$ClN$_4$O$_7$P.0.4 CH$_2$Cl$_2$: C, 47.18; H, 4.59; N, 10.28. Found: C, 46.97; H, 4.59; N, 10.11.

The following examples were synthesized as described in steps A-C of example 16.1, utilizing the phosphorylating agents of examples 1-15.

16.2: 4-amino-7-(cis-5'-O-[4-(2,5-difluorophenyl)-2-oxo-1,3,2-dioxaphosphorinan-2-yl]-2'-C-methyl-beta-D-ribofuranosyl)-7H-pyrrolo[2,3-d]pyrimidine

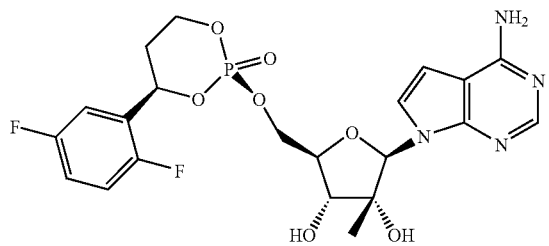

$R_f$=0.35 (10% MeOH in CH$_2$Cl$_2$). mp 145-148° C. Anal Calcd for C$_{21}$H$_{23}$N$_4$O$_7$F$_2$P.1.35 H$_2$O.1.0 CF$_3$CO$_2$H: C, 42.45; H, 4.14 ; N, 8.62. Found: C, 42.18; H, 3.77; N, 8.42.

16.3: 4-amino-7-(cis-5'-O-[4-(3-chloro-4-fluorophenyl)-2-oxo-1,3,2-dioxaphosphorinan-2-yl]-2'-C-methyl-beta-D-ribofuranosyl)-7H-pyrrolo[2,3-d]pyrimidine

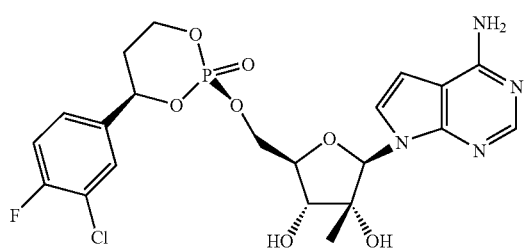

$R_f$=0.30 (10% MeOH in CH$_2$Cl$_2$). mp 128-130° C. Anal Calcd for C$_{21}$H$_{23}$N$_4$O$_7$FClP.2H$_2$O.1.9CF$_3$CO$_2$H: C, 38.11; H, 3.73; N, 7.17. Found: C, 38.04; H, 3.28; N, 7.02.

16.4: 4-amino-7-(cis-5'-O-[6,6-dimethyl-4-phenyl-2-oxo-1,3,2-dioxaphosphorinan-2-yl]-2'-C-methyl-beta-D-ribofuranosyl)-7H-pyrrolo[2,3-d]pyrimidine

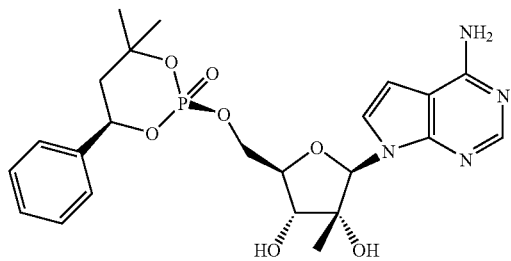

$R_f$=0.40 (10% MeOH in CH$_2$Cl$_2$). mp 140-142° C. Anal Calcd for C$_{23}$H$_{29}$N$_4$O$_7$P.1H$_2$O.0.4 CF$_3$CO$_2$H: C, 50.32; N, 5.57; N, 9.86. Found: C, 50.38; H, 5.12; N, 9.96.

16.5: 4-amino-7-(cis-5'-O-[4-(S)-(3-chlorophenyl)-2-oxo-1,3,2-dioxaphosphorinan-2-yl]-2'-C-methyl-beta-D-ribofuranosyl)-7H-pyrrolo[2,3-d]pyrimidine

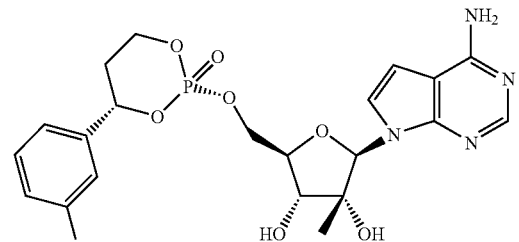

$R_f$=0.45 (10% MeOH in CH$_2$Cl$_2$). mp 135-138° C. Anal Calcd for C$_{21}$H$_{24}$ClN$_4$O$_7$P.0.2 H$_2$O.0.4 CH$_2$Cl$_2$: C, 46.87; H, 4.63; N, 10.22. Found: C, 47.02; H, 4.25; N, 9.99.

16.6: 4-amino-7-(cis-5'-O-[4-(S)-(3-chlorophenyl)-2-oxo-1,3,2-dioxaphosphorinan-2-yl]-2'-C-methyl-beta-D-ribofuranosyl)-7H-pyrrolo[2,3-d]pyrimidine methanesulfonic acid salt

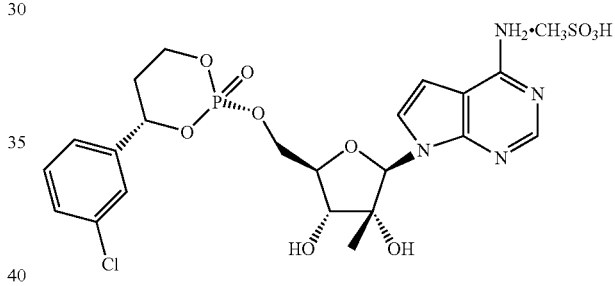

$R_f$=0.45 (10% MeOH in CH$_2$Cl$_2$). mp 125-128° C. Anal Calcd for C$_{21}$H$_{24}$N$_4$O$_7$ClP.1.6 CH$_3$SO$_3$H.1.0 H$_2$O: C, 39.76; H, 4.78; N, 8.21; S, 7.52. Found: C, 39.39; H, 4.30; N, 8.30; S, 7.96.

16.7: 4-amino-7-(cis-5'-O-[4-(S)-(pyridin-4-yl)-2-oxo-1,3,2-dioxaphosphorinan-2-yl]-2'-C-methyl-beta-D-ribofuranosyl)-7H-pyrrolo[2,3-d]pyrimidine

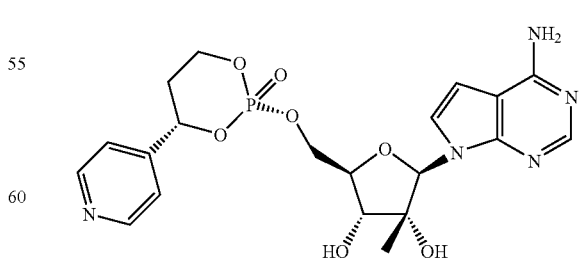

$R_f$=0.40 (15% MeOH in CH$_2$Cl$_2$-1% NH$_4$OH). mp 183-185° C. Anal Calcd for C$_{20}$H$_{24}$N$_5$O$_7$P. 1.6H$_2$O: C, 47.45; H, 5.42; N, 13.83. Found: C, 47.78; H, 5.47; N, 13.77.

16.8: 4-amino-7-(cis-5'-O-[4-(3-fluorophenyl)-2-oxo-1,3,2-dioxaphosphorinan-2-yl]-2'-C-methyl-beta-D-ribofuranosyl)-7H-pyrrolo[2,3-d]pyrimidine

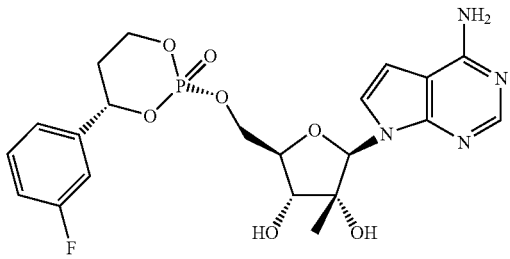

$R_f$=0.15 (10% MeOH in CH$_2$Cl$_2$). Anal Calcd for C$_{21}$H$_{24}$FN$_4$O$_7$P. 0.3 H$_2$O: C, 50.46; H, 4.96; N, 11.21. Found: C, 50.63; H, 5.35; N, 10.94.

16.9: 4-amino-7-(cis-5'-O-[4-(3-bromophenyl)-2-oxo-1,3,2-dioxaphosphorinan-2-yl]-2'-C-methyl-beta-D-ribofuranosyl)-7H-pyrrolo[2,3-d]pyrimidine.

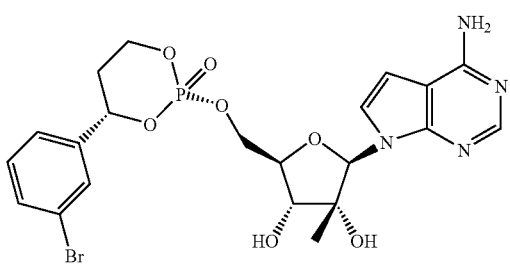

Rf=0.48 (15% MeOH in CH$_2$Cl$_2$-1% NH$_4$OH). Anal Calcd for C$_{21}$H$_{24}$BrN$_4$O$_7$P. 0.5 H$_2$O: C, 44.70; H, 4.47; N, 9.93. Found: C, 44.58; H, 4.52; N, 9.56.

16.10: 4-amino-7-(cis-5'-O-[4-(2-bromophenyl)-2-oxo-1,3,2-dioxaphosphorinan-2-yl]-2'-C-methyl-beta-D-ribofuranosyl)-7H-pyrrolo[2,3-d]pyrimidine

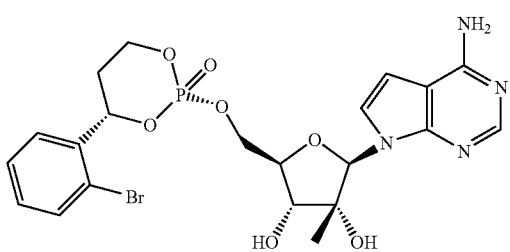

$R_f$=0.15 (10% MeOH in CH$_2$Cl$_2$). mp 132-135° C. Anal Calcd for C$_{21}$H$_{24}$BrN$_4$O$_7$P. 0.5 H$_2$O: C, 44.7; H, 4.47; N, 9.93. Found: C, 44.73; H, 4.69; N, 9.82.

16.11: 4-amino-7-(cis-5'-O-[4-(5-bromopyridin-3-yl)-2-oxo-1,3,2-dioxaphosphorinan-2-yl]-2'-C-methyl-beta-D-ribofuranosyl)-7H-pyrrolo[2,3-d]pyrimidine

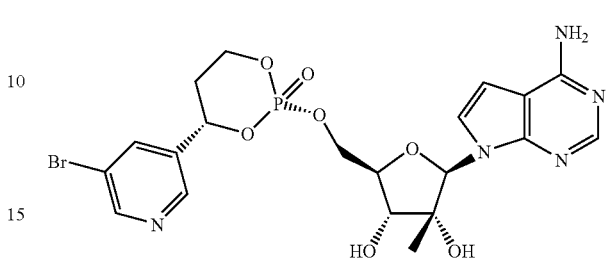

$R_f$=0.35 (10% MeOH in EtOAc) mp 132-135° C. Anal Calcd for C$_{20}$H$_{23}$N$_5$O$_7$BrP. 0.5 H$_2$O. 0.5 EtOAc: C, 43.36; H, 4.63; N, 11.49.
Found: C, 43.37; H, 4.80; N, 11.16.

16.12: 4-amino-7-(cis-5'-O-[4-(S)-phenyl-2-oxo-1,3,2-dioxaphosphorinan-2-yl]-2'-C-methyl-beta-D-ribofuranosyl)-7H-pyrrolo[2,3-d]pyrimidine

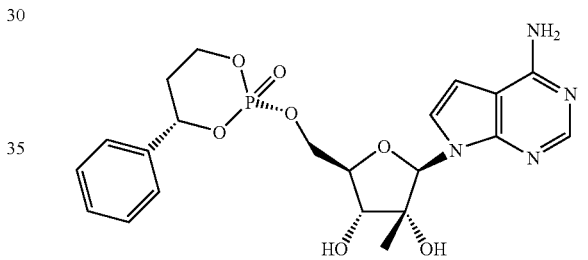

$R_f$=0.42 (15% MeOH in CH$_2$Cl$_2$-1% NH$_4$OH). mp 115-118° C. Anal Calcd for C$_{21}$H$_{25}$N$_4$O$_7$P. 0.4 EtOAc. 1.0 H$_2$O: C, 51.25; H, 5.75; N, 10.58. Found: C, 51.07; H, 5.88; N, 10.35.

16.13: 4-amino-7-(cis-5'-O-[4,5-cis-diphenyl-2-oxo-1,3,2-dioxaphosphorinan-2-yl]-2'-C-methyl-beta-D-ribofuranosyl)-7H-pyrrolo[2,3-d]pyrimidine trifluoroacetic Acid Salt

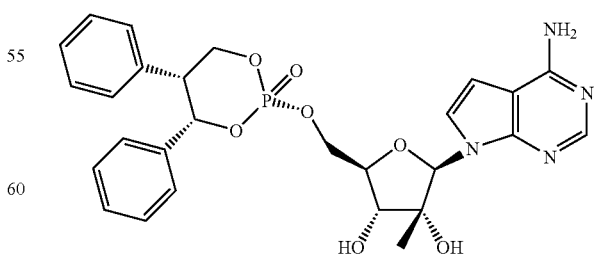

$R_f$=0.45 (10% MeOH in CH$_2$Cl$_2$). mp 174-177° C. Anal Calcd for C$_{29}$H$_{30}$F$_3$N$_4$O$_9$P.1.75 H$_2$O: C, 49.90; H, 4.48; N, 8.03. Found: C, 49.68; H, 4.82; N, 8.1.

16.14: 4-amino-7-(cis-5'-O-[4-(2-chlorophenyl)-2-oxo-1,3,2-dioxaphosphorinan-2-yl]-2'-C-methyl-beta-D-ribofuranosyl)-7H-pyrrolo[2,3-d]pyrimidine

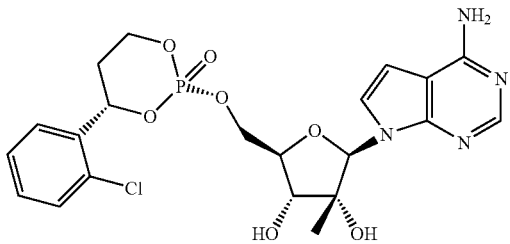

$R_f$=0.48 (10% MeOH in CH$_2$Cl$_2$). mp 187-190° C. Anal Calcd for C$_{21}$H$_{24}$ClN$_4$O$_7$P.H$_2$O.0.2 DMF: C, 47.72; H, 5.05; N, 10.77. Found: C, 47.66; H, 5.02; N, 10.96.

16.15: 4-amino-7-(cis-5'-O-[4-(2-fluoro-5-bromophenyl)-2-oxapbospborinan-2-yl]-2'-C-methyl-beta-D-ribofuranosyl)-7H-pyrrolo[2,3-d]pyrimidine

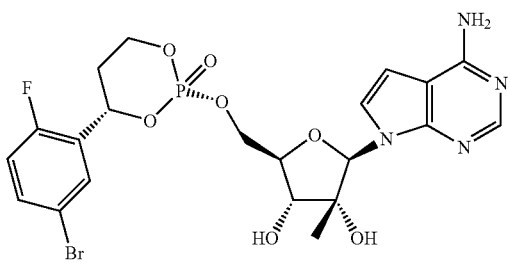

$R_f$=0.48 (15% MeOH in CH$_2$Cl$_2$-1% NH$_4$OH). Anal Calcd for C$_{21}$H$_{23}$BrFN$_4$O$_7$P.1.3H2O: C, 42.27; H, 4.32; N, 9.39. Found: C, 42.26; H, 4.03; N, 9.36.

16.16: 4-amino-7-(cis-5'-O-[4,6-cis-diphenyl-2-oxo-1,3,2-dioxaphosphorinan-2-yl]-2'-C-methyl-beta-D-ribofuranosyl)-7H-pyrrolo[2,3-d]pyrimidine trifluoroacetic acid salt

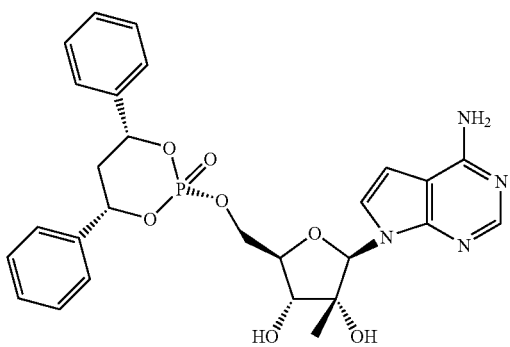

$R_f$=0.20 (10% MeOH in CH$_2$Cl$_2$). mp 140-143° C. Anal Calcd for C$_{27}$H$_{29}$N$_4$O$_7$P.1.25 H$_2$O.CF$_3$CO$_2$H: C, 50.55; H, 4.75; N, 8.13. Found: C, 50.25; H, 4.88; N, 7.99.

16.17: 4-amino-7-(cis-5'-O-[4(3,5-bis-trifluoromethylpheny)-2-oxo-1,3,2-dioxaphosphorinan-2-yl]-2'-C-methyl-beta-D-ribofuranosyl)-7H-pyrrolo[2,3-d]pyrimidine

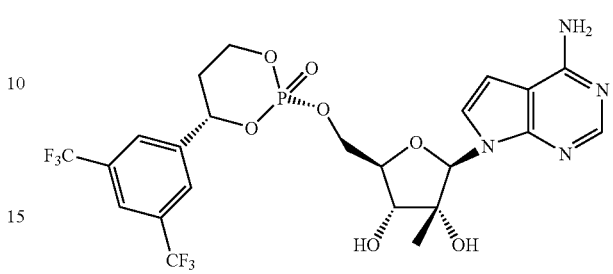

$R_f$=0.15 (10% MeOH in CH$_2$Cl$_2$). mp 130-134° C. Anal Calcd for C$_{23}$H$_{23}$N$_4$O$_7$P.0.6 H$_2$O: C, 44.33; H, 3.91; N, 8.99. Found: C, 44.29; H, 4.13; N, 8.98.

16.18: 4-amino-7-(trans-5'-O-[4,6-cis-diphenyl-2-oxo-1,3,2-dioxaphosphorinan-2-yl]-2'-C-methyl-beta-D-ribofuranosyl)-7H-pyrrolo[2,3-d]pyrimidine trifluoroacetic acid salt

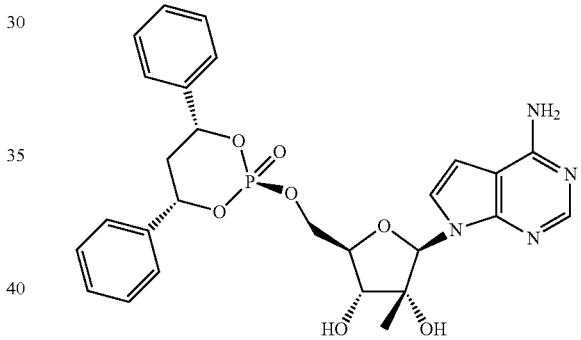

Rf=0.48 (15% MeOH in CH$_2$Cl$_2$-1% NH$_4$OH). mp >220° C. Anal Calcd for C$_{27}$H$_{29}$N$_4$O$_7$P.0.9 H$_2$O: C, 57.02; H, 5.46; N, 9.85. Found: C, 57.55; H, 5.97; N, 9.88.

16.19: 4-amino-7-(trans-5'-O-[4-(3-bromo-pyridin-4-yl)-2-oxo-1,3,2-dioxaphosphorinan-2-yl]-2'-C-methyl-beta-D-ribofuranosyl)-7H-pyrrolo[2,3-d]pyrimidine

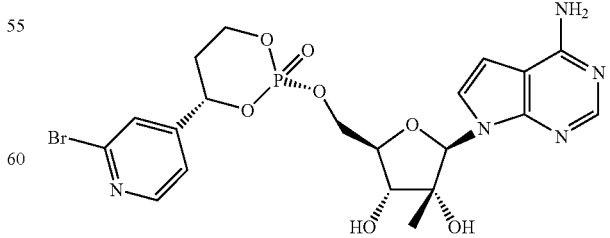

$R_f$=0.3 (10% MeOH in EtOAc). mp 116-120° C. Anal Calcd for C$_{20}$H$_{23}$N$_5$O$_7$BrP.1 H2O. 0.6 EtOAc: C, 42.90; H, 4.79; N, 11.17 Found: C, 42.90; H, 4.42; N, 10.82.

16.20: 4-amino-7-(trans-5'-O-[4-(2,4-dichlorophenyl)-2-oxo-1,3,2-dioxaphosphorinan-2-yl]-2'-C-methyl-beta-D-ribofuranosyl)-7H-pyrrolo[2,3-d]pyrimidine

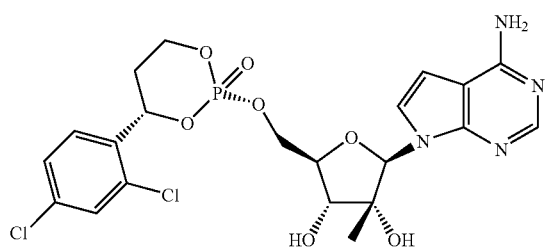

$R_f$=0.15 (10% MeOH in CH$_2$Cl$_2$). mp 184-188° C. Anal Calcd for C$_{22}$H$_{24}$F$_3$N$_4$O$_7$P. 0.6 H$_2$O: C, 47.59; H, 4.57; N, 10.09. Found: C, 47.46; H, 4.96; N, 10.10.

16.21: 4-amino-7-(trans-5'-O-[4-(3-trifluoromethylphenyl)-2-oxo-1,3,2-dioxaphosphorinan-2-yl]-2'-C-methyl-beta-D-ribofuranosyl)-7H-pyrrolo[2,3-d]pyrimidine

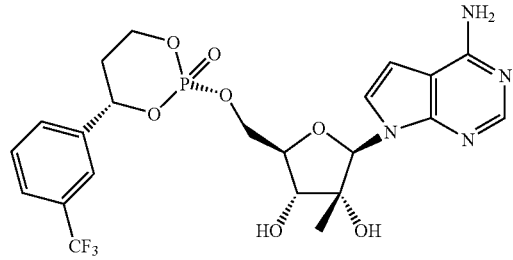

$R_f$=0.15 (10% MeOH in CH$_2$Cl$_2$). mp 120-124° C. Anal Calcd for C$_{21}$H$_{23}$Cl$_2$N$_4$O$_7$P.0.5 H$_2$O: C, 45.50; H, 4.36; N, 10.11. Found: C, 45.32; H, 4.58; N, 10.26.

16.22: 4-amino-7-(trans-5'-O-[4,5-cis-diphenyl-2-oxo-1,3,2-dioxaphosphorinan-2-yl]-2'-C-methyl-beta-D-ribofuranosyl)-7H-pyrrolo[2,3-d]pyrimidine

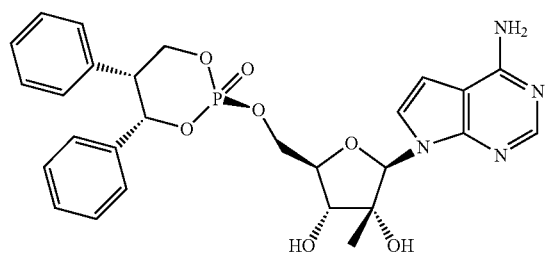

$R_f$=0.75 (15% MeOH in CH$_2$Cl$_2$-1% NH$_4$OH). mp 160-163° C. Anal Calcd for C$_{27}$H$_{29}$N$_4$O$_7$P.1.2 H$_2$O: C, 56.48; H, 5.51; N, 9.76. Found: C, 56.34, H, 5.75; N, 9.71.

16.23: 4-amino-7-(cis-5'-O-[cis-(5-methoxy-4-phenyl)2-oxo-1,3,2-dioxaphosphorinan-2-yl]-2'-C-methyl-beta-D-ribofuranosyl)-7H-pyrrolo[2,3-d]pyrimidine trifluoroacetic acid salt

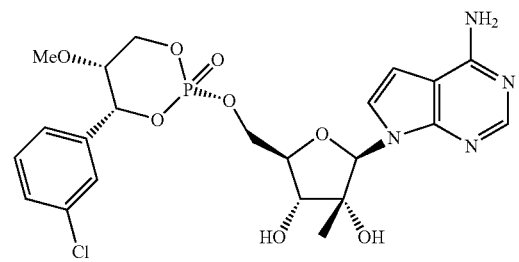

$R_f$=0.25 (10% MeOH in CH$_2$Cl$_2$). mp 116-120° C. Anal Calcd for C$_{22}$H$_{26}$N$_4$O$_8$PCl.1.75 H$_2$O.1.5 CF$_3$CO$_2$H: C, 40.39; H, 4.20; N, 7.54. Found: C, 39.95; H, 3.85; N, 7.38.

16.24: 4-amino-7-(cis-5'-O-[trans-(5-methoxy-4-phenyl)2-oxo-1,3,2-dioxaphosphorinan-2-yl]-2'-C-methyl-beta-D-ribofuranosyl)-7H-pyrrolo[2,3-d]pyrimidine trifluoroacetic acid salt

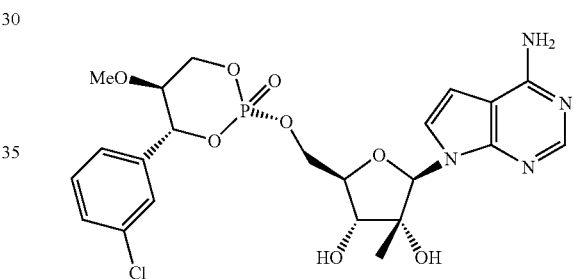

$R_f$=0.30 (10% MeOH in CH$_2$Cl$_2$). mp 140-143° C. Anal Calcd for C$_{22}$H$_{26}$N$_4$O$_8$PCl.2.5 H$_2$O.2.2 CF$_3$CO$_2$H: C, 37.89; H, 4.00; N, 6.70. Found: C, 37.73; H, 3.61; N, 6.85.

16.25: 4-amino-7-(cis-5'-O-[4-(2-bromo-5-chlorophenyl)-2-oxo-1,3,2-dioxaphosphorinan-2-yl]-2'-C-methyl-beta-D-ribofuranosyl)-7H-pyrrolo[2,3-d]pyrimidine

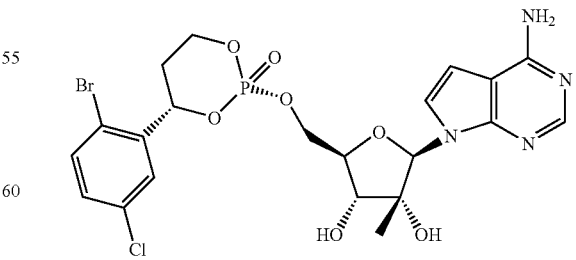

$R_f$=0.3 (10% MeOH in CH$_2$Cl$_2$). mp 193-196° C. Anal Calcd for C$_{21}$H$_{23}$N$_4$O$_7$PClBr.1.75 H$_2$O.1 CF$_3$CO$_2$H: C, 37.57; H, 3.77; N, 7.62. Found: C, 37.20; H, 3.49; N, 7.36.

16.26: 4-amino-7-(cis-5'-O-[4-(3,5-dichlorophenyl)-2-oxo-1,3,2-dioxaphosphorinan-2-yl]-2'-C-methyl-beta-D-ribofuranosyl)-7H-pyrrolo[2,3-d]pyrimidine

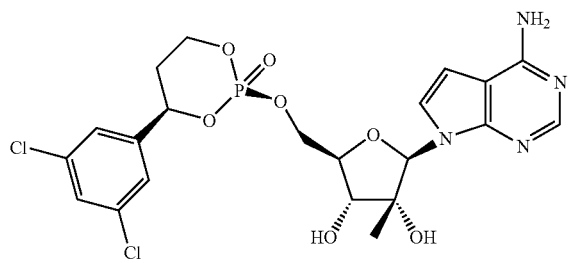

$R_f$=0.3 (10% MeOH in CH$_2$Cl$_2$). mp 182-185° C. Anal Calcd for C$_{21}$H$_{23}$N$_4$O$_7$Cl$_2$P.0.3 MeOH.0.5 H$_2$O: C, 45.37; H, 4.50; N, 9.93. Found: C, 45.36; H, 4.18; N, 9.58.

16.27: 4-amino-7-(cis-5'-O-[4-(3,5-difluorophenyl)-2-oxo-1,3,2-dioxaphosphorinan-2-yl]-2'-C-methyl-beta-D-ribofuranosyl)-7H-pyrrolo[2,3-d]pyrimidine

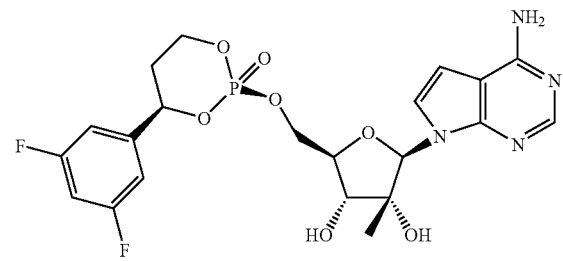

$R_f$=0.35 (10% MeOH in CH$_2$Cl$_2$). mp 135-140° C. Anal Calcd for C$_{21}$H$_{23}$N$_4$O$_7$F$_2$P.1.0 H$_2$O: C, 47.55; H, 4.75; N, 10.56. Found: C, 47.29; H, 4.51; N, 10.28.

16.28: 4-amino-7-(cis-5'-O-[4-(R)-(3-chlorophenyl)-2-oxo-1,3,2-dioxaphosphorinan-2-yl]-2'-C-methyl-beta-D-ribofuranosyl)-7H-pyrrolo[2,3-d]pyrimidine

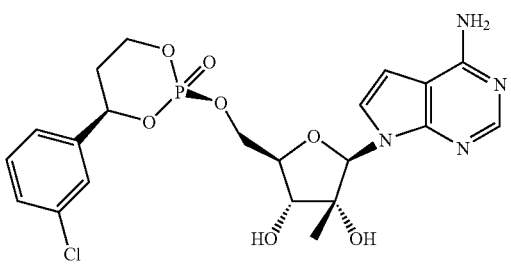

Rf=0.45 (10% MeOH in CH$_2$Cl$_2$). mp 126-128° C. Anal Calcd for C$_{21}$H$_{24}$ClN$_4$O$_7$P.1.0 H$_2$O: C, 47.69; H, 4.96; N, 1059. Found: C, 47.31; H, 4.77; N, 10.3.

16.29: 4-amino-7-(cis-5'-O-[4-(2-trifluoromethylphenyl)-2-oxo-1,3,2-dioxaphosphorinan-2-yl]-2'-C-methyl-beta-D-ribofuranosyl)-7H-pyrrolo[2,3-d]pyrimidine

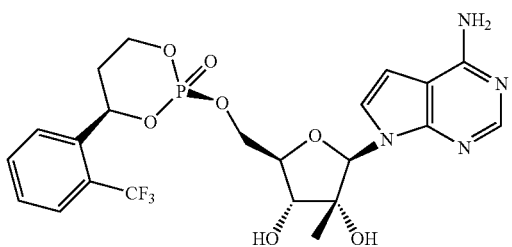

Rf=0.5 (10% MeOH in CH$_2$Cl$_2$). mp 115-120° C. Anal Calcd for C$_{22}$H$_{24}$F$_3$N$_4$O$_7$P.1.0 H$_2$O.1.0 CF$_3$CO$_2$H: C, 42.61; H, 4.02; N, 8.28. Found: C, 42.78; H, 4.07; N, 8.27.

16.30: 4-amino-7-(cis-5'-O-[4-(R)-(pyridin-4-yl)-2-oxo-1,3,2-dioxaphosphorinan-2-yl]-2'-C-methyl-beta-D-ribofuranosyl)-7H-pyrrolo[2,3-d]pyrimidine

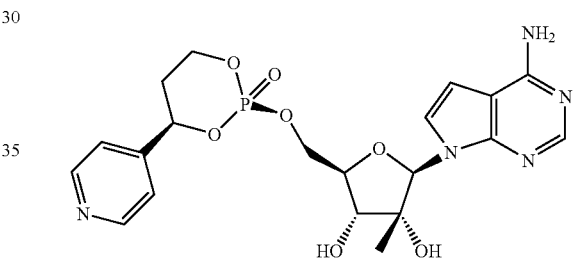

$R_f$=0.3 (20% MeOH in EtOAc). mp 132-136° C. Anal Calcd for C$_{20}$H$_{24}$N$_5$O$_7$P.0.03 H$_2$O.0.7 CH$_2$Cl$_2$: C, 46.52; H, 4.79; N, 13.14. Found: C, 46.13; H, 4.39; N, 13.50.

16.31: 4-amino-7-(cis-5'-O-[4-(3-bromo-4-fluorophenyl)-2-oxo-1,3,2-dioxaphosphorinan-2-yl]-2'-C-methyl-beta-D-ribofuranosyl)-7H-pyrrolo[2,3-d]pyrimidine

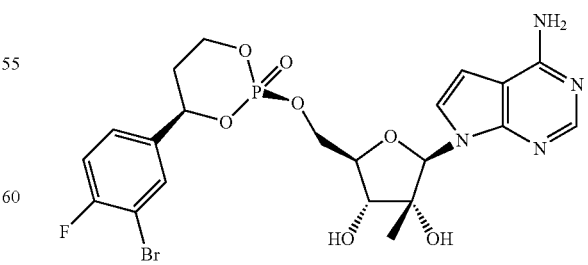

$R_f$=0.35 (10% MeOH in EtOAc). mp 122-125° C. Anal Calcd for C$_{21}$H$_{23}$N$_4$O$_7$FBrP.0.2 CF$_3$CO$_2$H: C, 43.12; H, 3.92; N, 9.40. Found: C, 42.82; H, 3.76; N, 9.57.

16.32: 4-amino-7-(cis-5'-O-[4-(pyridin-3-yl)-2-oxo-1,3,2-dioxaphosphorinan-2-yl]-2'-C-methyl-beta-D-ribofuranosyl)-7H-pyrrolo[2,3-d]pyrimidine

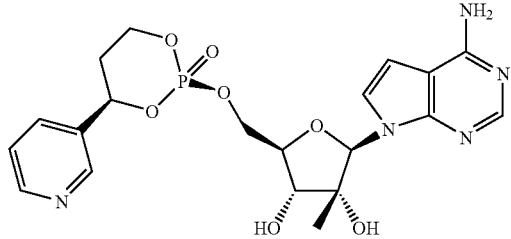

$R_f$=0.30 (10% MeOH in EtOAc). mp 134-138° C. Anal Calcd for $C_{20}H_{24}N_5O_7P.1.5H_2O$: C, 47.62; H, 5.40; N, 13.88. Found: C, 47.89; H, 5.08; N, 13.97.

16.33: 4-amino-7-(cis-5'-O-[4-(pyridin-2-yl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

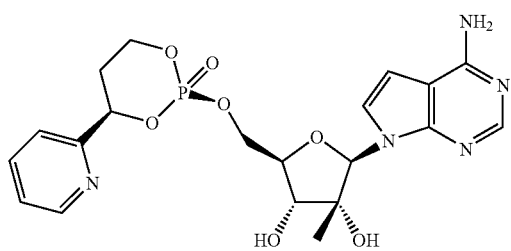

$R_f$=0.50 (10% MeOH in $CH_2Cl_2$). mp 88-90° C. Anal Calcd for $C_{20}H_{24}N_5O_7P.2.3H_2O.1.3CF_3CO_2H$: C, 40.69; H, 4.52; N, 10.50. Found: C, 40.38; H, 4.86; N, 10.90.

16.34: 4-amino-7-(cis-5'-O-[4-(R)-(phenyl)-2-oxo-1,3,2-dioxaphosphorinan-2-yl]-2'-C-methyl-beta-D-ribofuranosyl)-7H-pyrrolo[2,3-d]pyrimidine

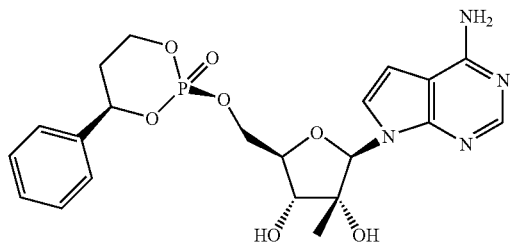

$R_f$=0.30 (10% MeOH in $CH_2Cl_2$). mp 177-180° C. Anal Calcd for $C_{21}H_{25}N_4O_7P$. 0.1 EtOAc. 0.2 $CF_3CO_2H$: C, 51.54; H, 5.16; N, 11.03. Found: C, 51.92; H, 4.78; N, 10.75.

16.35: 4-amino-7-(cis-5'-[4-(4-chlorophenyl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

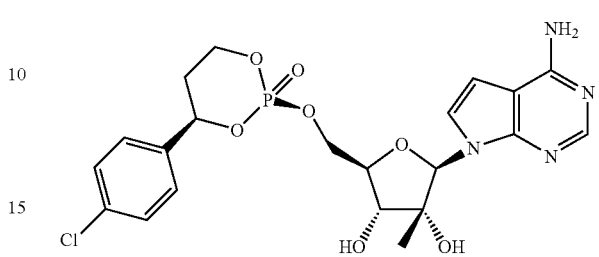

$R_f$=0.45 (10% MeOH in $CH_2Cl_2$). mp 182-184° C. Anal Calcd for $C_{21}H_{24}N_4O_7ClP.2.0H_2O.2.9CF_3CO_2H$: C, 36.68; H, 3.55; N, 6.38. Found: C, 36.33; H, 3.35; N, 6.44.

16.36: 4-amino-7-(cis-5'-O-[4-(2,3-difluorophenyl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

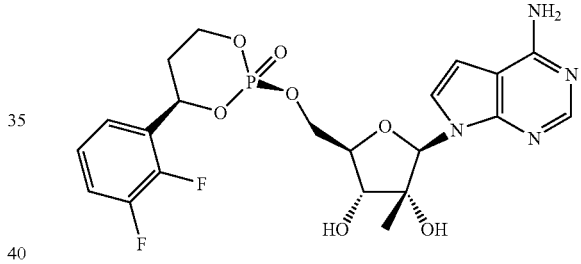

$R_f$=0.5 (10% MeOH in $CH_2Cl_2$). mp 177-180° C. Anal Calcd for $C_{21}H_{23}F_2N_4O_7P.1.9H_2O.1.1CF_3CO_2H$: C, 41.46; H, 4.18; N, 8.34. Found: C, 42.07; H, 4.02; N, 8.68.

16.37: 4-amino-7-(cis-5'-O-[4-(2-fluoro-5-methoxyphenyl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

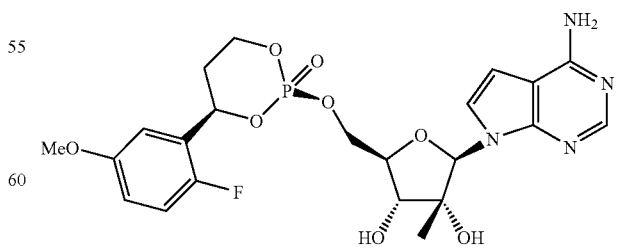

$R_f$=0.4 (10% MeOH in $CH_2Cl_2$). mp 80-85° C. Anal Calcd for $C_{22}H_{26}N_4O_8FP.0.4H_2O.2.0CF_3CO_2H$: C, 41.11; H, 3.82; N, 7.37. Found: C, 41.13; H, 3.50; N, 7.54.

16.38: 4-amino-7-(cis-5'-O-[4-(2-chloro-4-fluorophenyl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

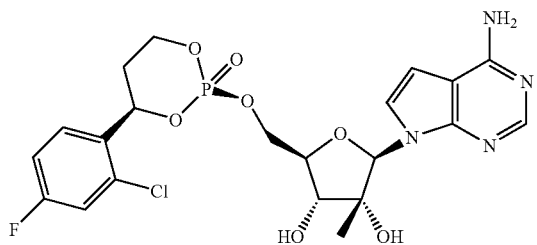

Rf=0.46 (15% MeOH in CH$_2$Cl$_2$). mp 138-141° C. Anal Calcd for C$_{21}$H$_{23}$ClFN$_4$O$_7$P. 0.3 H$_2$O. 0.9 CF$_3$CO$_2$H: C, 43.00; H, 3.88; N, 8.80. Found: C, 42.73; H, 4.21; N, 8.55.

16.39: 4-amino-7-(cis-5'-O-[4-(2-fluorophenyl)-2-oxo-1,3,2-dioxaphosphorinan-2-yl]-2'-C-methyl-beta-D-ribofuranosyl)-7H-pyrrolo[2,3-d]pyrimidine

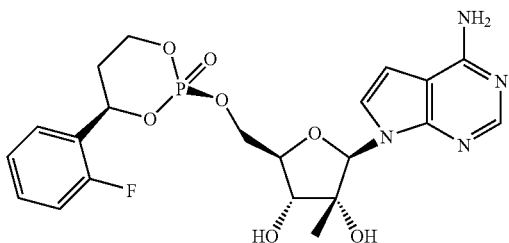

Rf=0.48 (15% MeOH in CH$_2$Cl$_2$-1%NH$_4$OH). mp 101-103° C. Anal Calcd for C$_{21}$H$_{24}$FN$_4$O$_7$P. 1.5 H$_2$O: C, 48.37; H, 5.22; N, 10.74. Found: C, 48.70; H, 5.47; N, 10.43.

16.40: 4-amino-7-(cis-5'-O-[4-(2-cyanophenyl)-2-oxo-1,3,2-dioxaphosphorinan-2-yl]-2'-C-methyl-beta-D-ribofuranosyl)-7H-pyrrolo[2,3-d]pyrimidine

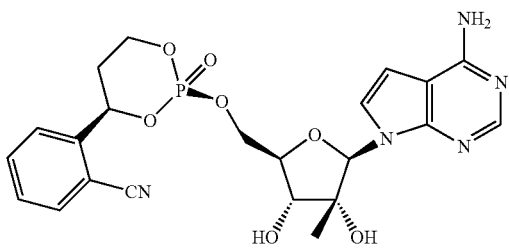

Rf=0.42 (15% MeOH in CH$_2$Cl$_2$-1%NH$_4$OH). Anal Calcd for C$_{22}$H$_{24}$N$_5$O$_7$P. 2 H$_2$O. 0.1 CF$_3$CO$_2$H: C, 48.58; H, 5.16; N, 12.76. Found: C, 48.86; H, 5.51; N, 12.70.

16.41: 4-amino-7-(cis-5'-O-[4-(S)-(3-chlorophenyl)-2-oxo-1,3,2-dioxaphosphorinan-2-yl]-2'-C-methyl-beta-D-ribofuranosyl)-7H-pyrrolo[2,3-d]pyrimidine trifluoroacetic acid salt

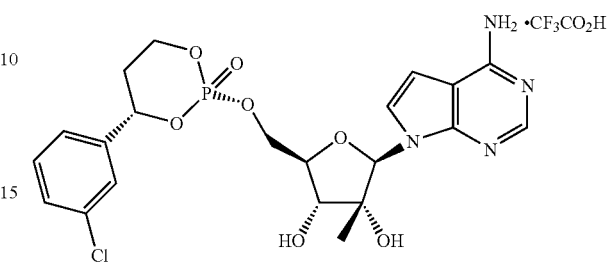

R$_f$=0.45 (10% MeOH in CH$_2$Cl$_2$). mp 145-148° C. Anal Calcd for C$_{21}$H$_{24}$N$_4$O$_7$PCl.0.7 CH$_2$Cl$_2$.1.2 CF$_3$CO$_2$H: C, 40.93; H, 3.79; N, 7.92; F, 9.67.
Found: C, 40.43; H, 3.77; N, 8.22; F, 9.47.

16.42: 4-amino-7-(cis-5'-O-[4-phenyl-5,6-tetramethylene-2-oxo-1,3,2-dioxaphosphorinan-2-yl]-2'-C-methyl-beta-D-ribofuranosyl)-7H-pyrrolo[2,3-d]pyrimidine

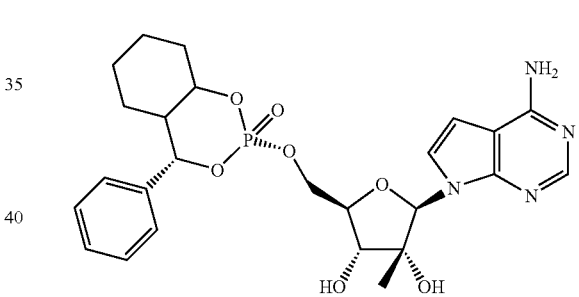

R$_f$=0.24 (15% MeOH in CH$_2$Cl$_2$-1%NH$_4$OH). mp 110-113° C. Anal Calcd for C$_{25}$H$_{31}$N$_4$O$_7$P. 2.0 H$_2$O: C, 53.00; H, 6.23; N, 9.89. Found: C, 53.03; H, 5.93; N, 9.91.

16.43: 4-amino-7-(cis-5'-O-[4-(3-cyanophenyl)-2-oxo-1,3,2-dioxaphosphorinan-2-yl]-2'-C-methyl-beta-D-ribofuranosyl)-7H-pyrrolo[2,3-d]pyrimidine

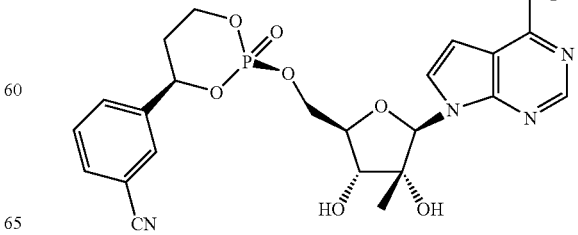

$R_f$=0.51 (15% MeOH in CH$_2$Cl$_2$-1%NH$_4$OH). mp 157-160° C. Anal Calcd for C$_{22}$H$_{24}$N$_5$O$_7$P. 2.5H$_2$O: C, 48.35; H, 5.35; N, 12.82. Found: C, 48.50; H, 5.72; N, 12.77.

Example 17

Preparation of prodrugs of 2'-C-beta-methyl-7-deazaguanosine via trans-phosphate addition The parent nucleoside 2-amino-7-(2-C-methyl-beta-D-ribofuranosyl)-7H-pyrrolo[2,3-d]pyrimidin-4(3H)-one was synthesized as described in US2002-0147160A1 and WO 02/057827.

The nucleoside was converted to corresponding prodrug following the procedures as in steps A, B and C of Example 16.

The following examples were synthesized as described steps A-C.

17.1: 2-amino-7-(cis-5'-O-[4-(3-chlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

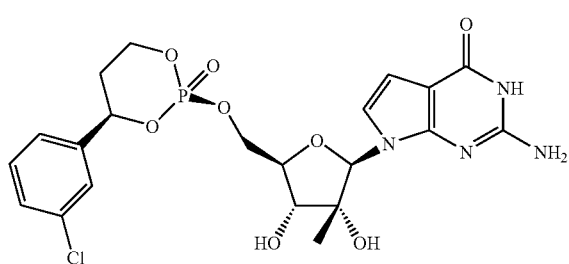

$R_f$=0.30 (10% MeOH in CH$_2$Cl$_2$). Anal calcd for C$_{21}$H$_{24}$ClN$_4$O$_8$P.1.2 CF$_3$CO$_2$NH$_4$.1.0 CF$_3$CO$_2$H: C, 38.22; H, 3.76; N, 9.13. Found: C, 37.93; N, 3.80; N, 9.40.

17.2: 2-amino-7-(cis-5'-O-[4-(S)-(3-chlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

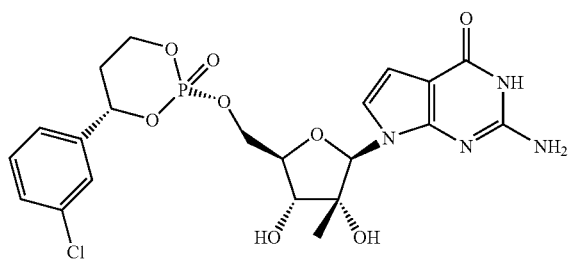

$R_f$=0.15 (10% MeOH in CH$_2$Cl$_2$). mp 175° C. Anal Calcd for C$_{21}$H$_{24}$ClN$_4$O$_8$P.0.5H$_2$O: C, 47.07; H, 4.70; N, 10.46. Found: C, 46.73; H, 4.90, N, 10.16.

17.3: 2-amino-7-(cis-5'-O-[4-(5-bromo-2-fluorophenyl)-2-oxo-1,3,2-dioxaphosphorinan-2-yl]-2'-C methyl-beta-D-ribofuranosyl)-7H-pyrrolo[2,3-d] pyrimidin-4(3H)-one

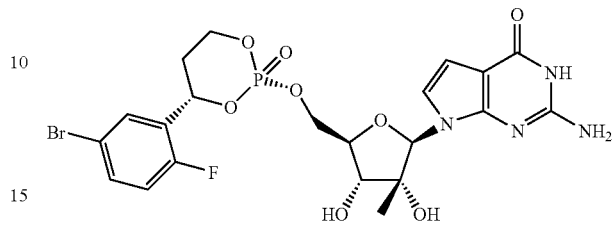

$R_f$=0.41 (15% MeOH in CH$_2$Cl$_2$-1% NH$_4$OH). Anal Calcd for C$_{21}$H$_{23}$BrFN$_4$O$_8$P. 0.5 H$_2$O. 0.2 CF$_3$CO$_2$H: C, 41.38; H, 3.93; N, 9.02. Found: C, 41.60; H, 4.32; N, 8.77.

17.4: 2-amino-7-(cis-5'-O-[4-(3-bromophenyl)-2-oxo-1,3,2-dioxaphosphorinan-2-yl]-2'-C methyl-beta-D-ribofuranosyl)-7H-pyrrolo[2,3-d]pyrimidin-4 (3H)-one trifluoroacetic acid salt

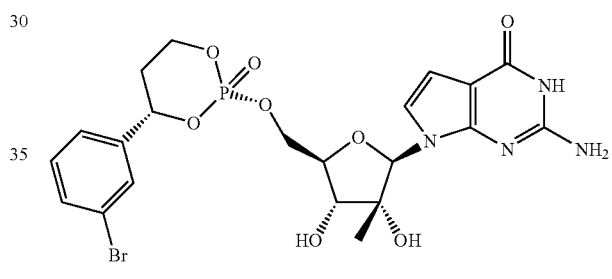

$R_f$=0.38 (15% MeOH in CH$_2$Cl$_2$-1% NH$_4$OH). mp 142-145° C. Anal Calcd for C$_{21}$H$_{24}$N$_4$O$_8$P. 0.7H$_2$O. 0.9 CF$_3$CO$_2$H: C, 39.89; H, 3.86; N, 8.16. Found: C, 39.53; H, 3.65; N, 8.43.

17.5: 2-amino-7-(cis-5'-O-[4-(3-Chloro-4-fluorophenyl)-2-oxo-1,3,2-dioxaphosphorinan-2-yl]-2'-C methyl-beta-D-ribofuranosyl)-7H-pyrrolo[2,3-d] pyrimidin-4(3H)-one

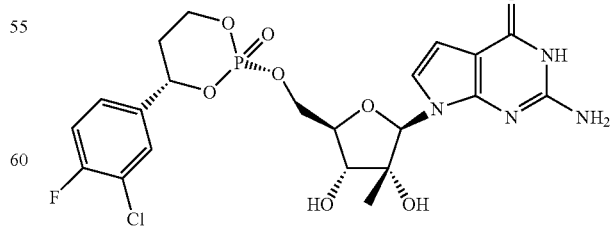

$R_f$=0.45 (20% MeOH in CH$_2$Cl$_2$. Anal Calcd for C$_{21}$H$_{23}$N$_4$O$_8$FClP. 1.4 H$_2$O: C, 44.24, H, 4.78; N, 9.83. Found: C, 43.77; H, 4.78; N, 10.31.

17.6: 2-amino-7-(cis-5'-O-[4-(2,5-difluorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

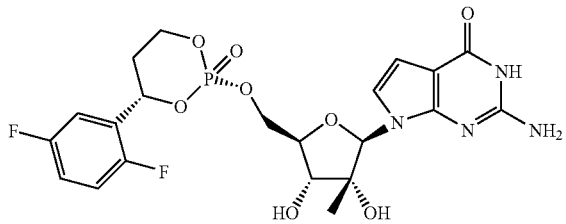

$R_f$=0.35 (20% MeOH in $CH_2Cl_2$). mp 170-173° C. Anal Calcd for $C_{21}H_{23}F_2N_4O_8P$·2.0 $H_2O$·0.4 $CF_3CO_2NH_4$: C, 42.45; H, 4.67; N, 9.99. Found: C, 42.28; H, 4.76 N, 9.96.

17.7: 2-amino-7-(cis-5'-O-[4-(2-chlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

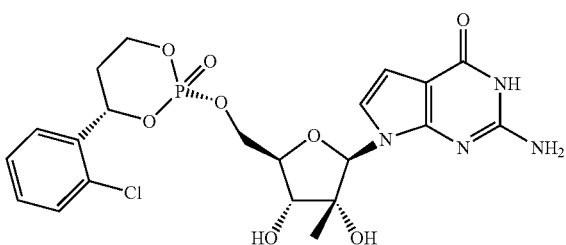

$R_f$=0.25 (15% MeOH in $CH_2Cl_2$–1% $NH_4OH$). Anal Calcd for $C_{21}H_{24}ClN_4O_8P$·1.25 $H_2O$·0.2 $CF_3CO_2H$: C, 44.92; H, 4.70; N, 9.79. Found: C, 44.93; H, 5.09; N, 10.08.

17.8: 2-amino-7-(cis-5'-O-[4-(pyridin-2-yl)-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

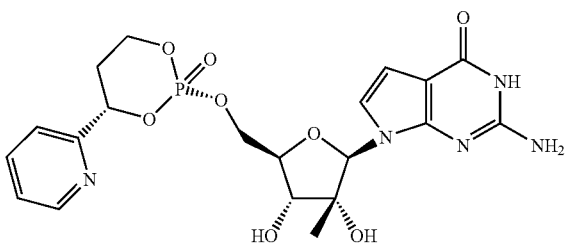

$R_f$=0.4 (15% MeOH in $CH_2Cl_2$). mp 180-190° C. Anal Calcd for $C_{20}H_{24}N_5O_8P$·1.3 $CF_3CO_2H$·0.3 $CH_2Cl_2$: C, 41.23; H, 3.91; N, 10.50. Found: C, 40.96; H, 3.46; N, 11.05.

17.9: 2-amino-7-(cis-5'-O-[4-(2-trifluoromethylphenyl)-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

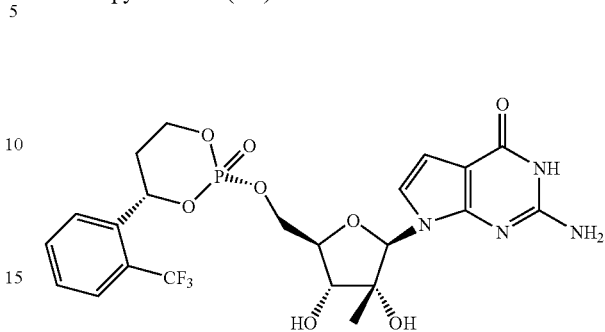

$R_f$=0.4 (10% MeOH in $CH_2Cl_2$). mp 185-188° C. Anal Calcd for $C_{22}H_{24}N_4O_8F_3P$·0.8 $CF_3CO_2H$: C, 43.50; H, 3.84; N, 8.60. Found: C, 43.55; H, 3.97; N, 8.98.

17.10: 2-amino-7-(cis-5'-O-[4-(R)-(3-chlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

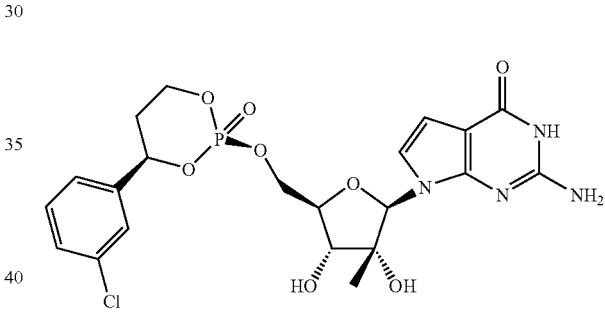

Rf=0.50 (15% MeOH in $CH_2Cl_2$). mp 170-180° C.

17.11: 2-amino-7-(cis-5'-O-[4-(3,5-difluorophenyl)-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

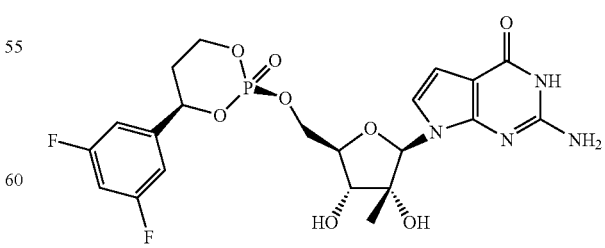

$R_f$=0.30 (10% MeOH in $CH_2Cl_2$) mp 182-185° C. Anal Calcd for $C_{21}H_{23}N_4O_8F_2P$·0.3 EtOAc. 0.2 $CF_3CO_2H$: C, 46.99; H, 4.47; N, 9.70. Found: C, 47.26; H, 4.32; N, 9.46.

17.12: 2-amino-7-(cis-5'-O-[4-(3,5-dichlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

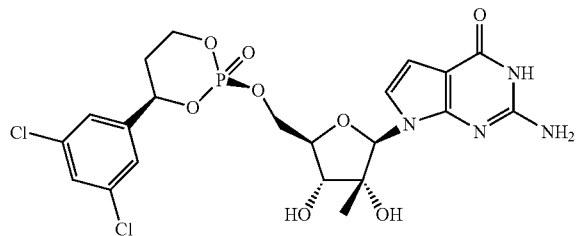

$R_f$=0.35 (10% MeOH in $CH_2Cl_2$). mp 177-180° C. Anal Calcd for $C_{21}H_{23}N_4O_8Cl_2P$.0.1 EtOAc .0.2 $CF_3CO_2H$. C, 44.16; H, 4.08; N, 9.45. Found: C, 44.33; H, 4.44; N, 9.18.

17.13: 2-amino-7-(cis-5'-O-[4-(S)-(pyridin-4-yl)-2-oxo-1,3,2-dioxaphosphorinan-2-yl]-2'-C methyl-beta-D-ribofuranosyl)-7H-pyrrolo[2,3-d]pyrimidin-4(3H)-one

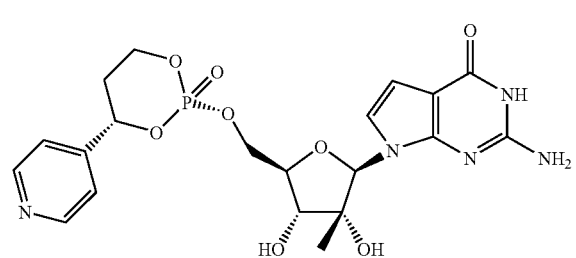

$R_f$=0.21 (15% MeOH in $CH_2Cl_2$-1% $NH_4OH$). mp 138-141° C. Anal Calcd for $C_{20}H_{24}N_5O_8P$. 2.2 $H_2O$: C, 45.07; H, 5.33; N, 13.14. Found: C, 45.12; H, 5.40; N, 12.89.

17.14: 2-amino-7-(cis-5'-O-[4-(3-fluorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

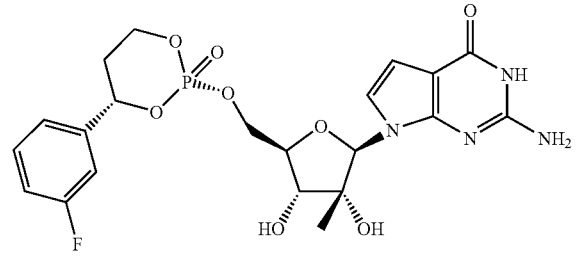

$R_f$=0.25 (10% MeOH in $CH_2Cl_2$). mp 170° C. Anal Calcd for $C_{21}H_{24}FN_4O_8P$.1.5 $H_2O$: C, 46.93; H, 5.06; N,10.42. Found: C, 46.92; H, 5.12; N, 10.44.

17.15: 2-amino-7-(cis-5'-O-[4-(3-bromo-4-fluorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

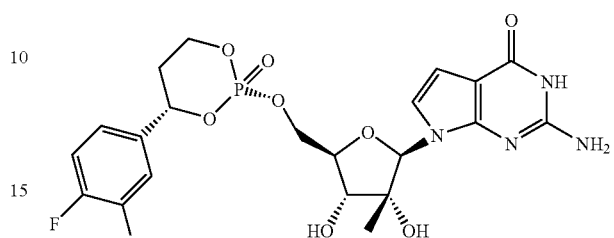

$R_f$=0.25 (10% MeOH in $CH_2Cl_2$). mp 175-179° C. Anal Calcd for $C_{21}H_{23}BrFN_4O_8P$.0.5 $H_2O$. 0.5 EtOAc: C, 43.01; H, 4.39; N, 8.72. Found: C, 43.03; H, 4.49; N, 8.49.

17.16: 2-amino-7-(cis-5'-O-[4-(R)-phenyl-2-oxo-1,3,2-dioxaphosphorinan-2-yl]-2'-C methyl-beta-D-ribofuranosyl)-7H-pyrrolo[2,3-d]pyrimidin-4(3H)-one

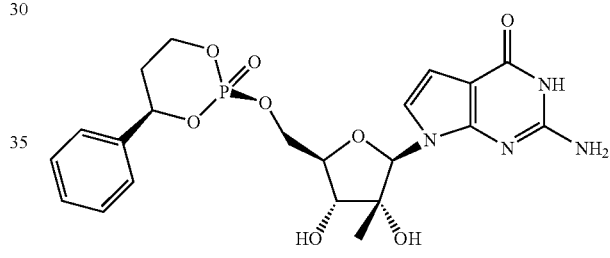

Rf=0.30 (10% MeOH in $CH_2Cl_2$) mp 128-133° C. Anal Calcd for $C_{21}H_{25}N_4O_8P$. 1.1 $H_2O$.0.3 $CF_3CO_2H$: C, 47.48; H, 5.07; N, 10.25. Found: C, 47.61; H, 5.36; N, 9.91.

17.17: 2-amino-7-(cis-5'-O-[4,5-cis-diphenyl-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

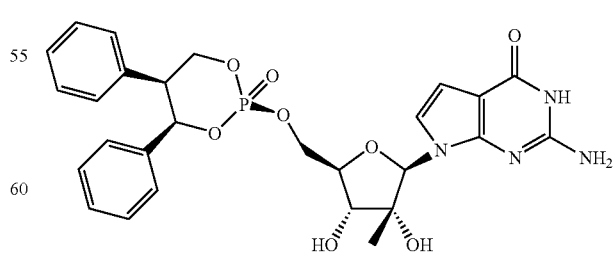

$R_f$=0.45 (20% MeOH in $CH_2Cl_2$). mp 187-190° C. Anal Calcd for $C_{27}H_{29}N_4O_8P$.2 $H_2O$.1.3 $CF_3CO_2H$: C, 47.23; H, 4.59; N, 7.44. Found: C, 46.83; H, 4.33; N, 7.31.

17.18: 2-amino-7-(cis-5'-O-[6,6-dimethyl-4-phenyl-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

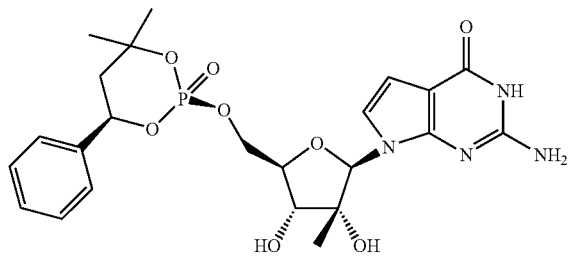

$R_f$=0.40 (20% MeOH in CH$_2$Cl$_2$). mp 192-194° C. Anal Calcd for C$_{23}$H$_{29}$N$_4$O$_8$P.2.0 H$_2$O.1.0 CF$_3$CO$_2$H: C, 44.78; H, 5.11; N, 8.36. Found: C, 44.40; H, 4.67; N, 8.22.

17.19: 2-amino-7-(cis-5'-O-[cis-(5-methoxy-4-phenyl)-2-oxo-1,3,2-dioxaphosphorinan-2-yl]-2'-C methyl-beta-D-ribofuranosyl)-7H-pyrrolo[2,3-d]pyrimidin-4(3H)-one

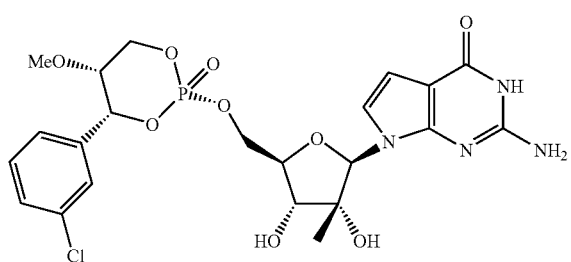

$R_f$=0.30 (20% MeOH in CH$_2$Cl$_2$). mp 148-151° C. Anal Calcd for C$_{22}$H$_{26}$N$_4$O$_9$ClP.1.0 H$_2$O: C, 45.96; H, 4.91; N, 9.75. Found: C, 46.03; H, 4.80; N, 9.64.

17.20: 2-amino-7-(cis-5'-O-[4-(2,3-difluorophenyl)-2-oxo-1,3,2-dioxaphosphorinan-2-yl]-2'-C methyl-beta-D-ribofuranosyl)-7H-pyrrolo[2,3-d]pyrimidin-4(3H)-one trifluoroacetic acid salt

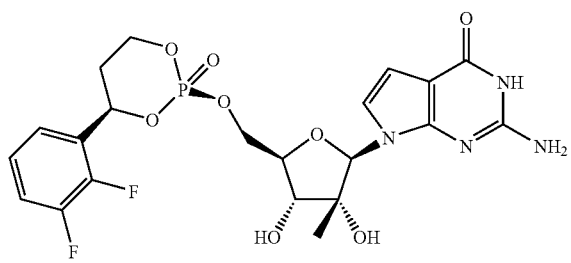

$R_f$=0.5 (10% MeOH in CH$_2$Cl$_2$). mp 215-220° C. Anal Calcd for C$_{21}$H$_{23}$N$_4$O$_8$F$_2$P.1.0 H$_2$O.1.0 CF$_3$CO$_2$H: C, 41.83; H, 3.97; N, 8.48. Found: C, 41.70; H, 3.77; N, 8.50.

17.21: 2-amino-7-(cis-5'-O-[4-(2-bromophenyl)-2-oxo-1,3,2-dioxaphosphorinan-2-yl]-2'-C methyl-beta-D-ribofuranosyl)-7H-pyrrolo[2,3-d]pyrimidin-4(3H)-one

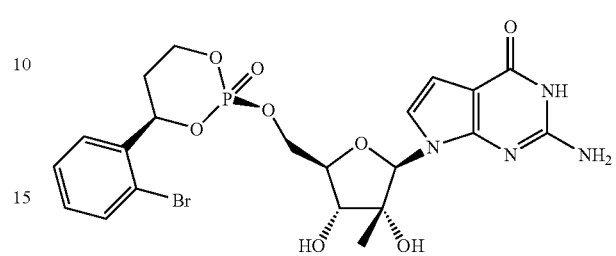

$R_f$=0.15 (10% MeOH in CH$_2$Cl$_2$). mp 180° C. Anal Calcd for C$_{21}$H$_{24}$BrN$_4$O$_8$P.1.1 H$_2$O: C, 42.67; H, 4.47; N, 9.48. Found: C, 42.51, H, 4.60; N, 9.58.

17.22: 2-amino-7-(cis-5'-O-[4-(3,4-dichlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

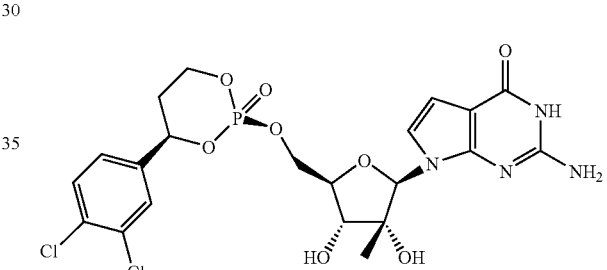

$R_f$=0.30 (10% MeOH in CH$_2$Cl$_2$). mp 192-195° C. Anal Calcd for C$_{21}$H$_{23}$N$_4$O$_8$Cl$_2$P.0.2 CF$_3$CO$_2$H. 0.2 EtOAc: C, 44.31; H, 4.15; N, 9.31. Found: C, 44.40; H, 3.94; N, 9.21.

17.23: 2-amino-7-(cis-5'-O-[4-(3,5-bis-(trifluoromethylphenyl)-2-oxo-1,3,2-dioxaphosphorinan-2-yl]-2'-C methyl-beta-D-ribofuranosyl)-7H-pyrrolo[2,3-d]pyrimidin-4(3H)-one

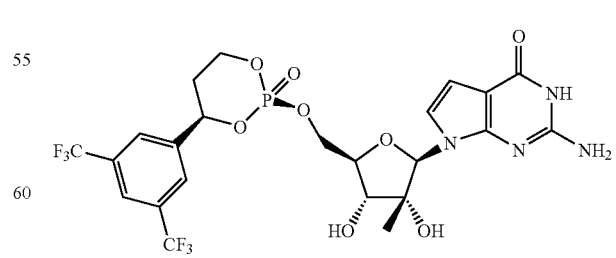

$R_f$=0.15 (10% MeOH in CH$_2$Cl$_2$) mp 155-175° C. Anal Calcd for C$_{23}$H$_{23}$F$_6$N$_4$O$_8$P.0.6 H$_2$O: C, 43.22; H, 3.82; N, 8.76. Found: C, 43.08; H, 4.03; N, 8.94.

17.24: 2-amino-7-(cis-5'-O-[4-(3-trifluoromethylphenyl)-2-oxo-1,3,2-dioxaphosphorinan-2-yl]-2'-C methyl-beta-D-ribofuranosyl)-7H-pyrrolo[2,3-d]pyrimidin-4(3H)-one

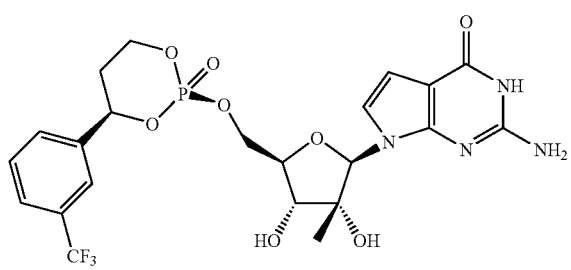

$R_f$=0.15 (10% MeOH in CH$_2$Cl$_2$). mp 145-165° C. Anal Calcd for C$_{22}$H$_{24}$F$_3$N$_4$O$_8$P.1 H$_2$O: C, 45.68; H, 4.53; N, 9.69. Found: C, 45.31; H, 4.88; N, 9.71.

17.25: 2-amino-7-(cis-5'-O-[4-(2,4-dichlorophenyl)-2-oxo-1,3,2-dioxaphosphorinan-2-yl]-2'-C methyl-beta-D-ribofuranosyl)-7H-pyrrolo[2,3-d]pyrimidin-4(3H)-one

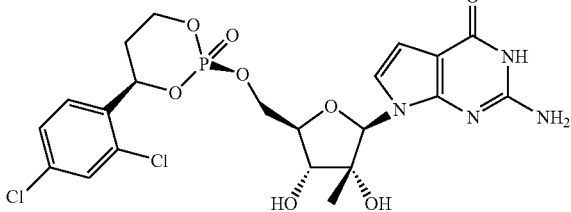

$R_f$=0.15 (10% MeOH in CH$_2$Cl$_2$) mp 175° C. Anal Calcd for C$_{21}$H$_{23}$C$_{12}$N$_4$O$_8$P.1H$_2$O: C, 43.54; H, 4.35; N, 9.67. Found: C, 43.32; H, 4.35; N, 9.55.

17.26: 2-amino-7-(cis-5'-O-[4-(5-bromo-pyridin-3-yl)-2-oxo-1,3,2-dioxaphosphorinan-2-yl]-2'-C methyl-beta-D-ribofuranosyl)-7H-pyrrolo[2,3-d]pyrimidin-4(3H)-one

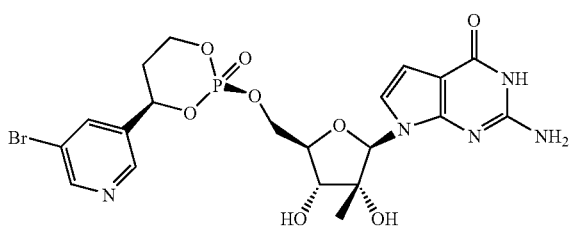

$R_f$=0.3 (10% MeOH in CH$_2$Cl$_2$) mp 185-189° C. Anal Calcd for C$_{20}$H$_{23}$N$_5$O$_8$BrP.1.5 CF$_3$CO$_2$H: C, 37.16; H, 3.32; N, 9.42. Found: C, 37.23; H, 3.44; N, 9.33.

17.27: 2-amino-7-(cis-5'-O-[4-(pyridin-3-yl)-2-oxo-1,3,2-dioxaphosphorinan-2-yl]-2'-C methyl-beta-D-ribofuranosyl)-7H-pyrrolo[2,3-d]pyrimidin-4(3H)-one

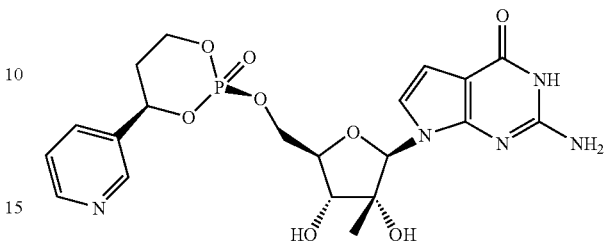

$R_f$=0.15 (10% MeOH in CH$_2$Cl$_2$); Anal Calcd for C$_{20}$H$_{24}$N$_5$O$_8$P.1 H$_2$O.0.4 EtOAc: C, 47.46; H, 5.38; N, 12.81. Found: C, 47.40; H, 5.17; N, 12.78.

Example 18

5'-O-[4-(3-chlorophenyl)-2-oxo-1,3,2-dioxaphosphorinan-2-yl]-2'-C-methyladenosine

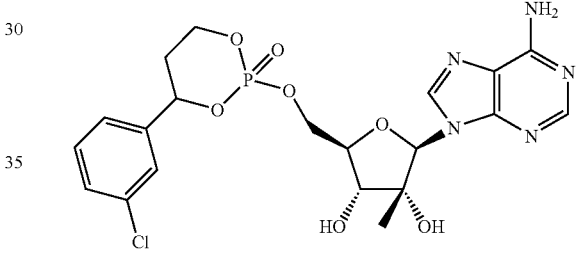

2'-C-methyl adenosine was made as described in WO01/90121.

Step A:

General procedure for synthesis of cyclic phosphoramidites from substituted diols:

To a solution of commercially available diisopropyl phosphoramidous dichloride (1 mmol) in THF (5 mL) was added 1,3-diol (1 mmol) and triethylamine (4 mmol) in THF (5 mL) at −78° C. over 30 min. The reaction was slowly warmed to room temperature and left stirring overnight. Reaction mixture was filtered to remove salts and filtrate was concentrated to give crude product. Silica gel column chromatography provided pure cyclic diisopropyl phosphoramidite of 1,3-diol.

Step B:

General procedure for nucleoside-cyclic phosphoramidite coupling and oxidation:

(*J. Org. Chem.*, 1996, 61, 7996)

To a solution of nucleoside (1 mmol) and cyclic phosphoramidite (1 mmol) in DMF (10 mL) was added benzimidazolium triflate (1 mmol). The reaction was stirred for 30 min at room temperature. The mixture was cooled to −40° C. before addition of t-butylhydro peroxide (2 mmol) and left at room temperature overnight. Concentration under reduced pressure and chromatography of crude product resulted in pure cyclic propyl prodrug.

$R_f$=0.46 (12% MeOH in CH$_2$Cl$_2$). mp 153° C. Anal calcd for C$_{20}$H$_{23}$ClN$_5$O$_7$P: C, 46.93; H, 4.53; N, 13.63. Found: C, 47.06; H, 4.36; N, 13.68.

Example 19 cis-5'-O-[4-(3-Chlorophenyl)-2-oxo-1,3,2-dioxaphosphorinan-2-yl]-2'-C-methyl-guanosine

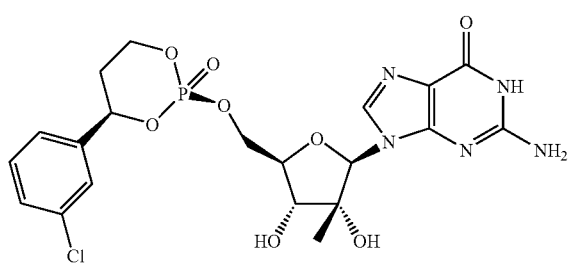

2'-C-Methyl guanosine was made as described in WO01/90121.

The nucleoside was converted to corresponding prodrug following the procedures as in steps A, B and C of Example 16.

$R_f$=0.35 (25% MeOH in CH$_2$Cl$_2$). mp>230° C. Anal calcd for C$_{20}$H$_{23}$ClN$_5$O$_8$P: C, 45.51; H, 4.39; N, 13.27. Found: C, 45.89; H, 4.44; N, 13.23.

Example 20 cis-5'-O-[4-(S)-(3-chlorophenyl)-2-oxo-1,3,2-dioxaphosphorinan-2-yl]-2'-C-beta-methyl-guanosine

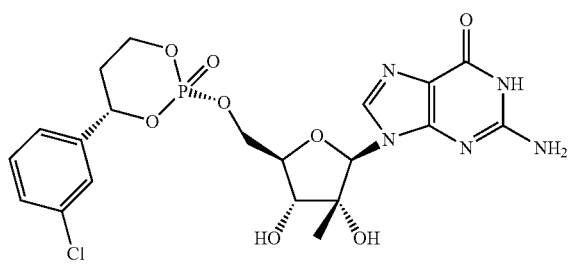

The compound was synthesized in a similar sequence as Example 19 using the phosphorylating agent whose preparation is described in Example 14.

$R_f$=0.35 (20% MeOH in CH$_2$Cl$_2$). mp>180° C. Anal calcd for C$_{20}$H$_{23}$N$_5$O$_8$ClP.1.0H$_2$O. 0.8 CF$_3$CO$_2$H: C, 40.72; H, 4.08; N, 10.99. Found: C, 40.43; N, 4.41; N, 11.34.

Example 21

Preparation of prodrugs of 2'-C-beta-methyl-adenosine via trans-phosphate addition 2'-C-methyl adenosine was made as described in WO01/90121.

The nucleoside was converted to corresponding prodrug following the procedures as in steps A, B and C of Example 16.

trans-phosphorylating agents utilized in step B are synthesized by the procedures as described in examples 1-15.

21.1: cis-5'-O-[4-(S)-(3-chlorophenyl)-2-oxo-1,3,2-dioxaphosphorinan-2-yl]-2'-C-beta-methyl-adenosine trifluoroacetic acid salt

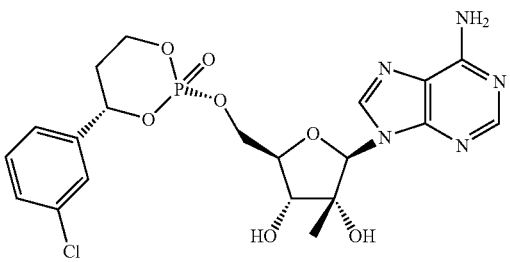

$R_f$=0.3 (5% MeOH in EtOAc). mp 125-128° C. Anal calcd for C$_{20}$H$_{23}$ClN$_5$O$_7$P.1.7 CF$_3$CO$_2$H: C, 39.83; H, 3.53; N, 9.92. Found: C; 39.52, H; 3.46, N; 10.21.

21.2: cis-5'-O-[4-(3-cyanophenyl)-2-oxo-1,3,2-dioxaphosphorinan-2-yl]-2'-C-beta-methyl-adenosine

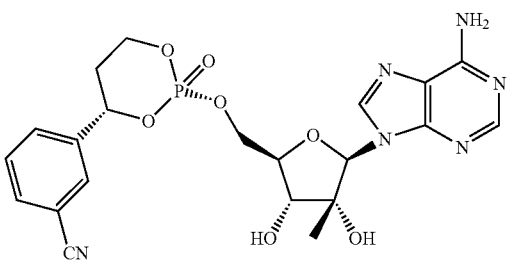

$R_f$=0.43 (15% MeOH in CH$_2$Cl$_2$–1% NH$_4$OH). mp 153-156° C. Anal calcd for C$_{21}$H$_{23}$N$_6$O$_7$P.1.1 H$_2$O: C, 48.30; H, 4.86; N, 16.09. Found: C, 48.53; H, 5.1 1; N, 15.75.

21.3: cis-5'-O-[4-(2,5difluorophenyl)-2-oxo-1,3,2-dioxaphosphorinan-2-yl]-2'-C-beta-methyl-adenosine

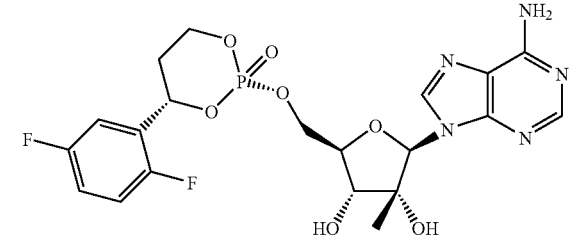

$R_f$=0.60 (15% MeOH in CH$_2$Cl$_2$–1% NH$_4$OH). mp 75-78°. Anal calcd for C$_{20}$H$_{22}$F$_2$N$_5$O$_7$P.0.3 CH$_2$Cl$_2$: C, 45.25; H, 4.23; N, 13.00. Found: C, 45.07; H, 3.94; N, 12.69.

21.4: cis-5'-O-[4-(3,5-difluorophenyl)-2-oxo-1,3,2-dioxaphosphorinan-2-yl]-2'-C-beta-methyl-adenosine

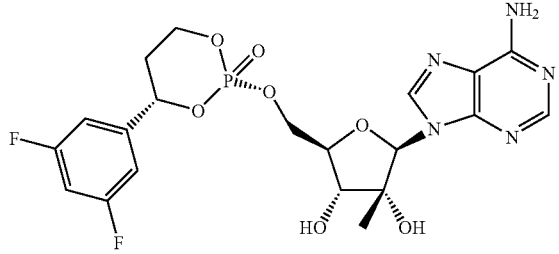

$R_f$=0.65 (15% MeOH in CH$_2$Cl$_2$–1% NH$_4$OH). mp 120-123° C. Anal calcd for C$_{20}$H$_{22}$F$_2$N$_5$O$_7$P.1.5 H$_2$O.0.1 C$_6$H$_{14}$: C, 45.07; H, 4.85; N, 12.76. Found: C, 45.04 ; H, 5.25; N, 12.59.

21.5: cis-5'-O-[4-(S)-(pyridin-4-yl)-2-oxo-1,3,2-dioxaphosphorinan-2-yl]-2'-C-beta-methyl-adenosine

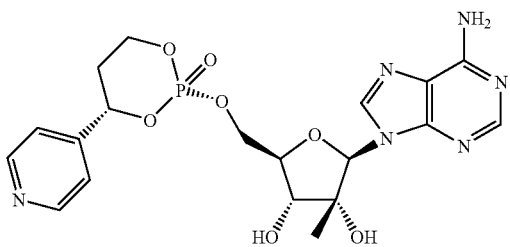

$R_f$=0.55 (15% MeOH in CH$_2$Cl$_2$-1% NH$_4$OH). Anal calcd for C$_{19}$H$_{23}$N$_6$O$_7$P.2.5H$_2$O: C, 43.60; H, 5.39; N, 16.06. Found: C, 43.35; H, 5.54; N, 16.05.

21.6: cis-5'-O-[4-(3-bromophenyl)-2-oxo-1,3,2-dioxaphosphorinan-2-yl]-2'-C-beta-methyl adenosine

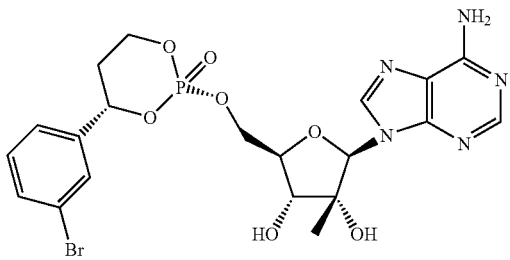

$R_f$=0.5 (10% MeOH in CH$_2$Cl$_2$). mp 108-110° C. Anal calcd for C$_{20}$H$_{23}$N$_5$O$_7$BrP.1.5 H$_2$O.0.4 CF$_3$CO$_2$H: C, 39.72; H, 4.23; N, 11.14. Found: C, 39.44; H, 4.55; N, 11.18.

21.7: cis-5'-O-[4-(pyridin-2-yl)-2-oxo-1,3,2-dioxaphosphorinan-2-yl]-2'-C-beta-methyl-adenosine trifluoroacetic acid salt

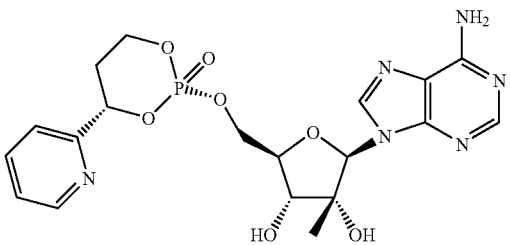

$R_f$=0.4 (10% MeOH in CH$_2$Cl$_2$). mp 118-120° C. Anal calcd for C$_{19}$H$_{23}$N$_6$O$_7$P.2.0 H$_2$O.1.0 CF$_3$CO$_2$H: C, 40.14; H, 4.49; N, 13.37. Found: C, 40.36; H, 4.92; N, 13.63.

21.8: cis-5'-O-[4-(4-methylsulfonylphenyl)-2-oxo-1,3,2-dioxaphosphorinan-2-yl]-2'-C-beta-methyl-adenosine trifluoroacetic acid salt

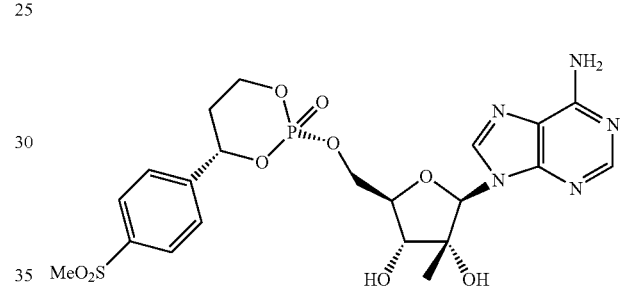

$R_f$=0.3 (10% MeOH in CH$_2$Cl$_2$). mp 185-187° C. Anal calcd for C$_{21}$H$_{26}$N$_5$O$_9$PS.0.6 H$_2$O.0.6 CF$_3$CO$_2$H: C, 42.01; H, 4.41; N, 11.03. Found: C, 41.93; H, 4.73; N, 10.97.

21.9: cis-5'-O-[4-(pyridine-3-yl)-2-oxo-1,3,2-dioxaphosphorinan-2-yl]-2'-C-beta-methyl-adenosine

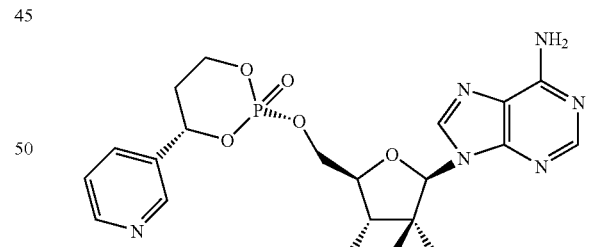

$R_f$=0.2 (10% MeOH in EtOAc). mp 137-140° C. Anal calcd for C$_{19}$H$_{23}$N$_6$O$_7$P.1.5 H$_2$O.0.4 EtOAc. C, 45.76; H, 15.54; N, 5.44. Found: C; 45.88; H, 15.19; N, 5.09.

Example 22

General procedure for preparation of 3'-acetyl prodrugs of 2'-C-beta-methyl-7-deazaadenosine cyclic prodrugs To a solution of 5'-substituted cyclic propyl prodrug (0.3 mmol) in pyridine (3 mL) was added acetic anhydride (0.6 mL) at 0° C. The reaction was left at 0° C. for 18 h. Excess acetic anhydride was quenched with ethanol (3 mL). The mixture was concentrated and azeotroped with additional ethanol (2×5 mL). The crude residue was chromatographed to get pure monoacetylated compound as a solid.

22.1: 4-amino-7-(3'-acetyl-cis-5'-O-[4-(S)-(pyridin-4-yl)-2-oxo-1,3,2-dioxaphosphorinan-2-yl]-2'-C-methyl-beta-D-ribofuranosyl)-7H-pyrrolo[2,3-d]pyrimidine

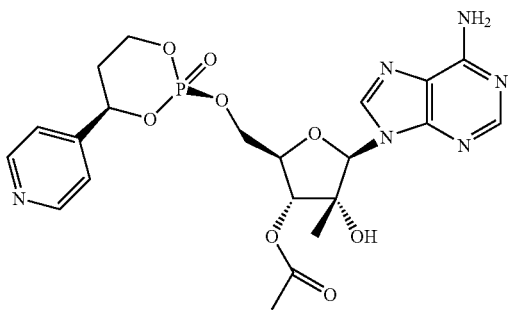

$R_f$=0.35 (15% MeOH in $CH_2Cl_2$). mp 182-185° C. Anal calcd for $C_{22}H_{26}N_5O_8P \cdot 1.5\ H_2O \cdot 0.2\ CH_2Cl_2$: C, 47.32; H, 5.56; N, 12.43. Found: C, 47.19; H, 4.78; N, 12.09.

22.2: 4-amino-7-(3'-acetyl-cis-5'-O-[4-(S)-(3-chlorophenyl)-2-oxo-1,3,2-dioxaphosphorinan-2-yl]-2'-C-methyl-beta-D-ribofuranosyl)-7H-pyrrolo[2,3-d]pyrimidine

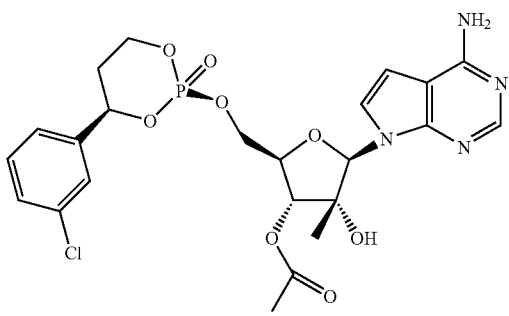

$R_f$=0.35 (10% MeOH in $CH_2Cl_2$). mp 90-93° C. Anal calcd for $C_{23}H_{26}N_4O_8ClP \cdot 1.0\ H_2O$: C, 48.39; H, 4.94; N, 9.81. Found: C, 48.79; H, 4.85; N, 9.91.

Example 23

General procedure for preparation of 2',3'-cyclic carbonate prodrugs of 2'-C-beta-methyl-7-deazaadenosine cyclic prodrugs To a solution of 5'-substituted cyclic propyl prodrug (0.25 mmol) in DMF (2.5 mL) was added carbonyl diimidazole (CDI) (0.5 mmol) at 0° C. The reaction was warmed to room temperature and stirred for 4 h. Solvent was removed under reduced pressure and the crude product was chromatographed to give 2',3'-carbonate as a solid.

23.1: 4-amino-7-(2',3'-carbonyl-cis-5'-O-[4-(S)-(3-chlorophenyl)-2-oxo-1,3,2-dioxaphosphorinan-2-yl]-2'-C-methyl-beta-D-ribofuranosyl)-7H-pyrrolo[2,3-d]pyrimidine

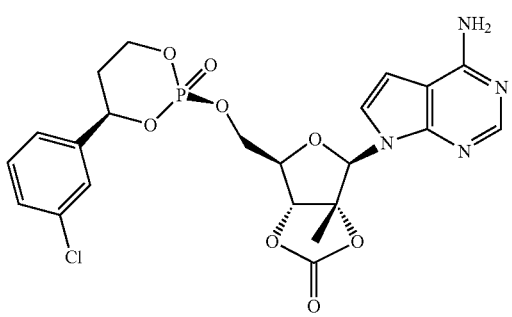

$R_f$=0.45 (10% MeOH in $CH_2Cl_2$). mp 127-130° C. Anal calcd for $C_{22}H_{22}N_4O_8PCl \cdot 1.0\ H_2O$: C, 47.62; H, 4.36; N, 10.10. Found: C, 47.94; H, 4.10; N, 10.13.

23.2: 4-amino-7-(2',3'-carbonyl-cis-5'-O-[4-(S)-(pyridin-4-yl)-2-oxo-1,3,2-dioxaphosphorinan-2-yl]-2'-C-methyl-beta-D-ribofuranosyl)-7H-pyrrolo[2,3-d]pyrimidine

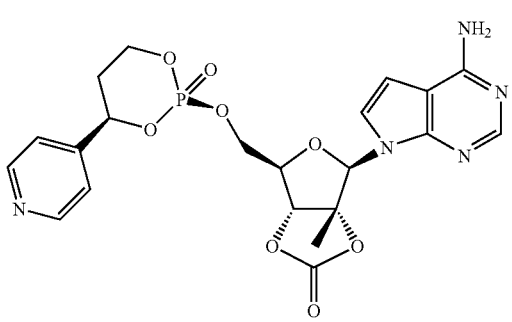

$R_f$=0.4 (20% MeOH in $CH_2Cl_2$). mp 192-195° C. Anal calcd for $C_{21}H_{22}N_5O_8P \cdot 1.0\ H_2O$: C, 48.37; H, 4.64; N, 13.43. Found: C, 48.41; H, 4.39; N, 13.60.

Example 24

Preparation of 3'-L-valinyl ester prodrugs of 2'-C-beta-methyl-7-deazaadenosine cyclic prodrugs 24.1: 4-amino-7-(cis-5'-O-[4-(S)-(3-chlorophenyl)-2-oxo-1,3,2-dioxaphosphorinan-2-yl]-2'-C-methyl-3'-L-valinyl-beta-D-ribofuranosyl)-7H-pyrrolo[2,3-d]pyrimidine 5'-substituted cyclic prodrug (16.5) was made as described in example 16.

Step A:

To a solution of BOC-L-Val (217 mg, 1.0 mmol) in THF (5 mL) was added carbonyl diimidazole (CDI) (162 mg, 1 mmol). The reaction was warmed to 50° C. and allowed to stir for 1 h. The resulting mixture was added to a solution of 5'-substituted cyclic prodrug (16.5) (0.50 mmol) in DMF (3 mL) followed by triethylamine (1.5 mL) and 4-dimethylamino pyridine (6 mg, 0.05 mmol). The reaction was heated at 80° C. for 3 h. The reaction mixture was concentrated under reduced pressure and the crude was extracted with 10% MeOH—$CH_2Cl_2$. The organic extract was washed with water, dried and concentrated. The crude residue was chromatographed by eluting with 5%-10% MeOH—$CH_2Cl_2$ to give 3'-BOC-L-Val adduct of 5'-cyclic propyl prodrug (200 mg).

Step B:

The BOC protected prodrug (200 mg) was dissolved in pre-cooled 70% aqueous trifluoroacetic acid (10 mL) at 0° C. The reaction was stirred at 0° C. for 3 h. The mixture was concentrated under reduced pressure and azeotroped with ethanol (2×5 mL). The crude residue was chromatographed by eluting with 5%-20% MeOH in $CH_2Cl_2$ to give the BOC deprotected prodrug (140 mg).

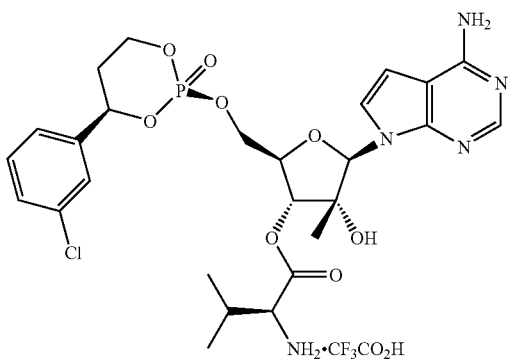

$R_f$=0.35 (15% MeOH in $CH_2Cl_2$). mp 132-135° C.

Anal calcd for $C_{26}H_{33}N_5O_8ClP \cdot 2.3\, CF_3CO_2H \cdot 2.1\, H_2O$: C, 40.38; H, 4.37; N, 7.70. Found: C, 39.94; H, 3.93; N, 7.48.

Example 25

Preparation of 6-azido prodrug of 2'-C-beta-methyl-7-deazaadenosine 5'-monophosphate cyclic prodrugs 4-Chloro-7-(2'-C-methyl-beta-D-ribofuranosyl)-7H-pyrrolo[2,3-d]pyrimidine was prepared as described in WO 02/057287.

Step A:

To a solution of 4-chloro-7-(2'-C-methyl-beta-D-ribofuranosyl)-7H-pyrrolo[2,3-d]pyrimidine (162 mg, 0.54 mmol) in DMF (5 mL) was added sodium azide (70 mg, 1.08 mmol) at room temperature. The reaction was heated to 60° C. and stirred for 18 h. The mixture was concentrated and chromatographed by eluting with $CH_2Cl_2$ to 5% MeOH—$CH_2Cl_2$ to give the azido substitution product (102 mg).

25.1: 4-azido-7-(2'-C-methyl-beta-D-ribofuranosyl)-7H-pyrrolo[2,3-d]pyrimidine

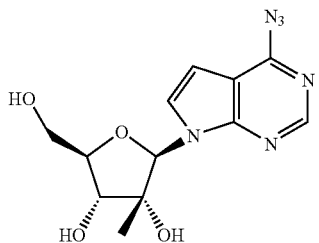

$R_f$=0.4 (5% MeOH in $CH_2Cl_2$). mp 179-180° C. Anal calcd for $C_{12}H_{14}N_6O_4$: C, 47.06; H, 4.61; N, 27.44. Found: C, 46.97; H, 4.71; N, 27.28.

Step B:

5'-substituted monophosphate cyclic prodrug of 4-Azido-7-(2'-C-methyl-beta-D-ribofuranosyl)-7H-pyrrolo[2,3-d]pyrimidine is made as described in Example 16.

Biological Examples

Examples of use of the method of the invention include the following. It will be understood that these examples are exemplary and that the method of the invention is not limited solely to these examples.

For the purposes of clarity and brevity, chemical compounds are referred to as synthetic example numbers in the biological examples below.

Example A

In Vitro Activation of Prodrug Analogues by Rat Liver Microsomes. Quantification by By-Product Capture The prodrug analogues were tested for activation in rat liver microsomes by means of a prodrug byproduct capture assay.

Methods:

Prodrugs were tested for activation by liver microsomes isolated from rats induced with dexamethasone to enhance CYP3A4 activity (Human Biologics Inc., Phoenix Ariz.). The study was performed at 2 mg/mL rat liver microsomes, 100 mM $KH_2PO_4$, 10 mM glutathione, 25 µM or 250 µM compound, and 2 mM NADPH for 0-7.5 min. in an Eppendorf Thermomixer 5436 at 37° C., speed 6. The reactions were initiated by addition of NADPH following a 2-min. preincubation. Reactions were quenched with 60% methanol at 0, 2.5, 5, and 7.5 min. L-Glutamyl-L-(S-(3-oxo-3-(3-chlorophenyl)propyl)cysteinylglycine, a glutathione adduct of the by-product of prodrug activation, 3-chlorophenyl vinyl ketone, was quantified following extraction of the reaction with 1.5 volumes of methanol. The extracted samples were centrifuged at 14,000 rpm in an Eppendorf microfuge and the supernatant analyzed by HPLC for L-glutamyl-L-(S-(3-oxo-3-(3-chlorophenyl)propyl)cysteinylglycine content. Spiked L-glutamyl-L-(S-(3-oxo-3-(3-chlorophenyl)propyl)cysteinylglycine standards (1-30 µM) were prepared in 2 mg/mL microsomes under reaction conditions and then quenched and processed in an identical fashion to unknown samples. For HPLC analysis, the loading mobile phase buffer (Buffer A)

consisted of a 9:1 ratio (v/v) of 20 mM potassium phosphate, pH 6.2 and acetonitrile. Extract (100 μL) was injected onto a Beckman Ultrasphere ODS column (4.6×250 mM, part# 235329). The column was eluted with a gradient to 60% acetonitrile. The elution of L-glutamyl-L-(S-(3-oxo-3-(3-chlorophenyl)propyl)cysteinylglycine (retention time 10.4 min.) was monitored at 245 nm.

Results:

Activation of Compounds in Rat Liver Microsomes

| Compound | Activation (250 μM) (nmol/mg/min) |
|---|---|
| 18 | 4.7 |
| 16.5 | 0.24 |
| 17.2 | 0.397 |

Conclusion:

Formation of product, L-glutamyl-L-(S-(3-oxo-3-(3-chlorophenyl)propyl) cysteinylglycine indicated activation of Compound 18 prodrug at a rate of 4.7 nmol/mg/min.

Example B

In Vitro Activation of Prodrug Analogues by Rat Liver Microsomes. Quantification by LC-MS/MS Prodrug analogues were tested for activation to NMP in reactions catalyzed by the microsomal fraction of rat liver.

Methods:

Prodrugs were tested for activation by liver microsomes isolated from rats induced with dexamethasone to enhance CYP3A4 activity (Human Biologics Inc., Phoenix Ariz.). Reactions were conducted in 0.1 M $KH_2PO_4$, pH 7.4, in the presence of 2 mM NADPH and liver microsomes (1 mg/mL). Reaction mixtures were incubated for 5 min. in an Eppendorf Thermomixer 5436 (37° C., speed 6). Reactions were terminated by the addition of 1.5 volumes of methanol. The resulting extracts were clarified by centrifugation at 14,000 rpm in an Eppendorf microfuge (20 min.). The supernatants (200 μL) were evaporated under vacuum and heat to dryness. The dried residue was reconstituted with 200 μL of water and the mixture was centrifuged for 10 min at 14,000 rpm. A mixture of 35 μL aliquot of supernatant and 35 μL of mobile phase A (20 mM N-N-dimethylhexylamine and 10 mM propionic acid in 20% methanol) was analyzed by LC-MS/MS (Applied Biosystems, API 4000) equipped with an Agilent 1100 binary pump and a LEAP injector. NMP was detected by using MS/MS mode (M⁻/78.8) and quantified based on comparison to a standard of lamivudine monophosphate.

Results:

Activation of Compounds in Rat Liver Microsomes

| Compound | Activation (250 μM) (nmol/mg/min) |
|---|---|
| 16.2 | 0.158 |
| 16.3 | 0.159 |
| 16.4 | 0.020 |
| 16.5 | 0.195 |
| 16.7 | 0.365 |
| 17.2 | 1.764 |
| 16.8 | 0.160 |
| 16.9 | 0.126 |
| 16.10 | 0.077 |
| 16.11 | 0.142 |
| 16.12 | 0.070 |
| 16.13 | 0.001 |
| 16.14 | 0.082 |
| 16.15 | 0.215 |
| 16.16 | 0.070 |
| 16.17 | 0.006 |
| 16.18 | 0.058 |
| 16.19 | 0.213 |
| 16.20 | 0.063 |
| 16.21 | 0.040 |
| 16.22 | 0.081 |
| 16.23 | 0.001 |
| 16.24 | 0.004 |
| 16.25 | 0.068 |
| 16.26 | 0.256 |
| 16.27 | 0.286 |
| 16.28 | 0.121 |
| 17.3 | 1.119 |
| 16.29 | 0.172 |
| 17.4 | 0.862 |
| 17.5 | 1.173 |
| 17.6 | 1.758 |
| 16.30 | 0.108 |
| 16.31 | 0.217 |
| 16.32 | 0.186 |
| 17.7 | 0.761 |
| 17.8 | 0.264 |
| 17.9 | 0.488 |
| 17.10 | 1.033 |
| 17.11 | 1.996 |
| 17.12 | 0.918 |
| 17.13 | 1.039 |
| 17.14 | 1.636 |
| 17.15 | 0.969 |
| 17.16 | 0.863 |
| 17.18 | 0.095 |
| 17.20 | 1.091 |
| 17.21 | 0.623 |
| 17.22 | 0.599 |
| 17.23 | 0.094 |
| 17.24 | 0.240 |

Example C

In Vitro Activation in Human Liver Microsomes. Quantification by By-Product Capture The prodrug analogues are tested for activation in human liver microsomes.

Methods:

Human liver microsomes are purchased from In Vitro Technologies (IVT1032). The study is performed at 2 mg/mL human liver microsomes, 100 mM $KH_2PO_4$, 10 mM glutathione, 25 μM or 250 μM compound, and 2 mM NADPH for 0-7.5 min. in an Eppendorf Thermomixer 5436 at 37° C., speed 6. The reactions are initiated by addition of NADPH following a 2-min. preincubation. Reactions are quenched with 60% methanol at 0, 2.5, 5, and 7.5 min. L-Glutamyl-L-(S-(3-oxo-3-(3-chlorophenyl)propyl)cysteinylglycine, a glutathione adduct of the by-product of prodrug activation, 3-chlorophenyl vinyl ketone, is quantified following extraction of the reaction with 1.5 volumes of methanol. The extracted samples are centrifuged at 14,000 rpm in an Eppendorf microfuge and the supernatant analyzed by HPLC for L-glutamyl-L-(S-(3-oxo-3-(3-chlorophenyl)propyl)cysteinylglycine content. Spiked L-glutamyl-L-(S-(3-oxo-3-(3-chlorophenyl)propyl)cysteinylglycine standards (1-30 μM) are prepared in 2 mg/mL microsomes under reaction conditions and then quenched and processed in an identical fashion to unknown samples. For HPLC analysis, the loading mobile phase buffer (Buffer A) consists of a 9:1 ratio (v/v) of 20 mM potassium phosphate, pH 6.2 and acetonitrile. Extract (100 μL) is injected onto a Beckman Ultrasphere ODS column (4.6×250 mM, part# 235329). The column is eluted with a gradient to 60% acetonitrile. The elution of L-glutamyl-L-(S-(3-oxo-3-(3-chlorophenyl)propyl)cysteinylglycine (retention time 10.4 min.) is monitored at 245 nm.

Conclusion:

Formation of product, L-glutamyl-L-(S-(3-oxo-3-(3-chlorophenyl)propyl) cysteinylglycine indicates the prodrugs are activated in vitro in human liver microsomes.

Example D

In Vitro Activation of Prodrug Analogues by Human Liver Microsomes. Quantification by LC-MS/MS Prodrug analogues were tested for activation to NMP in reactions catalyzed by the microsomal fraction of human liver.

Methods:

Prodrugs were tested for activation by human liver microsomes purchased from In Vitro Technologies (IVT1032) Reactions were conducted in 0.1 M KH$_2$PO$_4$, pH 7.4, in the presence of 2 mM NADPH and liver microsomes (1 mg/mL). Reaction mixtures were incubated for 5 min. in an Eppendorf Thermomixer 5436 (37° C., speed 6). Reactions were terminated by the addition of 1.5 volumes of methanol. The resulting extracts were clarified by centrifugation at 14,000 rpm in an Eppendorf microfuge (20 min.). The supernatants (200 μL) were evaporated under vacuum and heated to dryness. The dried residue was reconstituted with 200 μL of water and the mixture was centrifuged for 10 min at 14,000 rpm. A mixture of 35 μL aliquot of supernatant and 35 μL of mobile phase A (20 mM N-N-dimethylhexylamine and 10 mM propionic acid in 20% methanol) was analyzed by LC-MS/MS (Applied Biosystems, API 4000) equipped with an Agilent 1100 binary pump and a LEAP injector. NMP was detected by using MS/MS mode (M$^-$/78.8) and quantified based on comparison to a standard of lamivudine monophosphate.

Results:

Activation of Compounds in Human Liver Microsomes

| Compound | Activation (250 μM) (nmol/mg/min) |
|---|---|
| 16.2 | 0.301 |
| 16.3 | 0.162 |
| 16.4 | 0.049 |
| 16.5 | 0.463 |
| 16.7 | 0.213 |

-continued

| Compound | Activation (250 μM) (nmol/mg/min) |
|---|---|
| 17.2 | 2.040 |
| 16.8 | 0.436 |
| 16.9 | 0.316 |
| 16.10 | 0.241 |
| 16.11 | 0.100 |
| 16.12 | 0.394 |
| 16.13 | 0.002 |
| 16.14 | 0.282 |
| 16.15 | 0.335 |
| 16.16 | 0.075 |
| 16.17 | 0.021 |
| 16.18 | 0.044 |
| 16.19 | 0.171 |
| 16.20 | 0.137 |
| 16.21 | 0.043 |
| 16.22 | 0.077 |
| 16.23 | 0.013 |
| 16.24 | 0.031 |
| 16.25 | 0.242 |
| 16.26 | 0.223 |
| 16.27 | 0.455 |
| 16.28 | 0.293 |
| 17.3 | 1.677 |
| 17.4 | 1.324 |
| 17.5 | 0.952 |
| 17.6 | 2.086 |
| 16.30 | 0.037 |
| 16.31 | 0.138 |
| 16.32 | 0.074 |
| 17.7 | 1.024 |
| 17.8 | 0.322 |
| 17.9 | 0.314 |
| 17.10 | 0.626 |
| 17.11 | 1.439 |
| 17.12 | 0.750 |
| 17.13 | 0.499 |
| 17.14 | 1.164 |
| 17.15 | 0.733 |
| 17.16 | 0.497 |
| 17.18 | 0.085 |
| 17.20 | 1.381 |
| 17.21 | 0.626 |
| 17.22 | 0.484 |
| 17.23 | 0.089 |
| 17.24 | 0.455 |

Example E

NTP Accumulation in Hepatocytes Following Incubation with Nucleoside Analogues and their Prodrugs Nucleoside analogues and their prodrugs were evaluated for their ability to generate NTPs in freshly isolated rat hepatocytes. It is generally accepted that the NTP form of a nucleoside is the active antiviral agent.

Methods:

Hepatocytes were prepared from fed Sprague-Dawley rats (250-300 g) according to the procedure of Berry and Friend (Berry, M. N. Friend, D. S., *J. Cell Biol.* 43:506-520 (1969)) as modified by Groen (Groen, A. K. et al., *Eur. J. Biochem* 122:87-93 (1982)). Hepatocytes (20 mg/mL wet weight, >85% trypan blue viability) were incubated at 37° C. in 2 mL of Krebs-bicarbonate buffer containing 20 mM glucose, and 1 mg/mL BSA for 2 h in the presence of 1-250 μM nucleoside or prodrug (from 25 mM stock solutions in DMSO). Following the incubation, 1600 μL aliquot of the cell suspension was centrifuged and 300 μL of acetonitrile was added to the pellet, vortexed and sonicated until the pellet broke down. Then 200

µL of water was added to make a 60% acetonitrile solution. After 10 min centrifugation at 14,000 rpm, the resulting supernatant was transferred to a new vial and evaporated to near dryness in a Savant SpeedVac Plus at room temperature. The dried residue was reconstituted with 200 µL of water and the mixture was centrifuged for 10 min at 14,000 rpm. A mixture of 35 µL aliquot of supernatant and 35 µL of mobile phase A (20 mM N—N-dimethylhexylamine and 10 mM propionic acid in 20% methanol) was analyzed by LC-MS/MS (Applied Biosystems, API 4000) equipped with an Agilent 1100 binary pump and a LEAP injector. NTP was detected by using MS/MS mode (M$^-$/78.8) and quantified based on comparison to a standard of lamivudine triphosphate.

Results:

Following the incubation of 25 µM or 250 µM nucleosides and prodrugs with primary rat hepatocytes, NTP formation observed over the course of 2 h was measured as nmol/g.

| Compound | NTP formation from 25 µM compound (nmol/g) | NTP formation from 250 µM compound (nmol/g) |
|---|---|---|
| 2'-C-methyladenosine | 193 | 798 |
| 2'-C-methylguanosine | 1.3 | 4.7 |
| 19 | 13.8 | 56.7 |
| 18 | | 51.8 |
| 16.1 | 85 | 160 |
| 19 | | 130.9 |
| 16.2 | | 130.3 |
| 16.3 | | 102.6 |
| 16.4 | | 55.0 |
| 16.7 | | 347.7 |
| 17.2 | | 4.2 |
| 16.8 | | 160.6 |
| 16.9 | | 115.1 |
| 16.10 | | 17.6 |
| 16.11 | | 63.2 |
| 16.12 | | 18.3 |
| 16.13 | | 3.4 |
| 16.14 | | 18.6 |
| 16.15 | | 34.5 |
| 16.16 | | 6.3 |
| 16.17 | | 7.2 |
| 16.18 | | 13.8 |
| 16.19 | | 70.1 |
| 16.20 | | 19.4 |
| 16.21 | | 10.2 |
| 16.22 | | 10.9 |
| 16.23 | | 2.7 |
| 16.24 | | 4.4 |
| 16.25 | | 22.5 |
| 16.26 | | 58.5 |
| 16.27 | | 63.9 |
| 16.28 | | 19.8 |
| 17.3 | | 2.2 |
| 16.29 | | 14.1 |
| 17.4 | | 3.1 |
| 17.5 | | 2.0 |
| 17.6 | | 3.5 |
| 16.30 | | 36.7 |
| 16.31 | | 16.5 |
| 16.32 | | 49.5 |
| 17.7 | | 1.3 |
| 17.8 | | 1.6 |
| 17.9 | | 2.0 |
| 17.10 | | 2.1 |
| 17.11 | | 3.4 |
| 17.12 | | 1.9 |
| 17.13 | | 3.8 |
| 17.14 | | 4.0 |
| 17.15 | | 1.8 |
| 17.16 | | 1.5 |
| 17.17 | | 0.2 |
| 17.18 | | 4.1 |
| 17.19 | | 0.1 |
| 17.20 | | 2.1 |
| 17.21 | | 1.2 |
| 17.22 | | 1.8 |
| 17.23 | | 0.3 |
| 17.24 | | 3.9 |

Conclusion:

Compounds of this invention showed an ability to generate NTP in freshly isolated rat hepatocytes.

Example F

HCV-Infected Human Liver Slice Assay

Inhibition of HCV replication in human liver tissue was evaluated using the following assay.

Methods:

Procurement:

Liver from a brain-dead HCV antibody-positive human patient was perfused with ice-cold Viaspan (Dupont Pharmaceutical) preservation solution and received on ice in Viaspan.

Precision-cut liver slices of ~200-250 µm thickness and 8 cm diameter were prepared and cultured in Waymouth's cell culture medium (Gibco, Inc.) that was supplemented with 10% fetal bovine serum and 10 mL/L Fungi-Bact at 37° C., and gassed with carbogen (95% $O_2$, 5% $CO_2$) at 0.75 liters/min. Tissue slices were maintained in culture for 72 h. Cell culture medium containing test compound in solution was changed on a daily basis.

At appropriate times of liver slice incubation, liver slices and medium were collected for analysis of HCV RNA (tissue and medium) and nucleotide levels (NTP). All collected media and tissue slices were maintained in liquid $N_2$ until analysis.

Medium and tissue samples were analyzed for HCV RNA levels according to published procedures (Bonacini et. al., 1999) which utilize an automated, multicycle, polymerase chain reaction (PCR)-based technique. This assay has a lower limit of detection for HCV RNA of 100 viral copies/ml.

Analysis of Tissue NTPs:

Frozen liver slices were disrupted by using a combination of ultrasound probe sonication, Branson Sonifier 450 (Branson Ultrasonics, Danbury, Conn.) and homogenization using a Dounce conical pestle in 200 µls of 10% (v/v) perchloric acid (PCA). After a 5 min centrifugation at 2,500×g, the supernatants were neutralized using 3 M KOH/3 M $KHCO_3$ and mixed thoroughly. The neutralized samples were centrifuged at 2,500 g for 5 min and NTP levels were determined by ion exchange phase HPLC (Hewlett Packard 1050) using a Whatman Partisil 5 SAX (5 µm, 4.6×250 mm) column. Samples (50 µL) were injected onto the column in 70% 10 mM ammonium phosphate buffer and 30% 1 M ammonium phosphate buffer, both at pH 3.5 and containing 6% ethanol. Nucleoside triphosphates were eluted from the column using a linear gradient to 80% 1 M ammonium phosphate pH 3.5/6% ethanol buffer, at a flow rate of 1.25 mL/min and detected by UV absorbance (254 nm).

Results:

HCV RNA levels present in the liver slice culture media decreased from the levels present in control, untreated slices following incubation with 2'-C-methylguanosine and compound 19.

| Concentration of Compound (µM) | Log$_{10}$ decrease in viral RNA from control at 48-72 h following treatment with 2'-C-methylguanosine | Log$_{10}$ decrease in viral RNA from control at 48-72 h following treatment with compound 19 |
| --- | --- | --- |
| 0.25 | 0.51 | 1.27 |
| 1 | — | 1.61 |
| 2.5 | 1.74 | 1.70 |
| 25 | 1.48 | 1.72 |

Conclusion:

Treatment of HCV-infected human liver slices with 2'-C-methylguanosine or compound 19 for 72 h decreased the amount of HCV RNA released into the culture medium from 48-72 h. Treatment with the prodrug, compound 19 was more effective than treatment with the nucleoside, 2'-C-methylguanosine, at lowering viral RNA production in the culture medium.

Example G

Liver Targeting of Nucleoside Analogues and their Prodrugs

The liver specificity of the compound 19 prodrug was compared relative to the parent nucleoside, 2'-C-methylguanosine, and for compound 21.1 prodrug relative to its parent nucleoside, 2'-C-methyladenosine, by measuring the generation of NTP in the liver compared to nucleoside in the plasma.

Methods:

Compound 19 or 2'-C-methylguanosine were administered intraperitoneally to C57BL/6 mice at a dose of 30 mg/kg based on nucleoside equivalents (30 mg/kg 2'-C-methylguanosine and 53.27 mg/kg compound 19). Compound 21.1 or 2'-C-methyladenosine were administered intravenously to C57BL/6 mice at dose of about 5.5 mg/kg nucleoside equivalents (5.5 mg/kg 2'-C-methyladenosine and 10 mg/kg compound 21.1). Plasma concentrations of 2'-C-methylguanosine, compound 19, 2'-C-methyladenosine, and compound 21.1 were determined by HPLC-UV and the liver concentrations of the 5'-triphosphate of 2'-C-methylguanosine and 2'-C-methyladenosine were measured by LC-MS using the standard ion-pairing chromatography method for triphosphate as described in Example E. Conventional SAX HPLC-UV could not differentiate between endogenous GTP and 2'-C-methylguanosine triphosphate. Since an authentic standard of 2'-C-methylguanosine triphosphate was not available, the liver concentrations of the nucleotide were approximated as described in Example E.

Results:

Liver targeting of compound 19 as the triphosphate of 2'-C-methylguanosine and of compound 21.1 as the triphosphate of 2'-C-methyladenosine were clearly demonstrated with the prodrugs. The relative liver NTP AUC values, plasma nucleoside AUC values, the liver targeting ratio (liver/plasma), and the fold-improvement with the prodrugs are summarized in the table below. Compound 19 showed a 30-fold prodrug improvement of liver targeting over free nucleoside. Compound 21.1 showed a greater than 32-fold prodrug improvement of liver targeting over free nucleoside, which was below the limit of quantitation in the plasma following dosing of compound 21.1.

| Nucleoside [Prodrug] | Liver NTP AUC (nmol * h/g) | Plasma Nucleoside AUC (µM * h) | Liver Targeting Index (Liver/Plasma) | Prodrug Improvement (Fold) |
| --- | --- | --- | --- | --- |
| 2'-C-methylguanosine | 64 | 73.7 | 0.87 | — |
| 19 | 485 | 18.5 | 26.2 | 30 |
| 2'-C-methyladenosine | 119 | 26.8 | 4.4 | — |
| 21.1 | 502 | <3.6 | >141.4 | >32 |

Example H

Tissue Distribution Following Oral Administration of Nucleoside Analogues and their Prodrugs The liver specificity of prodrugs are compared relative to their parent nucleoside analog inhibitors in liver and other organs that could be targets of toxicity.

Methods:

Nucleoside analogues and their prodrugs are administered at 30 mg/kg (in terms of nucleoside equivalents) to fasted rats by oral gavage. Plasma concentrations of nucleoside and prodrug are determined by HPLC-UV, as described in Example J, and the liver, skeletal muscle, cardiac, kidney, small intestine, and other organ concentrations of the 5'-triphosphate of the nucleoside are measured by LC-MS using the standard ion-pairing chromatography method for triphosphate as described in Example E.

Results:

The results demonstrate the liver targeting of the nucleoside analog prodrugs and provide evidence for improved safety of the prodrugs over that of the nucleosides alone. This can occur solely by the liver targeting provided by the prodrug or by additional liver metabolism of nucleoside derived following dephosphorylation of the nucleoside monophosphate. In the latter case, the nucleoside can escape from the liver into the periphery leading to exposure of other tissues to the nucleoside and potential extrahepatic toxicity. The release of nucleoside from the liver can be reduced by metabolism of the nucleoside monophosphate or the nucleoside in the liver cell, e.g. the breakdown of adenosine-based nucleoside monophosphates to inosine via adenylate deaminase and nucleotidase, or the breakdown of adenosine-based nucleoside to inosine and hypoxanthine by adenosine deaminase and purine nucleoside phosphorylase, respectively.

Example I

Assessment of the Oral Bioavailability of Nucleoside Analogues and their Prodrugs in Normal Male Rats The oral bioavailability (OBAV) of the nucleoside analogues and their prodrugs were evaluated in the normal male rat.

Methods:

The compounds were solubilized in a suitable vehicle for intravenous and oral administration. The OBAV was assessed by calculating the ratio of the AUC values of the liver organ concentration-time profile of NTP following oral and i.v. or i.p. administration of 30 mg/kg (in terms of nucleoside equivalents) of the compound to groups of four rats. Liver organ samples were taken at 20 min and 1, 3, 5, 8, 12, and 24 h following dosing. Liver organ concentrations of NTP were determined as determined by LC-MS/MS (Example E) or HPLC (Example F) analysis.

Results:

Oral Bioavailability in the Normal Male Rat

| Compound | % F |
|---|---|
| 16.32 | 31.7 |

Example J

Susceptibility of Nucleoside Analogues to Metabolism in Rat Liver S9 Fraction or Isolated Hepatocytes The susceptibility of the purine nucleoside analogues to metabolism is assessed in rat liver S9 fraction or isolated rat hepatocytes.

Methods: Purine nucleoside analogues (100 µM) (e.g., 2'-C-methyladenosine) are incubated in rat liver S9 fraction or with isolated rat hepatocytes at 37° C. The reactions are terminated at time points up to 2 h and then deproteinized by extraction with 60% acetonitrile. Following centrifugation, the supernatants are evaporated to dryness and the resulting residues are reconstituted with aqueous mobile phase. These samples are analyzed for potential metabolites by a single HPLC system equipped with a diode array detector. Nucleosides (e.g., 2'-C-methylinosine) and bases (e.g., hypoxanthine) are separated and quantified on a Beckman Ultrasphere C-18 reverse phase column (4.5×250 mm) using a gradient of Buffer A (100 mM potassium phosphate pH 6) and Buffer B (25% v/v methanol) at a flow rate of 1.5 mL/min. The column is developed over 40 min using a nonlinear gradient of 0% Buffer B to 100% Buffer B (% pump Buffer B=100×(time [min]/40)$^3$) and monitored by UV absorbance at 260 nm. Metabolites are identified by coelution with authentic standards and/or UV spectrum matching.

Results:

The susceptibility of the purine nucleoside analogues to metabolism is dependent upon the type and location of the structural modification of the congener. The inclusion of certain pharmacophores (such as the 2'-C-methyl group of 2'-C-methyladenosine] leads to increased resistance to metabolism by purine salvage pathway enzymes [such as adenosine deaminase and purine nucleoside phosphorylase).[1]

[1] Eldrup A B, Allerson C R, Bennett C F, et al. (2004) *J. Med. Chem.* 47(9): 2283-2295, "Structure-activity relationship of purine ribonucleotides for inhibition of hepatitis C virus RNA-dependent RNA polymerase."

We claim:

1. A compound of Formula II:

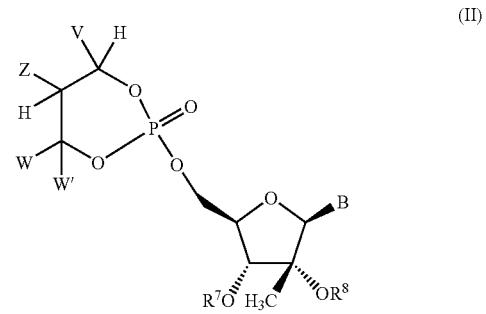

(II)

wherein:

B is selected from the group consisting of

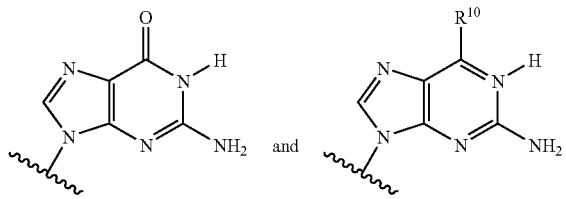

V is selected from the group consisting of optionally substituted monocyclic aryl and unsubstituted or substituted monocyclic heteroaryl wherein said substituted monocyclic aryl and said substituted monocyclic heteroaryl are substituted with 1-6 substituents selected from the group consisting of lower alkyl, lower alkoxy, lower perhaloalkyl, halogen, hydroxy, cyano, amino, —OR$^3$, —OR$^{12}$, —COR$^3$, —CO$_2$R$^3$, —NR$^3{}_2$, —NR$^{12}{}_2$, —CO$_2$NR$_2{}^2$, —SR$^3$, —SO$_2$R$^3$, and —SO$_2$NR$_2{}^2$;

W and W' are independently selected from the group consisting of —H, methyl, and V, or W and W' are each methyl, with the proviso that when W is V, then W' is H;

Z is selected from the group consisting of —H, —OMe, —OEt, phenyl, C$_1$-C$_3$ alkyl, —NR$^4{}_2$, —SR$^4$, —(CH$_2$)$_p$—OR$^6$, —(CH$_2$)$_p$—SR$^6$ and —OCOR$^5$; or together V and Z are connected via an additional 3-5 atoms to form a cyclic group, containing 0-1 heteroatom, that is fused to an aryl group at the beta and gamma position to the O attached to the phosphorus; or together Z and W are connected via an additional 3-5 atoms to form a cyclic group, containing 0-1 heteroatom; or together W and W' are connected via an additional 2-5 atoms to form a cyclic group;

R$^2$ is selected from the group consisting of R$^3$ and hydrogen;

R$^3$ is selected from the group consisting of alkyl, aryl, heterocycloalkyl, and aralkyl;

$R^4$ is $C_1$-$C_4$ alkyl;

$R^5$ is selected from the group consisting of $C_1$-$C_4$ alkyl, monocyclic aryl, and monocyclic aralkyl; and $R^6$ is $C_1$-$C_4$ acyl; and together $R^7$ and $R^8$ form a cyclic carbonate; and $R^{10}$ is selected from the group consisting of $OR^4$, $OR^6$, $NH_2$, $NHR^4$, halogen, and H;

or a pharmaceutically acceptable salt thereof.

2. The compound of claim 1, wherein:

V is selected from the group consisting of phenyl, substituted phenyl with 1-3 substituents independently selected from the group consisting of halogen, $C_1$-$C_6$ alkyl, —$CF_3$, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, —$SO_2NR_2{}^2$ and —CN, monocyclic heteroaryl, and substituted monocyclic heteroaryl with 1-2 substituents independently selected from the group consisting of halogen, $C_1$-$C_6$ alkyl, —$CF_3$, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, —$SO_2NR_2{}^2$ and —CN, and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 3-5 atoms to form a cyclic group, containing 0-1 heteroatom, that is fused to an aryl group at the beta and gamma position to the O attached to the phosphorus; and $R^3$ is $C_1$-$C_6$ alkyl.

3. The compound of claim 2 wherein:

V is selected from the group consisting of phenyl, substituted phenyl with 1-3 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN, monocyclic heteroaryl, and substituted monocyclic heteroaryl with 1-2 substituents independently selected from the group consisting of —Cl, —Br, —F, $C_1$-$C_3$ alkyl, —$CF_3$, —$COCH_3$, —OMe, —$NMe_2$, —OEt, —$CO_2$t-butyl, —$CO_2NH_2$, —SMe, —$SO_2Me$, —$SO_2NH_2$ and —CN and wherein said monocyclic heteroaryl and substituted monocyclic heteroaryl has 1-2 heteroatoms that are independently selected from the group consisting of N, O, and S with the provisos that a) when there are two heteroatoms and one is O, then the other can not be O or S, and b) when there are two heteroatoms and one is S, then the other can not be O or S; or together V and Z are connected via an additional 4 atoms to form a 6-membered ring that is fused to a phenyl or substituted phenyl at the beta and gamma position to the O attached to the phosphorus, wherein said substituted phenyl is substituted with 1-6 substituents selected from the group consisting of lower alkyl, lower alkoxy, lower perhaloalkyl, halogen, hydroxy, cyano, amino, —$OR^3$, —$OR^{12}$, —$COR^3$, —$CO_2R^3$, —$NR^3{}_2$, —$NR^{12}{}_2$, —$CO_2NR_2{}^2$, —$SR^3$, —$SO_2R^3$, and —$SO_2NR_2{}^2$.

4. The compound of claim 1 wherein V is selected from the group consisting of phenyl; substituted phenyl with 1-2 substituents independently selected from the group consisting of —Cl, —Br, —F, $C_1$-$C_3$ alkyl, and —$CF_3$; pyridyl; substituted pyridyl with 1 substituent independently selected from the group consisting of —Cl, —Br, —F, $C_1$-$C_3$ alkyl, and —$CF_3$; furanyl; substituted furanyl with 1 substituent independently selected from the group consisting of —Cl, —Br, —F, $C_1$-$C_3$ alkyl, and —$CF_3$; thienyl; and substituted thienyl with 1 substituent independently selected from the group consisting of —Cl, —Br, —F, $C_1$-$C_3$ alkyl, and —$CF_3$;

and wherein Z, W, and W' are each —H.

5. The compound of claim 4 wherein V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl.

6. The compound of claim 5 wherein V is selected from the group consisting of 3-chlorophenyl, 3-bromophenyl, 2-bromophenyl, 3,5-dichlorophenyl, 3-pyridyl, and 4-pyridyl.

7. The compound of claim 1, wherein said compound is a compound of Formula III:

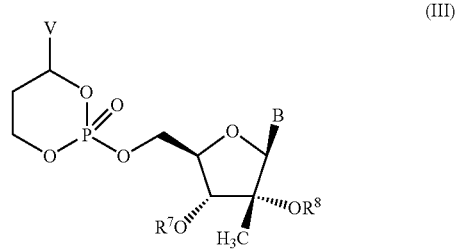

(III)

wherein:

V and the 5'oxymethylene group of the ribose sugar moiety are cis to one another and wherein V is selected from the group consisting of 3-chlorophenyl, 3-bromophenyl, 2-bromophenyl, 3,5-dichlorophenyl, 3-pyridyl, and 4-pyridyl.

8. The compound of claim 7, wherein said compound has R-stereochemistry at the V-attached carbon and has S-stereochemistry at the phosphorus center.

9. The compound of claim 7 wherein said compound has S-stereochemistry at the V-attached carbon and has R-stereochemistry at the phosphorus center.

10. A compound of Formula I:

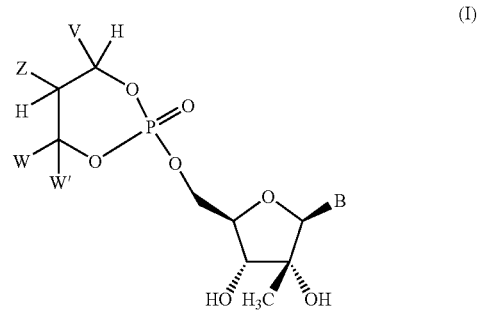

(I)

wherein:

B is

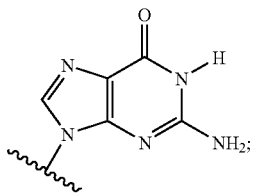

V is phenyl optionally substituted by one or two halogen atoms, or V is pyridyl;

and W, W' and Z are all —H;

or a pharmaceutically acceptable salt thereof.

11. The compound of claim 10, wherein V is selected from the group consisting of phenyl, 3-chlorophenyl, 3-bromophenyl, 2-bromophenyl, 3,5-dichlorophenyl, 3-bromo-4-fluorophenyl, 2-pyridyl, 3-pyridyl, and 4-pyridyl.

12. The compound of claim 11, wherein V is selected from the group consisting of 3-chlorophenyl, 3-bromophenyl, 2-bromophenyl, 3,5-dichlorophenyl, and 4-pyridyl.

13. The compound of claim 12, wherein V and the 5'oxymethylene group of the ribose sugar moiety are cis to one another.

14. The compound of claim 13, wherein said compound has R-stereochemistry at the V-attached carbon and has S-stereochemistry at the phosphorus center.

15. The compound of claim 13, wherein said compound has S-stereochemistry at the V-attached carbon and has R-stereochemistry at the phosphorus center.

16. The compound of claim 10 wherein said compound is:

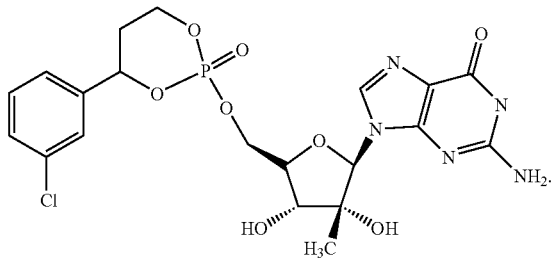

17. The compound of claim 10, wherein said compound is:

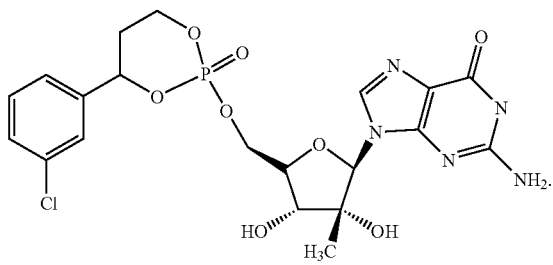

18. A pharmaceutical composition comprising a pharmaceutically effective amount of a compound of claim 1 and a pharmaceutically acceptable carrier.

19. A pharmaceutical composition comprising a pharmaceutically effective amount of a compound of claim 10 and a pharmaceutically acceptable carrier.

20. A method of inhibiting viral replication in a human patient comprising administering to said human patient a therapeutically effective amount of a compound of claim 1.

21. The method of claim 20, wherein said viral replication is RNA-dependent RNA viral replication.

22. The method of claim 20, wherein said viral replication is HCV replication.

23. A method of inhibiting viral replication in a human patient comprising administering to said human patient a therapeutically effective amount of a compound of claim 10.

24. The method of claim 23, wherein said viral replication is RNA-dependent RNA viral replication.

25. The method of claim 23, wherein said viral replication is HCV replication.

26. A method of treating a viral infection in a human patient comprising administering to said human patient a therapeutically effective amount of a compound of claim 1.

27. The method of claim 26, wherein said viral infection is RNA-dependent RNA viral infection.

28. The method of claim 26, wherein said viral infection is HCV infection.

29. The method of claim 26, wherein said compound is used in combination with a therapeutically effective amount of a second agent active against HCV.

30. The method of claim 29, wherein said second agent active against HCV is ribavirin; levovirin; viramidine; thymosin alpha-1; interferon-β; an inhibitor of NS3 serine protease; an inhibitor of inosine monophosphate dehydrogenase; interferon-α or pegylated interferon-α, alone or in combination with ribavirin or levovirin.

31. The method of claim 30, wherein said second agent active against HCV is interferon-α or pegylated interferon-α, alone or in combination with ribavirin or levovirin.

32. A method of treating a viral infection in a human patient comprising administering to said human patient a therapeutically effective amount of a compound of claim 10.

33. The method of claim 32, wherein said viral infection is RNA-dependent RNA viral infection.

34. The method of claim 32, wherein said viral infection is HCV infection.

35. The method of claim 34, wherein said compound of Formula I is used in combination with a therapeutically effective amount of a second agent active against HCV.

36. The method of claim 35, wherein said second agent active against HCV is ribavirin; levovirin; viramidine; thymosin alpha-1; interferon-β; an inhibitor of NS3 serine protease; an inhibitor of inosine monophosphate dehydrogenase; interferon-α or pegylated interferon-α, alone or in combination with ribavirin or levovirin.

37. The method of claim 36, wherein said second agent active against HCV is interferon-α or pegylated interferon-α, alone or in combination with ribavirin or levovirin.

* * * * *

UNITED STATES PATENT AND TRADEMARK OFFICE
CERTIFICATE OF CORRECTION

PATENT NO.        : 7,666,855 B2                                   Page 1 of 2
APPLICATION NO. : 11/589363
DATED             : February 23, 2010
INVENTOR(S)       : K. Raja Reddy and Mark D. Erion It is certified that error appears in the above-identified patent and that said Letters Patent is hereby corrected as shown below:

Column 1,
Line 37, "(NMP) is" should read --(NMP), is--.

Column 24,
Line 61, "-SO$_2$NH$_2$and" should read -- -SO$_2$NH$_2$ and--.

Column 27,

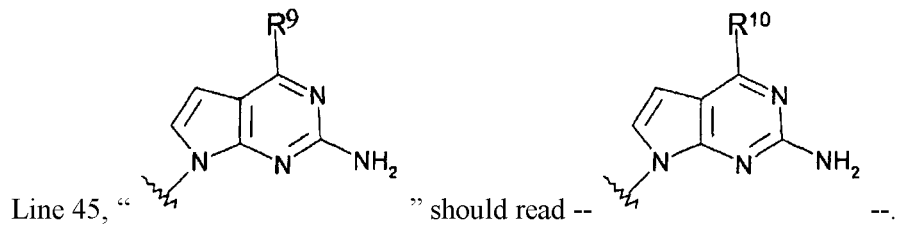

Line 45, " " should read -- --.

Column 64,
Line 29, "J. Ore. Chem" should read --J. Org. Chem.--.
Line 29, "H, 5.1 1;" should read --H, 5.11;--.

Column 70,
Line 45, "fornic acid" should read --formic acid--.

Column 81,
Line 47, "C$_{15}$H$_{12}$C$_2$NO$_6$P" should read --C$_{15}$H$_{12}$Cl$_2$NO$_6$P--.

Column 95,
Line 22, "1,3,2-dioxapbospborinan" should read --1,3,2-dioxaphosphorinan--.

Column 116,
Line 46, "BH$_3$THF" should read --BH$_3$THF--.

Signed and Sealed this

Twenty-second Day of June, 2010

David J. Kappos
*Director of the United States Patent and Trademark Office*

Column 132,
Line 40, "consisting of optionally substituted" should read
--consisting of unsubstituted or substituted--.
Column 135,
Lines 35-45, " 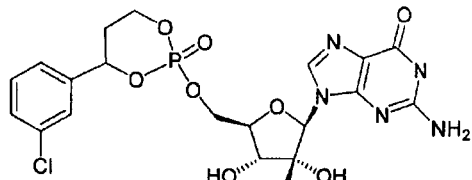 " should read
-- 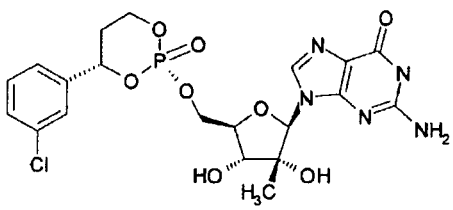 --.

UNITED STATES PATENT AND TRADEMARK OFFICE
CERTIFICATE OF CORRECTION

PATENT NO. : 7,666,855 B2
APPLICATION NO. : 11/589363
DATED : February 23, 2010
INVENTOR(S) : K. Raja Reddy and Mark D. Erion It is certified that error appears in the above-identified patent and that said Letters Patent is hereby corrected as shown below:

Column 1,
Line 37, "(NMP) is" should read --(NMP), is--.

Column 24,
Line 61, "-SO$_2$NH$_2$and" should read -- -SO$_2$NH$_2$ and--.

Column 27,
Line 45, " 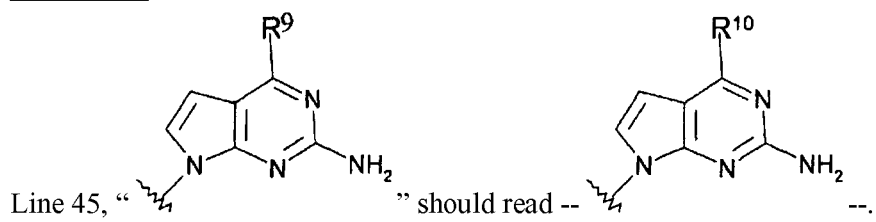 " should read -- --.

Column 64,
Line 29, "J. Ore. Chem" should read --J. Org. Chem.--.

Column 70,
Line 45, "fornic acid" should read --formic acid--.

Column 81,
Line 47, "C$_{15}$H$_{12}$C$_2$NO$_6$P" should read --C$_{15}$H$_{12}$Cl$_2$NO$_6$P--.

Column 95,
Line 22, "1,3,2-dioxapbospborinan" should read --1,3,2-dioxaphosphorinan--.

This certificate supersedes the Certificate of Correction issued June 22, 2010.

Signed and Sealed this
Twenty-second Day of February, 2011

David J. Kappos
*Director of the United States Patent and Trademark Office*

CERTIFICATE OF CORRECTION (continued)

Column 116,
Line 46, "H,5.1 1;" should read --H,5.11;--.

Column 132,
Line 40, "consisting of optionally substituted" should read
--consisting of unsubstituted or substituted--.

Column 135,

Lines 35-45, " 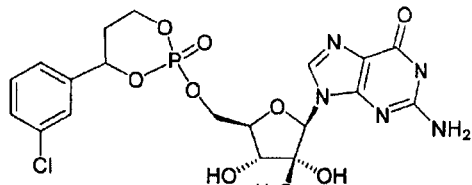 " should read

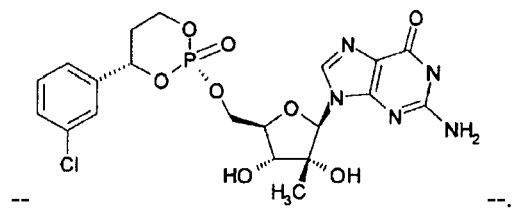

-- --.